US008980907B2

(12) United States Patent
Baker, Jr. et al.

(10) Patent No.: US 8,980,907 B2
(45) Date of Patent: Mar. 17, 2015

(54) DENDRIMER CONJUGATES

(71) Applicant: The Regents of the University of Michigan, Ann Arbor, MI (US)

(72) Inventors: James R. Baker, Jr., Ann Arbor, MI (US); Xue-min Cheng, Ann Arbor, MI (US); Abraham F. L. Van Der Spek, Ann Arbor, MI (US); Baohua Mark Huang, Ann Arbor, MI (US); Thommey P. Thomas, Dexter, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/107,817

(22) Filed: Dec. 16, 2013

(65) Prior Publication Data

US 2014/0128327 A1 May 8, 2014

Related U.S. Application Data

(63) Continuation of application No. 12/570,977, filed on Sep. 30, 2009.

(60) Provisional application No. 61/101,461, filed on Sep. 30, 2008.

(51) Int. Cl.
*A61K 31/5513* (2006.01)
*A61K 31/485* (2006.01)
*A61K 31/5377* (2006.01)
*C07D 489/02* (2006.01)
*C07D 413/06* (2006.01)
*A61K 47/48* (2006.01)

(52) U.S. Cl.
CPC ......... *A61K 47/483* (2013.01); *A61K 47/48207* (2013.01); *A61K 31/485* (2013.01)
USPC .......... 514/282; 514/237.2; 424/78.3; 546/46

(58) Field of Classification Search
USPC .................. 514/282, 237.2; 424/78.3; 546/46
See application file for complete search history.

(56) References Cited

U.S. PATENT DOCUMENTS

| | | | |
|---|---|---|---|
| 4,161,948 A | 7/1979 | Bichon |
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,708,930 A | 11/1987 | Kortright et al. |
| 4,713,975 A | 12/1987 | Tomalia et al. |
| 4,737,550 A | 4/1988 | Tomalia et al. |
| 4,743,543 A | 5/1988 | Kortright |
| 4,827,945 A | 5/1989 | Groman |
| 4,857,599 A | 8/1989 | Tomalia et al. |
| 4,871,779 A | 10/1989 | Killat et al. |
| 4,892,935 A | 1/1990 | Yoshida et al. |
| 4,914,021 A | 4/1990 | Toth |
| 4,918,164 A | 4/1990 | Hellstrom et al. |
| 4,921,789 A | 5/1990 | Salem et al. |
| 4,921,790 A | 5/1990 | O'Brien |
| 4,939,240 A | 7/1990 | Chu et al. |
| 4,946,778 A | 8/1990 | Ladner et al. |
| 4,963,484 A | 10/1990 | Kufe |
| 4,965,128 A | 10/1990 | Greidanus |
| 5,041,516 A | 8/1991 | Frechet et al. |
| 5,053,489 A | 10/1991 | Kufe |
| 5,110,911 A | 5/1992 | Samuel et al. |
| 5,270,163 A | 12/1993 | Gold et al. |
| 5,338,532 A | 8/1994 | Tomalia et al. |
| 5,354,308 A | 10/1994 | Simon et al. |
| 5,387,617 A | 2/1995 | Hedstrand et al. |
| 5,393,795 A | 2/1995 | Hedstrand et al. |
| 5,393,797 A | 2/1995 | Hedstrand et al. |
| 5,475,096 A | 12/1995 | Gold et al. |
| 5,512,443 A | 4/1996 | Schlom et al. |
| 5,527,524 A | 6/1996 | Tomalia et al. |

(Continued)

FOREIGN PATENT DOCUMENTS

| | | |
|---|---|---|
| CA | 2187921 | 11/1995 |
| CA | 2386998 | 4/2001 |

(Continued)

OTHER PUBLICATIONS

Maini, et al., "Infliximab (chimeric anti-tumour necrosis factor monoclonal antibody) versus placebo in rheumatoid arthritis patients receiving concomitant methotrexate: a randomised phase III trial," Lancet (1999) vol. 354, pp. 1932-1939.

Chandrasekar, Durairaj, et al., "The development of folate-PAMAM dendrimer conjugates for targeted delivery of anti-arthritic drugs and their pharmacokinetics and biodistribution in arthritic rats," Biomaterials (2007) vol. 28, pp. 504-512.

Mullen, Douglas G., "A Quantitative Assessment of Nanoparticle— Ligand Distributions: Implications for Targeted Drug and Imaging Delivery in Dendrimer Conjugates," ACS Nano (2010), 4(2), pp. 657-670.

(Continued)

*Primary Examiner* — Anoop Singh
*Assistant Examiner* — Anna Falkowitz
(74) *Attorney, Agent, or Firm* — Casimir Jones S.C.

(57) ABSTRACT

The present invention relates to novel therapeutic and diagnostic dendrimers. In particular, the present invention is directed to dendrimer-linker conjugates, methods of synthesizing the same, compositions comprising the conjugates, as well as systems and methods utilizing the conjugates (e.g., in diagnostic and/or therapeutic settings (e.g., for the delivery of therapeutics, imaging, and/or targeting agents (e.g., in disease (e.g., cancer) diagnosis and/or therapy, pain therapy, etc.)). Accordingly, dendrimer-linker conjugates of the present invention may further comprise one or more components for targeting, imaging, sensing, and/or providing a therapeutic or diagnostic material and/or monitoring response to therapy.

5 Claims, 50 Drawing Sheets

(56) References Cited

U.S. PATENT DOCUMENTS

| | | |
|---|---|---|
| 5,545,530 A | 8/1996 | Satomura et al. |
| 5,560,929 A | 10/1996 | Hedstrand et al. |
| 5,631,329 A | 5/1997 | Yin et al. |
| 5,661,025 A | 8/1997 | Szoka et al. |
| 5,674,192 A | 10/1997 | Sahatjian |
| 5,693,014 A | 12/1997 | Abele et al. |
| 5,693,763 A | 12/1997 | Codington et al. |
| 5,714,166 A | 2/1998 | Tomalia et al. |
| 5,733,303 A | 3/1998 | Israel et al. |
| 5,755,722 A | 5/1998 | Barry et al. |
| 5,773,527 A | 6/1998 | Tomalia et al. |
| 5,792,105 A | 8/1998 | Lin |
| 5,795,582 A | 8/1998 | Wright |
| 5,800,391 A | 9/1998 | Kontos |
| 5,800,508 A | 9/1998 | Goicoechea et al. |
| 5,800,519 A | 9/1998 | Sandock |
| 5,808,005 A | 9/1998 | Codington et al. |
| 5,843,089 A | 12/1998 | Sahatjian |
| 5,851,228 A | 12/1998 | Pinheiro |
| 5,855,866 A | 1/1999 | Thorpe |
| 5,855,881 A | 1/1999 | Loike et al. |
| 5,857,998 A | 1/1999 | Barry |
| 5,861,319 A | 1/1999 | Lin et al. |
| 5,866,561 A | 2/1999 | Ungs |
| 5,868,719 A | 2/1999 | Tsukernik |
| 5,876,445 A | 3/1999 | Andersen |
| 5,892,019 A | 4/1999 | Schlom |
| 5,892,020 A | 4/1999 | Mezes |
| 5,898,005 A | 4/1999 | Singh |
| 5,902,863 A | 5/1999 | Dvornic et al. |
| 5,908,413 A | 6/1999 | Lange |
| 5,913,894 A | 6/1999 | Schmitt |
| 5,922,887 A | 7/1999 | Dondio et al. |
| 5,933,145 A | 8/1999 | Meek |
| 5,935,114 A | 8/1999 | Jang |
| 6,051,429 A | 4/2000 | Hawley-Nelson et al. |
| 6,054,444 A | 4/2000 | Jackson |
| 6,267,987 B1 | 7/2001 | Park et al. |
| 6,312,679 B1 | 11/2001 | Tomalia et al. |
| 6,471,968 B1 | 10/2002 | Baker et al. |
| 6,485,718 B1 | 11/2002 | Parthasarathy |
| 6,585,956 B2 | 7/2003 | Malik et al. |
| 6,869,772 B2 | 3/2005 | Lichtman et al. |
| 7,078,461 B2 | 7/2006 | Tomalia |
| 7,097,856 B2 | 8/2006 | Frechet |
| 7,208,486 B2 | 4/2007 | Burnett |
| 7,261,875 B2 | 8/2007 | Li |
| 7,368,512 B2 | 5/2008 | Newkome |
| 7,459,145 B2 | 12/2008 | Bao |
| 7,745,229 B2 | 6/2010 | Wang |
| 2001/0031498 A1 | 10/2001 | Leclercq |
| 2002/0165179 A1 | 11/2002 | Baker, Jr. |
| 2003/0129158 A1 | 7/2003 | Matthews et al. ........... 424/78.17 |
| 2003/0180250 A1 | 9/2003 | Chauhan et al. |
| 2004/0109842 A1 | 6/2004 | Baker, Jr. |
| 2004/0120979 A1 | 6/2004 | Roessler et al. |
| 2005/0214247 A1 | 9/2005 | Shaunak |
| 2006/0057211 A1 | 3/2006 | Chorny |
| 2007/0020620 A1 | 1/2007 | Finn |
| 2007/0041934 A1* | 2/2007 | William et al. ............... 424/78.3 |
| 2007/0122348 A1 | 5/2007 | Kaiko et al. ................. 424/10.1 |
| 2007/0298006 A1 | 12/2007 | Tomalia et al. |
| 2008/0045689 A1 | 2/2008 | Stumbe et al. |
| 2008/0171067 A1 | 7/2008 | Govindan et al. |
| 2008/0200562 A1 | 8/2008 | Yin |
| 2008/0312344 A1 | 12/2008 | Liskamp et al. |
| 2009/0012035 A1 | 1/2009 | Jacobson et al. |
| 2009/0053139 A1 | 2/2009 | Shi |
| 2009/0069561 A1 | 3/2009 | Fokin et al. |
| 2009/0082537 A1 | 3/2009 | Ramon Hernandez et al. |
| 2009/0088376 A1 | 4/2009 | Baker, Jr. |
| 2009/0104119 A1 | 4/2009 | Majoros |
| 2009/0208580 A1 | 8/2009 | Shi |
| 2009/0287005 A1 | 11/2009 | Baker, Jr. |
| 2010/0136614 A1* | 6/2010 | Luo et al. ..................... 435/68.1 |
| 2010/0158850 A1 | 6/2010 | Baker, Jr. |
| 2010/0160299 A1 | 6/2010 | Baker, Jr. |
| 2010/0183749 A1 | 7/2010 | Brey |

FOREIGN PATENT DOCUMENTS

| | | |
|---|---|---|
| CN | 101267803 | 9/2008 |
| EP | 0099758 | 10/1984 |
| EP | 0271180 | 6/1988 |
| EP | 1941861 | 7/2008 |
| JP | 2002-265495 | 9/2002 |
| WO | 88/01178 | 2/1988 |
| WO | 88/01180 | 2/1988 |
| WO | 90/02545 | 3/1990 |
| WO | 95/24221 | 9/1995 |
| WO | 95/28641 | 10/1995 |
| WO | 9707398 | 2/1997 |
| WO | 97/38134 | 10/1997 |
| WO | 98/33941 | 8/1998 |
| WO | 99/02651 | 1/1999 |
| WO | 99/07724 | 2/1999 |
| WO | 9961662 | 2/1999 |
| WO | 99/10362 | 3/1999 |
| WO | 99/58656 | 11/1999 |
| WO | 00/16807 | 3/2000 |
| WO | 01/87348 | 11/2001 |
| WO | 0102861 | 11/2001 |
| WO | 03/003975 | 1/2003 |
| WO | 03/011115 | 2/2003 |
| WO | 03/055935 | 7/2003 |
| WO | 2006/033766 | 3/2006 |
| WO | 2007/011967 | 1/2007 |
| WO | 2007012001 | 1/2007 |
| WO | 2007/034750 | 3/2007 |
| WO | 2007/080114 | 7/2007 |
| WO | 2008/008483 | 1/2008 |
| WO | 2011002852 | 1/2011 |
| WO | 2011028334 | 3/2011 |
| WO | 2011/059609 | 5/2011 |
| WO | 2011053618 | 5/2011 |
| WO | 2011/072290 | 6/2011 |

OTHER PUBLICATIONS

Mullen, et al., "Design, synthesis, and biological functionality of a dendrimer-based modular drug delivery platform," Bioconjugate Chemistry, vol. 22, No. 4, pp. 679-689 (Mar. 22, 2011).

Frechet, Jean M.J., et al., "Reversed-phase high-performance liquid chromatographyj of functionalized dendritic macromolecules," Journal of Chromatography A, 667 (1994), pp. 284-289.

Opsteen, et al., "Modular synthesis of block copolymers via cycloaddition of terminal azide and alkyne functionalized polymers", Chemical Communicaitons, vol. 1, pp. 57-59 (2005).

Yim, et al., "Versatile conjugation of octreotide to dendrimers by cycloaddition ("Click") chemistry to yield high-affinity mulivalent cyclic peptide dendrimers," Bioconjugate Chemistry, vol. 20, No. 7, pp. 1323-1331 (2009).

Huang, B., et al., "Copper-free click conjugation of methotrexate to a PAMAM dendrimer platform", Tetrahedron Letters, E-pub, Dec. 10, 2010, v. 52, pp. 1411-1414.

Dijk, M.V., et al., "Synthesis and Applications of Biomedical and Pharmaceutical Polymers via Click Chemistry Methodologies," Bioconjugate Chemistry, Nov. 2009, v. 20, No. 11, pp. 2011-2016.

Nimmo, C.M. et al., "Regenerative Biomaterials that 'Click': Simple, Aqueous-Based Protocols for Hydrogel Synthesis, Surface Immoboilization, and 3D Patterning" Bioconjugate Chemistry, Oct. 13, 2011, v. 22, pp. 2199-2209.

Huang, B., et al., "The facile synthesis of multifunctional PAMAM dendrimer conjugates through copper-free click chemistry" Bioorganic & Medicinal Chemistry Letters, Mar. 21, 2012, v. 22, pp. 3152-3156.

International Search Report and Written Opinion mailed Mar. 29, 2013, International Patent Application No. PCT/US2012/066104.

Majithia V, et al. Am. J. Med. (2007) 120 (11): 936-9.

Eichman et al. (2000) Pharm. Sci. Technolo. Today 3:232-245.

Lou et al. (2002) Macromol. 35:3456-3462.

Kobayashi et al. (2003) Bioconj. Chem. 14:388-394.

(56) References Cited

OTHER PUBLICATIONS

Wang, et al., "Synthesis and Application of Carbohydrate-Containing Polymers", Chem. Mater. (2002) 14, pp. 3232-3244.
Wangler, C., et al., "Antibody-dendrimer conjugates: the number, not the size of the dendrimers, determines the immunoreactivity," Bioconjug Chem., Apr. 2008, vol. 19(4), pp. 813-820.
Dirks, A. (Ton) J., et al., "Monitoring Protein—Polymer Conugation by a Fluorogenic (Cu(I)-Catalyzed Azide—Alkyne 1,3-Dipolar Cycloaddition," Bioconjugate Chemistry, vol. 20, No. 6, pp. 1129-1138 (Jun. 2006).
Lalwani, Sanjiv, et al., "Mimicking PAMAM Dendrimers with Amphoteric, Hybrid Triazine Dendrimers: A Comparison of Dispersity and Stability," Macromolecules, vol. 42, No. 17, pp. 6723-6732 (Aug. 12, 2009).
Rheumatoid arthiritis, Merck Manual Home Ed. Avaialble at http://wwww.merckmanuals.com/home/print/sec05/ch066/ch066b.html (printed Apr. 19, 2011).
Sottosanti, "Calcium Sulfate: A Biodegradable and Biocompatible Barrier for Guided Tissue Regeneration," Compendium 13(3):226-8, 230, 232-4 (1992).
Springer et al., "Blood Group Tn-Active Macromolecules from Human . . ." Carbohydr. Res. 178:271-292 (1988).
Stoddart, "Gene Delivery with Dendrimers", Chemical Biology 2006.
Talanian et al., "Substrate Specificities of Caspase Family Proteases," J. Biol. Chem., 272:9677 (1997).
Tang et al., "In Vivo Gene Delivery by Degraded Polyamidoamine Dendrimers," Biocong Chem 7:703 (1996).
Tjandra et al., "Application of mammary serum antigen assay in the management of breast cancer: a preliminary report," Br. J. Surg. 75:811-817 (1988).
Tomalia et al., "Starburst Dendrimers: Molecular-Level Control of Size, Shape, Surface chemistry, Topology, and Flexibility from Atoms to Macroscopic Matter," Chem. Int. Ed. Engl., 29:138-175(1990).
Tomalia et al., "Comb-Burst Dendrimer Topology. New Macromolecular Architecture Derived from Dendritic Grating,"Macromolecule 24:1435-1438 (1999).
Tomalia, "Starburst/Cascade Dendrimers: Fundamental Building Blocks for a New Nanoscopic Chemistry Set," Advanced Materials 6:529 (1994).
Tortora et al., "Synergistic Inhibition of Growth and Induction of Apoptosis by 8-Chloro-cAMP and Paclitaxel or Cisplatin in Human Cancer Cells," Cancer Research 57:5107 (1997).
Trainer, et al., "Gene delivery to the epidermis," Human Mol. Gen 6:1761 (1997).
Tuerk et al., "In vitro evolution of functional nucleic acids: high affinity FNA ligands of HIV-1 proteins," Gene 137 (1):33-9 (1993).
Uppuluri et al., Tecto(Dendrimer) Core-Shell Molecules: . . . PMSE 80:55 (1999).
Urdea and Horn, "Dendrimer Development," Science 261:534 (1993).
Van Hest et al., "Polystyrene-Dendrimer Amphiphilic Block Copolymers with a Generation-Dependent Aggregation," Science 268:1592-1595 (1995).
Vasey et al., "Phase I Clinicial and Pharmacokinetic Study of PK1 . . . ", Clin. Cancer Res. 5:83 (1999).
Wagner, "Effects of membrane-active agents in gene delivery," Journal of controlled Release 53:155-158 (1998).
Webber et al., "Characterisation of soluble, salt-loaded, degradable PLGA films and their release of tetracycline," J. Biomed Mater Res 41:18 (1998).
White, et al., "Viral Recptors of the Immunoglobulin Superfamily," Cell 56:725 (1989).
Wiener et al., "Dendrimer-Based Metal Chelates: A New Class of Magnetic Resonance Imaging Contrast Agents," Magn Reson. Med. 31:1 (1994).
Wiener et al., "Targeting Dendrimer-Chelates to Tumors and Tumor Cells Expressing the High-Affinity Folate Receptor," Invest. Radiol. 32:748 (1997).

Wies, et al., "Structure of the influenza virus haemagglutinin complexed with its recptor, sialic acid," Nature 333:426 (1988).
Wilbur et al., "Biotin Reagents for Antibody Pretargeting . . . " Bioconjugate Chem., 9:813 (1998).
Winter, "Formation of the Scab and the Rate of Epithelization of Superficial Wounds in the Skin of the Young Domestic Pig," Nature 193:293 (1962).
Wong et al., "Accuracy and Precision of in Vitro Volumetric Measurements by Three-Dimensional Sonography," Ivest. Rad.31:26 (1996).
Wu et al., "Metal-Chelate-Dendrimer-Antibody Constructs for Use in Radioimmunotherapy and Imaging," Bioorg. Med. Chem. Lett., 4:449 (1994).
Wyrick et al., "Entry of Genital *Chlamydia trachomatis* into Polarized Human Epithelial Cells," Infect. Imm. 57:2378 (1989).
Ye, et al., "Targeted gene correction: a new strategy for molecular medicine" Mol. Med. Today 4:431 (1998).
Yew et al., "Optimization of Plasmid Vectors for High-Level Expression in Lung Epithelial Cells," Human Gene Ther. 8:575 (1997).
Yin et al., "Architectural Copolymers: Rod-Shaped, Cylindrical Dendrimers," J. Am. Chem. Soc., 120:2678 (1998).
Yu, et al., "Overexpression of ErbB2 blocks Taxol-Induced Apoptosis by Upregulation of p21(cip1), which Inhibits p34 (Cdc2) Kinase," Molecular Cell, 2:581 (1998).
Zaffaroni et al., "Induction of apoptosis by taxol and cisplatin and effect on cell cycle-related proteins in cisplatin-sensitive and resistance human ovarian cancer cells," Brit. J. Cancer 77:1378 (1998).
Zhuo et al. 1999, in vitro release of 5-fluorouracil with cyclic core dendritic polymer, J. of Controlled Release 57:249-257.
Zimmerman et al., "Self-Assembling Dendrimers," Science 271:1095-1098 (1996).
Suzawa, et al., "Synthesis of a Novel Duocarmycin Derivative Du-257 . . . ", Bioorganic & Medicinal Chemistry 8 (2000) 2175-2184.
Yang, Cancer Research, 1997, vol. 53, pp. 4333-4339.
Mojoros et al., Macromolecules, 2003, vol. 36, pp. 5526-5529.
Wu et al., Anti-Cancer Agents in Medicinal Chemistry, Mar. 2006, vol. 6, pp. 167-184.
International Search Report dated Jan. 5, 2010, PCT/US2009/036992, filed Mar. 12, 2009.
Jesse B. Wolinsky and Mark W. Grinstaff, "Therapeutic and diagnostic application of dendrimers for cancer treatment," Advanced Drug Delivery Reviews, Mar. 4, 2008, vol. 60, pp. 1037-1055.
Ulrik Boas and Peter M. H. Heegaard, "Dendrimers in drug research," Chemical Society Review, 2004, vol. 33, pp. 43-63.
Istvan J. Majoros, et al., "Poly(amidoamine) dendrimer-based multifunctional engineered nanodevice for cancer therapy," Journal of Medicinal Chemistry, 2005, vol. 48, pp. 5892-5899.
Tooru Ooya, Jaehwei Lee and Kinam Park, "Hydrotropic dendrimers of generations 4 and 5: Synthesis, characterization and hydrotropic solubilization of paclitaxel," Bioconjugate Chemistry, 2004, vol. 15, pp. 1221-1229.
Anil K. Patri, et al., "Synthesis and in vitro testing of J591 antibody-dendrimer conjugates for targeted prostage cancer therapy," Bioconjugate Chemistry 2004, vol. 15, pp. 1174-1181.
Thomas, Thommey, et al., "Detection and Analysis of Tumor Fluorescence Using a Two-Photon Optical Fiber Probe," Biophysical Journal, vol. 86, Jun. 2004, pp. 3959-3965.
Kolb, et al. (2001) Angewandte Chemie Intl. Ed. 40:2004-2011.
Evans (2007) Australian J. Chem. 60:384-395.
Carlmark, et al. (2009) Chem. Soc. Rev. 38:352-362.
Allen, T.M., Nature Reviews Cancer (2002) 2, (1), pp. 750-763.
Peer, D., et al., Nature Nanotechnology (2007), 2, pp. 751-760.
Svensson, J.-O, Journal of Chromatography B., Biomedical Sciences and Applications ()1986) 375, pp. 174-178.
Tebbett, I.R. Chromatographia (187) 23(5), pp. 377-378, 1987.
Stamford, J.A., Journal of Neuroscience Methods, (1990), 34(1-3), pp. 67-72.
Toner, C.C., and J.A. Stamford, Journal of Neuroscience Methods (1996) 67(2), pp. 133-140.
Toner, C.D. and J.A. Stamford, Neuroscience (1997), 81(4), pp. 999-1007.

(56) References Cited

OTHER PUBLICATIONS

Kimiskidis, V., et al., 2007, "Development and validation of a high performance liquid chromatographic method for the determination of oxcarbazepine and its main metabolites in human plasma and cerebrospinal fluid and its application to pharmacokinetic study", J Pharm Biomed Anal.; 43(2):763-8.
Achilli, G., et al., Journal of Chromatography, A. (1996) 729(1-2), pp. 273-277.
Horner, K.A., et al., Brain Research (2004) 1028(2): pp. 121-132.
Childers, S.R. and S.R. Childers, Life Sciences (1991) 48(21): pp. 1991-2003.
Adams, J.D., Jr., et al. Biomedical Mass Spectometry (1981) 8(11): pp. 527-538.
Millhorn et al, 1996, "Regulation of ionic conductances and gene expression by hypoxia in an oxygen sensitive cell line.", Adv Exp Med Biol. 410:135-42.
Cai, Y.C., et al., "Molecular Pharmacology," (1997) 51(4), pp. 583-587.
Franklin, R,B., et al., BMC Biochemistry (2006) 7: p. 10.
Kukanich, B., et al., Therapeutic Drug Monitoring (2005) 27(3), pp. 389-392.
Cucullo, L., et al., Current Opinion in Drug Discovery & Development (2005) 8(1), pp. 88-99.
Nambiar, M.P., et al., Toxicology and Applied Pharmacology (2007) 219(2-3), pp. 142-150.
Shih, T.M., T.C. Rowland and J.H. McDonough, Journal of Pharmacology and Experimental Therapeutics (2007) 320 (1), pp. 154-161.
Schulte, H., A. Sollevi and M. Segeradahl, Pain, (2005) 116(3), pp. 366-374.
Loetsch, J., et al., Clinical Pharmacology and Therapeutics (1996) 60(3): pp. 316-325.
Hill, H.F., et al., Pain (1990) 43(1), pp. 57-79.
Worek, F., et al., Toxicology (2008). 244: pp. 35-41.
Hong, S., et al., Chemistry & Biology (2007), 14 (1), pp. 105-113.
Mammen, M., et al., Angewandte Chemie-International Edition (1998), 37 (20), pp. 2755-2794.
Hong, S.P., et al., Bioconjugate Chmistry (2004) 15, (4), pp. 774-782.
Svenson, S., et al., Advanced Drug Delivery Reviews (2005), 57 (15), pp. 2106-2129.
Hong, S.P., et al., Bioconjugate Chmistry (2006) 17(3), pp. 728-734.
Leroueil, P.R., Acc. Chem. Res. 40(5) (2007) pp. 335-342.
Thomas, T.P., et al., Biomacromoledules (2004) 5, (6) pp. 2269-2274.
Shukla, R., et al., Bioconjugate Chemistry (2006), 17 (5), pp. 1109-1115.
Wu, G., et al., Molecular Cancer Therapeutics (2006) 5(1) pp. 52-59.
Wu, G., et al., Bioconjugate Chemistry (2004) 15(1), pp. 185-194.
Backer, M.V., et al., Molecular Cancer Therapeutics (2005) 4(9), pp. 1423-1429.
Shukla, R., et al., Chemical Communications (2005) 46, pp. 5739-5741.
Sheng, K.C., et al., European Journal of Immunology (2008), 38, pp. 424-436.
Baek, M.G., et al., Bioorganic & Medicinal Chemistry (2002) 10 (1) pp. 11-17.
Taite, L.J, et al., Journal of Biomaterials Science-Polymer Edition (2006) 17(10), pp. 1159-1172.
Kono, K., et al., Bioconjugate Chemistry (1999) 10(6), pp. 1115-1121.
Shukla, S., et al., Bioconjugate Chemistry (2003) 14(1), pp. 158-167.
Thomas, t.p., et al., Journal of Medicinal Chemistry (2005), 48 (11), pp. 3729-3735.
Myc, A., et al., Anti-Cancer Drugs (2008) 19, pp. 143-149.
Majoros, I.J., et al., Journal of Medicinal Chmistry (2005) 48 (19) pp. 5892-5899.
Kukowska-Latallo, J.F., et al., Cancer Research (2005) 65(12) pp. 5317-5324.
Myc, A., et al., Biomacromolecules (2007) 8, pp. 2986-2989.
Myc, A., et al., Biomacromolcules (2007) 8 (1), pp. 13-18.
Landmark, K.J., et al., ACS Nano (2008) 2 (4), pp. 773-783.
Mullen, D.G., Bioconjug. Chem. 19(9) (2008) pp. 1748-1752.
Choi, Y., Nanostructured Supramolecular Arrays Based on Dendrimers Using DNA: Desgin, Synthesis and Biological Evaluation. Biomed. Eng. (NY), vol. Ph.D., Dissertation, University of Michigan, Ann Arbor, MI (2005), p. 191.
Lee, J.W., Macromolecules 39(6) (2006), pp. 2418-2422.
Wu, P., Chem. Commun. (46) (2005), pp. 5775-5777.
Goyal, P., Chem. Eur. J. 13 (2007), pp. 8801-8810.
Yoon, K., Org. Letter 9(11) (2007), pp. 2051-2054.
Choi, Y.S., et al., Nano Letter 4(3) (2004), pp. 391-397.
Demattie, C.R., et al., Nano Letters 4(5) (2004), pp. 771-777.
Choi, Y., et al., Chem. Biol. 12(1) (2005), pp. 35-43.
Rostovtsev, V.V., et al., Angewandte Chemie-Inernational Edition (2002) 41 (14), p. 2596.
Wu, P., et al., Angewandte Chemie-International Edition (2004) 43 (30) pp. 3928-3932.
Wu, P., et al., Aldrichimica Acta 40(1) (2007), pp. 7-17.
Lee, J.W., et al., Bioconjugate Chemistry (2007) 18(2), pp. 579-584.
Lee, J.W., et al., Journal of Polymer Science Part a-Pollymer Chemistry (2008) 46, pp. 1083-1097.
Lee, J.W., et al., Tetrahedron (2006) 62(5), pp. 894-900.
Hoffman, R.E., Magn. Reson. Chem. (2006), 44, pp. 606-616.
De Groot, Franciscus, M.H., "Cascade-Release Dendrimers", Liberate All End Groups Upon a Single Triggering Event in the Dendritic Core, Angew. Chem. Int. Ed. (2003), vol. 42, pp. 4490-4494.
Lee, Cameron C., et al., "Designing Dendrimers for Biological Applications," Nature Biotechnology, Dec. 2005, vol. 23, No. 12, pp. 1517-1526.
Bloodworth, D., Phys. Med. Rehabil Clin. N. Am., (2006) 17(2), pp. 355-379.
Liu, J.K., et al., Neurobiology of Disease (2005) 1993), pp. 407-418.
Beall, H.D., et al., Journal of Medicinal Chemistry (1998) 41(24), pp. 4755-4766.
Ferrer, S., D.P. Naughton and M.D. Threadgill, Tetrahedron (2003) 59(19), pp. 3445-3454.
Naylor, M.A., et al., Journal of Medicinal Chemistry (1997) 40(15), pp. 2335-2346.
Phillips, R.M., et al., Journal of Medicinal Chemistry (1997) 40(15), pp. 2335-2346.
Phillips, R.M., et al., Journal of Medicinal Chemistry (1999) 42(20), pp. 4071-4080.
Zhang, Z., et al., Organic & Biomolecular Chemistry (2005) 3(10), pp. 1905-1910.
Esfand et al., "Synthesis, Complexation and Pharmaceutical Applications of Tetra-directional Cascade Dendrimers," Pharm Sci., 2:157 (1996).
Farkas et al., "Microscopic and Mesoscopic Spectral Bio-Imaging," SPEI 2678:200 (1997).
Fidler et al., "The Implications of Angiogenesis for the Biology and Therapy of Cancer Metastatis," Cell, 79:185 (1994).
Firey and Rodgers, "Photo-Properties of a Silicon Naphthalocyanine: . . . " Photochem. Photobiol., 45:535-38 (1997).
Folkman et al., "Antiogenesis," Journ. of Biol. Chem. 267(16):10931 (1992).
Folkman et al., "Angiogenic Factors," Science, 235:442 (1987).
Folkman, "Clinical Applications of Research on Angiogenesis," New Eng. J. Med. 333(26):1757 (1995).
Fracasso, et al., "Anti-tumor effects of toxins targeted to the prostate specific membrane antigen," The Prostate, 2002, 53: 9-23.
Frechet, et al., "Self-Condensing Vinyl Polymerization: An Approach to Dendritic Materials," Science 269:1080-1083 (1995).
Frechet, "Functional Polymers and Dendrimers: Reactivity, Molecular Architechture, and Interfacial Energy," Science 263:1710-1715 (1994).
Friedman, "Gene Therapy of Cancer Through Restoration of Tumor-Suppressor Functions?J" Cancer 70:1810 (1992).
Fujiwara et al., "Therapeutic Effect of a Retroviral Wild-Type p53 Expression Vector in an Orthotopic Lung Cancer Model," J. Natl. Cancer Inst., 86:458 (1994).
Gac et al., "Synthesis, Characterisation and in Vivo Behaviour of a Norfloxacin-Poly(L-Lysine Citramide Imide) Conjugate Beraing Mannosyl Residues," J. Drug Target 7(5):393 (2000).

(56) References Cited

OTHER PUBLICATIONS

Garcia-Contreras et al., "Biodegradable Cisplatin Microspheres for Direct Brain Injection: Preparation and Characterization," Pharm Dev Tech 2:53 (1997).
Gerwitz et al., "Nucleic Acid Therapeutics: State of the Art and Future Prospects," Blood 92:712 (1998).
Gibb, "Apoptosis as a Measure of Chemosensitivity to Cisplatin and Taxol Therapy in Ovarian Cancer Cell Lines," Gynecologoic Oncology 65:13 (1997).
Goodwin and Meares, Cancer (suppl.) 80:2675 (1997).
Haensler et al., "Polyamidoamine Cascade Polymers Mediate Efficient Transfection of Cells in Culture," Bioconjugate Chem. 4:373-379 (1993).
Hanisch et al., "Structural Studies on Oncofetal Carbohydrate . . . " Carbohydr. Res. 178:29-47 (1988).
Hawker et al., "Unimolecular Micelles and Globular Amphiphiles: Dendritic Macromolecules as Novel Recyclable Solubilization Agents," J. Chem. Soc. Perkins Trans. 12:1287-1297 (1993).
Hinoda et al., "Immunochemical Characterization of Adenocarcinoma-Associated Antigen YH206," Cancer J. 42:653-658 (1988).
Hockenbery et al., "Bcl-2 Functions in an Antioxidant Pathway to Prevent Apoptosis," Cell 75:241 (1993).
Holister et al., "Dendrimers" 2003 Technology White Papers pp. 1-15.
Huse, et al., "Generation of a Large Combinatorial Library of the Immunoglobulin Repertoire in Phage Lambda," Science 246:1275-1281 (1989).
International Search Report mailed Sep. 8, 2008, PCT/US2007/15976.
International Search Report dated Jul. 8, 2002, PCT/US01/15204.
International Search Report dated Nov. 20, 2001, PCT/US01/40824.
International Search Report mailed Jul. 17, 2006, PCT/US05/30278.
International Search Report PCT/US2001/15204 mailed Jul. 8, 2002.
International Search Report, PCT/Us2008/061023, dated Dec. 16, 2008.
Ishida et al., "Related Glycoproteins from Normal Secretory and Malignant Breast Cells," Tumor Biol. 10:12-22 (1989).
Jain et al., "Controlled Drug Delivery by Biodegradable Poly(Ester) Devices: Different Preparative Approaches," Drug Dev Ind Pharm 24:703 (1998).
Jane et al., "Vector development: a major obstacle in human gene therapy," Annals of Med 30:413 (1998).
Jansen et al., "The Dendritic Box: Shape-Selective Liberation of Encapsulated Guests," J. Am. Chem. Soc. 117:4417-4418 1995.
Jellinek, et al., "Inhibition of Receptor Binding by High-Affinity RNA Ligands to Vascular Endothelial Growth Factor," Biochem 83(34):10450-6 (1994).
Kaner et al., "Fibroblast Growth Factor Receptor is a Portal of Cellular Entry for Herpes Simplex Virus Type 1," Science 248:1410 (1990).
Kannon and Garrett, "Moist Wound Healing with Occlusive Dressings," Ermatol. Surg. 21:583 (1995).
Kerr et al., "Apoptosis: Its Significance in Cancer and Cancer Therapy," Cancer 73:2013 (1994).
Klatzman et al., "T-lymphocyte T4 molecule behaves as the receptor fro human retrovirus LAV," Nature 312:767 (1984).
Kirpotin et al., "Sterically Stabilized Anti-HER2 Immunoliposomes: Design and Targeting to Human Breast Cancer Cells in Vitro," Biochem., 36:66 (1997).
Kjeldsen et al., "Preparation and Characterization of Monoclonal Antibodies Directed to the Tumor-associated O-linked . . . " Cancer Res. 48:2214-2220 (1988).
Kohler and Milstein, "Continuous cultures of fused cells secreting antibody of predefined specificity," Nature 256:495-497 (1975).
Kozbor et al. "The production of monoclonal antibodies from human lymphocytes," Immunol. Today 4:72 (1983).
Krah, "Characterization of Octyl Glucoside-Solubilized Cell Membrane Receptors for Binding Measles Virus," Virology 172:386 (1989).
Kuhlmann et al., "Reduction of cisplatin toxicity in cultured renal tubular cells by the bioflavonoid quercetin," Arch. Toxicol. 72:536 (1998).
Kukowska-Latallo et al., "Efficient transfer of genetic material into mammalian cells using Starburst polyamidoamine dendrimers," Proc. Natl. Acad. Sci. USA 93:4897-4902 (1996).
Lan et al., "Isolation and Properties of a Human Pancreatic Adenocarcinoma-associated . . . " Cancer Res. 45:305-310 (1985).
Lanni et al., "p53-independent apoptosis induced by paclitaxel througho an indirect mechanism," Proc. Natl. Acad. Sci., 94:9679 (1997).
Lentz, et al., "Is the Acetylcholine Rectpor a Rabies Virus Receptor," Science 215:182 (1982).
Lester et al., "Infrared Microspectroscopic Imaging of the Cerebellum of Normal and Cytarabine Treated Rats," Cell Mol. Biol. 44:29 (1998).
Levi-Montalcini, "The Nerve Growth Factor Thirty-Five Years Later," in Vitro Cell., Devl. Biol. 23:227 (1987).
Liao, et al., "Chromophore-assisted laser inactivation of proteins is mediated by the photogeneration of free radicals," PNAS 91:2659 (1994).
Luck et al., "Plasma protein adsorption on biodegradable microspheres . . . " J. Control. Rel 55:107 (1998).
Madihally and Matthew, "Porous chitosan scaffolds for tissue engineering," Biomaterials 20(12):1133 (1999).
Majoros and Tomalia, Mar. 18, 2006 Abstract Only printed Apr. 20, 2009, "Synthesis and Characterization of Novel POPAM-PAMAM (POMAM) Hybrid Dendrimers as Reactive Modules for Nanodevice Construction" Eight Foresight Conference on Molecular Nanotechnology.
Majoros et al., "PAMAM Dendrimer-based multifunctional conjugate for cancer therapy: syntheis, characterization and functionality," Biomacromolecules, 2006, vol. 7, pp. 572-579.
Majoros, et al., "Acetylation of Poly(amidoamine) Dendrimers," Macromolecules 2003, 36, 5526-5529.
Malik et al., "A PAMAM Dendrimer-Platinate," Proc. Int'l Symp. Control. Rel. Bioact. Mater, 24:107 (1997).
Malik et al., "Dendrimers: Relationshipo between structure and biocompatibility in vitro, and preliminary studies on the biodistribution of (125)I-labelled polyamidoamine dendrimers in vivo," Journal of Controlled Relief 65:133-148 (2000).
Marlin et al., "A soluble form of intercellular adhesion molecule-1 inhibits rhinovirus infection," Nature 344:70 (1990).
Mayer et al., "Matrices for tissue engineering-scaffold structure for a bioartificial liver support system," J. Controlled Release 64(1-3):81 (2000).
Mendelsohn et al., "Cellular Receptor for Poliovirus: Molecular Cloning, . . . " Cell 56:855 (1989).
Monsigny et al., "Characterization and biological implications of membrane lectins in tumor, lymphoid and myeloid cells," Biochemie 70:1633 (1988).
Mosmann, "Rapid Colorimetric Assay for Cellular Growth and Survival: Application to Proliferation and Cytotoxity Assays," J. Immunol. Meth, 65:55 (1983).
Murphy, et al., "Photolytic Release of Nitric Oxide Modulates NMDA Receptor-mediated Transmission but Does not Induce Long-term Potentiation at Hippocampal Synapses," Neuropharm. 33:1375-85 (1994).
Naylor et al., Starburst Dendrimers. 5. Molecular Shape Control, J. Am. Chem. Soc. 111:2339-2341 (1989).
Niemiec et al., "Perifollicular Transgenic Expression of Human Interleukin-1 Rectpro Antagonist Protein following Topical Application of Novel Liposome-Plasmid DNA Formulations in Vivo," J. Pharm Sci. 86:701 (1997).
Orentas et al., "Detection of Epstein-Barr virus EBER sequence in post-transplant lymphoma patients with DNA dendrimers," Journal of Virological Methods 77:153-163 (1999).
Ottl, et al., "Preparation and Photoactivation of Caged Fluorophores and Caged Proteins Using a New Class of Heterobifunctional, Photocleavable Cross-Linking Reagents," Bioconjugate Chem. 9:143 (1998).

(56) References Cited

OTHER PUBLICATIONS

Page and Roy, "Synthesis and Biological Properties of Mannosylated Starburst Poly(amidoamine) Dendrimers," Bioconjugate Chem., 8:714 (1997).
Pan, et al., "Dendrimer modified magnetite nanoparticles for protein immobilization," Journal of Colloid and Interface Science, 2005, vol. 284, pp. 1-6.
Pandey, et al., "Chlorin and Porphyrine Derivatives as Potential Photosensitizers in Photodynamic Therapy," Photochem., Photobiol., 53:65-72 (1991).
Park et al., "Anti-HER2 immunoliposomes for targeted therapy of human tumors," Cancer Lett., 118:153 (1997).
Pasani et al., "Antitumor Complexes of Platinum with Carrier Molecules," Inorg. Chim. Acta 80:99 (1983).
Pavlova et al., "Biocompatible and biodegradable polyurethane polymers," Biomaterials 14(13):1024 (1993).
Pegram et al., Proc. Am. Soc. Clin. Oncol. 14:106 (1995).
Penault-Llorca et al., "Expression of FGF and FGF Receptor Genes in Human Breast Cancer," Int. J. Cancer 61:170 (1995).
Pillai V.N.R., "Photoremovable Protecting Groups in Organic Synthesis," Synthesis: 1-26 (1980).
Pratap Singh, "Terminal Groups in Starburst Dendrimers: Activation and Reaction with Proteins", 1998 Bioconnugate Chem. 9:54-63.
Press et al., "Expression of the HER-2/neu proto-oncogene in normal human adult and fetal tissues," Oncogene 5:953 (1990).
Quintana, et al., "Design and Function of a Dendrimer-Based Therapeutic Nanodevice Targeted to Tumor Cells Through the Folate Receptor," Pharmaceutical Research, vol. 19, No. 9, Sep. 2002.
Raczka et al., "The effect of synthetic surfactant Exosurf on gene transfer in mouse lung in vivo," Gene Ther 5:1333 (1998).
Riley, "Wound Healing," Am Fam. Physician 24:107 (1981).
Rinberg "Pnuematic capillary gun for ballistic delivery of microparticles" 2005 Applied Physics Letters vol. 87 pp. 1-3.
Roberts, et al., "Preliminary biological evaluation of oplyamidoamine (PAMAM) Starburst dendrimers," J. Biomed Mater res 30:53 (1996).
Roessler et al., "Substituted β-Cyclodextrins Interact with PAMAM Dendrimer-DNA Complexes and Modify Transfection Efficiency," Biochem. 124-129 (2001).
Ruff, et al., "CD4 receptor binding peptides that block HIV infectivity cause human monocyte chemotaxis," FEBS Letters 211:17 (1987).
Ruponen et al., "Interactions of polymeric and liposomal gene delivery systems with extracellular glycosaminoglycans: physicochemical and transfection studies," Biochmica ET Biophysica Acta 1415:331-341 (1999).
Sacerdote et al., "Vasoactive Intestinal Peptide 1-12: . . . " J. of Neuroscience Research 18:102 (1987).
Schneider, et al., "Distance-dependent fluorescence quenching on gold nanoparticles ensheathed with layer-by-layer assembled polyelectrolytes," Nano Letters, 2006, vol. 6, pp. 530-536.
Segura and Shea, "Materials for Non-Viral Gene Delivery" 2001 Annual Review of Materials Research, vol. 31 pp. 25-46.
Selman et al., "Copper Benzochlorin, a Novel Photosensitizer for Photodynamic Therapy . . . " Photochem. Photobio, 57:681-85 (1993).
Sessler et al., "Tripyrroledimethine-derived ("texaphyrine"-type) . . . " Proc. SPIE, 1426:318-29 (1991).
Sharon and Lis, "Lectins as Cell Recognition Molecules," Science 246:227 (1989).
Shchepinov et al., "Oligonucleotide dendrimers: synthesis and use as polylabelled DNA probes," Nucleic Acids Research 25:4447-4454 (1997).
Shea, "DNA delivery from polymer matrices for tissue engineering," Jun. 1999, Nature Biotechnology.
Shephey et al., "Monoclonal antibody identificaiton ofa 100-kDa membrane protein in HeLa cells and human spinal cord involved in poliovirus attachment," Proc. Natl. Acad. Sci. 85:7743 (1988).
Shortreed, et al., "Directed Energy Transfer Funnels in Dendrimetric Antenna Supermolecules," J. Phys. Chem. 101-6318 (1997).
Singh et al., "Starburst Dendrimers: Enhanced Performance and Flexibility for Immunoassays," Clin. Chem. 40:1845 (1994).
Sooklal, "A Blue-Emitting CdS/Dendrimer Nanocomposite," Adv. Mater, 10:1083 (1998).
Damen, E.W.P., et al., Biorganic & Medicinal Chemistry (2002) 10(1), pp. 71-77.
Hay, M.P., et al., Journal of Medicinal Chemistry (2003) 46(25), pp. 5533-5545.
Hay, M.P., et al., Journal of the Chemical Society-Perkin Transactions 1 (1999 (19), pp. 2759-2770.
Daniels, T.R., et al., Clinical Immunology (2006) 121(2), pp. 144-176.
Smith, M.W., and m. Gumbleton, Journal of Drug Targeting (2006) 14(4), pp. 191-214.
Koch, 1990, Angew. Chem. Int. Ed. Engl., 29:183-5.
Tomalia, et al., Chem. Int. Ed. Engl. 29:5305 (1990).
Yin, et al., J. Am. Chem. Soc., 120:2678 (1998).
Carelli, V., et al., Bioorganic & Medicinal Chemistry Letters (2003) 13(21), pp. 3765-3769.
Christrup, L.L., et al., International Journal of Pharmaceutics (1997). 154(2): pp. 157-165.
Drustrup, J., et al., International Journal of Pharmaceutics (1991), 71(1-2), pp. 105-116.
Groth, L., et al., International Journal of Pharmaceutics (1997) 154(2), pp. 149-155.
Mignat, C., et al., Journal of Pharmaceutical Sciences (1996) 85(7), pp. 690-694.
Hay, M.P., W.R. Wilson and W.A. Denny, Tetrahedron (2000) 56(4):, pp. 645-657.
de Groot, F.M.H., E.W.P. Damen, and H.W. Scheeren, Curr. Med. Chem.—Anti-Cancer Agents (2001) 8, pp. 1093-1122.
Dubowchik, G.M., and M.A. Walker, Pharmacology & Therapeutics (1999) 83, pp. 67-123.
Papot, S., et al., 2002, "Design of selectively activated anticancer prodrugs: elimination and cyclization strategies.", Curr Med Chem Anticancer Agents.; 2(2):155-85.
De Groot, F.M.H., et al., J. Org. Chem., 2001. 66, pp. 8815-8830.
Greenwald, R.B., et al., J. Med. Chem. (1999). 42: pp. 3657-3667.
Greenwald, R.B., et al., Bioconjugate Chem. (2003) 14, pp. 395-403.
Zhang, Z., et al., Pharmaceutical Research (2005) 22, pp. 381-389.
Antczak, C., et al., Bioorg. & Med. Chem (2001), 9: pp. 2843-2848.
Pohl, T., and H. Waldmann, J. Am. Chem. Soc. (1997), 119, pp. 6702-6710.
Sauerbrei, B., V. Jungmann, and H. Waldmann, Angew. Chem. Int. Ed. (1998), 37: pp. 1143-1146.
Leung, L.Y. and T.A. Baillie, J. Med. Chem. (1986), 29, pp. 2396-2399.
Woolf, T., et al., J. Org. Chem. (1984) 49. pp. 3305-3310.
Nudelman, A., R.J. McCaully and S.C. Bell, J. Pharm. Sci. (1974) 63, pp. 1880-1885.
Esfand, R. and D.A. Tomalila, Drug Discovery Today (2001). 6, pp. 427-436.
Jansen, J.F.G.A., E.M.M. de Brabander van den Berg and E.W. Maijer, Science (1994). 266, pp. 1226-1229.
Kolhe, P., et al., International Journal of Pharmaceutics (2003), 259, pp. 143-160.
Man, N., et al., European Journal of Medicinal Chemistry (2006), 41, pp. 670-674.
Morgan, M.T., et al., J. Am. Chem., Soc. (2003), 125(50): pp. 15485-15489.
Papagiannaros, A., et al., International Journal of Pharmaceutics (2005), 302, pp. 29-38.
Patri, A.K., J.F. Kukowska-Latallo, and J.R. Baker, Advanced Drug Delivery Reviews (2005) 57(15), pp. 2203-2214.
Patri, A.K., I.J Majoros and J.R. Baker Jr., Current Opinion in Chemical Biology (2002) 6, pp. 466-471.
Qiu, L.Y., and Y.H. Bae, Pharmaceutical Research (2006) 23, p. 1-30.
Schcharbin, D. and B.M., Biochmica et Biophysica Acta (2006) 1760, pp. 1021-1026.
Shi, X., et al., Electrophoresis (2006) 27(9), pp. 1758-1767.
Islam, M.T., I.J., Majoros and J.R. Baker, Journal of Chromatography B-Analytical Technologies in the Biomedical and Life Sciences (2005) 822(1-2): p. 21-26).

(56) References Cited

OTHER PUBLICATIONS

Islam, MT., et al., Analytical Chemistry (2005) 77(7): p. 2063-2070.
Shi, X., et al., Polymer (2005) 46: p. 3022-3034.
Shi, X., et al. Colloids Surf., A., (2006), 272, pp. 139-150.
Shi, X., I.J, Majoros and J.R. Baker, Jr., Mol. Pharm (2005), 2, pp. 278-294.
Shi, X.Y., et al., Electrophoresis (2005) 26(15), pp. 2949-2959.
Shi, X.Y., et al., Analysis (2006) 131(7): p. 842-848.
Shi, X.Y., et al. Analysis (2006) 131(3), pp. 374-381.
Shi, X.Y., et al. Electrophoresis (2005) 26(15): pp. 2960-2967.
Kuracka, L., et al., Clinical Chemistry (1996) 42(5), pp. 756-760.
Orlovic, D., et al., Chromatographia (2000) 52(11/12), pp. 732-734.
Svensson, J., et al., Journal of Chromatography B: Biomedical Sciences and Applications (1982), 230(2), pp. 427-432.
Abel et al., "The Selective Concentration of Sulpha-diazine and Related Compounds in Malignant Tissue," Eur. J. Cancer 9:4 (1973).
Abrams, et al., "Programmed cell death during Drosophila embryogenesis," Development 117:29 (1993).
Adlish et al., "Identification of a Putative Cell Receptor for Human Cytomegalovirus," Virology 176:337 (1990).
Akutsu et al., "Schedule-dependent Interaction Between Paclitaxel and Doxorubicin in Human Cancer Cell Lines in Vitro," Eur. J. Cancer 31A:2341 (1995).
Australian First Report on Application No. 2005287375 dated Jun. 10, 2008.
Babiuk, Shawn, Foldvari, Marianna, et al., "Cutaneous vaccination: the skin as an immunologically active tissue and the challenge of antigen delivery," Journal of Controlled Release, vol. 66 Issues 2-3, May 15, 2000 pp. 199-214.
Baker et al., "The Synthesis and Testing of Anti-Cancer Therapeutic Nanodevices," Kluwer Academic Publishers, Manufactured in the Netherlands 61-690 (2001).
Baldwin and Saltzman et al., "Materials for protein delivery in tissue engineering" 1998 Advanced Drug Delivery Reviews vol. 33, pp. 71-86.
Balogh and Tomalia, J. Am. Che. Soc. 120:7355 (1998).
Balogh et al., "Formation and Characterization of Dendrimer-Based Water Soluble Inorganic Nanocomposites," Proc. of ACS PMSE 77:118 (1997).
Banga et al., "Assessing the potential of skin electroporation for the delivery of protein- and gene-based drugs," Trends in Biotechnology vol. 16 Issue 10, Oct. 1, 1998 pp. 408-412.
Baker et al., "Utilization of Lipophilic Ionic Additives in Liquid Polymer Film Optodes for Selective Anion Activity Measurements," Anal. Chem. 69:990 (1997).
Barth et al., "Boron Neutron Capture Therapy of Brain Tumors: Past History, Current Status, and Future Potential," Cancer Invetigation 14:534 (1996).
Barth, et al., "Boronated Starburst Dendrimer-Monoclonal Antibody Immunoconjugates: Evaluation as a Potential Delivery System for Neutron Capture therapy," Bioconjugate Chem. 5:58 (1994).
Baumann et al., "Simultaneous Visualliztion of the Yellow and Green Forms of the Green Fluorescent Protein in Lying Cells," J. Histochem. Cytochem. 46:1073 (1998).
Bell, "Molecular Trees: A New Branch of Chemistry," Science 271:1077-1078 (1996).
Bielinska A. et al., "Regulation of in Vitro Gene Expression Using Antisense Oligonucleotides or . . . " Jun. 1, 1996 Nucleic Acids Research, Oxford University Press, Surrey, GB vol. 24 No. 11.
Bielinska et al. Bioconj Chem 10:843-850 (1999).
Bielinska et al., "Application of membrane-based dendrimer/DNA complexes for solid phase transfection in vitro and in vivo" May 2000 Biomaterials vol. 21, Issue 9, pp. 877-887.
Bielinska et al., "The Interaction of Plasmid DNA with polyamidoamine dendrimers: . . . " Biochimica et Biophysica Acta 1353:180-190 (1997).
Binkley et al., "FNA ligands to human nerve growth factor," Nuc. Acids Res. 23(16):3198-205 (1995).

Block, Lawrence, "Medicated Applications", Remington's Pharmaceutical Sciences, edited by Gennaro, 1990, 18th Edition, pp. 1596 and 1597.
Botchway, et al., "Novel Visible and Ultraviolet Light Photogeneration of . . . " Photochem., Photobiol. 67(7):635-40 (1998).
Bourassa et al., "Photochemistry of Roussin's Red Salt . . . " JACS 119:2853-60 (1997).
Bourne, et al., "Evaluation of the Effects of Intravascular MR Contrast Media (Gadolinium Dendrimer) on 3D Time of Flight Magnetic Resonance Angiography of the Body,"J. Magn. Reson. Imag., 6:305 (1996).
Brandl et al., "Plastics from Bacteria and for Bacteria: . . . ", Adv. Biochem Eng Biotechnol, 41:77 (1990).
Brasseur et al., "Biological Activities of Phthalocyanines . . . " Photochem., Photobiol., 47:705-11 (1988).
Braunegg et al., "Polyhydroxyalkanoates, biopolyesters from renewable resources: Physiological and engineering aspects,"J. Biotechnol 65(2-3):127 (1998).
Brazeau et al., "In vitro myotoxicity of selected cationic macromolecules used in non-viral gene delivery," Pharm Research 15:680-684 (1998).
Capale et al., "Boronated Epidermal Growth Factor as a Potential Targeting Agent for Boron Neutron Capture Therapy of Brain Tumors," Bioconjugate Chem., 7:7 (1996).
Carel et al., "Structural Requirements for C3d,g/Epstein-Barr Virus Receptor (CR2/CD21) Ligand Binding, Internalization, and Viral Infection," J. Biol. Chem. 265:12293 (1990).
Chan and Nie, "quantum Dot Bioconjugates for Ultrasensitive Nonisotopic Detection," Science 281:2016 (1998).
Chang, et al., "Synthetic Appropaches to Long-Wavelength Absorbing Photosensitizers: Porphyrinone and Derivatives," Proc. SPIE, 1203:281-86 (1990).
Chinese Office Action dated Jan. 16, 2009, CN Patent Application No. 200580034777.9.
Choate et al., "Direct Cutaneous Gene Delivery in Human Genetic Skin Disease," Human Gene Ther 8:1659 (1997).
Choi et al., "Poly(ethylene glycol)-block-poly(L-lysine) Dendrimer: . . . ", Bioconjugate Chem. 10:62-65 (1999).
Cincotta, et al., "Novel Benzophenothiazinium Photosensitizers: Preliminary In-Vivo Results," SPIE Proc. SPIE 1203:202-10 (1990).
Co et al., "Isolation and biochemical characterization of the mammalian reovirus type 3 cell-surface receptor," Proc Natl. Acad. Sci 82:1494 (1985).
Cohen and Tohoku, Exp. Med. 168:351 (1992), Abstract printed on May 1, 2002 (1 page).
Cole et al., "The EBV-Hybridoma Technique and its Application to Human Lung Cancer," in Monoclonal Antibodies and Cancer Therapy, Alan R. Liss, Inc., pp. 77-96 (1985).
Cortese et al., "Identification of biologically active peptides using random libraries displayed on phage," Curr. Opin. Biotechol., 6:73 (1995).
Cote et al., "Generation of Human monclonal antibodies reactive with cellular antigens," Proc. Natl. Acad. Sci. U.S.A. 80:2026-2030 (1983).
Davies, "Synthetic materials for covering burn woulds: Progress towards perfection. Part I. Short term dressing materials," Burns 10:94 (1983).
De Leo and Ford, "Reversible Photolabilzation of NO from Chromium (III)-Coordinated Nitrite. A New Strategy for Nitric Oxide Delivery," JACS 121:1980-81 (1999).
Duncan and Malik, Control Rel. Bioact. Mater. 23:105 (1996).
Duncan and Sat, "Tumour targeting by enhanced permeability and retention (EPR) effect," Ann. Oncol. 9:39 (1998).
Duncan et al., "Polymer Conjugates for Anti-Cancer Agent and DNA Delivery," Polymer Preprints 39:180 (1998).
Dvornic and Tomalia, "Dendritic polymers divergent synthesis: starburst poly(amidoamine) dendrimers," in Salamone (ed.) The Polymeric Materials Encyclopedia: Synthesis, Proper, 1996.
EP Patent Application No. EP 01 935 316.8, Office Action dated Nov. 30, 2007.
Eppstein et al., "Epidermal growth factor receptor occupancy inhibits vaccinia virus infection," Nature 318:663 (1985).

(56) References Cited

OTHER PUBLICATIONS

CN Office Action mailed Aug. 14, 2013, CN Patent Application No. 201080059383.

Bhanja, et al., "Protective role of R-spondin1, an intestinal stem cell growth factor, against radiation-induced gastrointestinal syndrome in mice," Plos One, vol. 4, Issue 11, Article No. e8014, pp. 1-10 (Nov. 24, 2009).

Zhao, et al., "R-spondin1 protects mice from chemotheray or radiation-induced oral mucositis through the canonical Wnt/B-catein pathway," PNAS, vol. 106, No. 7, pp. 2331-2336 (Feb. 17, 2009).

Zhou, et al., "Slit-Robo signaling induces malignant transormation through Hakai-mediated E-cadher in degration during colorectal epithelial cell carcinogenesis", Cell Research, vol. 21, No. 4, pp. 609-626 (Feb. 1, 2011).

Wang, eet al., "Induction of tumor angiogenesis by Slit-Robo signaling and inhibition of cancer growth by blocking Robo activity," Cancer Cell, vol. 4, Issue 1, pp. 19-29 (Jul. 2003).

Takashima et al., "The Wnt agonist R-spondin1 regulates systemic graft-versus-host disease by protecting intestinal stem cells," The Journal of Experimental Medicine, vol. 208, No. 2, pp. 285-294 (Jan. 31, 2011).

Zhou, et al., "Induction of intestinal stem cells by R-spondin1 and slit2 augments chemoradioprotection," Nature, vol. 501, No. 7465, pp. 107-111 (Sep. 2013).

\* cited by examiner

Scheme 1. Drug releasing mechanism of the tripartite prodrug strategy

Where Y axis is Amount Released (arbitrary units)
Where X axis is Time (minutes)

Glucuronidase
induced cleavage

Factors that affect the effectiveness of the linker

X = O, NR

X = O, NH   Additional self-degradable linkers
Y = (CH$_2$)nX

X = O, NH   Additional self-degradable linkers
Y = (CH$_2$)nX

Simple esters

Esters with an 1,6-elimination spacer will drive the hydrolysis to completion:

10-Hydroxycamptothecin (SN-38)

Irinotecan w/ or w/out triggering unit inserted

Morphine  Hydromorphone

Indolequinone-based Naloxone Pro-drug

*In vitro* studies showed that we could obtain a sustained release of Morphine using a Morphine Pro-drug

*In vitro* release kinetics of free Morphine from Prodrug B by different plasma samples

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

His Leu Asn Ile Leu Ser Thr Leu Trp Lys Tyr Arg
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: The residue at this position is linked to
      7-methoxycoumarin-4-yl acetyl
<220> FEATURE:
<221> NAME/KEY: MISC_FEATURE
<222> LOCATION: (7)..(7)
<223> OTHER INFORMATION: The residue at this position is linked to a
      2,4-dinitrophenyl group and NH2

<400> SEQUENCE: 2

Tyr Glu Val Asp Gly Trp Lys
1               5
```

DENDRIMER CONJUGATES

CROSS-REFERENCE TO RELATED APPLICATIONS

The present application is a continuation of U.S. patent application Ser. No. 12/570,977, filed Sep. 30, 2009, which claims priority to U.S. Provisional Patent Application No. 61/101,461, filed Sep. 30, 2008, hereby incorporated by reference in their entireties.

STATEMENT REGARDING FEDERALLY SPONSORED RESEARCH OR DEVELOPMENT

This invention was made with government support under CA119409 awarded by the National Institutes of Health and W911NF-07-1-0437 awarded by the Army/ARO. The Government has certain rights in the invention.

FIELD OF THE INVENTION

The present invention relates to novel therapeutic and diagnostic dendrimers. In particular, the present invention is directed to dendrimer-linker conjugates, methods of synthesizing the same, compositions comprising the conjugates, as well as systems and methods utilizing the conjugates (e.g., in diagnostic and/or therapeutic settings (e.g., for the delivery of therapeutics, imaging, and/or targeting agents (e.g., in disease (e.g., cancer) diagnosis and/or therapy, pain therapy, etc.)). Accordingly, dendrimer-linker conjugates of the present invention may further comprise one or more components for targeting, imaging, sensing, and/or providing a therapeutic or diagnostic material and/or monitoring response to therapy.

BACKGROUND OF THE INVENTION

Cancer remains the number two cause of mortality in the United States, resulting in over 500,000 deaths per year. Despite advances in detection and treatment, cancer mortality remains high. New compositions and methods for the imaging and treatment (e.g., therapeutic) of cancer may help to reduce the rate of mortality associated with cancer.

Severe, chronic pain is observed a variety of subjects. For example, there exist large numbers of individuals with sever pain associated with arthritis, autoimmune disease, injury, cancer, and a host of other conditions.

A vast number of different types of pain medications exist. For example, a number natural and synthetic alkaloids of opium (i.e., opioids) are useful as analgesics for the treatment of severe pain. However, a number of severe side effects associated with opioid and other pain medication usage exist. For example, administration of opioid agonists often results in intestinal dysfunction due to action of the opioid agonist upon the large number of receptors in the intestinal wall. Opioids are generally known to cause nausea and vomiting as well as inhibition of normal propulsive gastrointestinal function in animals, resulting in side effects such as constipation.

Pain medication (e.g., opioid)-induced side effects are a serious problem for patients being administered pain medications (e.g., opioid analgesics) for both short term and long term pain management. For instance, more than 250,000 terminal cancer patients each year take opioids, such as morphine, for pain relief, and about half of those patients experience severe constipation. At present, patients receiving opioid pain medications face the difficult choice of suffering burdensome adverse effects (e.g., constipation) or ineffective analgesia.

There exists a need for compositions, methods and systems for delivering agents (e.g., diagnostic and/or therapeutic (e.g., cancer and/or pain therapeutics) to subjects that provide effective therapy (e.g., disease treatment, symptom relief, etc.) with reduced or eliminated side effects, even when administered in high doses.

SUMMARY

Battlefield trauma covers a range of injuries caused by different mechanisms resulting at times in severe disturbances of vital functions, disability, fear and pain (see, e.g., Conventional warfare: ballistic, blast, and burn injuries. 1990, Department of the Army, Office of the Surgeon General, Borden Institute. 396; herein incorporated by reference in its entirety). Depending on the military situation, initial reliance for first aid must either be administered by oneself, other troops or field medics. It is not until the injured reach a Forward Surgical Team (FST) or a Battalion Aid Station (BAS) that trained personnel can administer traditional pain and anxiolytic medications due to the need for frequent assessment of the medications' side effects and need for supportive measures to prevent drug-induced deterioration of vital functions (see, e.g., Anesthesia and perioperative care of the combat casualty. 1995, Department of the Army, Office of the Surgeon General, Borden Institute. 931; herein incorporated by reference in its entirety). Unfortunately, the time for an injured soldier to arrive at a FST or BAS unit can be delayed for hours to days. Adequate pain therapy may be markedly delayed resulting in problems such as long term, psychological-psychiatric effects, chronic pain syndromes and Post Traumatic Stress Disorders. This prolonged exposure of service members to inadequately treated pain is associated with considerable cost to the soldier and society (see, e.g., Bloodworth, D., Phys Med Rehabil Clin N Am, 2006. 17(2): p. 355-79; herein incorporated by reference in its entirety).

If one were to attempt to administer potent pain and anxiolytic/amnestic medications to injured soldiers on the battlefield, it is important to understand the compensatory physiological responses required to preserve vital functions during trauma and evaluate how these medications' side effects could potentiate combat-induced pathophysiology. Ventilation with oxygenation and perfusion of vital organs—the heart, lungs and brain—must be preserved in the face of major injuries and blood loss, while at the same time perfusion of other organ systems may virtually shut down. Such a reduced flow state may be maintained for hours or days depending on the soldier's condition, environment and other factors. Disturbance of this delicate cardio respiratory balance by pain medications needs to be considered carefully lest it be detrimental or even fatal to the injured. Reports of blood gasses of injured personnel taken at the time of admission to the FST unit illustrate the degree of cardio, respiratory and metabolic compromise that occur in non-fatal injuries. Approximately 35% of injured entrants had pH levels in the range of 7.0 to 7.20, and as low as 6.9 while pCO2 levels were often in the 50-60 mmHg range and could be as high as 80-90 mmHg in severe trauma. Oxygen saturation levels were as low as 40% while the lowest hematocrit encountered was 9 mg/dl. This shows the dire nature of combat injuries, and provides an insight into why the administration of analgesic and anxiolytic/amnestic medications with vasodilatory and respiratory depressive side effects has been avoided. It also suggests the need for physiologically triggered feedback regulation to prevent worsening of these derangements.

The unique conditions of battlefield trauma require a complex pain relief solution. For example, there is a need for a form of sustained therapeutic that could relieve pain over many hours or even days. This situation is further complicated by the need for battlefield therapeutics to be easily administered, preferably without the technical challenge of intravenous access or continuous administration. Therapy should not require monitoring, since uninjured soldiers will be involved in ongoing combat. Some effective pain medications (e.g., narcotic analgesics) have serious limitations. For example, narcotic analgesics are short acting, the therapeutic index is relatively narrow, and the doses of drug that cause analgesia are not greatly separated from those that cause serious side effects, including respiratory depression and hypotension due to vasodilatation (see, e.g., Bloodworth, D., Phys Med Rehabil Clin N Am, 2006. 17(2): p. 355-79; herein incorporated by reference in its entirety). Such side effects can actually worsen the physiological derangements of acute trauma. Respiratory depression leads to respiratory acidosis that can cause metabolic derangements. This can also exacerbate metabolic acidosis due to traumatic injury, and sustained depression can lead to death from hypoxia due to respiratory failure. Hypotension can trigger shock and cardiovascular collapse, especially in an individual who has already suffered traumatic blood loss. Thus, to provide autonomously effective narcotic analgesia over long periods of time in the battlefield, a need exists for a sustained release narcotic with a widened therapeutic index allowing for sustained analgesia in the absence of respiratory depression. This formulation should also be easily administered (e.g., through intramuscular auto-injector). Finally, lack of sedation and an absence of systemic side effects are acutely important given the fact that individuals with traumatic injuries in the battlefield may need to participate in self-extraction to safety.

The present invention provides compositions and related methods addressing such needs. In particular, the present invention provides compositions comprising dendrimer molecules (e.g., polyamideamine (PAMAM) dendrimers, polypropylamine (POPAM) dendrimers, or PAMAM-POPAM dendrimers) conjuguated to one or more pain relief agents (e.g., prodrug analgesic molecules, prodrug anxiolytic drugs, prodrug amnestic drugs). In some embodiments, the dendrimers conjugated to one or more pain relief agents are configured for controlled and/or sustained release of the pain relief agents (e.g., through use of targeting agents, linking agents, and/or trigger agents conjugated to the dendrimer and/or pain relief agent). In some embodiments, the pain relief agent conjugated to the dendrimer is active upon administration to a subject. In some embodiments, sustained release (e.g., slow release over a period of 24-48 hours) of the pain relief drug is accomplished through conjugating the pain relief drug to the dendrimer through, for example, a linkage agent connected to a trigger agent that slowly degrades in a biological system (e.g., ester linkage). In some embodiments, constitutively active release of the pain relief drug is accomplished through conjugating the pain relief drug to the dendrimer through, for example, a linkage agent connected to a trigger agent that renders the pain relief agent constitutively active in a biological system (e.g., amide linkage, ether linkage). In some embodiments, sustained release (e.g., a slow release mechanism that achieves analgesic concentrations over a period of, for example, 24-48 hours) of the pain relief agent prevents adverse side effects of the pain relief agent (e.g., respiratory failure, adverse cardiovascular consequences).

In certain embodiments, the compositions comprising dendrimer molecules conjugated to one or more pain relief agents are co-administered with additional agents designed to prevent adverse side effects of pain relief agents (e.g., respiratory failure, adverse cardiovascular consequences). In some embodiments, the compositions comprising dendrimer molecules conjuguated to one or more pain relief agents (e.g., narcotic prodrugs) are co-administered with a pain relief agent antagonist (e.g., a narcotic antagonist that is modulated to permit analgesia while preventing respiratory depression). In some embodiments, a feedback system is employed so as to prevent respiratory failure and adverse cardiovascular consequences while still maintaining analgesia. In some embodiments, the "feedback" component is a rapid-acting narcotic antagonist (e.g., Naloxone) released only upon detection of symptoms of respiratory depression. In some embodiments, the biomarker used to monitor respiratory depression and trigger the release of the antagonist is hypoxia (low pO2). Hypoxia is a sensitive and important marker as it is the direct cause of tissue injury from respiratory failure. It is also more specific than lowered serum pH, a marker of respiratory acidosis, since this is also observed in acute trauma situations as a result of metabolic derangements. A fast acting antagonist released in response to hypoxia rapidly reverses respiratory depression, which thereby increases the pO2, reversing the hypoxia and stopping the release of the antagonist. In contrast, the narcotic itself would continue to be released at a slow and predictable rate. In this way, appropriate analgesia is achieved that is reversed only when absolutely necessary to prevent respiratory failure. This would allow maintenance of analgesia in the battlefield for prolonged periods of time without monitoring of the wounded. In some embodiments, as shown in FIG. 32A, the present invention provides compositions comprising a plurality of pain relief agents coupled to dendrimers with a linkage agent connected to a trigger agent that slowly degrades in a biological system (e.g., ester linkage) (as shown in FIG. 32A, the trigger agent is an ester bond that is released by serum esterases to mediate sustained-release analgesia). When administered together, the plurality of pain relief agents (e.g., Ketamine and Lorazepam) have favorable analgesic and anxiolytic/amnestic qualities, and relatively broad therapeutic indexes. Compositions comprising a plurality of pain relief agents (e.g., Ketamine and Lorazepam) provide analgesia without the cardiovascular effects of opioids and minimize their major complication, that being respiratory depression. As a feedback mechanism, compositions of the invention comprising a pain relief agent antagonist (e.g., Doxapram) are complexed with a dendrimer through charge interaction (e.g., that is releasable by, for example, acidosis). While acidosis may be observed from causes other than respiratory depression, this feedback mechanism is unique in that Doxapram stimulates respirations without reducing analgesia. As such, the present invention provides release of Doxapram regardless of the source of the acidosis (e.g., traumatic injuries, hemorrhagic shock, burns or rhabdomyolysis). Thus, the present invention provides a safe analgesia with easily achieved physiological feedback.

In some embodiments, targeting agents are conjugated to the dendrimers for delivery of the dendrimers to desired body regions (e.g., to the central nervous system (CNS). The targeting agents are not limited to targeting specific body regions. In some embodiments, the targeting agents target the central nervous system (CNS). In some embodiments, targeting agents target the peripheral nervous system, specific nerves (e.g., perception nerves, pain nerves, pressure nerves, etc.), muscles, and/or tendons. In some embodiments, where the targeting agent is specific for the CNS, the targeting agent is transferrin (see, e.g., Daniels, T. R., et al., Clinical Immunology, 2006. 121(2): p. 159-176; Daniels, T. R., et al., Clinical Immunology, 2006. 121(2): p. 144-158; each herein incorporated by reference in their entireties). In some embodiments, the targeting agents target neurons within the central nervous system (CNS). In some embodiments, where the targeting agent is specific for neurons within the CNS, the targeting agent is a synthetic tetanus toxin fragment (e.g., a 12 amino acid peptide (Tet 1)) (see, e.g., Liu, J. K., et al., Neurobiology of Disease, 2005. 19(3): p. 407-418; herein incorporated by reference in its entirety). In some embodiments, locking agents designed to retain the dendrimer within a particular body region are conjugated to the dendrimer (e.g., locking agents designed to prevent back diffusion of a dendrimer across the blood brain barrier (BBB) (e.g., pyridinium molecule, which when activated by enzymatic reduction, becomes charged and locks the dendrimer in the CNS)). In some embodiments, trigger agents are conjugated to the dendrimers so as to permit a controlled release of a particular agent (e.g., a narcotic and/or narcotic antagonist). The dendrimers are not limited to particular types of trigger agents. In some embodiments, sustained release (e.g., slow release over a period of 24-48 hours) of the pain relief drug is accomplished through conjugating the pain relief drug to the dendrimer through, for example, a linkage agent connected to a trigger agent that slowly degrades in a biological system (e.g., ester linkage). In some embodiments, constitutively active release of the pain relief drug is accomplished through conjugating the pain relief drug to the dendrimer through, for example, a linkage agent connected to a trigger agent that renders the pain relief agent constitutively active in a biological system (e.g., amide linkage, ether linkage). In some embodiments, the trigger agent is designed to permit release of the drug conjugated to the dendrimer in the presence of brain enzymes (e.g., the trigger agent indolequinone is reduced by brain enzymes such as, for example, diaphorase). In some embodiments, the trigger agent is designed to permit release of the drug conjugated to the dendrimer upon detection of reduced pO2 concentrations (e.g., through use of a trigger agent that detects reduced pO2 levels (e.g., a re-dox linker)). The use of a re-dox linker provides direct physiological feed back in order to prevent consequences of opoid-induced respiratory depression (e.g., cerebral hypoxia).

FIG. 32B shows two dendrimer conjugates designed for pain management in a subject. One of the dendrimers is conjugated to a morphine drug through a linkage agent connected to a trigger agent (e.g., ester linkage) permitting sustained release. The other dendrimer is conjugated to a morphine antagonist (e.g., Naloxone) through a linkage agent connected to a trigger agent (e.g., re-dox linker) permitting release of the morphine antagonist upon detection of reduced pO2 levels. Each of the dendrimers are targeted for CNS delivery through conjugation of targeting agents specific for the CNS (e.g., transferrin, a synthetic tetanus toxin fragment). Each of the dendrimers are designed for retention within the CNS through conjugation of locking agents designed to prevent back diffusion of the dendrimer across the BBB (e.g., pyridinium molecule, which when activated be enzymatic reduction, becomes charged and locks the dendrimer in the CNS).

These two characteristics differentiate the sustained release of a narcotic, and the feedback release of a narcotic antagonist. For example, in some embodiments, the narcotic is linked such that it would remain constitutively active while coupled to the polymer or continuously released over time (e.g., through triggering agents designed to permit sustained release) to provide prolonged activity, whereas, in some embodiments, the antagonist is active when released during hypoxia to prevent respiratory failure. In some embodiments, the antagonist and agonist are attached to two identical populations of dendrimers in a very consistent manner, and administered together (or separately) to form a single drug delivery system.

Accordingly, the present invention provides compositions, systems and methods for treating and/or managing pain in a subject through use of dendrimers conjugated to pain relief agents and/or pain relief agent antagonists. The following discussion describes individual component parts of the dendrimer and methods of making and using the same in some embodiments of the present invention. To illustrate the design and use of the systems and compositions of the present invention, the discussion focuses on specific embodiments of the use of the compositions in the treatment and reduction of pain suffered by a subject. These specific embodiments are intended only to illustrate certain preferred embodiments of the present invention and are not intended to limit the scope thereof. For example, although some discussion of the present invention involves battlefield injuries, other types apply (e.g., general trauma settings).

In certain embodiments, the present invention provides compositions comprising a dendrimer linked to a moiety comprising a trigger agent, a linkage agent, a targeting agent, and at least one therapeutic agent, wherein the therapeutic agent is a pain relief agent designed to reduce and/or eliminate pain in a subject and/or a pain relief agent antagonist. The composition are not limited to particular dendrimers. In some embodiments, the dendrimer is, for example, a polyamideamine (PAMAM) dendrimer, a polypropylamine (POPAM) dendrimer, and a PAMAM-POPAM dendrimer. The compositions are not limited to particular linkage agents (e.g., a spacer comprising between 1 and 8 straight or branched carbon chains). In some embodiments, the linkage agent is substituted or unsubstituted straight or branched carbon chain. In some embodiments, straight or branched carbon chains are substituted with alkyls. In some embodiments, the dendrimers are acetylated.

The compositions are not limited to particular trigger agents. In some embodiments, the trigger agents are configured to delay release of the pain relief agent from the moiety (e.g., an ester bond). In some embodiments, the trigger agents are configured to constitutively release the therapeutic agent from the moiety (e.g., an amide bond, an ether bond). In some embodiments, the trigger agent is configured to release the therapeutic agent from the moiety under conditions of acidosis. In some embodiments, the trigger agent is configured to release the therapeutic agent from the moiety under conditions of hypoxia (e.g., indoquinones, nitroheterocyles, and nitroimidazoles). In some embodiments, the trigger agent is configured to release the therapeutic agent from the moiety in the presence of a brain enzyme (e.g., the trigger agent is indolequinone and the brain enzyme is diaphorase).

The compositions are not limited to particular targeting agents. In some embodiments, the targeting agent is configured to permit the composition to cross the blood brain barrier (e.g., transferrin). In some embodiments, the targeting agent is configured to permit the composition to bind with a neuron within the central nervous system (e.g., the targeting agent is a synthetic tetanus toxin fragment (e.g., an amino acid peptide fragment (e.g., HLNILSTLWKYR (SEQ ID NO:1))).

In some embodiments, the moiety further comprises a locking agent. The compositions are not limited to particular locking agents. In some embodiments, the locking agent, upon activation, prevents transfer of the composition across the blood brain barrier. In some embodiments, the locking agent is a pyridinium molecule which is activated by enzymes specific to the central nervous system. In some embodiments, the locking agent is a re-dox system. In some embodiments, the re-dox system is the 1,4-dihydrotrigonelline⇌trigonelline (coffearine) re-dox system, wherein conversion of lipophilic 1,4-dihydro form (L) in vivo to the hydrophilic quaternary form (L$^+$) by oxidation prevents the composition from diffusing across the blood brain barrier.

The compositions are not limited to particular pain relief agents. In some embodiments, the pain relief agents include, but are not limited to, analgesic drugs, anxiolytic drugs, anesthetic drugs, antipsychotic drugs, hypnotic drugs, sedative drugs, and muscle relaxant drugs.

In some embodiments, the analgesic drugs include, but are not limited to, non-steroidal anti-inflammatory drugs, COX-2 inhibitors, and opiates. In some embodiments, the non-steroidal anti-inflammatory drugs are selected from the group consisting of Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate, Salicylamide, arylalkanoic acids, Diclofenac, Aceclofenac, Acemethacin, Alclofenac, Bromfenac, Etodolac, Indometacin, Nabumetone, Oxametacin, Proglumetacin, Sulindac, Tolmetin, 2-arylpropionic acids, Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids, Mefenamic acid, Flufenamic acid, Meclofenamic acid, Tolfenamic acid, pyrazolidine derivatives, Phenylbutazone, Ampyrone, Azapropazone, Clofezone, Kebuzone, Metamizole, Mofebutazone, Oxyphenbutazone, Phenazone, Sulfinpyrazone, oxicams, Piroxicam, Droxicam, Lornoxicam, Meloxicam, Tenoxicam, sulphonanilides, nimesulide, licofelone, and omega-3 fatty acids. In some embodiments, the COX-2 inhibitors are selected from the group consisting of Celecoxib, Etoricoxib, Lumiracoxib, Parecoxib, Rofecoxib, and Valdecoxib. In some embodiments, the opiate drugs are selected from the group consisting of natural opiates, alkaloids, morphine, codeine, thebaine, semi-synthetic opiates, hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, ethylmorphine, fully synthetic opioids, fentanyl, pethidine, Oxycodone, Oxymorphone, methadone, tramadol, Butorphanol, Levorphanol, propoxyphene, endogenous opioid peptides, endorphins, enkephalins, dynorphins, and endomorphins.

In some embodiments, the anxiolytic drugs include, but are not limited to, benzodiazepines, alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze, Triazolam, serotonin 1A agonists, Buspirone (BuSpar), barbituates, amobarbital (Amytal), pentobarbital (Nembutal), secobarbital (Seconal), Phenobarbital, Methohexital, Thiopental, Methylphenobarbital, Metharbital, Barbexaclone), hydroxyzine, cannabidiol, valerian, kava (Kava Kava), chamomile, Kratom, Blue Lotus extracts, Sceletium tortuosum (kanna) and bacopa monniera.

In some embodiments, the anesthetic drugs include, but are not limited to, local anesthetics, procaine, amethocaine, cocaine, lidocaine, prilocaine, bupivacaine, levobupivacaine, ropivacaine, dibucaine, inhaled anesthetics, Desflurane, Enflurane, Halothane, Isoflurane, Nitrous oxide, Sevoflurane, Xenon, intravenous anesthetics, Barbiturates, amobarbital (Amytal), pentobarbital (Nembutal), secobarbital (Seconal), Phenobarbital, Methohexital, Thiopental, Methylphenobarbital, Metharbital, Barbexaclone)), Benzodiazepines, alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam, Etomidate, Ketamine, and Propofol.

In some embodiments, the antipsychotic drugs include, but are not limited to, butyrophenones, haloperidol, phenothiazines, Chlorpromazine (Thorazine), Fluphenazine (Prolixin), Perphenazine (Trilafon), Prochlorperazine (Compazine), Thioridazine (Mellaril), Trifluoperazine (Stelazine), Mesoridazine, Promazine, Triflupromazine (Vesprin), Levomepromazine (Nozinan), Promethazine (Phenergan)), thioxanthenes, Chlorprothixene, Flupenthixol (Depixol and Fluanxol), Thiothixene (Navane), Zuclopenthixol (Clopixol & Acuphase)), clozapine, olanzapine, Risperidone (Risperdal), Quetiapine (Seroquel), Ziprasidone (Geodon), Amisulpride (Solian), Paliperidone (Invega), dopamine, bifeprunox, norclozapine (ACP-104), Aripiprazole (Abilify), Tetrabenazine, and Cannabidiol.

In some embodiments, the hypnotic drugs include, but are not limited to, Barbiturates, Opioids, benzodiazepines, alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam, nonbenzodiazepines, Zolpidem, Zaleplon, Zopiclone, Eszopiclone, antihistamines, Diphenhydramine, Doxylamine, Hydroxyzine, Promethazine, gamma-hydroxybutyric acid (Xyrem), Glutethimide, Chloral hydrate, Ethchlorvynol, Levomepromazine, Chlormethiazole, Melatonin, and Alcohol.

In some embodiments, the sedative drugs include, but are not limited to, barbituates, amobarbital (Amytal), pentobarbital (Nembutal), secobarbital (Seconal), Phenobarbital, Methohexital, Thiopental, Methylphenobarbital, Metharbital, Barbexaclone), benzodiazepines, alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam, herbal sedatives, ashwagandha, catnip, kava (Piper methysticum), mandrake, marijuana, valerian, solvent sedatives, chloral hydrate (Noctec), diethyl ether (Ether), ethyl alcohol (alcoholic beverage), methyl trichloride (Chloroform), nonbenzodiazepine sedatives, eszopiclone (Lunesta), zaleplon (Sonata), zolpidem (Ambien), zopiclone (Imovane, Zimovane)), clomethiazole (clomethiazole), gamma-hydroxybutyrate (GHB), Thalidomide, ethchlorvynol (Placidyl), glutethimide (Doriden), ketamine (Ketalar, Ketaset), methaqualone (Sopor, Quaalude), methyprylon (Noludar), and ramelteon (Rozerem).

In some embodiments, the muscle relaxant drugs include, but are not limited to, depolarizing muscle relaxants, Succinylcholine, short acting non-depolarizing muscle relaxants, Mivacurium, Rapacuronium, intermediate acting non-depolarizing muscle relaxants, Atracurium, Cisatracurium, Rocuronium, Vecuronium, long acting non-depolarizing muscle relaxants, Alcuronium, Doxacurium, Gallamine, Metocurine, Pancuronium, Pipecuronium, and d-Tubocurarine.

The compositions are not limited to particular pain relief agent antagonists. In some embodiments, the pain relief agent antagonists include drugs that counter the effect of a pain relief agent (e.g., an anesthetic antagonist, an analgesic antagonist, a mood stabilizer antagonist, a psycholeptic drug antagonist, a psychoanaleptic drug antagonist, a sedative drug antagonist, a muscle relaxant drug antagonist, and a hypnotic drug antagonist). In some embodiments, pain relief agent antagonists include, but are not limited to, a respiratory stimulant, Doxapram, BIMU-8, CX-546, an opiod receptor antagonist, Naloxone, naltrexone, nalorphine, levallorphan, cyprodime, naltrindole, norbinaltorphimine, buprenorphine, a benzodiazepine antagonist, flumazenil, a non-depolarizing muscle relaxant antagonist, and neostigmine.

In some embodiments, the moiety comprises a plurality of therapeutic agents (e.g., 2, 3, 4, 5, 10, 15, 50, 100, at any desired ratio). In some embodiments, the moeity comprises a plurality of pain relief agents (e.g., ketamine and lorazepam). In some embodiments, the therapeutic agent is a pain relief agent, wherein the pain relief agent is morphine. In some embodiments, the therapeutic agent is a pain relief agent antagonist, wherein the pain relief agent antagonist is Doxapram. In some embodiments, the therapeutic agent is a pain relief agent antagonist, wherein the pain relief agent antagonist is Naloxone.

In certain embodiments, the present invention provides methods for reducing pain in a subject (e.g., cat, dog, human, monkey, ape, cow, etc.) comprising administering to the subject at least one composition comprising a dendrimer linked to a moiety comprising a trigger agent, a linkage agent, a targeting agent, and at least one therapeutic agent, wherein the therapeutic agent is a pain relief agent designed to reduce and/or eliminate pain in a subject and/or a pain relief agent antagonist (as described above).

In some embodiments, the two compositions are administered to the subject such that one of the compositions comprises a pain relief agent and one of the compositions comprises a pain relief agent antagonist. In such embodiments, for example, the pain relief agent is morphine and the pain relief agent antagonist is Naloxone. In such embodiments, for example, the pain relief agent is ketamine and/or lorazepam and the pain relief agent antagonist is Doxapram.

In some embodiments, the present invention provides methods for treating cancer localized with a subject's central nervous system (e.g., brain) administering to the subject at least one composition comprising a dendrimer linked to a moeity comprising a trigger agent (e.g., a trigger agent that is sensitive to (e.g., is cleaved by) hypoxia) (e.g., a trigger agent that is sensitive to (e.g., is cleaved by) tumor associated enzymes), a linkage agent, a targeting agent configured to cross the blood brain barrier, and at least one therapeutic agent configured for treating cancer. In some embodiments, the dendrimers are designed for retention within the CNS through conjugation of locking agents designed to prevent back diffusion of the dendrimer across the BBB (e.g., pyridinium molecule, which when activated by enzymatic reduction, becomes charged and locks the dendrimer in the CNS).

DEFINITIONS

Figure 1:
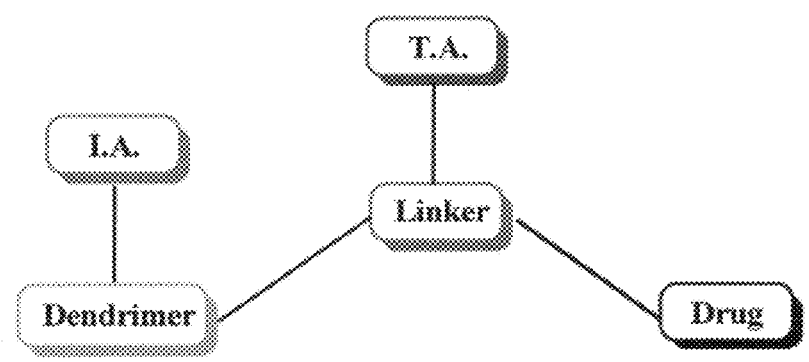
FIG. 1 shows a diagram of a dendrimer conjugate provided in some embodiments of the present invention.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "antagonist" or "pain relief agent antagonist" refers to an agent able to counter the effect of a pain relief agent and/or the effect of a pain relief agent (e.g., respiratory distress, cardiovascular distress).

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to a test result of initial cancer diagnosis that reveals the presence or absence of cancerous cells (e.g., using a biopsy and histology).

As used herein, the term "identifying the risk of said tumor metastasizing" refers to the relative risk (e.g., the percent chance or a relative score) of a tumor metastasizing.

As used herein, the term "identifying the risk of said tumor recurring" refers to the relative risk (e.g., the percent chance or a relative score) of a tumor recurring in the same organ as the original tumor.

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer on a subject's future health (e.g., expected morbidity or mortality, the likelihood of getting cancer, and the risk of metastasis).

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "drug" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "purified" or "to purify" or "compositional purity" refers to the removal of components (e.g., contaminants) from a sample or the level of components (e.g., contaminants) within a sample. For example, unreacted moieties, degradation products, excess reactants, or byproducts are removed from a sample following a synthesis reaction or preparative method.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using screening methods known in the art.

As used herein, the term "NAALADase inhibitor" refers to any one of a multitude of inhibitors for the neuropeptidase NAALADase (N-acetylated-alpha linked acidic dipeptidase). Such inhibitors of NAALADase have been well characterizied. For example, an inhibitor can be selected from the group comprising, but not limited to, those found in U.S. Pat. No. 6,011,021, herein incorporated by reference in its entirety.

As used herein, the term "nanodevice" or "nanodevices" refer, generally, to compositions comprising dendrimers of the present invention. As such, a nanodevice may refer to a composition comprising a dendrimer and metal nanoparticles (e.g., iron oxide nanoparticles (e.g., poly(styrene sulfonate) (PSS)-coated iron oxide nanoparticles)) of the present invention that may contain one or more functional groups (e.g., a therapeutic agent) conjugated to the dendrimer. A nanodevice may also refer to a composition comprising two or more different dendrimers of the present invention.

As used herein, the term "degradable linkage," when used in reference to a polymer (e.g., PEG-hRNase conjugate of the present invention), refers to a conjugate that comprises a physiologically cleavable linkage (e.g., a linkage that can be hydrolyzed (e.g., in vivo) or otherwise reversed (e.g., via enzymatic cleavage). Such physiologically cleavable linkages include, but are not limited to, ester, carbonate ester, carbamate, sulfate, phosphate, acyloxyalkyl ether, acetal, and ketal linkages (See, e.g., U.S. Pat. No. 6,838,076, herein incorporated by reference in its entirety). Similarly, the conjugate may comprise a cleavable linkage present in the linkage between the polymer and hRNase, or, may comprise a cleavable linkage present in the polymer itself (e.g., such that when cleaved, a small portion of the polymer remains on the hRNase molecule) (See, e.g., U.S. Pat. App. Nos. 20050158273 and 20050181449, each of which is herein incorporated by reference in its entirety). For example, a PEG polymer comprising an ester linkage can be utilized for conjugation to hRNase to create a PEG-hRNase conjugate (See, e.g., Kuzlowski et al., Biodrugs, 15, 419-429 (2001). A conjugate that comprises a degradable linkage of the present invention is capable of generating hRNase that is free (e.g., completely or partially free) of the polymer (e.g., in vivo after hydrolysis of the linkage).

A "physiologically cleavable" or "hydrolysable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond (e.g., typically a covalent bond) that is substantially stable in water (i.e., does not undergo hydrolysis under physiological conditions to any appreciable extent over an extended period of time). Examples of hydrolytically stable linkages include, but are not limited to, carbon-carbon bonds (e.g., in aliphatic chains), ethers, amides, urethanes, and the like.

As used herein, the term "click chemistry" refers to chemistry tailored to generate substances quickly and reliably by joining small modular units together (see, e.g., Kolb et al. (2001) Angewandte Chemie Intl. Ed. 40:2004-2011; Evans (2007) Australian J. Chem. 60:384-395; Carlmark et al. (2009) Chem. Soc. Rev. 38:352-362; each herein incorporated by reference in its entirety).

As used herein, the term "one-pot synthesis reaction" or equivalents thereof, e.g., "1-pot", "one pot", etc., refers to a chemical synthesis method in which all reactants are present in a single vessel. Reactants may be added simultaneously or sequentially, with no limitation as to the duration of time elapsing between introduction of sequentially added reactants.

As used herein, an "ester coupling agent" refers to a reagent that can facilitate the formation of an ester bond between two reactants. The present invention is not limited to any particular coupling agent or agents. Examples of coupling agents include but are not limited to 2-chloro-1-methylpyridium iodide and 4-(dimethylamino) pyridine, or dicyclohexylcarbodiimide and 4-(dimethylamino) pyridine or diethyl azodicarboxylate and triphenylphosphine or other carbodiimide coupling agent and 4-(dimethylamino)pyridine.

As used herein, the term "glycidolate" refers to the addition of a 2,3-dihydroxylpropyl group to a reagent using glycidol as a reactant. In some embodiments, the reagent to which the 2,3-dihydroxylpropyl groups are added is a dendrimer. In some embodiments, the dendrimer is a PAMAM dendrimer. Glycidolation may be used generally to add terminal hydroxyl functional groups to a reagent.

As used herein, the term "ligand" refers to any moiety covalently attached (e.g., conjugated) to a dendrimer branch; in preferred embodiments, such conjugation is indirect (e.g., an intervening moiety exists between the dendrimer branch and the ligand) rather than direct (e.g., no intervening moiety exists between the dendrimer branch and the ligand). Indirect attachment of a ligand to a dendrimer may exist where a scaffold compound (e.g., triazine scaffold) intervenes. In preferred embodiments, ligands have functional utility for specific applications, e.g., for therapeutic, targeting, imaging, or drug delivery function(s). The terms "ligand", "conjugate", and "functional group" may be used interchangeably.

DETAILED DESCRIPTION OF THE INVENTION

The present invention relates to novel therapeutic and diagnostic dendrimers. In particular, the present invention is directed to dendrimer-linker conjugates, methods of synthesizing the same, compositions comprising the conjugates, as well as systems and methods utilizing the conjugates (e.g., in diagnostic and/or therapeutic settings (e.g., for the delivery of therapeutics, imaging, and/or targeting agents (e.g., in disease (e.g., cancer) diagnosis and/or therapy, pain therapy, etc.)). Accordingly, dendrimer-linker conjugates of the present invention may further comprise one or more components for targeting, imaging, sensing, and/or providing a therapeutic or diagnostic material and/or monitoring response to therapy.

Accordingly, in some embodiments, the present invention provides a linker conjugated to an agent (e.g., therapeutic agent, imaging agent, targeting agent, triggering agent) (e.g., that can be conjugated to a dendrimer (e.g., for specific targeting and/or therapeutic use of the dendrimer)). Thus, in some embodiments, the present invention provides methods of synthesizing dendrimer conjugates (e.g., PAMAM dendrimers) comprising linkers (e.g., conjugated to a trigger moiety, therapeutic moiety and/or other type of moiety), compositions comprising the same, and methods of using the same in the diagnosis, imaging and treatment of disease (e.g., cancer, inflammatory disease, chronic pain, etc.).

The present invention provides a multiplicity of linkers and agents (e.g., therapeutic agent, imaging agent, targeting agent, triggering agent) that find use in the present invention. Indeed, the present invention is not limited to any particular linker or to any particular targeting agent or to any particular dendrimer. In some embodiments, the present invention provides a dendrimer conjugated to a linker that is conjugated to an agent (e.g., therapeutic agent, imaging agent, targeting agent, triggering agent), and methods of generating and using the same (e.g., to treat cancer, pain and/or inflammation, etc.). In some embodiments, a dendrimer conjugated to a linker that is conjugated to an agent (e.g., therapeutic agent, imaging agent, targeting agent, triggering agent) decreases the number of conjugation steps required to form a dendrimer (e.g., a dendrimer conjugate (e.g., a dendrimer conjugated to a targeting agent, imaging agent, therapeutic agent and/or triggering agent)). For example, in some embodiments, the present invention provides a customizable dendrimer wherein one or a plurality of linkers (e.g. attached to one or a plurality of targeting agents, triggering agents and/or therapeutic agents) are conjugated to a dendrimer, thereby decreasing the number of conjugation steps used to form a dendrimer (e.g., versus a dendrimer that is conjugated to a targeting moiety in one step and that is separately conjugated to a linker (e.g., comprising a therapeutic agent, imaging agent, triggering agent or other moiety) in an additional conjugation step). In some embodiments, a linker conjugated to one or more agents (e.g., therapeutic agents, imaging agents, targeting agents, triggering agents) is conjugated to one or more additional moieties including, but not limited to, a therapeutic agent, a triggering agent, an imaging agent, a triggering agent, etc. Thus, in some embodiments, the present invention provides a dendrimer with increased load capacity (e.g., increased load of therapeutic, imaging agent, etc. on the dendrimer). In some embodiments, two or more linkers (e.g., conjugated to one or a plurality of targeting agents) are conjugated to a dendrimer via the same or different linkage (e.g., covalent linkage).

Several different schemes were evaluated for generating dendrimer conjugates wherein a dendrimer is conjugated to one or more linkers that comprise multiple sites for binding (e.g., covalent binding) moieties. For example, in one embodiment, a linker may comprise a chemical structure that allows, for example, conjugation of a targeting moiety and a therapeutic compound to the linker. Thus, in some embodiments, a dendrimer conjugate of the present invention permits control of the stoichiometry between targeting agent and therapeutic compound (e.g., generation of one to one ratio, two to one ratio, one to two ratio, one to three ratio etc. between targeting and therapeutic moieties).

In some embodiments, a dendrimer conjugated to a linker that is conjugated to a targeting agent and/or therapeutic agent comprises a linker that is configured to be irreversibly degraded (e.g., that is non-reversible (e.g., that permits drug delivery at the correct time and/or at the correct place)).

In some embodiments, the present invention provides dendrimer molecules (e.g., polyamideamine (PAMAM) dendrimers, polypropylamine (POPAM) dendrimers, or PAMAM-POPAM dendrimers) conjuguated to one or more pain relief agents (e.g., prodrug analgesic molecules). In some embodiments, the dendrimers conjugated to one or more pain relief agents (e.g., prodrug analgesic molecules) are configured for controlled and/or sustained release of the pain relief agents (e.g., through use of targeting agents, linking agents, and/or trigger agents conjugated to the dendrimer and/or pain relief agent). In some embodiments, the pain relief agent conjugated to the dendrimer is active upon administration to a subject. In some embodiments, sustained release (e.g., slow release over a period of 24-48 hours) of the pain relief agent is accomplished through conjugating the pain relief agent to the dendrimer through, for example, a linkage agent connected to a trigger agent that slowly degrades in a biological system (e.g., ester linkage). In some embodiments, constitutively active release of the pain relief agent is accomplished through conjugating the pain relief agent to the dendrimer through, for example, a linkage agent connected to a trigger agent that renders the pain relief agent constitutively active in a biological system (e.g., amide linkage, ether linkage). In some embodiments, the dendrimers conjugated to one or more pain relief agents simultaneously configured for sustained release (e.g., a slow release mechanism that achieves analgesic concentrations over a period of, for example, 24-48 hours) of the pain relief agent prevents adverse side effects of the pain relief agent (e.g., respiratory failure, adverse cardiovascular consequences). The present invention further provides systems and methods for treating and/or managing pain through utilization of dendrimers conjugated to one or more pain relief agents.

In some embodiments, as shown in FIG. 32A, the present invention provides compositions comprising a plurality of pain relief agents (e.g., Ketamine and Lorazepam) coupled to dendrimers with a linkage agent connected to a trigger agent that slowly degrades in a biological system (e.g., amide linkage, ester linkage, ether linkage) (as shown in FIG. 32A, the trigger agent is an ester bond that is released by serum esterases to mediate sustained-release analgesia). When administered together, Ketamine and Lorazepam have favorable analgesic and anxiolytic/amnestic qualities, and relatively broad therapeutic indexes. Such compositions comprising Ketamine and Lorazepam provide analgesia without the cardiovascular effects of opioids and minimize their major complication, that being respiratory depression. As a feedback mechanism, compositions comprising a pain relief agent antagonist (e.g., Doxapram) complexed with dendrimer through charge interaction that would be released by, for example, acidosis. While acidosis could be observed from causes other than respiratory depression, this feedback mechanism is unique in that Doxapram stimulates respirations without reducing analgesia. As such, there would not be an issue in releasing the Doxapram regardless of the source of the acidosis. Indeed, the increased respiratory drive would be of benefit to compensate acidosis even when caused by metabolic sources from traumatic injuries, hemorrhagic shock, burns or rhabdomyolysis. One advantage to this approach is that it provides safe analgesia with easily achieved physiological feedback.

For example, in some embodiments, G5 dendrimers with different percentages of succinamic acid termini (Scheme 3) wherein Doxapram molecules are encapsulated in the interior of dendrimers, In such embodiments, the negative charges on the dendrimer surface prevent the release of the drug due to the strong electrostatic interaction with the positively charged Doxapram hydrochloride. In such embodiments, the drug is released once the dendrimer surface carboxyl groups are protonated with decreasing pH.

Scheme 3. Molecular structure of Doxapram

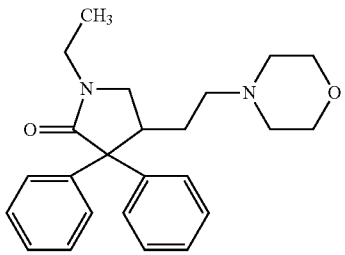

In some embodiments, as shown in FIG. 32B shows two dendrimer conjugates designed for pain management in a subject. One of the dendrimers is conjugated to a morphine drug through a linkage agent connected to a trigger agent (e.g., ester, amide) permitting sustained release. The other dendrimer is conjugated to a morphine antagonist (e.g., Naloxone) through a linkage agent connected to a trigger agent (e.g., re-dox linker) permitting release of the morphine antagonist upon detection of reduced pO2 levels. Each of the dendrimers are targeted for CNS deliver through conjugation of targeting agents specific for the CNS (e.g., transferrin, a synthetic tetanus toxin fragment). Each of the dendrimers are designed for retention within the CNS through conjugation of locking agents designed to prevent back diffusion of the dendrimer across the BBB (e.g., pyridinium molecule, which when activated be enzymatic reduction, becomes charged and locks the dendrimer in the CNS).

Figure 33:
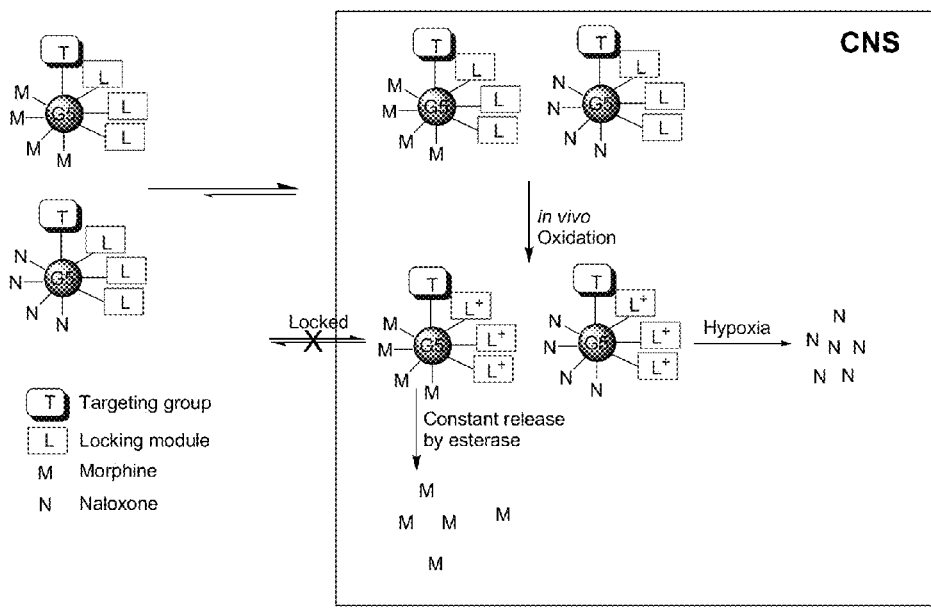
FIG. 33 shows a schematic representation of CNS locking targeted drug.

In some embodiments, as shown in FIG. 33, the present invention provides dendrimer conjugates configured to provide effective analgesia (e.g., narcotic analgesia (e.g., Morphine)) over prolonged time periods. In some embodiments, the dendrimer conjugates shown in FIG. 33 are transported to the CNS, and retained in the CNS to provide, for example, constitutive narcotic analgesia. Such embodiments permit the use of smaller analgesic doses, while reducing the peripheral adverse effects. In some embodiments, as shown in FIG. 33, the dendrimer conjugates comprise i) a targeting agent that enables the conjugate to cross the BBB and target neurons, ii) a locking agent (e.g., a re-dox locking module) to prevent the dendrimer conjugate from diffusing back across the BBB, and iii) a pain relief agent (e.g., narcotic analgesic (Morphine)) or pain relief agent antagonist (e.g., Naloxone) coupled by different linking agents and triggering agents. The dendrimer conjugates are not limited to particular targeting agents. In some embodiments, the targeting agent for CNS targeting through crossing the BBB is transferrin (see, e.g., Daniels, T. R., et al., Clinical Immunology, 2006. 121(2): p. 159-176; Daniels, T. R., et al., Clinical Immunology, 2006. 121(2): p. 144-158; each herein incorporated by reference in their entireties). In some embodiments, the targeting agent for neuron targeting is a 12 amino acid peptide (Tet 1) (see, e.g., Liu, J. K., et al., Neurobiology of Disease, 2005. 19(3): p. 407-418; herein incorporated by reference in its entirety). The dendrimer conjugates are not limited to particular locking agents. In some embodiments, the locking agent for locking the dendrimer conjugate within the CNS is the 1,4-dihydrotrigonelline⇌trigonelline (coffearine) re-dox system where the lipophilic 1,4-dihydro form (L) is converted in vivo to the hydrophilic quaternary form ($L^+$) by oxidation to prevent the dendrimer conjugate from diffusing back into the circulation (see, e.g., Bodor, N. and P. Buchwald, Drug Discovery Today, 2002. 7(14): p. 766-774; herein incorporated by reference in its entirety). In some embodiments, the dendrimer conjugate device is eliminated from the CNS (e.g., because of acquired hydrophilicity due to loss of the quaternary form). In some embodiments, the pain relief agent and/or pain relief agent antagonist is attached to the dendrimer through, for example, triggering agents designed for delayed release (e.g., ester bonds, amide bonds, ether bonds). In some embodiments wherein the dendrimer conjugate comprises a pain relief agent antagonist (e.g., Naloxone), the pain relief agent antagonist is attached to the dendrimer through a linkage agent connected to a trigger agent (e.g., re-dox linker) permitting release of the pain relief agent antagonist upon detection of reduced pO2 levels.

Figure 2A:
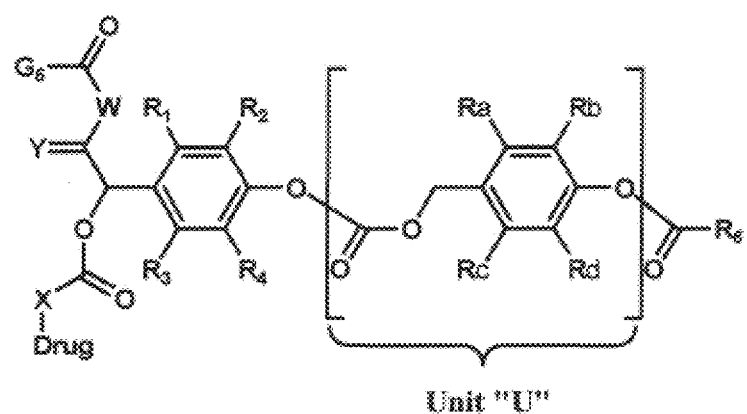
FIG. 2A, FIG. 2B and FIG. 2C show a diagram of a dendrimer conjugate provided in some embodiments of the present invention.
Figure 2B:
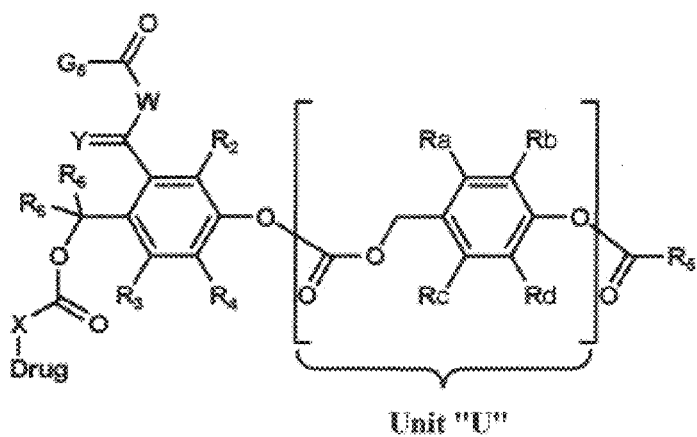
Figure 2C:
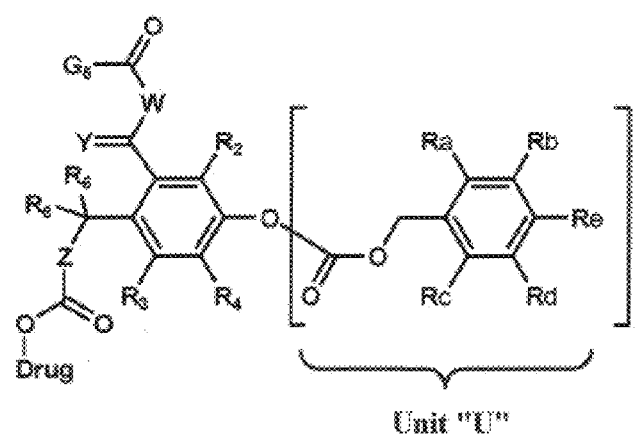

In some embodiments, the present invention provides a dendrimer conjugate as shown in FIG. 1. For example, FIG. 1 shows a targeting agent (T.A.) conjugated to a linker that is also conjugated to a drug, wherein the linker conjugated to a drug and targeting agent is conjugated to a dendrimer conjugated to an imaging agent (I.A.). In some embodiments, the present invention provides a dendrimer conjugate as shown in FIG. 2 (e.g., possessing targeted anticancer therapeutic moiety). For example, FIG. 2 shows several structures of dendrimer conjugates, wherein R1, R2, R3 and R4 are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid)). In some embodiments, the "U" moiety is present or absent. In some embodiments, when the "U" moiety is absent, one of the R1, R2, R3 and/or R4 groups is linked to a targeting agent through a linker and/or spacer. In some embodiments, R5 is an alkyl (e.g., that is straight chained, branched, cyclic (e.g., that is substituted or unsubtituted)). In some embodiments, R6 is a hydrogen or an alkyl (e.g., of 1-4 carbons (e.g., that are straight chained or cyclic (e.g., that is substituted or unsubtituted)). In some embodiments, Ra, Rb, Rc, Rd and Re are each independently selected from hydrogen, halogen, and alkyl. In some embodiments, the alkyl is straight or cyclic, unsubstituted or substituted (e.g., by from 1 to 4 substituents (e.g., selected from halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, the "U" moiety is present or absent. In some embodiments, when the "U" moiety is absent, one of the Ra, Rb, Rc, Rd and Re groups is linked to a targeting agent through a linker and/or spacer. In some embodiments, "Y" is an oxygen atom. In some embodiments, "Y" is two hydrogen atoms. In some embodiments, G5 is a generation five poly (amidoamine) (PAMAM) dendrimer (e.g., conjugated to one or more imaging agents (e.g., FITC, etc.), although higher (e.g., G6, G7, G8, G9, G10 or higher, or lower, G4, G3, or G2 dendrimers may also be used. In some embodiments, "W" is a linker comprising 1-8 carbon and/or nitrogen atoms (e.g., straight chanined, branched, or cyclic, unsubstituted or substituted by "R" groups as described above.

Figure 3:
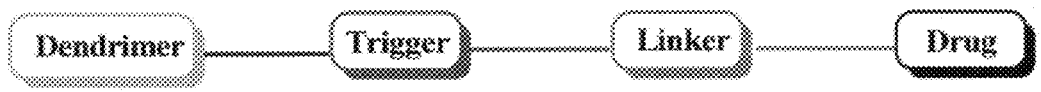
FIG. 3 shows a diagram of a dendrimer conjugate provided in some embodiments of the present invention.
Figure 4:
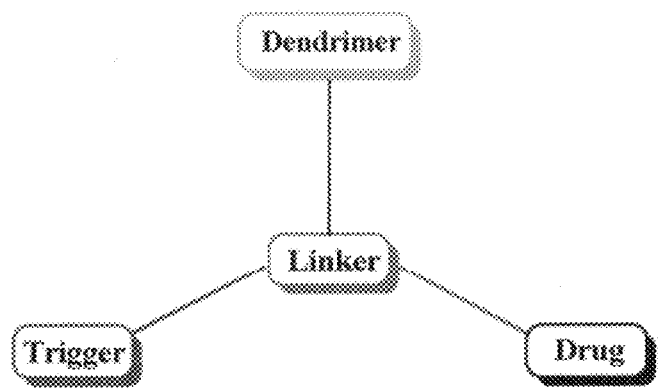
FIG. 4 shows a diagram of a dendrimer conjugate provided in some embodiments of the present invention.

In some embodiments, the present invention provides a dendrimer conjugate as shown in FIGS. 3 and 4. In particular, a dendrimer conjugate as shown in FIG. 3 comprises a dendrimer (e.g., a G5 PAMAM dendrimer conjugated to an imaging agent (e.g., FITC) and/or targeting agent) conjugated to a trigger molecule that is conjugated to a linker that is conjugated to a therapeutic. A dendrimer conjugate as shown in FIG. 4 comprises a dendrimer (e.g., a G5 PAMAM dendrimer conjugated to an imaging agent (e.g., FITC) and/or targeting agent) conjugated to a linker that is conjugated to a trigger and to a therapeutic moiety. The conjugates of FIGS. 3 and 4 are configured to be non-toxic to normal cells. For example, the conjugates are configured in such a way so as to release their therapeutic agent only at a specific, targeted site (e.g., through activation of a trigger molecule that in to leads to release of the therapeutic agent) For example, once a conjugate arrives at a target site in a subject (e.g., a tumor, or a site of inflammation), components in the target site (e.g., a tumor associated factor, or an inflammatory or pain associated factor) interacts with the trigger moiety thereby initiating cleavage of this unit from the linker. In some embodiments, once the trigger is cleaved from the linker (e.g., by a target associated moiety, the linker proceeds through spontaneous chemical breakdown thereby releasing the therapeutic agent at the target site (e.g., in its active form). The present invention is not limited to any particular target associated moiety (e.g., that interacts with and initiates cleavage of a trigger). In some embodiments, the target associated moiety is a tumor associated factor (e.g., an enzyme (e.g., glucuronidase and/or plasmin), a cathepsin, a matrix metalloproteinase, a hormone receptor (e.g., integrin receptor, hyaluronic acid receptor, luteinizing hormone-releasing hormone receptor, etc.), cancer and/or tumor specific DNA sequence), an inflammatory associated factor (e.g., chemokine, cytokine, etc.) or other moiety.

Figure 5:
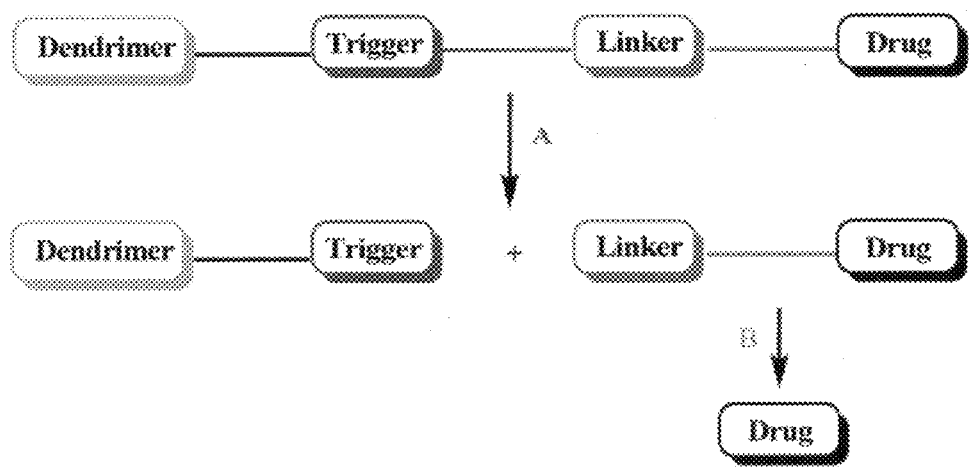
FIG. 5 shows a diagram of a dendrimer conjugate provided in some embodiments of the present invention.
Figure 6:
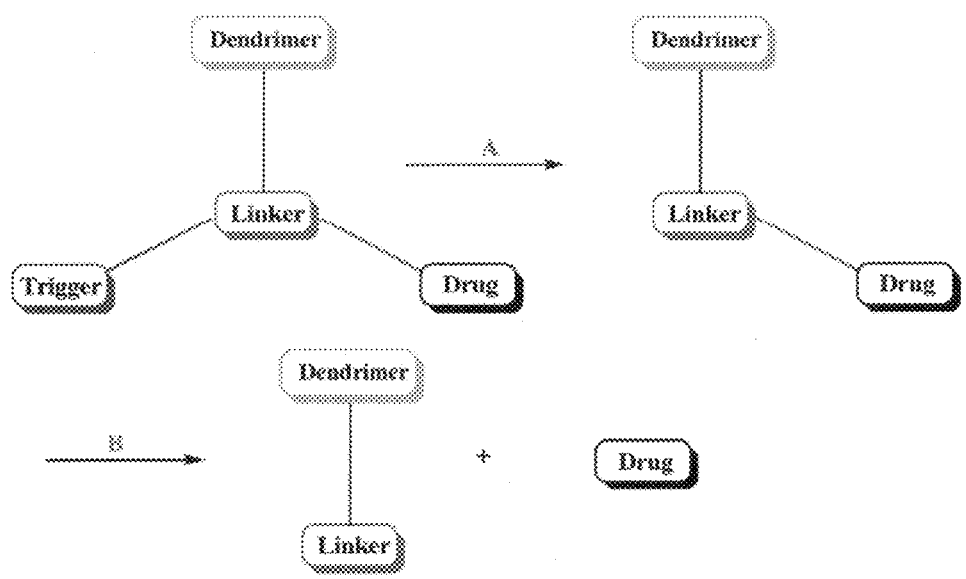
FIG. 6 shows a diagram of a dendrimer conjugate provided in some embodiments of the present invention.
Figure 7:
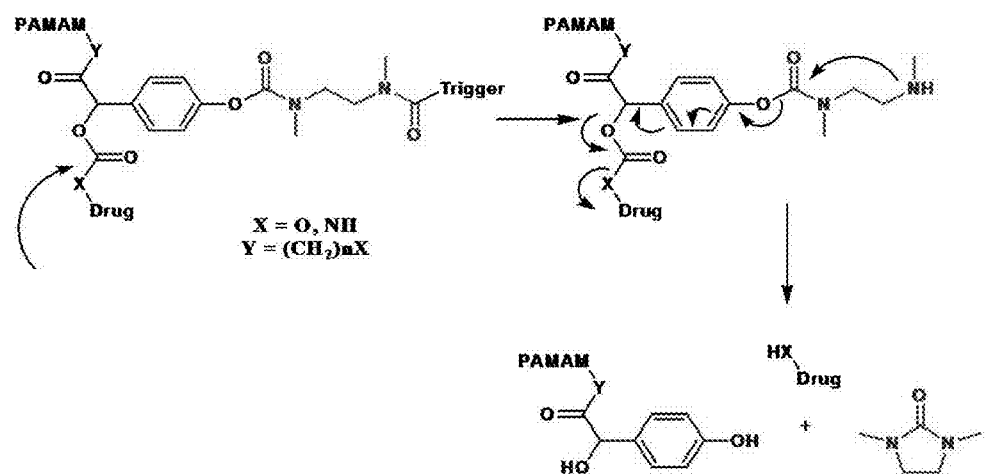
FIG. 7 shows the release of a therapeutic compound from a dendrimer conjugate in one embodiment of the invention.
Figure 8:
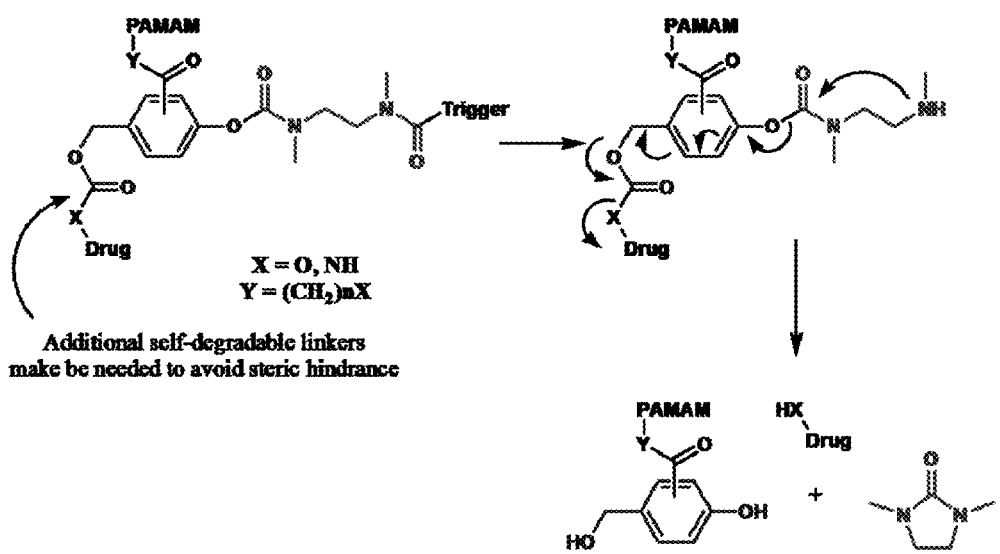
FIG. 8 shows the release of a therapeutic compound from a dendrimer conjugate in one embodiment of the invention.
Figure 9A:
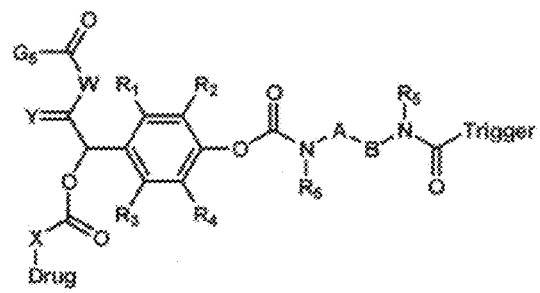
FIG. 9A, FIG. 9B, FIG. 9C and FIG. 9D show a diagram of a dendrimer conjugate provided in some embodiments of the present invention.
Figure 9B:
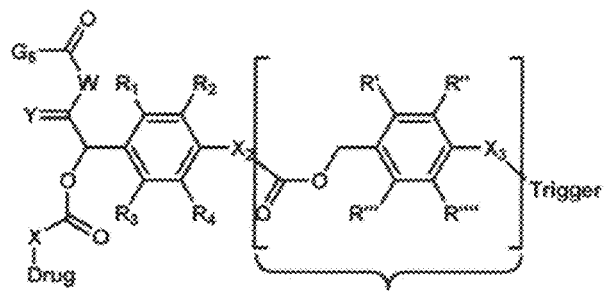
Figure 9C:
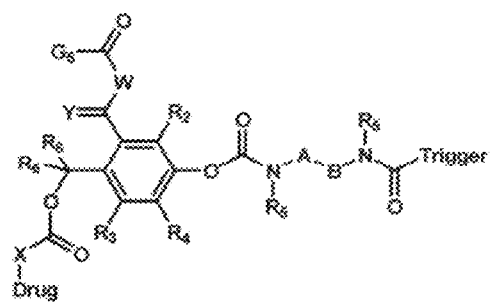
Figure 9D:
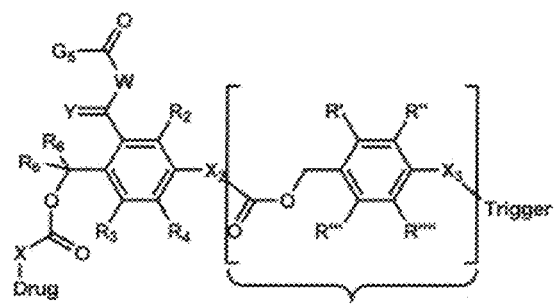
Figure 32:
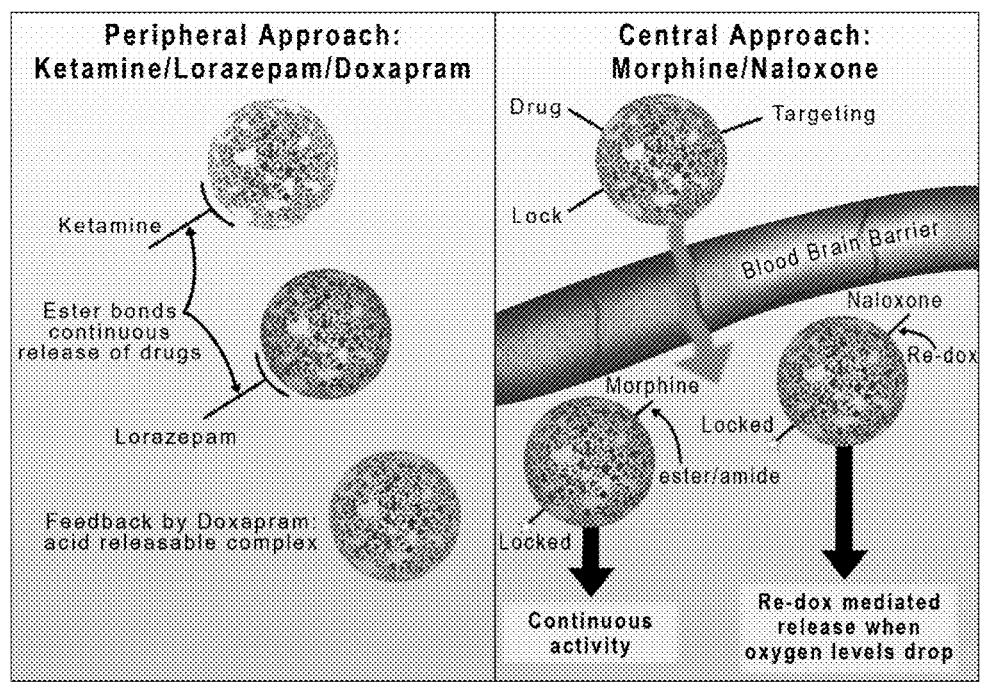
FIG. 32 shows two dendrimer conjugates.

Although an understanding of a mechanism of action is not necessary to practice the present invention, and the present invention is not limited to any particular mechanism of action, in some embodiments, a dendrimer conjugate as described in FIG. 3 or 4 provides a therapeutic to a site by a mechanism as shown in FIG. 5 or 6. For example, as shown in FIG. 5, a dendrimer conjugate comprising a dendrimer (e.g., a G5 PAMAM dendrimer conjugated to an imaging agent (e.g., FITC) and/or targeting agent) conjugated to a trigger molecule that is conjugated to a linker that is conjugated to a therapeutic (A) interacts with a target associated moiety thereby activating the trigger and initiating cleavage of same, releasing the linker therapeutic drug conjugate. Once cleavage of the trigger occurs, the linker (B) proceeds through a spontaneous chemical breakdown at the target site, releasing (e.g., irreversibly releasing) the therapeutic drug at the target site. In some embodiments, as shown in FIG. 6, a dendrimer conjugate comprising a dendrimer (e.g., a G5 PAMAM dendrimer conjugated to an imaging agent (e.g., FITC) and/or targeting agent) conjugated to a linker that is conjugated to a trigger and to a therapeutic moiety (A) interacts with a target associated moiety thereby activating the trigger and initiating cleavage of same, releasing a dendrimer-linker-therapeutic moiety from the trigger. Once cleavage of the trigger occurs, the linker (B) proceeds through a spontaneous chemical breakdown (e.g., to a point where the therapeutic drug is released from the dendrimer linker conjugate) at the target site, releasing (e.g., irreversibly releasing) the therapeutic drug at the target site. In some embodiments, cleavage of the trigger and subsequent linker breakdown is not necessary to deliver the therapeutic drug to the target site. Several design processes for generating a dendrimer conjugate comprising a trigger are shown in FIGS. 7 and 8. The dendrimer conjugates for the present invention (e.g., the dendrimer conjugates as shown in FIGS. 32, 3 and 4) are not limited to any particular dendrimer. Indeed, the conjugates may comprise a variety of different types of dendrimers. In some embodiments, the dendrimer is a PAMAM dendrimer (e.g., G3, G5 or G7 dendrimer). In some embodiments, one or more amino groups present on the dendrimer are linked (e.g., through a covalent bond) to one or more targeting agents (e.g., folic acid) and/or imaging agents (e.g., FITC) (e.g., as described in U.S. Pat. Nos. 6,471,968 and 7,078,461; U.S. Patent Pub. Nos. 20020165179 and 20070041934 and WO 06/033766, each of which is hereby incorporated by reference in its entirety for all purposes).

In some embodiments, the present invention provides a dendrimer conjugate as shown in FIG. 9. In particular, a dendrimer conjugate as shown in FIG. 9 comprises a dendrimer (e.g., a G5 PAMAM dendrimer conjugated to an imaging agent (e.g., FITC) and/or targeting agent) conjugated to a trigger molecule that is conjugated to a linker that is conjugated to a therapeutic, or a dendrimer (e.g., a G5 PAMAM dendrimer conjugated to an imaging agent (e.g., FITC) and/or targeting agent) conjugated to a linker that is conjugated to a trigger and to a therapeutic moiety). For example, FIG. 9 shows several structures of dendrimer conjugates, wherein R1, R2, R3 and R4 are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, R5 is an alkyl that is straight, branched or cyclic, that is unsubstituted or substituted. In some embodiments, R6 is a hydrogen or alkyl of 1-4 carbons that are straight, branched or cyclic, that is unsubstituted or substituted. In some embodiments, the two R6 are connected together to form a ring of 306 members. In some embodiments, R', R'', R''' and R'''' are each independently selected from hydrogen, halogen, and alkyl. In some embodiments, the alkyl is straight or cyclic, unsubstituted or substituted (e.g., by from 1 to 4 substituents (e.g., selected from the group comprising, but not limited to, halogen, amino, monoalkylamino, dialkylamino, hydroxy, alkoxy, nitro, aryl, cyano, carboxyl, carboxamide, monoalkylcarboxamide, dialkylcarboxamide, thiol, thioalkyl and sulfonic acid. In some embodiments, X, X2 and X3 are either oxygen or "NR", wherein "N" is a nitrogen atom, and "R" is an alkyl that is straight or branched or cyclic (e.g., substituted or unsubstituted). In some embodiments, "Y" is an oxygen atom or two hydrogen atoms. In some embodiments, A-B is an ethylene group (e.g., unsubstituted or substituted by alkyls (e.g., straight or cyclic). In some embodiments, A-B are connected by a carbon chain (e.g., of 2, 3, 4, 5, or more carbons) and/or hetero atoms (e.g., forming a saturated or unsaturated aromatic ring structure (e.g., comprising substituents such as R1, R2, R3 and R4). In some embodiments, G5 is a dendrimer (e.g., a G5 PAMAM dendrimer conjugated to an imaging agent (e.g., FITC) and/or targeting agent). As described herein, the present invention is not limited to any particular dendrimer. In some embodiments, "W" is a linker (e.g., comprising a carbon or nitrogen chain (e.g., 2, 3, 4, 5, 6, 7, 8, 9, or more carbons or nitrogens (e.g., straight or branched or cyclic (e.g., substituted or unsubstituted (e.g., with R groups as described above))).

The present invention is not limited by the type of dendrimer conjugate (e.g., comprising a trigger) for use in treating a subject. In some embodiments, the dendrimer conjugates of the present invention (see, e.g., FIGS. 32 and 33) are used as delivery agents for pain relief agents and pain relief agent antagonists. Such dendrimer conjugates are not limited to uses within particular settings. Indeed, the dendrimer conjugates of the present invention (see, e.g., FIGS. 32 and 33) may be used in any setting requiring treatment and/or management of pain (e.g., battlefield, ambulance, hospital, clinic, rescue, etc.). In addition, the present invention contemplates dendrimer conjugates comprising one or more pain relief agent prodrugs and/or pain relief agent antagonist prodrugs developed for site specific conversion to drug based on tumor associated factors (e.g., hypoxia and pH, tumor-associated enzymes, and/or receptors). In some embodiments, dendrimer conjugates of the present invention are configured such that a prodrug (e.g., pain relief agent prodrug, pain relief agent antagonist prodrug) is conjugated to a linker that is further conjugated to a targeting moiety (e.g., that targets the conjugate to a particular body region (e.g., CNS)). Although an understanding of the mechanism is not necessary for the present invention, and the present invention is not limited to any particular mechanism of action, in some embodiments, a trigger component serves as a precursor for site-specific activation. For example, in some embodiments, once the trigger recognizes a particular condition (e.g., hypoxia), cleavage and/or processing of the trigger is induced, thereby releasing the pain relief agent and/or pain relief antagonist.

The present invention is not limited to a particular trigger agent or to any particular cleavage and/or processing of the trigger agent. In some embodiments, the present invention provides pain relief agents and/or pain relief agent antagonists coupled to dendrimers with a linkage agent connected to a trigger agent that slowly degrades in a biological system (e.g., amide linkage, ester linkage, ether linkage) (as shown in FIG. 32A, the trigger agent is an ester bond that is released by serum esterases to mediate sustained-release analgesia).

Figure 18:
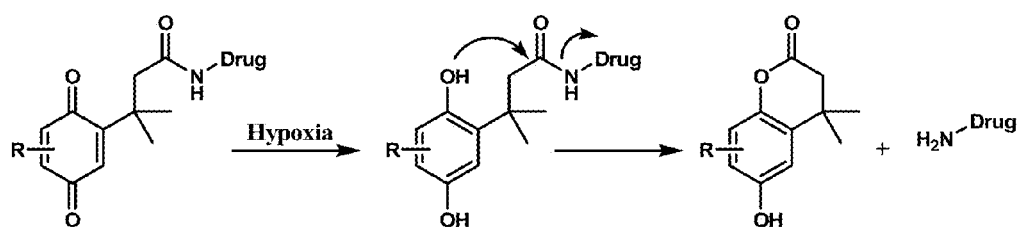
FIG. 18 shows an example of a dendrimer conjugate designed for hypoxia induced activation in one embodiment of the present invention.
Figure 19:
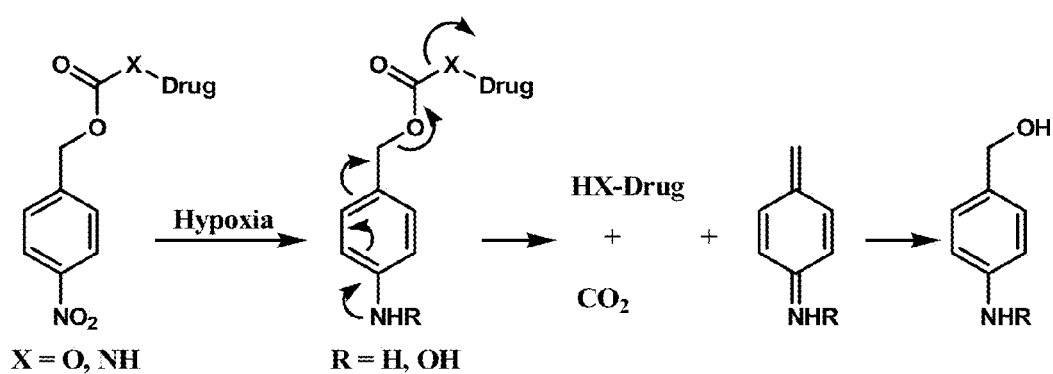
FIG. 19 shows that, in some embodiments, a heteroaromatic nitro compound present in a dendrimer conjugate of the present invention is reduced to either an amine or a hydroxylamine, thereby triggering the spontaneous release of a therapeutic agent/drug.

In some embodiments, the present invention provides a dendrimer conjugate comprising a trigger agent that is sensitive to (e.g., is cleaved by) hypoxia (e.g., as described in Example 8). Hypoxia is a feature of several disease states, including cancer, inflammation and rheumatoid arthritis, as well as an indicator of respiratory depression (e.g., resulting from analgesic drugs). Advances in the chemistry of bioreductive drug activation have led to the design of various hypoxia-selective drug delivery systems in which the pharmacophores of drugs are masked by reductively cleaved groups. In some embodiments, a dendrimer conjugate of the present invention utilizes a quinone, N-oxide and/or (hetero) aromatic nitro groups. For example, a quinone present in a dendrimer conjugate of the present invention is reduced to phenol under hypoxia conditions, with spontaneous formation of lactone that serves as a driving force for drug release (e.g., as shown in FIG. 18). In some embodiments, a heteroaromatic nitro compound present in a dendrimer conjugate of the present invention is reduced to either an amine or a hydroxylamine, thereby triggering the spontaneous release of a therapeutic agent/drug (e.g., as shown in FIG. 19). In some embodiments, the present invention provides pain relief agents and/or pain relief agent antagonists coupled to dendrimers with a linkage agent connected to a trigger agent that degrades upon detection of reduced pO2 concentrations (e.g., through use of a re-dox linker).

The concept of prodrug systems in which the pharmacophores of drugs are masked by reductively cleavable groups has been widely explored by many research groups and pharmaceutical companies (see, e.g., Beall, H. D., et al., Journal of Medicinal Chemistry, 1998. 41(24): p. 4755-4766; Ferrer, S., D. P. Naughton, and M. D. Threadgill, Tetrahedron, 2003. 59(19): p. 3445-3454; Naylor, M. A., et al., Journal of Medicinal Chemistry, 1997. 40(15): p. 2335-2346; Phillips, R. M., et al., Journal of Medicinal Chemistry, 1999. 42(20): p. 4071-4080; Zhang, Z., et al., Organic & Biomolecular Chemistry, 2005. 3(10): p. 1905-1910; each of which are herein incorporated by reference in their entireties). Several such hypoxia activated prodrugs have been advanced to clinical investigations, and work in relevant oxygen concentrations to prevent cerebral damage. The present invention is not limited to particular hypoxia activated trigger agents. In some embodiments, the hypoxia activated trigger agents include, but are not limited to, indoquinones, nitroimidazoles, and nitroheterocycles (see, e.g., Damen, E. W. P., et al., Bioorganic & Medicinal Chemistry, 2002. 10(1): p. 71-77; Hay, M. P., et al., Journal of Medicinal Chemistry, 2003. 46(25): p. 5533-5545; Hay, M. P., et al., Journal of the Chemical Society-Perkin Transactions 1, 1999(19): p. 2759-2770; each herein incorporated by reference in their entireties). The mechanism of re-dox triggered release of drugs from these linkers is shown in Scheme 2.

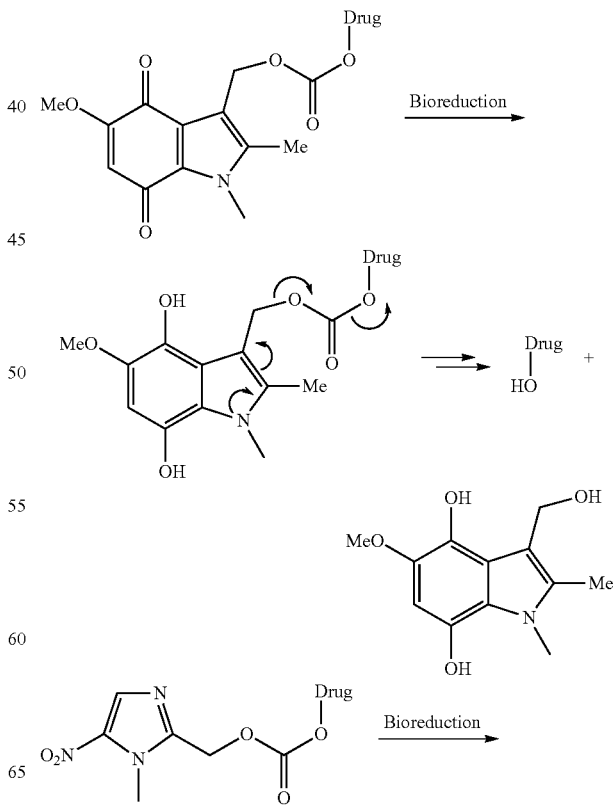

Scheme 2. Mechanism of re-dox triggered release of drug from dendritic polymers.

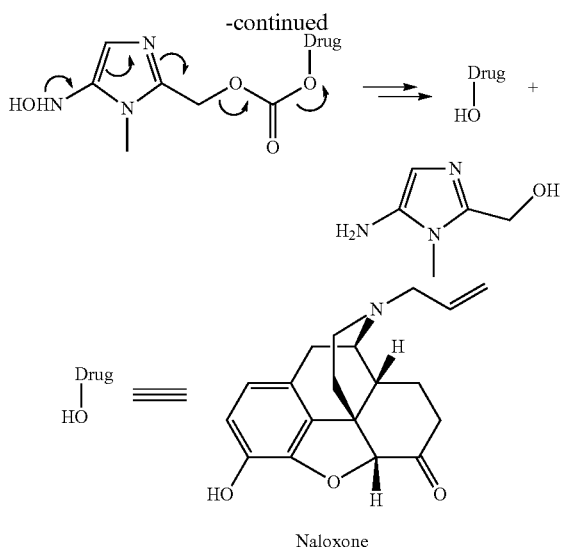

Naloxone

In some embodiments, the present invention provides a dendrimer conjugate comprising a trigger agent that is sensitive to (e.g., is cleaved by) and/or that associates with a tumor associated enzyme. In some embodiments, the present invention provides a dendrimer conjugate comprising a trigger that is sensitive to (e.g., is cleaved by) and/or that associates with a glucuronidase. Glucuronic acid can be attached to several anticancer drugs via various linkers. These anticancer drugs include, but are not limited to, doxorubicin, paclitaxel, docetaxel, 5-fluorouracil, 9-aminocamtothecin, as well as other drugs under development. These prodrugs are generally stable at physiological pH and are significantly less toxic than the parent drugs. In some embodiments, dendrimer conjugates comprising anticancer prodrugs find use for treating necrotic tumors (e.g., that liberate β-glucuronidase) or for ADEPT with antibodies that can deliver β-glucuronidase to target tumor cells.

In some embodiments, the present invention provides a dendrimer conjugate comprising a trigger agent that is sensitive to (e.g., is cleaved by) and/or that associates with brain enzymes. For example, trigger agents such as indolequinone are reduced by brain enzymes such as, for example, diaphorase (see, e.g., Damen, E. W. P., et al., Bioorganic & Medicinal Chemistry, 2002. 10(1): p. 71-77; herein incorporated by reference in its entirety). For example, in such embodiments, the antagonist is only active when released during hypoxia to prevent respiratory failure.

In some embodiments, the present invention provides a dendrimer conjugate comprising a trigger agent that is sensitive to (e.g., is cleaved by) and/or that associates with a protease. The present invention is not limited to any particular protease. In some embodiments, the protease is a cathepsin. In some embodiments, a trigger comprises a Lys-Phe-PABC moiety (e.g., that acts as a trigger). In some embodiments, a Lys-Phe-PABC moiety linked to doxorubicin, mitomycin C, and paclitaxel are utilized as a trigger-therapeutic conjugate in a dendrimer conjugate provided herein (e.g., that serve as substrates for lysosomal cathepsin B or other proteases expressed (e.g., overexpressed) in tumor cells. In some embodiments, utilization of a 1,6-elimination spacer/linker is utilized (e.g., to permit release of therapeutic drug post activation of trigger).

In some embodiments, the present invention provides a dendrimer conjugate comprising a trigger agent that is sensitive to (e.g., is cleaved by) and/or that associates with plasmin. The serine protease plasmin is over expressed in many human tumor tissues. Tripeptide specifiers (e.g., including, but not limited to, Val-Leu-Lys) have been identified and linked to anticancer drugs through elimination or cyclization linkers.

In some embodiments, the present invention provides a dendrimer conjugate comprising a trigger agent that is sensitive to (e.g., is cleaved by) and/or that associates with a matrix metalloproteases (MMPs). In some embodiments, the present invention provides a dendrimer conjugate comprising a trigger that is sensitive to (e.g., is cleaved by) and/or that associates with β-Lactamase (e.g., a β-Lactamase activated cephalosporin-based prodrug).

In some embodiments, the present invention provides a dendrimer conjugate comprising a trigger agent that is sensitive to (e.g., is cleaved by) and/or activated by a receptor (e.g., expressed on a target cell (e.g., a tumor cell)). Thus, in some embodiments, a dendrimer conjugate comprises a receptor binding motif conjugated to a therapeutic agent (e.g., cytotoxic drug) thereby providing target specificity. Examples include, but are not limited to, a dendrimer conjugate comprising a prodrug (e.g., of doxorubicin and/or paclitaxel) targeting integrin receptor, a hyaluronic acid receptor, and/or a hormone receptor In some embodiments, the present invention provides a dendrimer conjugate comprising a trigger agent that is sensitive to (e.g., is cleaved by) and/or activated by a nucleic acid. Nucleic acid triggered catalytic drug release can be utilized in the design of chemotherapeutic agents. Thus, in some embodiments, disease specific nucleic acid sequence is utilized as a drug releasing enzyme-like catalyst (e.g., via complex formation with a complimentary catalyst-bearing nucleic acid and/or analog). In some embodiments, the release of a therapeutic agent is facilitated by the therapeutic component being attached to a labile protecting group, such as, for example, cisplatin or methotrexate being attached to a photolabile protecting group that becomes released by laser light directed at cells emitting a color of fluorescence (e.g., in addition to and/or in place of target activated activation of a trigger component of a dendrimer conjugate). In some embodiments, the therapeutic device also may have a component to monitor the response of the tumor to therapy. For example, where a therapeutic agent of the dendrimer induces apoptosis of a target cell (e.g., a cancer cell (e.g., a prostate cancer cell)), the caspase activity of the cells may be used to activate a green fluorescence. This allows apoptotic cells to turn orange, (combination of red and green) while residual cells remain red. Any normal cells that are induced to undergo apoptosis in collateral damage fluoresce green.

In some embodiments, the present invention provides a dendrimer conjugate comprising a linker that connects to a therapeutic compound. In some embodiments, the linker is configured such that its decomposition leads to the liberation (e.g., non-reversible liberation) of the therapeutic agent (e.g., pain relief agent) (e.g., at the target site (e.g., site of tumor, CNS, and/or inflammatory site)). The linker may influence multiple characteristics of a dendrimer conjugate including, but not limited to, properties of the therapeutic agent (e.g., stability, pharmacokinetic, organ distribution, bioavailability, and/or enzyme recognition (e.g., when the therapeutic agent (e.g., prodrug)) is enzymatically activated)).

Figure 20:
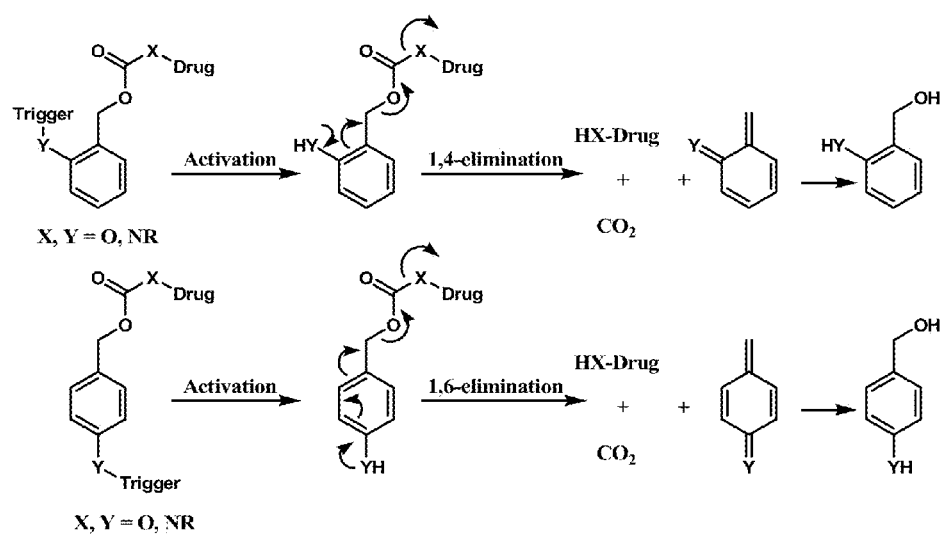
FIG. 20 depicts the activation of a dendrimer conjugate comprising either a 1,4 or a 1,6 elimination linker in embodiments of the present invention.
Figure 21:
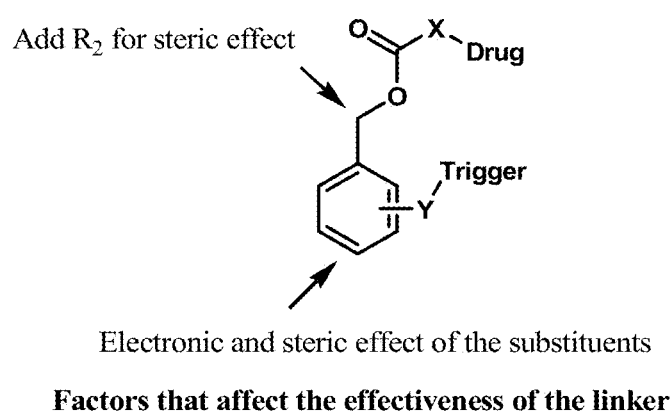
FIG. 21 shows that a spacer (R2) can be used to decrease steric hindrance in a dendrimer conjugate in some embodiments of the present invention.

In some embodiments, the linker is an elimination linker. For example, in some embodiments, in a dendrimer conjugate of the present invention, when a trigger is cleaved (e.g., enzymatically and/or chemically), a phenol or an aniline promotes a facile 1,4 or 1,6 elimination, followed by release of a $CO_2$ molecule and the unmasked therapeutic agent (e.g., drug) (See, e.g., FIG. 20). In some embodiments, a dendrimer conjugate of the present invention utilizes this configuration and/or strategy to mask one or more hydroxyl groups and/or amino groups of the therapeutic agents. In some embodiments, a linker present within a dendrimer conjugate of the present invention is fine tuned (e.g., to optimize stability and/or drug release from the conjugate). For example, the sizes of the aromatic substituents can be altered (e.g., increased or decreased) and/or alkyl substitutions at the benzylic position may be made to alter (e.g., increase or decrease) degradation of the linker and/or release of the therapeutic agent (e.g., prodrug). In some embodiments, elongated analogs (e.g., double spacers) are used (e.g., to decrease steric hindrance (e.g., for large therapeutic agents (e.g., See FIG. 21))). In some embodiments, a dendrimer conjugate of the present invention comprises an enol based linker (e.g., that undergoes an elimination reaction to release therapeutic agent (e.g., prodrug)).

Figure 22:
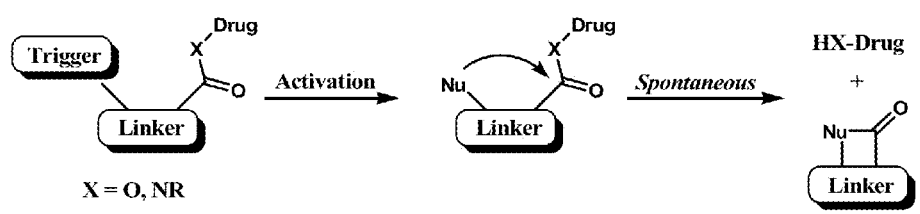
FIG. 22 depicts a dendrimer conjugate comprising a cyclization based linker in some embodiments of the present invention.
Figure 23:
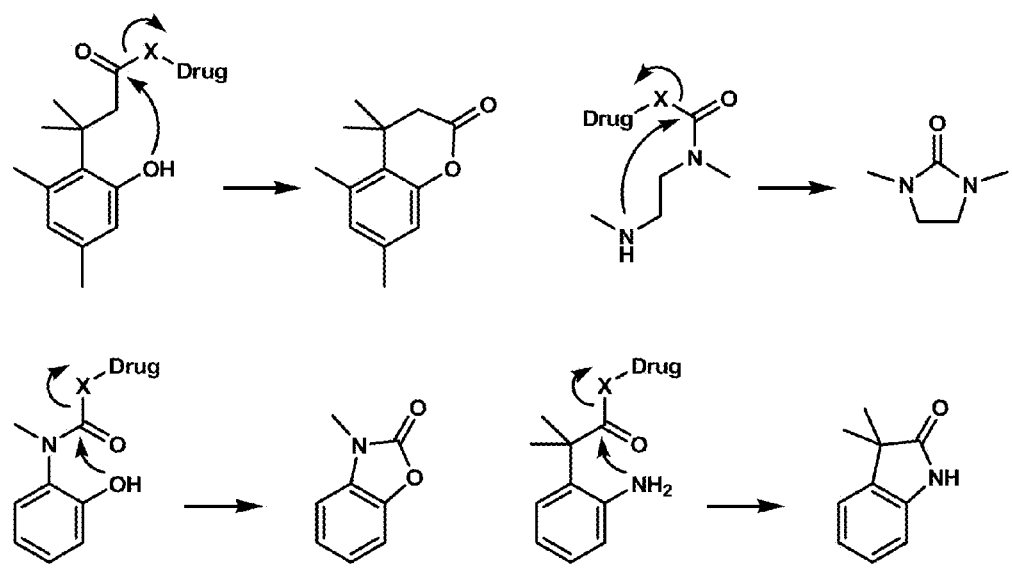
FIG. 23 depicts cyclization based linkers in some embodiments of the invention.

In some embodiments, the linker is a cyclization based linker. For example, one configuration for this approach is shown in FIG. 22. A nucleophilic group (e.g., OH or NHR) that becomes available once the trigger is cleaved attacks the carbonyl of the C(O)X-Therapeutic agent/drug (e.g., thereby leading to release of therapeutic agent-XH) and thereby to quickly release the Drug-XH. In some embodiments, a driving force that permits the reaction to reach completion is the stability of the cyclic product. In some embodiments, a cyclization based linker of a dendrimer conjugate of the present invention include, but are not limited to, those shown in FIG. 23.

Figure 24:
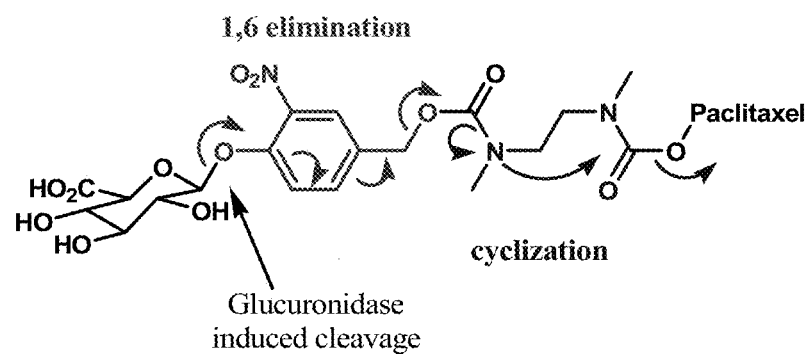
FIG. 24 depicts a linker utilized in a dendrimer conjugate in some embodiments of the present invention.

In some embodiments, a dendrimer conjugate of the present invention comprises a combination of one or more linkers. For example, in some embodiments, a dendrimer conjugate comprises a combination of two or more elimination linkers. In some embodiments, a dendrimer conjugate of the present invention comprises two or more cyclization linkers. In some embodiments, a dendrimer conjugate of the present invention comprises a one or more elimination linkers and one or more cyclization linkers, or a combination of one or more different types of linkers described herein. For example, in some embodiments, a dendrimer conjugate comprises a linker as shown in FIG. 24.

Figure 25:
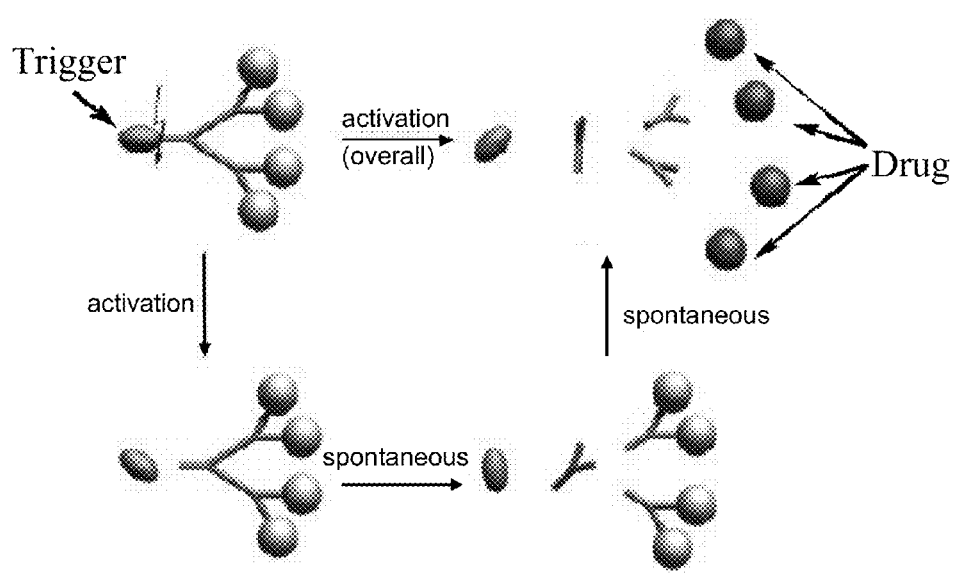
FIG. 25 shows branched self-elimination linkers utilized in a dendrimer conjugate in some embodiments of the present invention.

In some embodiments, a dendrimer conjugate of the present invention comprises branched self-elimination linkers (e.g., as shown in FIG. 25). Thus, in some embodiments, use of branched linkers provides a conjugate that can present increased concentrations of a therapeutic agent to a target site (e.g., inflammatory site, tumor site, etc.).

Figure 26A:
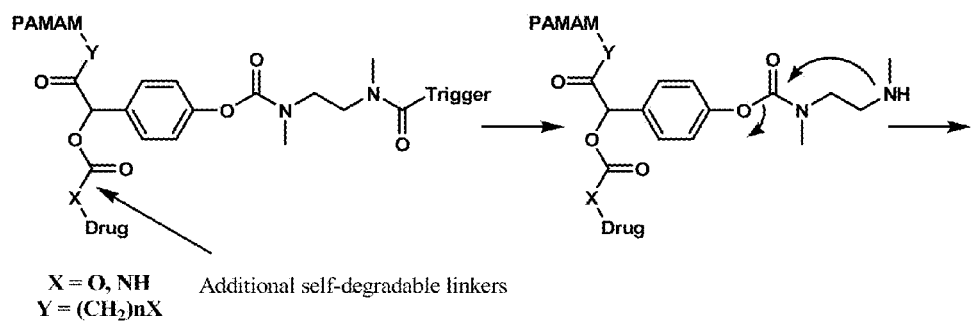
FIG. 26A and FIG. 26B depicts dendrimer conjugates provided in some embodiments of the present invention.
Figure 26A:
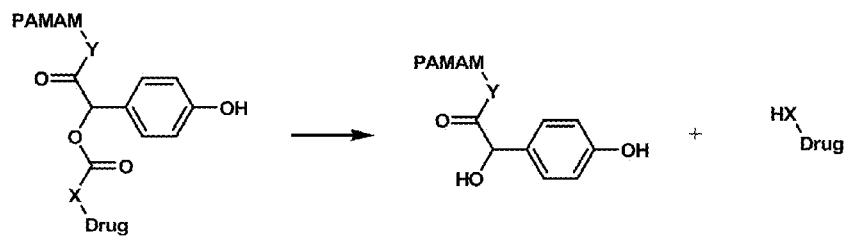
Figure 26B:
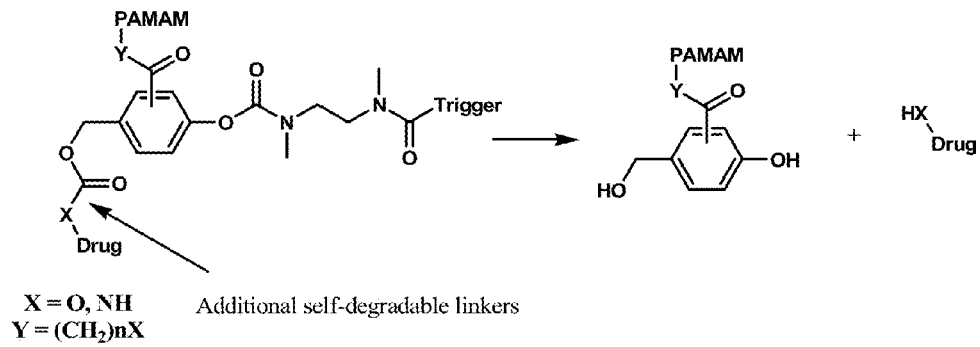

In some embodiments, a dendrimer conjugate of the present invention is generated by a process comprising conjugating a pre-formed tripartite piece (e.g., trigger, linker, and therapeutic agent) to a dendrimer (e.g., a G5 PAMAM dendrimer or other type of dendrimer described herein (e.g., conjugated to one or more different types of agents (e.g., imaging agent)). In some embodiments, linkage between a tripartite piece and a dendrimer comprises a non-cleavable bond (e.g., an ether or an amide bond (e.g., thereby decreasing unwanted activation of a trigger and/or degradation of a linker and/or release of therapeutic drug)). In some embodiments, a linker (e.g., linear or other type of linker described herein) is utilized to attach a tripartite moiety (e.g., trigger, linker, and therapeutic agent) to a dendrimer (e.g., in order to increase drug release, decrease steric hindrance, and/or increase stability of the dendrimer). For example, in some embodiments, the present invention provides a dendrimer conjugate as shown in FIG. 26A-B.

Figure 27:
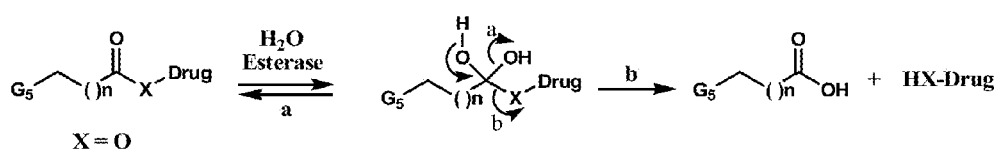
FIG. 27 shows a dendrimer comprising a simple ester (top portion of figure) and a dendrimer conjugate comprising an elimination linker (e.g., a 1, 6, elimination linker/spacer as shown in the bottom portion).
Figure 27:
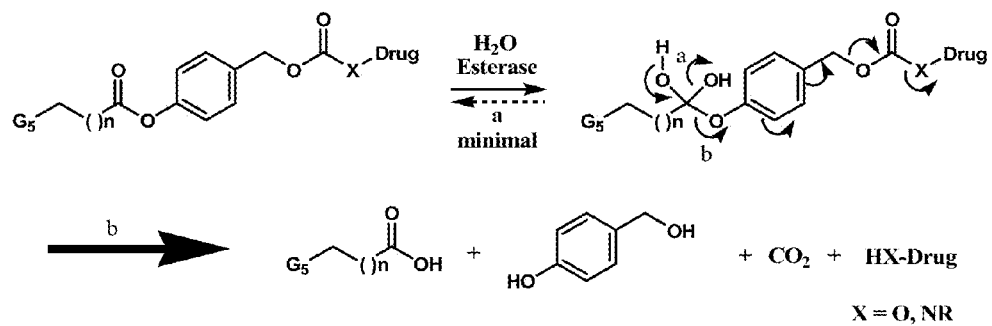

In some embodiments, a dendrimer conjugate of the present invention comprises a dendrimer conjugated to a linker (e.g., optionally conjugated to a trigger) that is conjugated to a therapeutic agent. In some embodiments, the dendrimer conjugate comprises a self-immolative connector between an ester bond (e.g., that is to be cleaved) and the therapeutic agent (e.g., thereby enhancing drug release). For example, although a mechanism is not necessary to practice the present invention and the present invention is not limited to any particular mechanism of action, in some embodiments, a dendrimer conjugate of the present invention comprising an ester linkage undergoes esterase catalyzed hydrolysis (e.g., as shown in FIG. 27 (e.g., G5 dendrimer comprising a self-degradable spacer and therapeutic agent)). Thus, in contrast to a dendrimer comprising a simple ester (e.g., a dendrimer in the top portion of FIG. 27 wherein therapeutic agent release may or may not occur, e.g., if x=NH), in some embodiments, the present invention provides a dendrimer conjugate comprising an elimination linker (e.g., a 1, 6, elimination linker/spacer as shown in the bottom portion of FIG. 27 (e.g., that permits complete hydrolysis of the linker (e.g., at a target site))).

The present invention is not limited by the type of linker configuration. In some embodiments, the linker is conjugated via a free amino group via an amide linkage (e.g., formed from an active ester (e.g., the N-hydroxysuccinimide ester)). In some embodiments, an ester linkage remains in the conjugate after conjugation. In some embodiments, linkage occurs through a lysine residue. In some embodiments, conjugation occurs through a short-acting, degradable linkage. The present invention is not limited by the type of degradable linkage utilized. Indeed, a variety of linkages are contemplated to be useful in the present invention including, but not limited to, physiologically cleavable linkages including ester, carbonate ester, carbamate, sulfate, phosphate, acyloxyalkyl ether, acetal, and ketal linkages. In some embodiments, a dendrimer conjugate comprises a cleavable linkage present in the linkage between the dendrimer and linker and/or targeting agent and/or therapeutic agent present therein (e.g., such that when cleaved, no portion of the linkage remains on the dendrimer). In some embodiments, a dendrimer conjugate comprises a cleavable linkage present in the linker itself (e.g., such that when cleaved, a small portion of the linkage remains on the dendrimer).

The present invention is not limited by the type of therapeutic agent delivered via a dendrimer of the present invention. For example, a therapeutic agent may be any agent selected from the group comprising, but not limited to, a pain relief agent, a pain relief agent antagonist, a chemotherapeutic agent, an anti-oncogenic agent, an anti-angiogenic agent, a tumor suppressor agent, an anti-microbial agent, or an expression construct comprising a nucleic acid encoding a therapeutic protein. Illustrative examples of these types of agents are described herein.

In some embodiments, the therapeutic agent is a pain relief agent. The dendrimer conjugates of the present invention are not limited to a particular type or kind of pain relief agent.

In some embodiments, the pain relief agents include several medications that have been used for field deployment and have a proven efficacy for military medical applications (see, e.g., Emergency war surgery. 3rd ed. 2004, Department of Defense, USA; herein incorporated by reference in its entirety) (see Table 1). These drugs include, but are not limited to, Ketamine, narcotics (e.g., Morphine, fentanyl, hydromorphone), benzodiazepines (e.g., midazolam, diazepam, Lorazepam) and the selective antagonist of narcotics (e.g., Naloxone) and benzodiazepines (e.g., flumazenil). Military relevance is supported by the fact, for example, that small amounts of Morphine and Ketamine are used by medics during extraction-evacuation of the injured from the battle field.

TABLE 1

Drug Levels to Target Per 12-Hour Period

| Drug | Infusion | Per Hour Delivery | 12-hour Coverage |
|---|---|---|---|
| Ketamine | 1 mg/kg/hr will provide analgesia and anesthesia. | 1 mg × 75 kg => 75 mg/hr release | 900 mg |
| Lorazepam | 50 µg/kg/hr for sedation | 50 µg × 75 = 3750 µg/hr or 3.75 mg/hr release | 45000 µg (45 mg) |
| Morphine | 30 µg/kg/hr provides "basal - low end" analgesia | 30 µg × 75 kg is 2250 ug/hr released | 27000 µg (27 mg) |
| Naloxone | 5 µg/k/hr provides basal reversal of narcotic induced side effects | 5 µg × 75 kg is 375 ug/hr released | 9000 µg (9 mg) |
| Doxapram | 2 (to 3) mg/kg/hr | 2 mg × 75 kg is 150 mg/hr released | 1800 mg |

µg = Micrograms Reference: Micromedex 2006. Assumptions: Requirements for a 75 Kg individual over a 12 hours period; delivered in one subcutaneous or intramuscular administration of maximal volume 5 ml.

In some embodiments, the pain relief agent is Ketamine. Ketamine is a potent analgesic, amnestic and anxiolytic, even in the low dose range while amnesia extends beyond its analgesic duration. Ketamine's therapeutic index is large and as levels are increased, general anesthesia is achieved. Unlike other current general anesthetic agents, vital functions (e.g., neuromuscular tone, airway patency, respirations, and cardiovascular function) are maintained. All narcotic agents (e.g., Morphine) display effects opposite of those of Ketamine with respect to vital functions. As narcotic levels are increased, respirations, neuromuscular tone, and airway patency are decreased while cardiovascular function may also be compromised, particularly due to peripheral vasodilatation. Ketamine also induces bronchodilation, which is particularly useful when irritants cause bronchoconstriction and coughing. Morphine suppresses coughing and either leaves bronchomotor tone unaltered or increases it (see, e.g., *Anesthesia*. 4th ed. 1994, Churchill Livingstone: New York; *Goodman & Gilman's the pharmacological basis of therapeutics*. 9th ed. 1996, McGraw-Hill, Health Professions Division: New York; each herein incorporated by reference in its entirety). When faced with severe injuries and blood loss, low dose Ketamine provides analgesia and amnesia while preserving homeostatic mechanisms and vital functions. Ketamine levels can be increased to achieve a state of "dissociation" in which major procedures (e.g., an amputation) can be accomplished with cardio respiratory stability while the individual seems unattached to the procedure. Dissociation is unique to Ketamine.

In some embodiments, the present invention provides dendrimer conjugates comprising Ketamine and Lorazepam. Unfortunately, disforic reactions can occur in a small percentage of recipients, but can be effectively treated with the concurrent administration of benzodiazepines (e.g., Lorazepam). Lorazepam has excellent amnestic and anxiolytic properties, which are very desirable in the severely injured combatant (see, e.g., *Anesthesia*. 4th ed. 1994, Churchill Livingstone: New York; *Goodman & Gilman's the pharmacological basis of therapeutics*. 9th ed. 1996, McGraw-Hill, Health Professions Division: New York; each herein incorporated by reference in its entirety). It does not have analgesic nor anesthetic properties. It has mild, centrally mediated muscle relaxant properties while it is an anticonvulsant. Its effects on homeostasis of the respiratory and hemodynamic system are mildly depressant when used in the dose range of its anxiolytic properties.

In some embodiments, the pain relief agent is Morphine. Morphine is the standard against which all other analgesics are compared. It is less potent as an analgesic when compared to Ketamine. Its sedation can be accompanied by euphoria, but its amnestic and anxiolytic effects are less when compared to Ketamine and Lorazepam. Even in high doses, Morphine is a poor anesthetic and an unreliable amnestic, but these properties may maintain co-operativity on the battlefield. Morphine's analgesic effects overlap closely with its effects on homeostasis of the respiratory and hemodynamic system. Thus as the dosage of Morphine is increased, depression of respirations, and loss of airway patency and reflexes become soon apparent relative to Ketamine's effect. Its hemodynamic effects include veno-vasodilatation within the range of Morphine's analgesia. Thus, in the severely injured with blood loss, Morphine's analgesic range is limited by its effects on homeostasis of vital functions. Morphine's therapeutic index, particularly in the setting of the severely injured combatant, is low compared to the index for Ketamine. Thus, Morphine has many good qualities but should be administered in a manner to avoid side effects.

In some embodiments, the pain relief agent antagonist is Doxapram. Doxapram is a respiratory stimulant causing an increase in tidal volume with an increase in respiratory rate used in acute respiratory insufficiency. It can improve cardiac output in the setting of hypovolemia. It may increase catecholamines release. Doxapram is useful as a respiratory and cardiovascular stimulant in the battlefield field setting to reduce or negate respiratory and hemodynamic effects of any proposed analgesic-amnestic-anxiolytic agents. Thus, the release of Doxapram is a viable counter-regulatory effect for respiratory depression whatever the cause.

In some embodiments, the pain relief agent antagonist is Naloxone. Naloxone is an effective, selective opioid (e.g., Morphine) antagonist. It reverses a range of Morphine's effects including Morphine's analgesia and respiratory depression. Although Morphine's analgesic and respiratory ranges overlap, low dose infusions of Naloxone can reverse Morphine's respiratory depression while its analgesic effect is relatively unaffected and pain-relief can remain present. Thus, it is a prime candidate for a dendrimer-drug delivery system requiring a Morphine feedback mechanism.

In some embodiments, pain relief agents include, but are not limited to, analgesic drugs and respective antagonists. Examples of analgesic drugs include, but are not limited to, paracetamol and Non-steroidal anti-inflammatory drugs (NSAIDs), COX-2 inhibitors, opiates and morphonimimetics, and specific analgesic agents.

Examples of NSAIDs include, but are not limited to, salicylates (e.g., Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate, Salicylamide), arylalkanoic acids (e.g., Diclofenac, Aceclofenac, Acemethacin, Alclofenac, Bromfenac, Etodolac, Indometacin, Nabumetone, Oxametacin, Proglumetacin, Sulindac, Tolmetin), 2-arylpropionic acids (profens) (e.g., Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, Tiaprofenic acid), N-arylanthranilic acids (fenamic acids) (e.g., Mefenamic acid, Flufenamic acid, Meclofenamic acid, Tolfenamic acid), pyrazolidine derivatives (e.g., Phenylbutazone, Ampyrone, Azapropazone, Clofezone, Kebuzone, Metamizole, Mofebutazone, Oxyphenbutazone, Phenazone, Sulfinpyrazone), oxicams (e.g., Piroxicam, Droxicam, Lornoxicam, Meloxicam, Tenoxicam), sulphonanilides (e.g., nimesulide), licofelone, and omega-3 fatty acids.

Examples of COX-2 inhibitors include, but are not limited to Celecoxib, Etoricoxib, Lumiracoxib, Parecoxib, Rofecoxib, Valdecoxib.

Examples of Opiates include, but are not limited to, natural opiates (e.g., alkaloids contained in the resin of the opium poppy including morphine, codeine and thebaine), semi-synthetic opiates (e.g., created from the natural opioids, such as hydromorphone, hydrocodone, oxycodone, oxymorphone, desomorphine, diacetylmorphine (Heroin), nicomorphine, dipropanoylmorphine, diamorphine, benzylmorphine, Buprenorphine, Nalbuphine, Pentazocine, meperidine, diamorphine, and ethylmorphine), fully synthetic opioids (e.g., such as fentanyl, pethidine, Oxycodone, Oxymorphone, methadone, tramadol, Butorphanol, Levorphanol, and propoxyphene), and endogenous opioid peptides (e.g., produced naturally in the body, such as endorphins, enkephalins, dynorphins, and endomorphins).

Additional analgesics include, but are not limited to, tricyclic antidepressants (e.g., amitriptyline, carbamazepine, gabapentin, and pregabalin), Tetrahydrocannabinol, ketamine, clonidine, $\alpha_2$-adrenoreceptor agonists, mexiletine, Orphenadrine, cyclobenzaprine, scopolamine, atropine, gabapentin, first-generation antidepressants and other drugs possessing anticholinergic and/or antispasmodic.

In some embodiments, pain relief agents include anesthetic drugs and respective antagonists. Examples of anesthetic drugs include, but are not limited to, local anesthetics (e.g., procaine, amethocaine, cocaine, lidocaine, prilocaine, bupivacaine, levobupivacaine, ropivacaine, dibucaine), inhaled anesthetics (e.g., Desflurane, Enflurane, Halothane, Isoflurane, Nitrous oxide, Sevoflurane, Xenon), intravenous anesthetics (e.g., Barbiturates (e.g., amobarbital (Amytal), pentobarbital (Nembutal), secobarbital (Seconal), Phenobarbital, Methohexital, Thiopental, Methylphenobarbital, Metharbital, Barbexaclone)), Benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), Etomidate, Ketamine, Propofol).

In some embodiments, pain relief agents include anticonvulsant drugs and respective antagonists. Examples of anticonvulsant drugs include, but are not limited to, aldehydes (e.g., paraldehyde), aromatic allylic alcohols (e.g., stiripentol), barbiturates (e.g., amobarbital (Amytal), pentobarbital (Nembutal), secobarbital (Seconal), Phenobarbital, Methohexital, Thiopental, Methylphenobarbital, Metharbital, Barbexaclone), benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), bromides (e.g., potassium bromide), carbamates (e.g., felbamate), carboxamides (e.g., carbamazepine, oxcarbazepine), fatty acids (e.g., valproates (e.g., valproic acid, sodium valproate, and divalproex sodium), Vigabatrin, Progabide, Tiagabine), fructose derivatives (e.g., topiramate), gaba analogs (e.g., gabapentin, pregabalin), hydantoins (e.g., Ethotoin, Phenytoin, Mephenytoin, Fosphenytoin), Oxazolidinediones (e.g., paramethadione, trimethadione, ethadione), priopionates (e.g., primidone), pyrrolidines (e.g., brivaracetam, levetiracetam, seletracetam), succinimides (e.g., Ethosuximide, Phensuximide, Mesuximide), sulfonamides (e.g., Acetazolamide, Sulthiame, Methazolamide, Zonisamide), triazines (e.g., lamotrigine), ureas (e.g., pheneturide, phenacemide), and valproylamdies (amide derivatives of valproate) (e.g., valpromide, valnoctamide).

In some embodiments, pain relief agents include mood stablizer drugs. Examples of mood stabilizer drugs include, but are not limited to, Lithium carbonate, lithium orotate, lithium salt, Valproic acid (Depakene), divalproex sodium (Depakote), sodium valproate (Depacon), Lamotrigine (Lamictal), Carbamazepine (Tegretol), Gabapentin (Neurontin), Oxcarbazepine (Trileptal), and Topiramate (Topamax).

In some embodiments, pain relief agents include psycholeptic drugs. Examples of psycholeptic drugs include, but are not limited to, anxiolytic drugs, antipsychotic drugs, and hypnotic drugs, and sedative drugs. Examples of anxiolytic drugs include, but are not limited to, benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), serotonin 1A agonists (e.g., Buspirone (BuSpar)), barbituates (e.g., amobarbital (Amytal), pentobarbital (Nembutal), secobarbital (Seconal), Phenobarbital, Methohexital, Thiopental, Methylphenobarbital, Metharbital, Barbexaclone), hydroxyzine, cannabidiol, and herbal treatments. (e.g., valerian, kava (Kava Kava), chamomile, Kratom, Blue Lotus extracts, Sceletium tortuosum (kanna) and bacopa monniera). are reputed to have anxiolytic properties. Examples of antipsychotic drugs include, but are not limited to, butyrophenones (e.g., haloperidol), phenothiazines (e.g., Chlorpromazine (Thorazine), Fluphenazine (Prolixin), Perphenazine (Trilafon), Prochlorperazine (Compazine), Thioridazine (Mellaril), Trifluoperazine (Stelazine), Mesoridazine, Promazine, Triflupromazine (Vesprin), Levomepromazine (Nozinan), Promethazine (Phenergan)), thioxanthenes (e.g., Chlorprothixene, Flupentixol (Depixol and Fluanxol), Thiothixene (Navane), Zuclopenthixol (Clopixol & Acuphase)), clozapine, olanzapine, Risperidone (Risperdal), Quetiapine (Seroquel), Ziprasidone (Geodon), Amisulpride (Solian), Paliperidone (Invega), dopamine, bifeprunox, norclozapine (ACP-104), Aripiprazole (Abilify), Tetrabenazine, and Cannabidiol. Examples of hypnotics include, but are not limited to, Barbiturates, Opioids, benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), nonbenzodiazepines (e.g., Zolpidem, Zaleplon, Zopiclone, Eszopiclone), antihistamines (e.g., Diphenhydramine, Doxylamine, Hydroxyzine, Promethazine), gamma-hydroxybutyric acid (Xyrem), Glutethimide, Chloral hydrate, Ethchlorvynol, Levomepromazine, Chlormethiazole, Melatonin, and Alcohol. Examples of sedatives include, but are not limited to, barbituates (e.g., amobarbital (Amytal), pentobarbital (Nembutal), secobarbital (Seconal), Phenobarbital, Methohexital, Thiopental, Methylphenobarbital, Metharbital, Barbexaclone), benzodiazepines (e.g., alprazolam, bromazepam (Lexotan), chlordiazepoxide (Librium), Clobazam, Clonazepam, Clorazepate, Diazepam, Midazolam, Lorazepam, Nitrazepam, temazepam, nimetazepam, Estazolam, Flunitrazepam, oxazepam (Serax), temazepam (Restoril, Normison, Planum, Tenox, and Temaze), Triazolam), Herbal sedatives (e.g., ashwagandha, catnip, kava (Piper methysticum), mandrake, marijuana, valerian), solvent sedatives (e.g., chloral hydrate (Noctec), diethyl ether (Ether), ethyl alcohol (alcoholic beverage), methyl trichloride (Chloroform)), nonbenzodiazepine sedatives (e.g., eszopiclone (Lunesta), zaleplon (Sonata), zolpidem (Ambien), zopiclone (Imovane, Zimovane)), clomethiazole (clomethiazole), gamma-hydroxybutyrate (GHB), Thalidomide, ethchlorvynol (Placidyl), glutethimide (Doriden), ketamine (Ketalar, Ketaset), methaqualone (Sopor, Quaalude), methyprylon (Noludar), and ramelteon (Rozerem).

In some embodiments, pain relief agents include psychoanaleptic drugs. Examples of psychoanaleptic drugs include, but are not limited to, antidepressants, psychostimulants, and anti-dementia drugs. Examples of antidepresants include, but are not limited to, selective serotonin reuptake inhibitors (SSRIs) (e.g., fluoxetine (Prozac), paroxetine (Paxil, Seroxat), escitalopram (Lexapro, Esipram), citalopram (Celexa), and sertraline (Zoloft)), serotonin-norepinephrine reuptake inhibitors (SNRIs) (e.g., venlafaxine (Effexor), and duloxetine (Cymbalta)), noradrenergic and specific serotonergic antidepressants (NASSAs) (e.g., mirtazapine (Avanza, Zispin, Remeron)), norepinephrine (noradrenaline) reuptake inhibitors (NRIs) (e.g., reboxetine (Edronax)), norepinephrine-dopamine reuptake inhibitors (e.g., bupropion (Wellbutrin, Zyban)), tricyclic antidepressants (TCAs) (e.g., amitriptyline and desipramine), monoamine oxidase inhibitor (MAOIs) (e.g., phenelzine (Nardil), moclobemide (Manerix), selegiline), and augmentor drugs (e.g., tryptophan (Tryptan) and buspirone (Buspar)). Examples of psychostimulants include, but are not limited to, amphetamine, methamphetamine, cocaine, methylphenidate, and arecoline). Examples of anti-dementia drugs include, but are not limited to, Acetylcholinesterase inhibitors (e.g., Tacrine (Cognex), donepezil (Aricept), galantamine (Razadyne), and rivastigmine (Exelon).

In some embodiments, pain relief agents include muscle relaxant drugs. Examples of muscle relaxant drugs include, but are not limited to, depolarizing muscle relaxants (e.g., Succinylcholine), short acting non-depolarizing muscle relaxants (e.g., Mivacurium, Rapacuronium), intermediate acting non-depolarizing muscle relaxants (e.g., Atracurium, Cisatracurium, Rocuronium, Vecuronium), and long acting non-depolarizing muscle relaxants (e.g., Alcuronium, Doxacurium, Gallamine, Metocurine, Pancuronium, Pipecuronium, d-Tubocurarine).

In some embodiments, the pain relief agent antagonists include drugs that counter the effect (e.g., side effect, main effect, cardiovascular effect) of a pain relief agent. The present invention is not limited to particular pain relief agent antagonists (e.g., Anesthetic antagonists, Analgesic antagonists, Anticonvulsant antagonists, Mood stabilizer antagonists, Psycholeptic drug antagonists, Psychoanaleptic drug antagonists, and muscle relaxant antagonists). In some embodiments, the pain relief agent antagonists include, but are not limited to, respiratory stimulants (e.g., Doxapram, BIMU-8, CX-546), opiod receptor antagonists (e.g., Naloxone, naltrexone, nalorphine, levallorphan, cyprodime, naltrindole, norbinaltorphimine, buprenorphine), agents that effect of benzodiazepines (e.g., flumazenil), agents that reverse the effect of non-depolarizing muscle relaxants (e.g., neostigmine).

Figure 28:
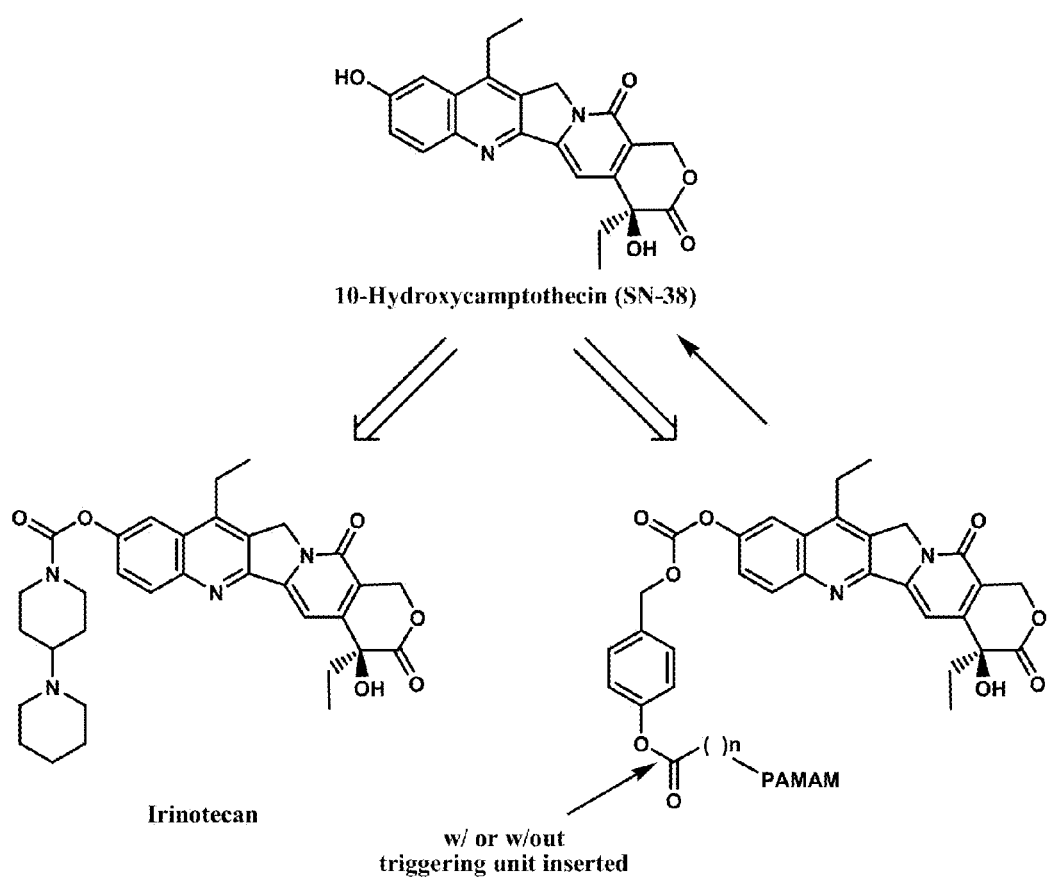
FIG. 28 shows a dendrimer conjugate comprising hydroxycamptothecin in some embodiments of the invention.

In some embodiments, a dendrimer conjugated comprising a linker may comprise nearly any therapeutic agent (e.g., pain relief agent, pain relief agent antagonist) comprising a hydroxyl and/or amino group. In some embodiments, the therapeutic agent is an anti-cancer drug or agent. For example, in some embodiments, the therapeutic agent is doxorubicin (or an analog thereof) or paclitaxel (or an analog thereof). In some embodiments, a dendrimer conjugate of the invention comprises a therapeutic agent comprising a single reactive group (e.g., at a primary or secondary position). In some embodiments, a dendrimer conjugate of the present invention is synthesized utilizing a selective protection/deprotection strategy if multiple functional groups are present within a therapeutic agent. In some embodiments, a dendrimer conjugate of the present invention provides the ability to deliver a therapeutic agent that, when not in the context of the dendrimer conjugate (e.g., in the absence of conjugation to a dendrimer (e.g., a dendrimer comprising a linker and a trigger (e.g., configured to shield and/or mask the therapeutic drug and/or prohibit release of the therapeutic drug until the dendrimer reaches and reacts with a target site))) is toxic to a subject (e.g., that is too toxic to be utilized to treat a subject). Thus, in some embodiments, the present invention provides dendrimer conjugates comprising therapeutic agents that suffer from delivery issues and/or toxicity issues and/or non-specificity issues in the absence of being conjugated to a dendrimer conjugate. For example, in some embodiments, the present invention provides a dendrimer conjugate comprising a therapeutic agent comprising a compound of the camptothecin family (e.g., IRINOTECAN). IRINOTECAN is a prodrug of 10-hydroxycamptothecin (SN-38), which is 1000-fold more cytotoxic than IRINOTECAN. It has been reported that the conversion of irinotecan to hydroxycamptothecin has very low efficiency. Thus, in some embodiments, the present invention provides a dendrimer conjugate comprising hydroxycamptothecin (See, e.g., FIG. 28).

In some embodiments of the present invention, the therapeutic agent includes, but is not limited to, a chemotherapeutic agent, an anti-oncogenic agent, an anti-angiogenic agent, a tumor suppressor agent, an anti-microbial agent, or an expression construct comprising a nucleic acid encoding a therapeutic protein, although the present invention is not limited by the nature of the therapeutic agent. In further embodiments, the therapeutic agent is protected with a protecting group selected from photo-labile, radio-labile, and enzyme-labile protecting groups. In some embodiments, the chemotherapeutic agent is selected from a group consisting of, but not limited to, platinum complex, verapamil, podophylltoxin, carboplatin, procarbazine, mechloroethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, bleomycin, etoposide, tamoxifen, paclitaxel, taxol, transplatinum, 5-fluorouracil, vincristin, vinblastin, bisphosphonate (e.g., CB3717), chemotherapeutic agents with high affinity for folic acid receptors, ALIMTA (Eli Lilly), and methotrexate. In some embodiments, the anti-oncogenic agent comprises an antisense nucleic acid (e.g., RNA, molecule). In certain embodiments, the antisense nucleic acid comprises a sequence complementary to an RNA of an oncogene. In preferred embodiments, the oncogene includes, but is not limited to, abl, Bcl-2, Bcl-xL, erb, fms, gsp, hst, jun, myc, neu, raf; ras, ret, src, or trk. In some embodiments, the nucleic acid encoding a therapeutic protein encodes a factor including, but not limited to, a tumor suppressor, cytokine, receptor, inducer of apoptosis, or differentiating agent. In preferred embodiments, the tumor suppressor includes, but is not limited to, BRCA1, BRCA2, C-CAM, p16, p21, p53, p73, Rb, and p27. In preferred embodiments, the cytokine includes, but is not limited to, GMCSF, IL-1, IL-2, IL-3, IL-4, IL-5, IL-6, IL-7, IL-8, IL-9, IL-10, IL-11, IL-12, IL-13, IL-14, IL-15, β-interferon, γ-interferon, and TNF. In preferred embodiments, the receptor includes, but is not limited to, CFTR, EGFR, estrogen receptor, IL-2 receptor, and VEGFR. In preferred embodiments, the inducer of apoptosis includes, but is not limited to, AdE1B, Bad, Bak, Bax, Bid, Bik, Bim, Harakid, and ICE-CED3 protease. In some embodiments, the therapeutic agent comprises a short-half life radioisotope.

In some embodiments of the present invention, the biological monitoring agent comprises an agent that measures an effect of a therapeutic agent (e.g., directly or indirectly measures a cellular factor or reaction induced by a therapeutic agent), however, the present invention is not limited by the nature of the biological monitoring agent. In some embodiments, the monitoring agent is capable of detecting (e.g., measuring) apoptosis caused by the therapeutic agent.

In some embodiments of the present invention, the imaging agent comprises a radioactive label including, but not limited to, $^{14}$C, $^{36}$Cl, $^{57}$Co, $^{58}$Co, $^{51}$Cr, $^{125}$I, $^{131}$I, $^{111}$Ln, $^{152}$Eu, $^{59}$Fe, $^{67}$Ga, $^{32}$P, $^{186}$Re, $^{35}$S, $^{75}$Se, Tc-99m, and $^{175}$Yb. In some embodiments, the imaging agent comprises a fluorescing entity. In a preferred embodiment, the imaging agent is fluorescein isothiocyanate or 6-TAMARA.

Dendrimer conjugates of the present invention are not limited by the type of anti-angiogenic agent used. Indeed, a variety of anti-angiogenic agents are contemplated to be useful in the compositions of the present invention including, but not limited to, Batimastat, Marimastat, AG3340, Neovastat, PEX, TIMP-1, -2, -3, -4, PAI-1, -2, uPA Ab, uPAR Ab, Amiloride, Minocycline, tetracyclines, steroids, cartilage-derived TIMP, αvβ3 Ab: LM609 and Vitaxin, RGD containing peptides, αvβ5 Ab, Endostatin, Angiostatin, aaAT, IFN-α, IFN-γ, IL-12, nitric oxide synthase inhibitors, TSP-1, TNP-470, Combretastatin A4, Thalidomide, Linomide, IFN-α, PF-4, prolactin fragment, Suramin and analogues, PPS, distamycin A analogues, FGF-2 Ab, antisense-FGF-2, Protamine, SU5416, soluble Flt-1, dominant-negative Flk-1, VEGF receptor ribosymes, VEGF Ab, Aspirin, NS-398, 6-AT, 6A5BU, 7-DX, Genistein, Lavendustin A, Ang-2, batimastat, marimastat, anti-αvβ3 monoclonal antibody (LM609) thrombospondin-1 (TSP-1) Angiostatin, endostatin, TNP-470, Combretastatin A-4, Anti-VEGF antibodies, soluble Flk-1, Flt-1 receptors, inhibitors of tyrosine kinase receptors, SU5416, heparin-binding growth factors, pentosan polysulfate, platelet-derived endothelial cell growth factor/Thymidine phosphorylase (PD-ECGF/TP), cox (e.g., cox-1 an cox-2) inhibitors (e.g., Celebrex and Vioxx), DT385, Tissue inhibitor of metalloprotease (TIMP-1, TIMP-2), Zinc, Plasminogen activator-inhibitor-1 (PAI-1), p53 Rb, Interleukin-10 Interleukin-12, Angiopoietin-2, Angiotensin, Angiotensin II (AT2 receptor), Caveolin-1, caveolin-2, Angiopoietin-2, Angiotensin, Angiotensin II (AT2 receptor), Caveolin-1, caveolin-2, Endostatin, Interferon-alpha, Isoflavones, Platelet factor-4, Prolactin (16 Kd fragment), Thrombospondin, Troponin-1, Bay 12-9566, AG3340, CGS 27023A, CGS 27023A, COL-3, (Neovastat), BMS-275291, Penicillamine, TNP-470 (fumagillin derivative), Squalamine, Combretastatin, Endostatin, Penicillamine, Farnesyl Transferase Inhibitor (FTI), -L-778,123, -SCH66336, -R115777, anti-VEGF antibody, Thalidomide, SU5416, Ribozyme, Angiozyme, SU6668, PTK787/ZK22584, Interferon-alpha, Interferon-alpha, Suramin, Vitaxin, EMD121974, Penicillamine, Tetrathiomolybdate, Captopril, serine protease inhibitors, CAI, ABT-627, CM101/ZDO101, Interleukin-12, IM862, PNU-145156E, those described in U.S. Patent App. No. 20050123605, herein incorporated by reference in its entirety, and fragments or portions of the above that retain anti-angiogenic (e.g., angiostatic or inhibitory properties).

The present invention is not limited to any particular targeting agent. In some embodiments, targeting agents are conjugated to the dendrimers for delivery of the dendrimers to desired body regions (e.g., to the central nervous system (CNS). The targeting agents are not limited to targeting specific body regions. In some embodiments, the targeting agents target the central nervous system (CNS). In some embodiments, where the targeting agent is specific for the CNS, the targeting agent is transferrin (see, e.g., Daniels, T. R., et al., Clinical Immunology, 2006. 121(2): p. 159-176; Daniels, T. R., et al., Clinical Immunology, 2006. 121(2): p. 144-158; each herein incorporated by reference in their entireties). Transferrin has been utilized as a targeting vector to transport, for example, drugs, liposomes and proteins across the BBB by receptor mediated transcytosis (see, e.g., Smith, M. W. and M. Gumbleton, Journal of Drug Targeting, 2006. 14(4): p. 191-214; herein incorporated by reference in its entirety). In some embodiments, the targeting agents target neurons within the central nervous system (CNS). In some embodiments, where the targeting agent is specific for neurons within the CNS, the targeting agent is a synthetic tetanus toxin fragment (e.g., a 12 amino acid peptide (Tet 1) (HLNILSTL-WKYR (SEQ ID NO; 1)) (see, e.g., Liu, J. K., et al., Neurobiology of Disease, 2005. 19(3): p. 407-418; herein incorporated by reference in its entirety).

In some embodiments, the targeting agent is a moiety that has affinity for a tumor associated factor. For example, a number of targeting agents are contemplated to be useful in the present invention including, but not limited to, RGD sequences, low-density lipoprotein sequences, a NAALA-Dase inhibitor, epidermal growth factor, and other agents that bind with specificity to a target cell (e.g., a cancer cell)). In some embodiments, the targeting agent is an antibody, receptor ligand, hormone, vitamin, or antigen. However, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, or VEGFR. In some embodiments, the receptor ligand is folic acid.

The present invention is not limited to cancer and/or tumor targeting agents. Indeed, dendrimers of the present invention can be targeted (e.g., via a linker conjugated to the dendrimer wherein the linker comprises a targeting agent) to a variety of target cells or tissues (e.g., to a biologically relevant environment) via conjugation to an appropriate targeting agent. For example, in some embodiments, the targeting agent is a moiety that has affinity for an inflammatory factor (e.g., a cytokine or a cytokine receptor moiety (e.g., TNF-α receptor)). In some embodiments, the targeting agent is a sugar, peptide, antibody or antibody fragment, hormone, hormone receptor, or the like.

In some embodiments of the present invention, the targeting agent includes, but is not limited to an antibody, receptor ligand, hormone, vitamin, and antigen, however, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

The present invention also provides a method of treating a medical condition and/or a disease (e.g., cancer, inflammatory disease, chronic pain, autoimmune disease, etc.) comprising administering to a subject suffering from or susceptible to medical condition and/or a disease a therapeutically effective amount of a composition comprising a dendrimer conjugate (e.g., comprising a linker and/or trigger and a therapeutic agent) described herein. In some embodiments, the medical condition and/or disease is pain (e.g., chronic pain, mild pain, recurring pain, severe pain, etc.). In some embodiments, the dendrimer conjugates are configured to deliver pain relief agents to a subject. In some embodiments, the dendrimer conjugates are configured to deliver pain relief agents and pain relief agent antagonists to counter the side effects of pain relief agents. The dendrimer conjugates are not limited to treating a particular type of pain and/or pain resulting from a disease. Examples include, but are not limited to, pain resulting from trauma (e.g., trauma experienced on a battlefield, trauma experienced in an accident (e.g., car accident)).

In some embodiments, the disease is cancer. In some embodiments, the dendrimers are designed for retention within the CNS through conjugation of locking agents designed to prevent back diffusion of the dendrimer across the BBB (e.g., pyridinium molecule, which when activated by enzymatic reduction, becomes charged and locks the dendrimer in the CNS). The present invention is not limited by the type of cancer treated using the compositions and methods of the present invention. Indeed, a variety of cancer can be treated including, but not limited to, cancers located within the CNS, prostate cancer, colon cancer, breast cancer, lung cancer and epithelial cancer. Similarly, the present invention is not limited by the type of inflammatory disease and/or chronic pain treated using the compositions of the present invention. Indeed, a variety of diseases can be treated including, but not limited to, arthritis (e.g., osteoarthritis, rheumatoid arthritis, etc.), inflammatory bowel disease (e.g., colitis, Crohn's disease, etc.), autoimmune disease (e.g., lupus erythematosus, multiple sclerosis, etc.), inflammatory pelvic disease, etc.

In preferred embodiments, dendrimer conjugates of the present invention are configured such that they are readily cleared from the subject (e.g., so that there is little to no detectable toxicity at efficacious doses). In some embodiments, the disease is a neoplastic disease, selected from, but not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, lymphoma, Hodgkin's disease, non-Hodgkin's disease, Multiple myeloma, Waldenstrom's macroglobulinemia, Heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma. In some embodiments, the disease is an inflammatory disease selected from the group consisting of, but not limited to, eczema, inflammatory bowel disease, rheumatoid arthritis, asthma, psoriasis, ischemia/reperfusion injury, ulcerative colitis and acute respiratory distress syndrome. In some embodiments, the disease is a viral disease selected from the group consisting of, but not limited to, viral disease caused by hepatitis B, hepatitis C, rotavirus, human immunodeficiency virus type I (HIV-I), human immunodeficiency virus type II (HIV-II), human T-cell lymphotropic virus type I (HTLV-I), human T-cell lymphotropic virus type II (HTLV-II), AIDS, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

The dendrimers of the present invention find use in the detection and treatment of a variety of cancers. Indeed, the present invention is not limited by the type of cancer to be treated. Thus, in some embodiments, the present invention provides compositions comprising dendrimer conjugates for the targeting and identification of angiogenesis associated with cancers (e.g., carcinomas). For example, in some embodiments, a dendrimer conjugate of the present invention further comprises a targeting agent (e.g., folic acid moiety) that associates with high affinity to a targeting agent ligand (e.g., receptor) on a cancer cell (e.g., carcinoma cells and/or solid tumor cells). In some embodiments, dendrimer conjugate and a targeting agent, that target and identify cancer cells and/or angiogenesis associated with cancer, further comprise a therapeutic agent that inhibits angiogenesis thereby treating the cancer. In some embodiments, treatment with dendrimer conjugates and an anti-angiogenic agent are used in combination with other dendrimers of the present invention, with other chemotherapeutic treatments, and/or as a treatment following surgical removal of a tumor or cancerous tissue. In some embodiments, a targeting moiety (e.g., folic acid or other targeting moiety described herein) possesses a high affinity for ligands (e.g., receptors or other types of proteins or molecules) present on cancer cell possessing such ligands thereby permitting the targeting, identification and treatment of disease (e.g., cancer) with little to no toxicity to surrounding healthy cells and tissue.

In some embodiments, the present invention also provides a kit comprising a composition comprising dendrimer conjugate comprising a linker and/or trigger and a therapeutic agent. In some embodiments, the kit comprises a fluorescent agent or bioluminescent agent.

Some embodiments of the present invention provide compositions comprising dendrimer conjugates further comprising one or more functional groups, the functional groups including, but not limited to, therapeutic agents, biological monitoring components, biological imaging components, targeting components, and components to identify the specific signature of cellular abnormalities. As such, in some embodiments, a therapeutic dendrimer conjugate of the present invention is made up of individual dendrimers, each with one or more functional groups being specifically conjugated with or covalently linked to the dendrimer.

As is clear from the above example, the use of the compositions of the present invention facilitates non-intrusive sensing, signaling, and intervention for treating and managing pain, cancer and other diseases and conditions. Since specific protocols of molecular alterations in cancer cells are identified using this technique, non-intrusive sensing through the dendrimers is achieved and may then be employed automatically against various tumor phenotypes. The present invention is not limited to a particular type of dendrimer.

Indeeed, dendrimeric polymers have been described extensively (See, e.g., Tomalia, Advanced Materials 6:529 (1994); Angew, Chem. Int. Ed. Engl., 29:138 (1990); incorporated herein by reference in their entireties). Dendrimer polymers are synthesized as defined spherical structures typically ranging from 1 to 20 nanometers in diameter. Methods for manufactureing a G5 PAMAM dendrimer with a protected core is shown (FIGS. 1-5). In preferred embodiments, the protected core diamine is NH2-CH2-CH2-NHPG. Molecular weight and the number of terminal groups increase exponentially as a function of generation (the number of layers) of the polymer (See, e.g., FIG. 9). Different types of dendrimers can be synthesized based on the core structure that initiates the polymerization process (See e.g., FIGS. 1-5).

The dendrimer core structures dictate several characteristics of the molecule such as the overall shape, density and surface functionality (See, e.g., Tomalia et al., Chem. Int. Ed. Engl., 29:5305 (1990)). Spherical dendrimers can have ammonia as a trivalent initiator core or ethylenediamine (EDA) as a tetravalent initiator core (See, e.g., FIG. 9). Recently described rod-shaped dendrimers (See, e.g., Yin et al., J. Am. Chem. Soc., 120:2678 (1998)) use polyethyleneimine linear cores of varying lengths; the longer the core, the longer the rod. Dendritic macromolecules are available commercially in kilogram quantities and are produced under current good manufacturing processes (GMP) for biotechnology applications.

Figure 10:
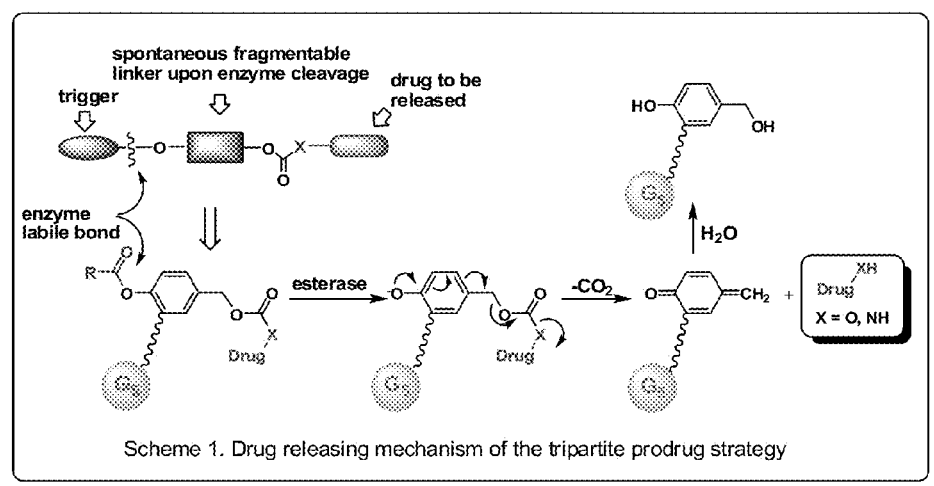
FIG. 10 shows the release of a therapeutic compound from esterase sensitive linker-dendrimer conjugate in one embodiment of the invention (Scheme 1).
Figure 13:
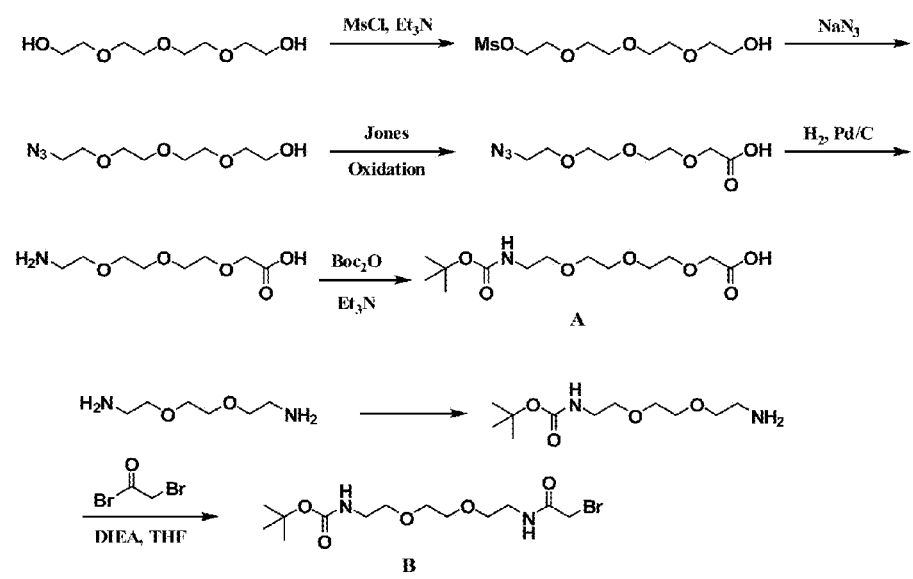
FIG. 13 shows dendrimer conjugate and methods of synthesizing the same in some embodiments of the invention.
Figure 14:
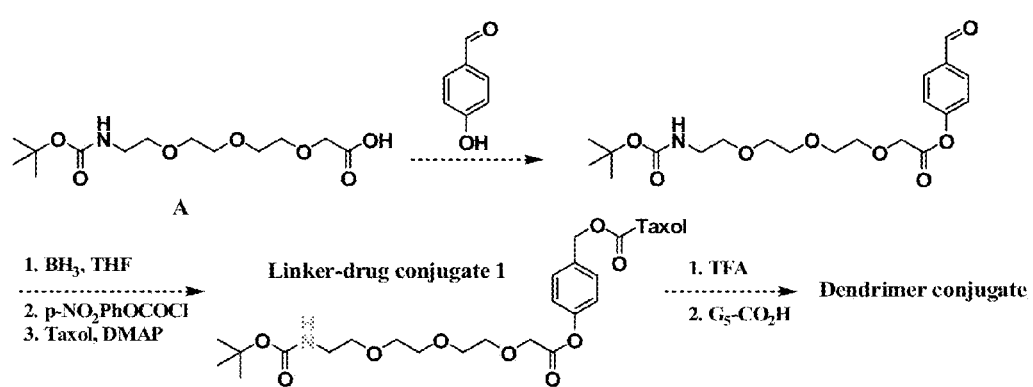
FIG. 14 shows a diagram of a dendrimer conjugate provided in some embodiments of the present invention.
Figure 17:
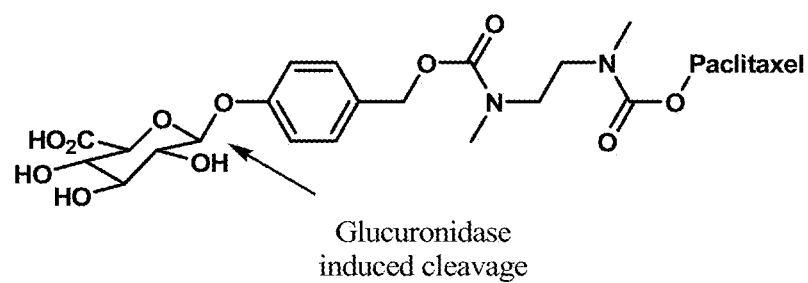
FIG. 17 shows an example of a dendrimer conjugate designed for glucuronidase triggered cleavage in one embodiment of the present invention.

Dendrimers may be characterized by a number of techniques including, but not limited to, electrospray-ionization mass spectroscopy, $^{13}$C nuclear magnetic resonance spectroscopy, $^{1}$H nuclear magnetic resonance spectroscopy (See, e.g., Example 5, FIG. 10(A) and Example 7, FIG. 14), high performance liquid chromatography (See, e.g., Example 5, FIG. 10(B); and Example 6, FIG. 13), size exclusion chromatography with multi-angle laser light scattering (See, e.g., Example 4, FIG. 8), ultraviolet spectrophotometry (See, e.g., Example 8, FIG. 17), capillary electrophoresis and gel electrophoresis. These tests assure the uniformity of the polymer population and are important for monitoring quality control of dendrimer manufacture for GMP applications and in vivo usage.

Numerous U.S. patents describe methods and compositions for producing dendrimers. Examples of some of these patents are given below in order to provide a description of some dendrimer compositions that may be useful in the present invention, however it should be understood that these are merely illustrative examples and numerous other similar dendrimer compositions could be used in the present invention.

U.S. Pat. Nos. 4,507,466, 4,558,120, 4,568,737, and 4,587,329 each describe methods of making dense star polymers with terminal densities greater than conventional star polymers. These polymers have greater/more uniform reactivity than conventional star polymers, i.e. 3rd generation dense star polymers. These patents further describe the nature of the amidoamine dendrimers and the 3-dimensional molecular diameter of the dendrimers.

U.S. Pat. No. 4,631,337 describes hydrolytically stable polymers. U.S. Pat. No. 4,694,064 describes rod-shaped dendrimers. U.S. Pat. No. 4,713,975 describes dense star polymers and their use to characterize surfaces of viruses, bacteria and proteins including enzymes. Bridged dense star polymers are described in U.S. Pat. Nos. 4,737,550, 4,857,599 and 4,871,779 describe dense star polymers on immobilized cores useful as ion-exchange resins, chelation resins and methods of making such polymers.

U.S. Pat. No. 5,338,532 is directed to starburst conjugates of dendrimer(s) in association with at least one unit of carried agricultural, pharmaceutical or other material. This patent describes the use of dendrimers to provide means of delivery of high concentrations of carried materials per unit polymer, controlled delivery, targeted delivery and/or multiple species such as e.g., drugs antibiotics, general and specific toxins, metal ions, radionuclides, signal generators, antibodies, interleukins, hormones, interferons, viruses, viral fragments, pesticides, and antimicrobials.

U.S. Pat. No. 6,471,968 describes a dendrimer complex comprising covalently linked first and second dendrimers, with the first dendrimer comprising a first agent and the second dendrimer comprising a second agent, wherein the first dendrimer is different from the second dendrimer, and where the first agent is different than the second agent.

Other useful dendrimer type compositions are described in U.S. Pat. Nos. 5,387,617, 5,393,797, and 5,393,795 in which dense star polymers are modified by capping with a hydrophobic group capable of providing a hydrophobic outer shell. U.S. Pat. No. 5,527,524 discloses the use of amino terminated dendrimers in antibody conjugates.

The use of dendrimers as metal ion carriers is described in U.S. Pat. Nos. 5,560,929. 5,773,527 discloses non-crosslinked polybranched polymers having a comb-burst configuration and methods of making the same. U.S. Pat. No. 5,631,329 describes a process to produce polybranched polymer of high molecular weight by forming a first set of branched polymers protected from branching; grafting to a core; deprotecting first set branched polymer, then forming a second set of branched polymers protected from branching and grafting to the core having the first set of branched polymers, etc.

U.S. Pat. No. 5,902,863 describes dendrimer networks containing lipophilic organosilicone and hydrophilic polyanicloamine nanscopic domains. The networks are prepared from copolydendrimer precursors having PAMAM (hydrophilic) or polyproyleneimine interiors and organosilicon outer layers. These dendrimers have a controllable size, shape and spatial distribution. They are hydrophobic dendrimers with an organosilicon outer layer that can be used for specialty membrane, protective coating, composites containing organic organometallic or inorganic additives, skin patch delivery, absorbants, chromatography personal care products and agricultural products.

U.S. Pat. No. 5,795,582 describes the use of dendrimers as adjuvants for influenza antigen. Use of the dendrimers produces antibody titer levels with reduced antigen dose. U.S. Pat. Nos. 5,898,005 and 5,861,319 describe specific immunobinding assays for determining concentration of an analyte. U.S. Pat. No. 5,661,025 provides details of a self-assembling polynucleotide delivery system comprising dendrimer polycation to aid in delivery of nucleotides to target site. This patent provides methods of introducing a polynucleotide into a eukaryotic cell in vitro comprising contacting the cell with a composition comprising a polynucleotide and a dendrimer polyeation non-covalently coupled to the polynucleotide.

Dendrimer-antibody conjugates for use in in vitro diagnostic applications have previously been demonstrated (See, e.g., Singh et al., Clin. Chem., 40:1845 (1994)), for the production of dendrimer-chelant-antibody constructs, and for the development of boronated dendrimer-antibody conjugates (for neutron capture therapy); each of these latter compounds may be used as a cancer therapeutic (See, e.g., Wu et al., Bioorg. Med. Chem. Lett., 4:449 (1994); Wiener et al., Magn. Reson. Med. 31:1 (1994); Barth et al., Bioconjugate Chem. 5:58 (1994); and Barth et al.).

Some of these conjugates have also been employed in the magnetic resonance imaging of tumors (See, e.g., Wu et al., (1994) and Wiener et al., (1994), supra). Results from this work have documented that, when administered in vivo, antibodies can direct dendrimer-associated therapeutic agents to antigen-bearing tumors. Dendrimers also have been shown to specifically enter cells and carry either chemotherapeutic agents or genetic therapeutics. In particular, studies show that cisplatin encapsulated in dendrimer polymers has increased efficacy and is less toxic than cisplatin delivered by other means (See, e.g., Duncan and Malik, Control Rel. Bioact. Mater. 23:105 (1996)).

Dendrimers have also been conjugated to fluorochromes or molecular beacons and shown to enter cells. They can then be detected within the cell in a manner compatible with sensing apparatus for evaluation of physiologic changes within cells (See, e.g., Baker et al., Anal. Chem. 69:990 (1997)). Finally, dendrimers have been constructed as differentiated block copolymers where the outer portions of the molecule may be digested with either enzyme or light-induced catalysis (See, e.g., Urdea and Hom, Science 261:534 (1993)). This allows the controlled degradation of the polymer to release therapeutics at the disease site and provides a mechanism for an external trigger to release the therapeutic agents.

In some embodiments, dendrimer conjugates of the present invention contain one or more signature identifying agents that are activated by, or are able to interact with, a signature component ("signature"). In preferred embodiments, the signature identifying agent is an antibody, preferably a monoclonal antibody, that specifically binds the signature (e.g., cell surface molecule specific to a cell to be targeted).

In some embodiments of the present invention, tumor cells are identified. Tumor cells have a wide variety of signatures, including the defined expression of cancer-specific antigens such as Mucl, HER-2 and mutated p53 in breast cancer. These act as specific signatures for the cancer, being present in 30% (HER-2) to 70% (mutated p53) of breast cancers. In some embodiments, a dendrimer of the present invention comprises a monoclonal antibody that specifically binds to a mutated version of p53 that is present in breast cancer. In some embodiments, a dendrimer of the present invention comprises an antibody (e.g., monoclonal antibody) with high affinity for a signature including, but not limited to, Mucl and HER-2.

In some embodiments of the present invention, cancer cells expressing susceptibility genes are identified. For example, in some embodiments, there are two breast cancer susceptibility genes that are used as specific signatures for breast cancer: BRCA1 on chromosome 17 and BRCA2 on chromosome 13. When an individual carries a mutation in either BRCA1 or BRCA2, they are at an increased risk of being diagnosed with breast or ovarian cancer at some point in their lives. These genes participate in repairing radiation-induced breaks in double-stranded DNA. It is thought that mutations in BRCA1 or BRCA2 might disable this mechanism, leading to more errors in DNA replication and ultimately to cancerous growth.

In addition, the expression of a number of different cell surface receptors find use as targets for the binding and uptake of a dendrimer conjugate. Such receptors include, but are not limited to, EGF receptor, folate receptor, FGR receptor 2, and the like.

In some embodiments of the present invention, changes in gene expression associated with chromosomal abborations are the signature component. For example, Burkitt lymphoma results from chromosome translocations that involve the Myc gene. A chromosome translocation means that a chromosome is broken, which allows it to associate with parts of other chromosomes. The classic chromosome translocation in Burkitt lymophoma involves chromosome 8, the site of the Myc gene. This changes the pattern of Myc expression, thereby disrupting its usual function in controlling cell growth and proliferation.

From the discussion above it is clear that there are many different tumor signatures that find use with the present invention, some of which are specific to a particular type of cancer and others which are promiscuous in their origin. The present invention is not limited to any particular tumor signature or any other disease-specific signature. For example, tumor suppressors that find use as signatures in the present invention include, but are not limited to, p53, Mucl, CEA, p16, p21, p27, CCAM, RB, APC, DCC, NF-1, NF-2, WT-1, MEN-1, MEN-II, p73, VHL, FCC and MCC.

In some embodiments of the present invention, a dendrimer conjugate comprises at least one imaging agent that can be readily imaged. The present invention is not limited by the nature of the imaging component used. In some embodiments of the present invention, imaging modules comprise surface modifications of quantum dots (See e.g., Chan and Nie, Science 281:2016 (1998)) such as zinc sulfide-capped cadmium selenide coupled to biomolecules (Sooklal, Adv. Mater., 10:1083 (1998)).

In some embodiments, the imaging module comprises dendrimers produced according to the "nanocomposite" concept (See, e.g., Balogh et al., Proc. of ACS PMSE 77:118 (1997) and Balogh and Tomalia, J. Am. Che. Soc., 120:7355 (1998)). In these embodiments, dendrimers are produced by reactive encapsulation, where a reactant is preorganized by the dendrimer template and is then subsequently immobilized in/on the polymer molecule by a second reactant. Size, shape, size distribution and surface functionality of these nanoparticles are determined and controlled by the dendritic macromolecules. These materials have the solubility and compatibility of the host and have the optical or physiological properties of the guest molecule (i.e., the molecule that permits imaging). While the dendrimer host may vary according to the medium, it is possible to load the dendrimer hosts with different compounds and at various guest concentration levels. Complexes and composites may involve the use of a variety of metals or other inorganic materials. The high electron density of these materials considerably simplifies the imaging by electron microscopy and related scattering techniques. In addition, properties of inorganic atoms introduce new and measurable properties for imaging in either the presence or absence of interfering biological materials. In some embodiments of the present invention, encapsulation of gold, silver, cobalt, iron atoms/molecules and/or organic dye molecules such as fluorescein are encapsulated into dendrimers for use as nanoscopi composite labels/tracers, although any material that facilitates imaging or detection may be employed. In a preferred embodiment, the imaging agent is fluorescein isothiocyanate In some embodiments of the present invention, imaging is based on the passive or active observation of local differences in density of selected physical properties of the investigated complex matter. These differences may be due to a different shape (e.g., mass density detected by atomic force microscopy), altered composition (e.g. radiopaques detected by X-ray), distinct light emission (e.g., fluorochromes detected by spectrophotometry), different diffraction (e.g., electron-beam detected by TEM), contrasted absorption (e.g., light detected by optical methods), or special radiation emission (e.g., isotope methods), etc. Thus, quality and sensitivity of imaging depend on the property observed and on the technique used. The imaging techniques for cancerous cells have to provide sufficient levels of sensitivity to is observe small, local concentrations of selected cells. The earliest identification of cancer signatures requires high selectivity (i.e., highly specific recognition provided by appropriate targeting) and the highest possible sensitivity.

In some embodiments, once a targeted dendrimer conjugate has attached to (or been internalized into) a target cell (e.g., tumor cell and or inflammatory cell), one or more modules on the device serve to image its location. Dendrimers have already been employed as biomedical imaging agents, perhaps most notably for magnetic resonance imaging (MRI) contrast enhancement agents (See e.g., Wiener et al., Mag. Reson. Med. 31:1 (1994); an example using PAMAM dendrimers). These agents are typically constructed by conjugating chelated paramagnetic ions, such as Gd(III)-diethylenetriaminepentaacetic acid (Gd(III)-DTPA), to water-soluble dendrimers. Other paramagnetic ions that may be useful in this context include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof. In some embodiments of the present invention, a dendrimer conjugate is also conjugated to a targeting group, such as epidermal growth factor (EGF), to make the conjugate specifically bind to the desired cell type (e.g., in the case of EGF, EGFR-expressing tumor cells). In a preferred embodiment of the present invention, DTPA is attached to dendrimers via the isothiocyanate of DTPA as described by Wiener (Wiener et al., Mag. Reson. Med. 31:1 (1994)).

Dendrimeric MRI agents are particularly effective due to the polyvalency, size and architecture of dendrimers, which results in molecules with large proton relaxation enhancements, high molecular relaxivity, and a high effective concentration of paramagnetic ions at the target site. Dendrimeric gadolinium contrast agents have even been used to differentiate between benign and malignant breast tumors using dynamic MRI, based on how the vasculature for the latter type of tumor images more densely (Adam et al., Ivest. Rad. 31:26 (1996)). Thus, MRI provides a particularly useful imaging system of the present invention.

Static structural microscopic imaging of cancerous cells and tissues has traditionally been performed outside of the patient. Classical histology of tissue biopsies provides a fine illustrative example, and has proven a powerful adjunct to cancer diagnosis and treatment. After removal, a specimen is sliced thin (e.g., less than 40 microns), stained, fixed, and examined by a pathologist. If images are obtained, they are most often 2-D transmission bright-field projection images. Specialized dyes are employed to provide selective contrast, which is almost absent from the unstained tissue, and to also provide for the identification of aberrant cellular constituents. Quantifying sub-cellular structural features by using computer-assisted analysis, such as in nuclear ploidy determination, is often confounded by the loss of histologic context owing to the thinness of the specimen and the overall lack of 3-D information. Despite the limitations of the static imaging approach, it has been invaluable to allow for the identification of neoplasia in biopsied tissue. Furthermore, its use is often the crucial factor in the decision to perform invasive and risky combinations of chemotherapy, surgical procedures, and radiation treatments, which are often accompanied by severe collateral tissue damage, complications, and even patient death.

A dendrimer conjugate of the present invention allows functional microscopic imaging of tumors and provide improved methods for imaging. The methods find use in vivo, in vitro, and ex vivo. For example, in one embodiment of the present invention, dendrimer conjugates of the present invention are designed to emit light or other detectable signals upon exposure to light. Although the labeled dendrimers may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multiwavelength sources (See, e.g., Farkas et al., SPEI 2678: 200 (1997)). In embodiments where the imaging agents are present in deeper tissue, longer wavelengths in the Near-infrared (NMR) are used (See e.g., Lester et al., Cell Mol. Biol. 44:29 (1998)). Dendrimeric biosensing in the Near-IR has been demonstrated with dendrimeric biosensing antenna-like architectures (See, e.g., Shortreed et al., J. Phys. Chem., 101:6318 (1997)). Biosensors that find use with the present invention include, but are not limited to, fluorescent dyes and molecular beacons.

In some embodiments of the present invention, in vivo imaging is accomplished using functional imaging techniques. Functional imaging is a complementary and potentially more powerful techniques as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce. When excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue. For example, in some embodiments of the present invention, biosensor-comprising dendrimers of the present invention are used to image upregulated receptor families such as the folate or EGF classes. In such embodiments, functional biosensing therefore involves the detection of physiological abnormalities relevant to carcinogenesis or malignancy, even at early stages. A number of physiological conditions may be imaged using the compositions and methods of the present invention including, but not limited to, detection of nanoscopic dendrimeric biosensors for pH, oxygen concentration, $Ca^{2+}$ concentration, and other physiologically relevant analytes.

In some embodiments, the present invention provides dendrimer conjugates having a biological monitoring component. The biological monitoring or sensing component of a dendrimer conjugate of the present invention is one that can monitor the particular response in a target cell (e.g., tumor cell) induced by an agent (e.g., a therapeutic agent provided by the therapeutic component of the dendrimer conjugate). While the present invention is not limited to any particular monitoring system, the invention is illustrated by methods and compositions for monitoring cancer treatments. In preferred embodiments of the present invention, the agent induces apoptosis in cells and monitoring involves the detection of apoptosis. In particular embodiments, the monitoring component is an agent that fluoresces at a particular wavelength when apoptosis occurs. For example, in a preferred embodiment, caspase activity activates green fluorescence in the monitoring component. Apoptotic cancer cells, which have turned red as a result of being targeted by a particular signature with a red label, turn orange while residual cancer cells remain red. Normal cells induced to undergo apoptosis (e.g., through collateral damage), if present, will fluoresce green.

In these embodiments, fluorescent groups such as fluorescein are employed in the monitoring component. Fluorescein is easily attached to the dendrimer surface via the isothiocyanate derivatives, available from MOLECULAR PROBES, Inc. This allows the dendrimer conjugate to be imaged with the cells via confocal microscopy. Sensing of the effectiveness of the dendrimer conjugates is preferably achieved by using fluorogenic peptide enzyme substrates. For example, apoptosis caused by the therapeutic agents results in the production of the peptidase caspase-1 (ICE). CALBIOCHEM sells a number of peptide substrates for this enzyme that release a fluorescent moiety. A particularly useful peptide for use in the present invention is:

```
                                        (SEQ ID NO: 2)
MCA-Tyr-Glu-Val-Asp-Gly-Trp-Lys-(DNP)-NH₂
``` where MCA is the (7-methoxycoumarin-4-yl)acetyl and DNP is the 2,4-dinitrophenyl group (See, e.g., Talanian et al., J. Biol. Chem., 272: 9677 (1997)). In this peptide, the MCA group has greatly attenuated fluorescence, due to fluorogenic resonance energy transfer (FRET) to the DNP group. When the enzyme cleaves the peptide between the aspartic acid and glycine residues, the MCA and DNP are separated, and the MCA group strongly fluoresces green (excitation maximum at 325 nm and emission maximum at 392 nm).

In some embodiments of the present invention, the lysine end of the peptide is linked to the dendrimer conjugate, so that the MCA group is released into the cytosol when it is cleaved. The lysine end of the peptide is a useful synthetic handle for conjugation because, for example, it can react with the activated ester group of a bifunctional linker such as Mal-PEG-OSu. Thus the appearance of green fluorescence in the target cells produced using these methods provides a clear indication that apoptosis has begun (if the cell already has a red color from the presence of aggregated quantum dots, the cell turns orange from the combined colors).

Additional fluorescent dyes that find use with the present invention include, but are not limited to, acridine orange, reported as sensitive to DNA changes in apoptotic cells (Abrams et al., Development 117:29 (1993)) and cis-parinaric acid, sensitive to the lipid peroxidation that accompanies apoptosis (Hockenbery et al., Cell 75:241 (1993)). It should be noted that the peptide and the fluorescent dyes are merely exemplary. It is contemplated that any peptide that effectively acts as a substrate for a caspase produced as a result of apoptosis finds use with the present invention.

In some embodiments, conjugation between a dendrimer (e.g., terminal arm of a dendrimer) and a functional group or between functional groups is accomplished through use of a 1,3-dipolar cycloaddition reaction ("click chemistry"). 'Click chemistry' involves, for example, the coupling of two different moieties (e.g., a therapeutic agent and a functional group) (e.g., a first functional group and a second functional group) via a 1,3-dipolar cycloaddition reaction between an alkyne moiety (or equivalent thereof) on the surface of the first moeity and an azide moiety (e.g., present on a triazine composition) (or equivalent thereof) (or any active end group such as, for example, a primary amine end group, a hydroxyl end group, a carboxylic acid end group, a thiol end group, etc.) on the second moiety (see, e.g., U.S. Provisional Patent App. No. 61/140,480, herein incorporated by reference in its entirety. 'Click' chemistry is an attractive coupling method because, for example, it can be performed with a wide variety of solvent conditions including aqueous environments. For example, the stable triazole ring that results from coupling the alkyne with the azide is frequently achieved at quantitative yields and is considered to be biologically inert (see, e.g., Rostovtsev, V. V.; et al., Angewandte Chemie-International Edition 2002, 41, (14), 2596; Wu, P.; et al., Angewandte Chemie-International Edition 2004, 43, (30), 3928-3932; each herein incorporated by reference in their entireties).

In some embodiments, conjugation between a dendrimer (e.g., a terminal arm of a dendrimer) and a functional ligand is accomplished during a "one-pot" reaction. The term "one-pot synthesis reaction" or equivalents thereof, e.g., "1-pot", "one pot", etc., refers to a chemical synthesis method in which all reactants are present in a single vessel. Reactants may be added simultaneously or sequentially, with no limitation as to the duration of time elapsing between introduction of sequentially added reactants. In some embodiments, a one-pot reaction occurs wherein a hydroxyl-terminated dendrimer (e.g., HO-PAMAM dendrimer) is reacted with one or more functional ligands (e.g., a therapeutic agent, a pro-drug, a trigger agent, a targeting agent, an imaging agent) in one vessel, such conjugation being facilitated by ester coupling agents (e.g., 2-chloro-1-methylpyridinium iodide and 4-(dimethylamino) pyridine) (see, e.g., U.S. Provisional Patent App. No. 61/226,993, herein incorporated by reference in its entirety).

Functionalized nanoparticles (e.g., dendrimers) often contain moieties (including but not limited to ligands, functional ligands, conjugates, therapeutic agents, targeting agents, imaging agents, fluorophores) that are conjugated to the periphery. Such moieties may for example be conjugated to one or more dendrimer branch termini. Classical multi-step conjugation strategies used during the synthesis of functionalized dendrimers generate a stochastic distribution of products with differing numbers of ligands attached per dendrimer molecule, thereby creating a population of dendrimers with a wide distribution in the numbers of ligands attached. The low structural uniformity of such dendrimer populations negatively affects properties such as therapeutic potency, pharmacokinetics, or effectiveness for multivalent targeting. Difficulties in quantifying and resolving such populations to yield samples with sufficient structural uniformity can pose challenges. However, in some embodiments, use of separation methods (e.g., reverse phase chromatography) customized for optimal separation of dendrimer populations in conjunction with peak fitting analysis methods allows isolation and identification of subpopulations of functionalized dendrimers with high structural uniformity (see, e.g., U.S. Provisional Pat. App. No. 61/237,172; herein incorporated by reference in its entirety). In certain embodiments, such methods and systems provide a dendrimer product made by the process comprising: a) conjugation of at least one ligand type to a dendrimer to yield a population of ligand-conjugated dendrimers; b) separation of the population of ligand-conjugated dendrimers with reverse phase HPLC to result in subpopulations of ligand-conjugated dendrimers indicated by a chromatographic trace; and c) application of peak fitting analysis to the chromatographic trace to identify subpopulations of ligand-conjugated dendrimers wherein the structural uniformity of ligand conjugates per molecule of dendrimer within said subpopulation is, e.g., approximately 80% or more.

As described above, another component of the present invention is that the dendrimer conjugate compositions are able to specifically target a particular tissue region and/or cell type (e.g., CNS). In some embodiments, the dendrimer conjugate targets the CNS (e.g., via transferrin), neurons within the CNS (e.g., via Tet1), the peripheral nervous system, muscles, and/or nerves.

In some embodiments of the present invention, targeting groups are conjugated to dendrimers and/or linkers conjugated to the dendrimers with either short (e.g., direct coupling), medium (e.g. using small-molecule bifunctional linkers such as SPDP, sold by PIERCE CHEMICAL Company), or long (e.g., PEG bifunctional linkers, sold by NEKTAR, Inc.) linkages. Since dendrimers have surfaces with a large number of functional groups, more than one targeting group and/or linker may be attached to each dendrimer. As a result, multiple binding events may occur between the dendrimer conjugate and the target cell. In these embodiments, the dendrimer conjugates have a very high affinity for their target cells via this "cooperative binding" or polyvalent interaction effect.

For steric reasons, in some embodiments, the smaller the ligands, the more can be attached to the surface of a dendrimer and/or linkers attached thereto. Recently, Wiener reported that dendrimers with attached folic acid would specifically accumulate on the surface and within tumor cells expressing the high-affinity folate receptor (hFR) (See, e.g., Wiener et al., Invest. Radiol., 32:748 (1997)). The hFR receptor is expressed or upregulated on epithelial tumors, including breast cancers. Control cells lacking hFR showed no significant accumulation of folate-derivatized dendrimers. Folic acid can be attached to full generation PAMAM dendrimers via a carbodiimide coupling reaction. Folic acid is a good targeting candidate for the dendrimers, with its small size and a simple conjugation procedure.

Antibodies can be generated to allow for the targeting of antigens or immunogens (e.g., tumor, tissue or pathogen specific antigens) on various biological targets (e.g., pathogens, tumor cells, normal tissue). Such antibodies include, but are not limited to polyclonal, monoclonal, chimeric, single chain, Fab fragments, and an Fab expression library.

In some embodiments, the antibodies recognize tumor specific epitopes (e.g., TAG-72 (See, e.g., Kjeldsen et al., Cancer Res. 48:2214-2220 (1988); U.S. Pat. Nos. 5,892,020; 5,892,019; and 5,512,443); human carcinoma antigen (See, e.g., U.S. Pat. Nos. 5,693,763; 5,545,530; and 5,808,005); TP1 and TP3 antigens from osteocarcinoma cells (See, e.g., U.S. Pat. No. 5,855,866); Thomsen-Friedenreich (TF) antigen from adenocarcinoma cells (See, e.g., U.S. Pat. No. 5,110,911); "KC-4 antigen" from human prostrate adenocarcinoma (See, e.g., U.S. Pat. Nos. 4,708,930 and 4,743,543); a human colorectal cancer antigen (See, e.g., U.S. Pat. No. 4,921,789); CA125 antigen from cystadenocarcinoma (See, e.g., U.S. Pat. No. 4,921,790); DF3 antigen from human breast carcinoma (See, e.g., U.S. Pat. Nos. 4,963,484 and 5,053,489); a human breast tumor antigen (See, e.g., U.S. Pat. No. 4,939,240); p97 antigen of human melanoma (See, e.g., U.S. Pat. No. 4,918,164); carcinoma or orosomucoid-related antigen (CORA) (See, e.g., U.S. Pat. No. 4,914,021); a human pulmonary carcinoma antigen that reacts with human squamous cell lung carcinoma but not with human small cell lung carcinoma (See, e.g., U.S. Pat. No. 4,892,935); T and Tn haptens in glycoproteins of human breast carcinoma (See, e.g., Springer et al., Carbohydr. Res. 178:271-292 (1988)), MSA breast carcinoma glycoprotein termed (See, e.g., Tjandra et al., Br. J. Surg. 75:811-817 (1988)); MFGM breast carcinoma antigen (See, e.g., Ishida et al., Tumor Biol. 10:12-22 (1989)); DU-PAN-2 pancreatic carcinoma antigen (See, e.g., Lan et al., Cancer Res. 45:305-310 (1985)); CA125 ovarian carcinoma antigen (See, e.g., Hanisch et al., Carbohydr. Res. 178:29-47 (1988)); YH206 lung carcinoma antigen (See, e.g., Hinoda et al., (1988) Cancer J. 42:653-658 (1988)). Each of the foregoing references are specifically incorporated herein by reference.

Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Kohler and Milstein (Kohler and Milstein, Nature 256:495-497 (1975)), as well as the trioma technique, the human B-cell hybridoma technique (See e.g., Kozbor et al. Immunol. Today 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc. Natl. Acad. Sci. U.S.A. 80:2026-2030 (1983)) or by transforming human B cells with EBV virus in vitro (Cole et al., in Monoclonal Antibodies and Cancer Therapy, Alan R. Liss, pp. 77-96 (1985)).

According to the invention, techniques described for the production of single chain antibodies (U.S. Pat. No. 4,946,778; herein incorporated by reference) can be adapted to produce specific single chain antibodies. An additional embodiment of the invention utilizes the techniques described for the construction of Fab expression libraries (Huse et al., Science 246:1275-1281 (1989)) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.).

The dendrimer conjugates of the present invention have many advantages over liposomes, such as their greater stability, better control of their size and polydispersity, and generally lower toxicity and immunogenicity (See e.g., Duncan et al, Polymer Preprints 39:180 (1998)). Thus, in some embodiments of the present invention, anti-HER2 antibody fragments, as well as other targeting antibodies are conjugated to dendrimers, as targeting agents for the nanodevices of the present invention.

The bifunctional linkers SPDP and SMCC and the longer Mal-PEG-OSu linkers are particularly useful for antibody-dendrimer conjugation. In addition, many tumor cells contain surface lectins that bind to oligosaccharides, with specific recognition arising chiefly from the terminal carbohydrate residues of the latter (See, e.g., Sharon and Lis, Science 246:227 (1989)). Attaching appropriate monosaccharides to nonglycosylated proteins such as BSA provides a conjugate that binds to tumor lectin much more tightly than the free monosaccharide (See, e.g., Monsigny et al., Biochemie 70:1633 (1988)).

Mannosylated PAMAM dendrimers bind mannoside-binding lectin up to 400 more avidly than monomeric mannosides (See, e.g., Page and Roy, Bioconjugate Chem., 8:714 (1997)). Sialylated dendrimers and other dendritic polymers bind to and inhibit a variety of sialate-binding viruses both in vitro and in vivo. By conjugating multiple monosaccharide residues (e.g., α-galactoside, for galactose-binding cells) to dendrimers, polyvalent conjugates are created with a high affinity for the corresponding type of tumor cell. The attachment reaction are easily carried out via reaction of the terminal amines with commercially-available α-galactosidyl-phenylisothiocyanate. The small size of the carbohydrates allows a high concentration to be present on the dendrimer surface.

Related to the targeting approaches described above is the "pretargeting" approach (See e.g., Goodwin and Meares, Cancer (suppl.) 80:2675 (1997)). An example of this strategy involves initial treatment of a subject with conjugates of tumor-specific monoclonal antibodies and streptavidin. Remaining soluble conjugate is removed from the bloodstream with an appropriate biotinylated clearing agent. When the tumor-localized conjugate is all that remains, a radiolabeled, biotinylated agent is introduced, which in turn localizes at the tumor sites by the strong and specific biotin-streptavidin interaction. Thus, the radioactive dose is maximized in dose proximity to the cancer cells and minimized in the rest of the body where it can harm healthy cells.

It has been shown that if streptavidin molecules bound to a polystyrene well are first treated with a biotinylated dendrimer, and then radiolabeled streptavidin is introduced, up to four of the labeled streptavidin molecules are bound per polystyrene-bound streptavidin (See, e.g., Wilbur et al., Bioconjugate Chem., 9:813 (1998)). Thus, biotinylated dendrimers may be used in the methods of the present invention, acting as a polyvalent receptor for the radiolabel in vivo, with a resulting amplification of the radioactive dosage per bound antibody conjugate. In the preferred embodiments of the present invention, one or more multiply-biotinylated module(s) on the clustered dendrimer presents a polyvalent target for radiolabeled or boronated (See, e.g., Barth et al., Cancer Investigation 14:534 (1996)) avidin or streptavidin, again resulting in an amplified dose of radiation for the tumor cells.

Dendrimers may also be used as clearing agents by, for example, partially biotinylating a dendrimer that has a polyvalent galactose or mannose surface. The conjugate-clearing agent complex would then have a very strong affinity for the corresponding hepatocyte receptors.

In other embodiments of the present invention, an enhanced permeability and retention (EPR) method is used in targeting. The enhanced permeability and retention (EPR) effect is a more "passive" way of targeting tumors (See, e.g., Duncan and Sat, Ann. Oncol., 9:39 (1998)). The EPR effect is the selective concentration of macromolecules and small particles in the tumor microenvironment, caused by the hyperpermeable vasculature and poor lymphatic drainage of tumors. The dendrimer compositions of the present invention provide ideal polymers for this application, in that they are relatively rigid, of narrow polydispersity, of controlled size and surface chemistry, and have interior "cargo" space that can carry and then release antitumor drugs. In fact, PAMAM dendrimer-platinates have been shown to accumulate in solid tumors (Pt levels about 50 times higher than those obtained with cisplatin) and have in vivo activity in solid tumor models for which cisplatin has no effect (See, e.g., Malik et al., Proc. Int'l. Symp. Control. Rel. Bioact. Mater., 24:107 (1997) and Duncan et al., Polymer Preprints 39:180 (1998)).

In some embodiments of the present invention, the preparation of PAMAM dendrimers is performed according to a typical divergent (building up the macromolecule from an initiator core) synthesis. It involves a two-step growth sequence that includes of a Michael addition of amino groups to the double bond of methyl acrylate (MA) followed by the amidation of the resulting terminal carbomethoxy, —($CO_2CH_3$) group, with ethylenediamine (EDA).

In the first step of this process, ammonia is allowed to react under an inert nitrogen atmosphere with MA (molar ratio: 1:4.25) at 47° C. for 48 hours. The resulting compound is referred to as generation=0, the star-branched PAMAM tri-ester. The next step involves reacting the tri-ester with an excess of EDA to produce the star-branched PAMAM tri-amine (G=0). This reaction is performed under an inert atmosphere (nitrogen) in methanol and requires 48 hours at 0° C. for completion. Reiteration of this Michael addition and amidation sequence produces generation=1.

Preparation of this tri-amine completes the first full cycle of the divergent synthesis of PAMAM dendrimers. Repetition of this reaction sequence results in the synthesis of larger generation (G=1-5) dendrimers (i.e., ester- and amine-terminated molecules, respectively). For example, the second iteration of this sequence produces generation 1, with an hexa-ester and hexa-amine surface, respectively. The same reactions are performed in the same way as for all subsequent generations from 1 to 9, building up layers of branch cells giving a core-shell architecture with precise molecular weights and numbers of terminal groups as shown above. Carboxylate-surfaced dendrimers can be produced by hydrolysis of ester-terminated PAMAM dendrimers, or reaction of succinic anhydride with amine-surfaced dendrimers (e.g., full generation PAMAM, POPAM or POPAM-PAMAM hybrid dendrimers).

Various dendrimers can be synthesized based on the core structure that initiates the polymerization process. These core structures dictate several important characteristics of the dendrimer molecule such as the overall shape, density, and surface functionality (See, e.g., Tomalia et al., Angew. Chem. Int. Ed. Engl., 29:5305 (1990)). Spherical dendrimers derived from ammonia possess trivalent initiator cores, whereas EDA is a tetra-valent initiator core. Recently, rod-shaped dendrimers have been reported which are based upon linear poly (ethyleneimine) cores of varying lengths the longer the core, the longer the rod (See, e.g., Yin et al., J. Am. Chem. Soc., 120:2678 (1998)).

In some embodiments, dendrimers of the present invention comprise a protected core diamine. In some embodiments, the protected initiator core diamine is $NH2\text{-}(CH2)_n\text{---}NHPG$, (n=1-10). In other embodiments, the intitor core is selected from the group comprising, but not limited to, $NH2\text{-}(CH2)_n\text{-}NH2$ (n=1-10), $NH2\text{-}((CH2)_nNH2)_3$ (n=1-10), or unsubstituted or substituted 1,2-; 1,3-; or 1,4-phenylenedi-n-alkylamine, with a monoprotected diamine (e.g., $NH2\text{-}(CH2)_n\text{-}NHPG$) used during the amide formation of each generation. In these approaches, the protected diamine allows for the large scale production of dendrimers without the production of non-uniform nanostructures that can make characterization and analysis difficult. By limiting the reactivity of the diamine to only one terminus, the opportunities of dimmer/polymer formation and intramolecular reactions are obviated without the need of employing large excesses of diamine. The terminus monoprotected intermediates can be readily purified since the protecting groups provide suitable handle for productive purifications by classical techniques like crystallization and or chromatography.

The protected intermediates can be deprotected in a deprotection step, and the resulting generation of the dendrimer subjected to the next iterative chemical reaction without the need for purification. The invention is not limited to a particular protecting group. Indeed a variety of protecting groups are contemplated including, but not limited to, t-butoxycarbamate (N-t-Boc), allyloxycarbamate (N-Alloc), benzylcarbamate (N-Cbz), 9-fluorenylmethylcarbamate (FMOC), or phthalimide (Phth). In preferred embodiments of the present invention, the protecting group is benzylcarbamate (N-Cbz). N-Cbz is ideal for the the present invention since it alone can be easily cleaved under "neutral" conditions by catalytic hydrogenation (Pd/C) without resorting to strongly acidic or basic conditions needed to remove an F-MOC group. The use of protected monomers finds particular use in high through-put production runs because a lower amount of monomer can be used, reducing production costs.

The dendrimers may be characterized for size and uniformity by any suitable analytical techniques. These include, but are not limited to, atomic force microscopy (AFM), electrospray-ionization mass spectroscopy, MALDI-TOF mass spectroscopy, $^{13}C$ nuclear magnetic resonance spectroscopy, high performance liquid chromatography (HPLC) size exclusion chromatography (SEC) (equipped with multi-angle laser light scattering, dual UV and refractive index detectors), capillary electrophoresis and get electrophoresis. These analytical methods assure the uniformity of the dendrimer population and are important in the quality control of dendrimer production for eventual use in in vivo applications. Most importantly, extensive work has been performed with dendrimers showing no evidence of toxicity when administered intravenously (Roberts et al., J. Biomed. Mater. Res., 30:53 (1996) and Boume et al., J. Magnetic Resonance Imaging, 6:305 (1996)).

In some embodiments of the present invention, the dendrimer conjugates comprise transgenes for delivery and expression to a target cell or tissue, in vitro, ex vivo, or in vivo. In such embodiments, rather than containing the actual protein, the dendrimer complex comprises an expression vector construct containing, for example, a heterologous DNA encoding a gene of interest and the various regulatory elements that facilitate the production of the particular protein of interest in the target cells.

In some embodiments, the gene is a therapeutic gene that is used, for example, to treat cancer, to replace a defective gene, or a marker or reporter gene that is used for selection or monitoring purposes. In the context of a gene therapy vector, the gene may be a heterologous piece of DNA. The heterologous DNA may be derived from more than one source (i.e., a multigene construct or a fusion protein). Further, the heterologous DNA may include a regulatory sequence derived from one source and the gene derived from a different source.

Tissue-specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters may be used to target gene expression in other tissues (e.g., insulin, elastin amylase, pdr-1, pdx-1 and glucokinase promoters target to the pancreas; albumin PEPCK, HBV enhancer, alpha fetoproteinapolipoprotein C, alpha-1 antitrypsin, vitellogenin, NF-AB and transthyretin promoters target to the liver; myosin H chain, muscle creatine kinase, dystrophin, calpain p94, skeletal alpha-actin, fast troponin 1 promoters target to skeletal muscle; keratin promoters target the skin; sm22 alpha; SM-.alpha.-actin promoters target smooth muscle; CFTR; human cytokeratin 18 (K18); pulmonary surfactant proteins A, B and Q CC-10; P1 promoters target lung tissue; endothelin-1; E-selectin; von Willebrand factor; KDR/flk-1 target the endothelium; tyrosinase targets melanocytes).

The nucleic acid may be either cDNA or genomic DNA. The nucleic acid can encode any suitable therapeutic protein. Preferably, the nucleic acid encodes a tumor suppressor, cytokine, receptor, inducer of apoptosis, or differentiating agent. The nucleic acid may be an antisense nucleic acid. In such embodiments, the antisense nucleic acid may be incorporated into the nanodevice of the present invention outside of the context of an expression vector.

In preferred embodiments, the nucleic acid encodes a tumor suppressor, cytokines, receptors, or inducers of apoptosis. Suitable tumor suppressors include BRCA1, BRCA2, C-CAM, p16, p211 p53, p73, or Rb. Suitable cytokines include GMCSF, IL-1, IL-2, IL-3, IL-4, IL-5, IL6, IL-7, IL-8, IL-9, IL-10, IL-11, IL-12, IL-13, IL-14, IL-15, β-interferon, γ-interferon, or TNF. Suitable receptors include CFTR, EGFR, estrogen receptor, IL-2 receptor, or VEGFR. Suitable inducers of apoptosis include AdE1B, Bad, Bak, Bax, Bid, Bik, Bim, Harakiri, or ICE-CED3 protease.

In some embodiments, more than one administration of the dendrimer conjugates of the present invention or the other agent are utilized. Various combinations may be employed, where the dendrimer is "A" (e.g., comprising a pain relief agent) and the other agent is "B" (e.g., comprising a pain relief agent antagonist), as exemplified below: A/B/A, B/A/B, B/B/A, A/A/B, B/A/A, A/B/B, B/B/B/A, B/B/A/B, A/A/B/B, A/B/A/B, A/B/B/A, B/B/A/A, B/A/B/A, A/B/A/B, B/B/B/A, A/A/A/B, B/A/A/A, A/B/A/A, A/A/B/A, A/B/B/B, B/A/B/B, B/B/A/B.

Other combinations are contemplated.

Other factors that may be used in combination therapy with the dendrimer conjugates of the present invention include, but are not limited to, factors that cause DNA damage such as gamma-rays, X-rays, and/or the directed delivery of radioisotopes to tumor cells. Other forms of DNA damaging factors are also contemplated such as microwaves and UV-irradiation. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In preferred embodiments of the present invention, the regional delivery of the dendrimer conjugates to patients with cancers is utilized to maximize the therapeutic effectiveness of the delivered agent. Similarly, the chemo- or radiotherapy may be directed to particular, affected region of the subjects body. Alternatively, systemic delivery of the immunotherapeutic composition and/or the agent may be appropriate in certain circumstances, for example, where extensive metastasis has occurred.

In addition to combining the dendrimer conjugates with chemo- and radiotherapies, it also is contemplated that traditional gene therapies are used. For example, targeting of p53 or p16 mutations along with treatment of the dendrimer conjugates provides an improved anti-cancer treatment. The present invention contemplates the co-treatment with other tumor-related genes including, but not limited to, p21, Rb, APC, DCC, NF-I, NF-2, BCRA2, p16, FHIT, WT-I, MEN-I, MEN-II, BRCA1, VHL, FCC, MCC, ras, myc, neu, raf erb, src, fms, jun, trk, ret, gsp, hst, bcl, and abl.

In vivo and ex vivo treatments are applied using the appropriate methods worked out for the gene delivery of a particular construct for a particular subject. For example, for viral vectors, one typically delivers $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies.

An attractive feature of the present invention is that the therapeutic compositions may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935,114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS (SCIMED LIFE SYSTEMS, Inc.), the SYMPHONY (Boston Scientific Corporation), the Wallstent (Schneider Inc.), the PRECEDENT II (Boston Scientific Corporation) and the NIR (Medinol Inc.). Such devices are delivered to and/or implanted at target locations within the body by known techniques.

In some embodiments, the therapeutic complexes of the present invention comprise a photodynamic compound and a targeting agent that is administered to a patient. In some embodiments, the targeting agent is then allowed a period of time to bind the "target" cell (e.g. about 1 minute to 24 hours) resulting in the formation of a target cell-target agent complex. In some embodiments, the therapeutic complexes comprising the targeting agent and photodynamic compound are then illuminated (e.g., with a red laser, incandescent lamp, X-rays, or filtered sunlight). In some embodiments, the light is aimed at the jugular vein or some other superficial blood or lymphatic vessel. In some embodiments, the singlet oxygen and free radicals diffuse from the photodynamic compound to the target cell (e.g. cancer cell or pathogen) causing its destruction.

Where clinical applications are contemplated, in some embodiments of the present invention, the dendrimer conjugates are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein.

In preferred embodiments, the dendrimer conjugates are used in conjunction with appropriate salts and buffers to render delivery of the compositions in a stable manner to allow for uptake by target cells. Buffers also are employed when the dendrimer conjugates are introduced into a patient. Aqueous compositions comprise an effective amount of the dendrimer conjugates to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active dendrimer conjugates may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some embodiments, a therapeutic agent is released from dendrimer conjugates within a target cell (e.g., within an endosome). This type of intracellular release (e.g., endosomal disruption of a linker-therapeutic conjugate) is contemplated to provide additional specificity for the compositions and methods of the present invention. In some embodiments, the dendrimer conjugates of the present invention contain between 100-150 primary amines on the surface. Thus, the present invention provides dendrimers with multiple (e.g., 100-150) reactive sites for the conjugation of linkers and/or functional groups comprising, but not limited to, therapeutic agents, targeting agents, imaging agents and biological monitoring agents.

The compositions and methods of the present invention are contemplated to be equally effective whether or not the dendrimer conjugates of the present invention comprise a fluorescein (e.g. FITC) imaging agent. Thus, each functional group present in a dendrimer composition is able to work independently of the other functional groups. Thus, the present invention provides dendrimer conjugates that can comprise multiple combinations of targeting, therapeutic, imaging, and biological monitoring functional groups. Additionally, in some embodiments, each functional group (e.g., therapeutic agents, targeting agents, imaging agents and biological monitoring agents) present in a dendrimer composition can function together with one or more of the functional groups (e.g., cooperative binding of multiple targeting ligands).

The present invention also provides a very effective and specific method of delivering molecules (e.g., therapeutic and imaging functional groups) to the interior of target cells (e.g., cancer cells). Thus, in some embodiments, the present invention provides methods of therapy that comprise or require delivery of molecules into a cell in order to function (e.g., delivery of genetic material such as siRNAs).

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, dendrimer conjugates are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. In addition, suppositories may be used in connection with colon cancer. The dendrimer conjugates also may be formulated as inhalants for the treatment of lung cancer and such like.

In some embodiments of the present invention methods and compositions are provided for the treatment of tumors in cancer therapy. It is contemplated that the present therapy can be employed in the treatment of any cancer for which a specific signature has been identified or which can be targeted. Cell proliferative disorders, or cancers, contemplated to be treatable with the methods of the present invention include human sarcomas and carcinomas, including, but not limited to, fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrbm's macroglobulinemia, and heavy chain disease.

In some embodiments of the present invention, methods and compositions are provided for the treatment of inflammatory diseases (e.g., dendrimers conjugated with therapeutic agents configured for treating inflammatory diseases). Inflammatory diseases include but are not limited to arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate 77mperfect (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

In some embodiments, the dendrimer conjugates configured for treating inflammatory disorders (e.g., rheumatoid arthritis) are co-administered to a subject (e.g., a human suffering from an inflammatory disorder) a therapeutic agent configured for treating inflammatory disorders (e.g., rheumatoid arthritis). Examples of such agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), and glucocorticoids (e.g., prednisone, methylprednisone).

The present invention also includes methods involving co-administration of the multifunctional dendrimers and components thereof described herein with one or more additional active agents. Indeed, it is a further aspect of this invention to provide methods for enhancing prior art therapies and/or pharmaceutical compositions by co-administering multifunctional dendrimers of this invention. In co-administration procedures, the agents may be administered concurrently or sequentially. In some embodiments, the multifunctional dendrimers described herein are administered prior to the other active agent(s). The agent or agents to be co-administered depends on the type of condition being treated. For example, when the condition being treated is cancer, the additional agent can be a chemotherapeutic agent or radiation. The additional agents to be co-administered, such as anticancer agents, can be any of the well-known agents in the art, including, but not limited to, those that are currently in clinical use. The determination of appropriate type and dosage of radiation treatment is also within the skill in the art or can be determined with relative ease.

Where clinical applications are contemplated, in some embodiments of the present invention, the dendrimer conjugates are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein. It is contemplated that the present therapy can be employed in the treatment of any pathogenic disease for which a specific signature has been identified or which can be targeted for a given pathogen. Examples of pathogens contemplated to be treatable with the methods of the present invention include, but are not limited to, Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus, human papilloma virus, human immunodeficiency virus, rubella virus, polio virus, and the like.

EXPERIMENTAL

The following examples are provided in order to demonstrate and further illustrate certain preferred embodiments and aspects of the present invention and are not to be construed as limiting the scope thereof.

Example 1

Experiments were conducted during development of embodiments of the invention in order to analyze and characterize various schemes for generating dendrimer conjugates wherein a dendrimer is conjugated to one or more linkers that comprise multiple sites for binding (e.g., covalent binding) moieties. A drug releasing mechanism for esterase sensitive linker-dendrimer conjugates was analyzed (See e.g., FIG. 10). In some embodiments, once the ester bond is cleaved (e.g., by esterases (e.g., present at a target site (e.g., intrinsic to the target))), irreversible decomposition of the linkers leads to release of drug and/or therapeutic agent (e.g., at the target site).

Figure 11:
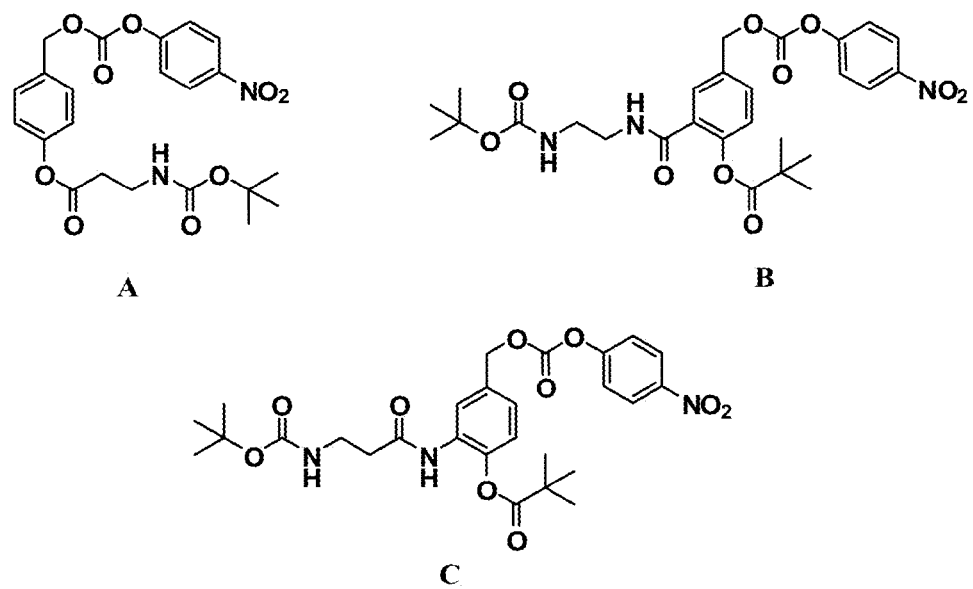
FIG. 11 shows examples of several (A, B, and C) elimination linkers designed for esterase triggered cleavage.

Three elimination linkers (See FIG. 11, A-C) designed for esterase triggered cleavage were synthesized. In some embodiments, the linkers are conjugated to a therapeutic agent and/or to a dendrimer (e.g., G5 dendrimer).

Example 2

Synthesis of Esterase Sensitive Linker 11A

A synthesis scheme of a dendrimer (e.g., G5 PAMAM dendrimer) conjugated to a therapeutic agent (e.g., TAXOL) with an esterase sensitive linker (esterase sensitive elimination linker 11A) is shown below.

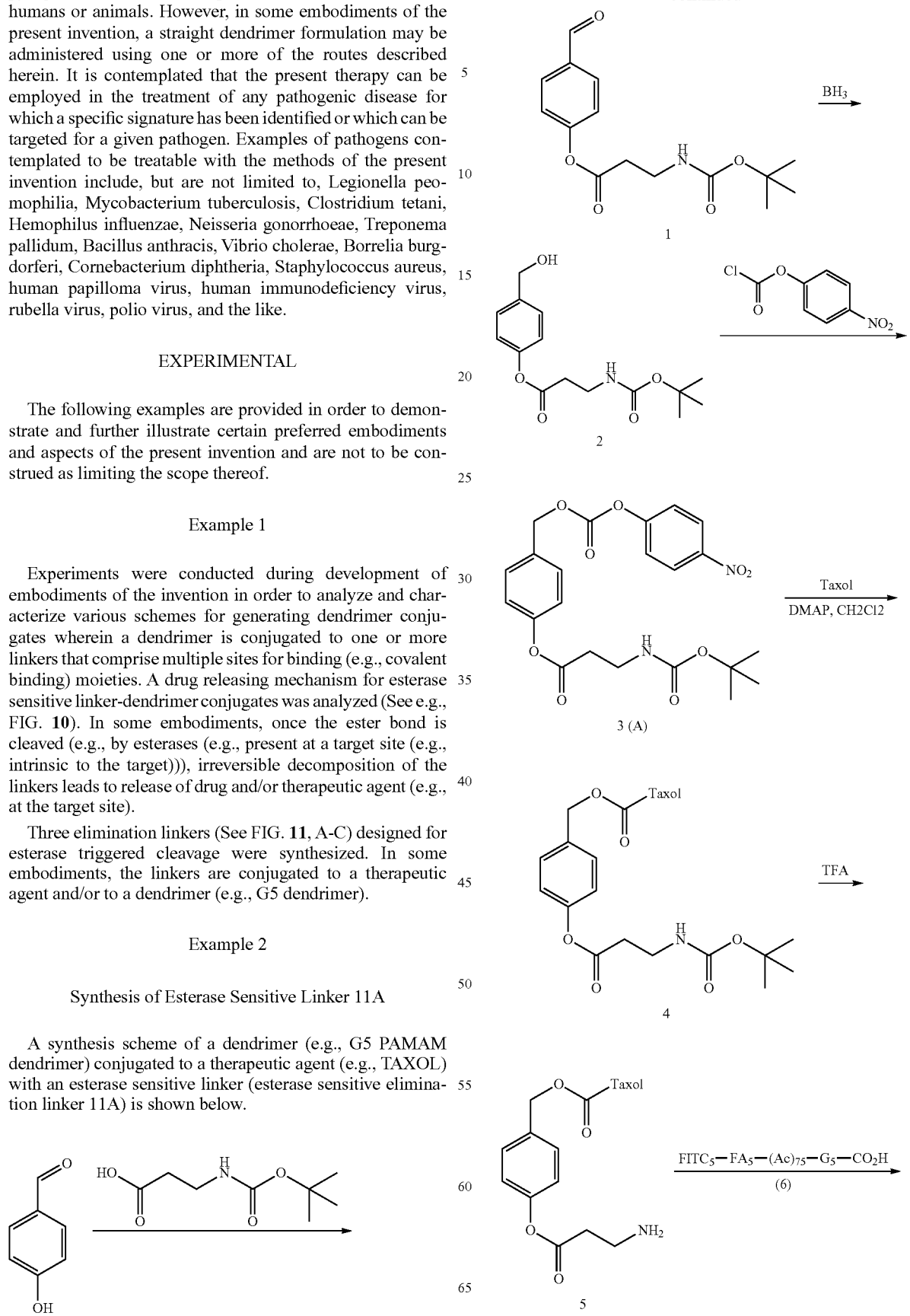

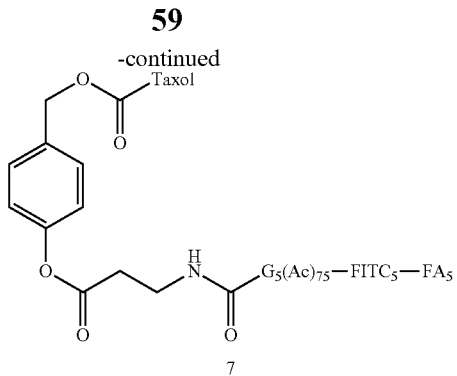

Step 1:

A 50 mL solution of Boc-β-alanine (500 mg, 2.64 mmol), EDC (506 mg, 2.64 mmol), and DMAP (322 mg, 2.64 mmol) in methylene chloride was stirred at 0° C. for 20 min. 4-Hydroxybenzaldehyde (323 mg, 2.64 mmol) was then added slowly. The reaction mixture was stirred at 0° C. for 2 hour before it was warmed to RT and continued for over night. The reaction mixture was then diluted with EtOAc and $H_2O$ and extractive work up to give a crude product which was purified by silica gel chromatography to afford a clear oil (712 mg, 92%).

MS (EI) m/e=294 (M+1)

Step 2:

The aldehyde 1 (775 mg, 2.64 mmol) was dissolved in 40 mL of dry THF and was cooled to 0° C. Boran in THF (1N solution, 2.64 mL) was added dropwise. The reaction mixture was for 2 h. MeOH (5 mL) was added slowly and the reaction mixture was warmed to RT in 1 h. Solvent was evaporated and the product was purified by chromatograph to afford the product as a white solid (625 mg, 80%).

MS (EI) m/e=296 (M+1)

Step 3:

The benzyl alcohol 2 (456 mg, 1.54 mmol) and p-nitrobenzyl chloroformate (934 mg, 4.63 mmol) were dissolved in 20 mL of methylene chloride. Pyridine (0.42 mL, 5.19 mmol) was added. White precipitate was formed during the addition process. The reaction mixture was stirred at RT over night. The reaction mixture was then diluted with EtOAc and water. Layers were separated and the aqueous layer was extracted with EtOAc×3. Combined organic solution was washed with 1N HCl, sat'd $NaHCO_3$ and brine. The crude mixture was purified by silica gel chromatography eluting with 15-25% EtOAc in Hexanes to afford the product as clear oil (520 mg, 73%).

MS (EI) m/e=461 (M+1)

Step 4:

Taxol (9.3 mg, 0.0103575 mmol) and 3 (4.75 mg, 0.0103575 mmol) were dissolved in dry methylene chloride (1 mL). A solution of DMAP (2.5 mg, 0.02715 mmol) in methylene chloride (1 mL) was added dropwise at room temperature. After addition, a light yellow color appeared. The reaction mixture was allowed to stir at room temperature for 3 hours when TLC indicated the reaction was complete. The reaction mixture was extracted with methylene chloride and water. The organic layers were combined and dried over $MgSO_4$. Solvent was evaporated after filtration. The residue was purified by column chromatography (silica gel, EtOAc: Hexanes 1:1) and pure product (10 mg, yield 82%) was obtained.

MS (EI) m/e=1197.5 (M+Na).

Step 5:

Taxol-linker conjugate 4 (10.0 mg, 0.008514 mmol) was dissolved in methylene chloride (1 mL). To above solution was added TFA (120 μL). The reaction mixture was stirred at room temperature and was checked with TLC until the reaction was complete in 20 minutes. The solvent was evaporated and the residue was purified by column chromatography (silica gel, $CH_2Cl_2$:MeOH 10:1). Product 5 was isolated as a white solid (8.0 mg, yield 87.4%).

MS (EI) m/e=1075.4 (M+H).

Step 6:

G5-Ac-Fl-FA-COOH (6), prepared as reported previously, (15.3 mg, 0.0004636 mmol) was dissolved in $H_2O$ (5.2 mL), EDM (10.6 mg, 0.03488 mmol) was added. The reaction mixture was stirred for 2 hour at room temperature. A solution of 5 (10 mg, 0.0093 mmol) in DMF (4.3 mL) and DMSO (3.4 mL) was added dropwise. The reaction was allowed to stir at room temperature for three days. The solvent was removed by membrane filtration through a 10,000 MWCO membrane. The residue was further purified by passing through a Sephdex G-25 column and extensively washed with PBS buffer and water. Lyophilization gave final product 7 as orange colored solid (15.1 mg, yield 90%).

Example 3

Synthesis of Esterase Sensitive Linker 11B

A synthesis scheme of a dendrimer (e.g., G5 PAMAM dendrimer) conjugated to a therapeutic agent (e.g., Taxol) with an esterase sensitive linker (esterase sensitive elimination linker 11B) is shown below.

Scheme 2. Synthesis of dendrimer-Taxol conjugate through an esterase-sensitive linker 11

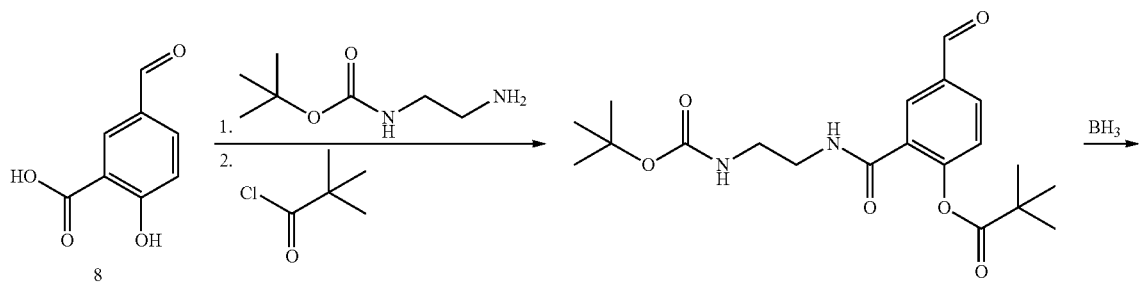

-continued
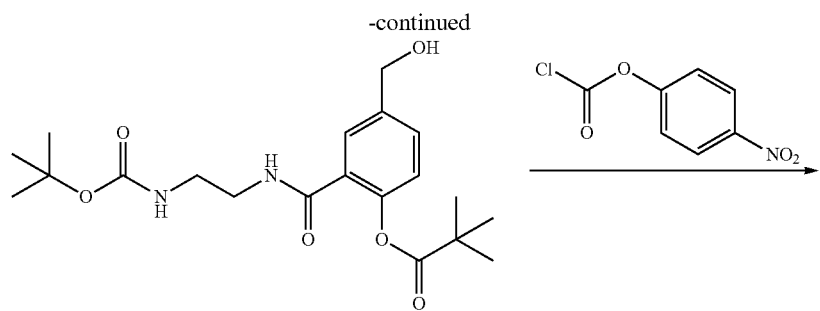
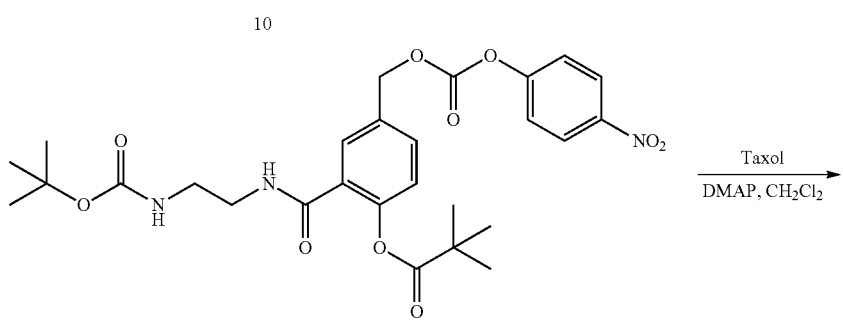
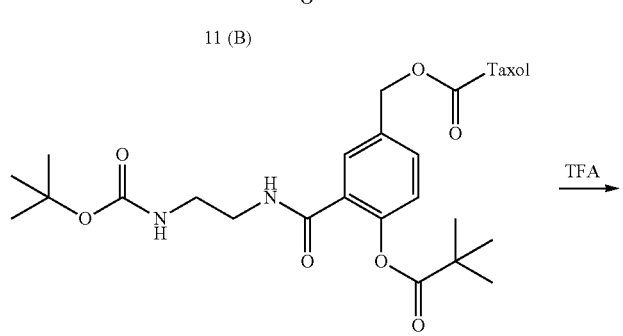
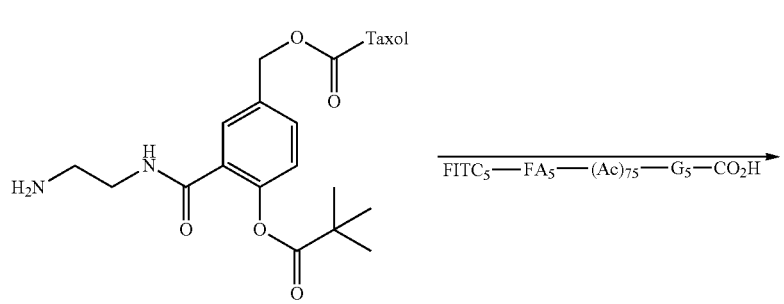
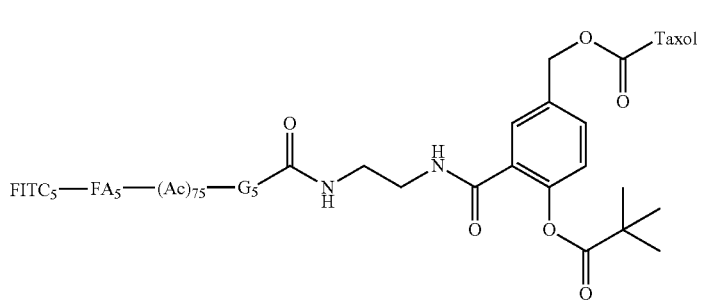

Step 1:

A mixture of 5-formyl-2-hydroxybenzoic acid 8 (1.66 g, 10 mmol), mono-Boc-ethylene diamine (1.60 g, 10 mmol), EDC methiodide (2.97 g, 10 mmol), and HOBT (1.35 g, 10 mmol) was dissolved in 40 mL of DMF at 0° C. The solution was stirred at this temperature for 1 h before it was warmed to RT. Stirring was continued for over night. The orange-yellow colored reaction mixture was cooled to 0° C. Triethylamine (2.8 mL, 20 mmol) was added followed by pivaloyl chloride (2.5 mL, 20 mmol). The reaction mixture was stirred for 2 hours and it was quenched by addition of 50 ml of water. EtOAc (200 mL) was added and the layers were separated. The aqueous layer was extracted with EtOAc×3. The combined organics was washed with 1N HCl, saturated NaHCO$_3$ solution, and brine sequentially and was dried with MgSO$_4$. After solvent was evaporated, the residue was purified by silica gel chromatography to afford the product 9 as a pale yellow solid (3.33 g, 85% 2 steps).

MS (EI) m/e=xxx (M+1)

Step 2:

The aldehyde 9 (2.04 g, 5.20 mmol) was dissolved in 60 mL of dry THF and was cooled to 0° C. Boran in THF (1N solution, 5.46 mL) was added dropwise. The reaction mixture was for 2 h. MeOH (10 mL) was added slowly and the reaction mixture was warmed to RT in 2 h. Solvent was evaporated and the product was purified by chromatograph to afford the product as a white solid (2.02 g, 98%).

MS (EI) m/e=xxx (M+1)

Step 3:

The benzyl alcohol 10 (1.185 g, 3.0 mmol) and p-nitrobenzyl chloroformate (908 mg, 4.50 mmol) were dissolved in 30 mL of methylene chloride. Pyridine (0.49 mL, 6.0 mmol) was added. White precipitate was formed during the addition process. The reaction mixture was stirred at RT over night. The reaction mixture was then diluted with EtOAc and water. Layers were separated and the aqueous layer was extracted with EtOAc×3. Combined organic solution was washed with 1N HCl, sat'd NaHCO$_3$ and brine. The crude mixture was purified by silica gel chromatography eluting with 15-25% EtOAc in Hexanes to afford the product 11 as white solid (1.38 g, 82%).

MS (EI) m/e=560 (M+1)

Step 4:

In a 5 mL round bottle flask, taxol (20 mg, 0.02227 mmol) and linker 11 (35.8 mg, 0.02810 mmol) were dissolved in dry methylene chloride (2 mL). A solution of DMAP (5.7 mg, 0.04666 mmol) in methylene chloride (1 mL) was added dropwise at room temperature. After addition, a light yellow appeared. The reaction mixture was allowed to stir at room temperature for 3 hours. The reaction was monitored with TLC until the reaction was complete. The reaction mixture was extracted with methylene chloride and water. The organic layer was collected and dried over MgSO$_4$ and evaporated. The residue was purified by column chromatography (silica gel, AcOEt:Hexanes 1:1) and pure product (25.3 mg, yield 89%) was obtained.

MS (EI) m/e=1296.5(M+Na).

Step 5:

To the taxol-linker conjugate 12 (12 mg, 0.009426 mmol) in methylene chloride (1 mL) was added TFA (120 µL). The reaction mixture was stirred at room temperature for 20 minutes and was checked with TLC until the reaction was complete. The solvent was evaporated and the residue was purified by column chromatography (silica gel, CH$_2$Cl$_2$:MeOH 10:1). Product 13 was isolated as a white solid (9.8 mg, yield 88%).

MS (EI) m/e=1174.5 (M+H).

Step 6:

G5-Ac-Fl-FA-COOH (6), prepared as reported previously, (13.8 mg, 0.00041818 mmol) was dissolved in H$_2$O (5.2 mL), EDM (9.32 mg, 0.03136 mmol) was added. The reaction mixture was stirred for 2 hour at room temperature. A solution of 13 (9.8 mg, 0.0093 mmol) in DMF (4.3 mL) and DMSO (3.4 mL) was added dropwise. The reaction was allowed to stir at room temperature for three days. The solvent was removed by membrane filtration through a 10,000 MWCO membrane. The residue was further purified by passing through a Sephdex G-25 column and extensively washed with PBS buffer and water. Lyophilization gave final product 14 as orange colored solid (15.1 mg, yield 87%).

Example 4

Synthesis of Esterase Sensitive Linker 11C

A synthesis scheme of a dendrimer (e.g., G5 PAMAM dendrimer) conjugated to a therapeutic agent (e.g., Taxol) with an esterase sensitive linker (esterase sensitive elimination linker 11C) is shown below.

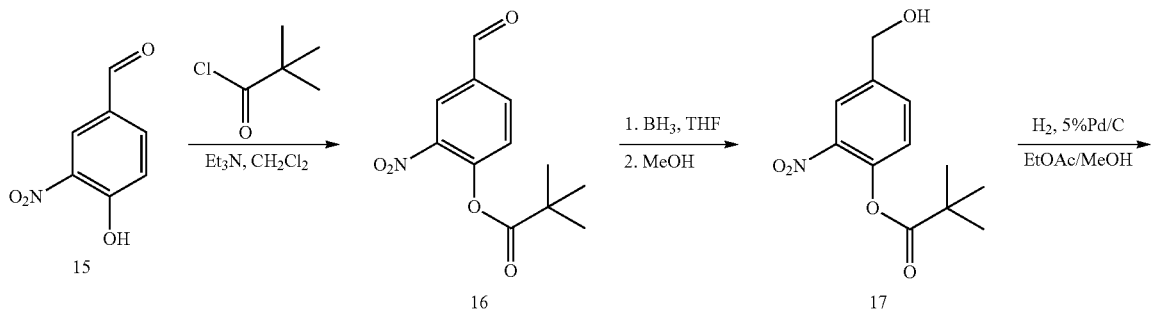

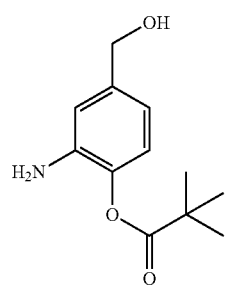

18

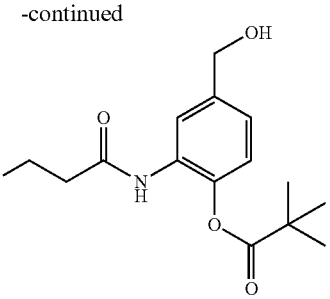

19

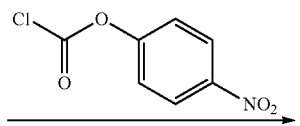

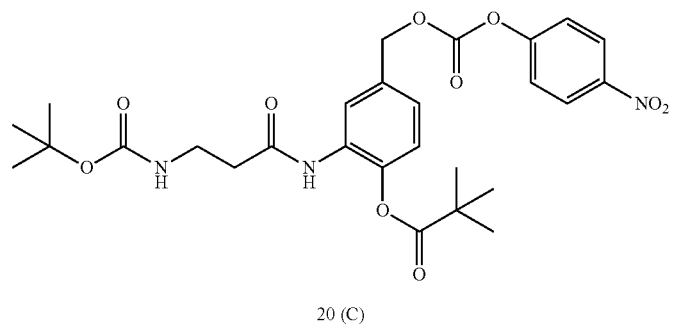

20 (C)

Example 5

Additional Self-Immorlative Linkers

The present invention is not limited by the type of self-immorlative linkers utilized. For example, cyclization based linkers can be used. Although a mechanism is not necessary to practice the present invention and the present invention is not limited to any particular mechanism, in some embodiments, a mechanism as shown below is utilized in a conjugate of the present invention:

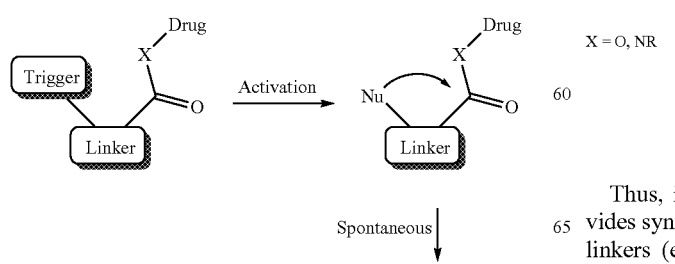

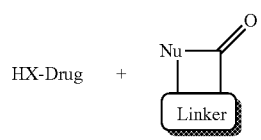

X = O, NR

Thus, in some embodiments, the present invention provides synthesis of dendrimer conjugates utilizing cyclization linkers (e.g., designed as esterase cleavage substrates) as shown below:

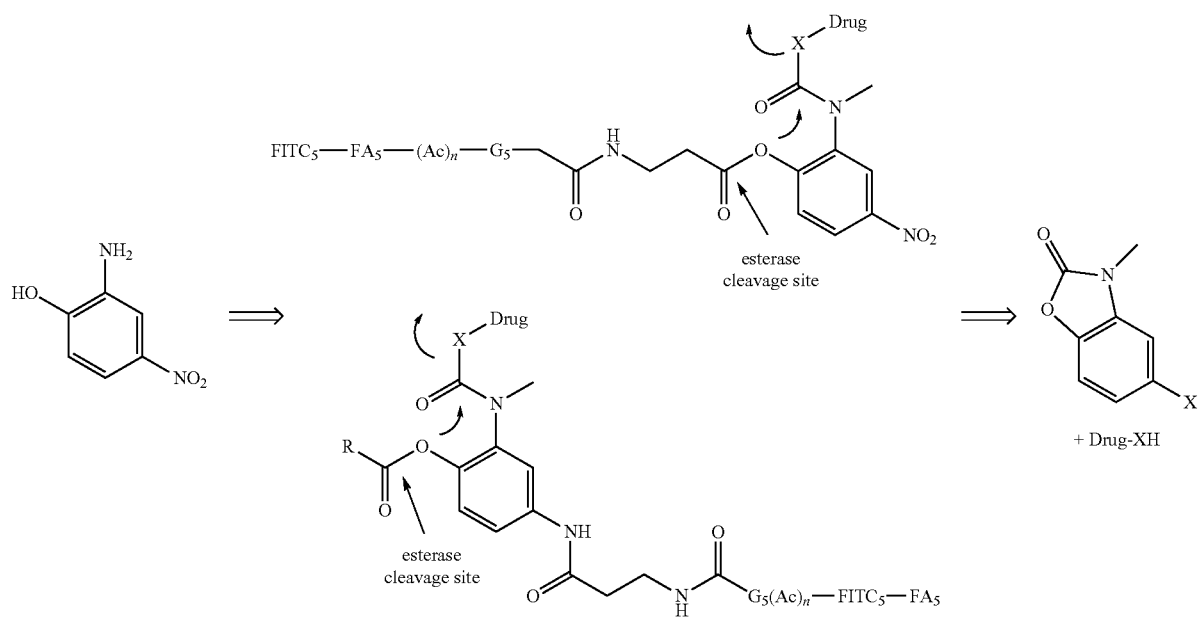
In some embodiments, the present invention provides syntheses of linkers C and D as shown below.
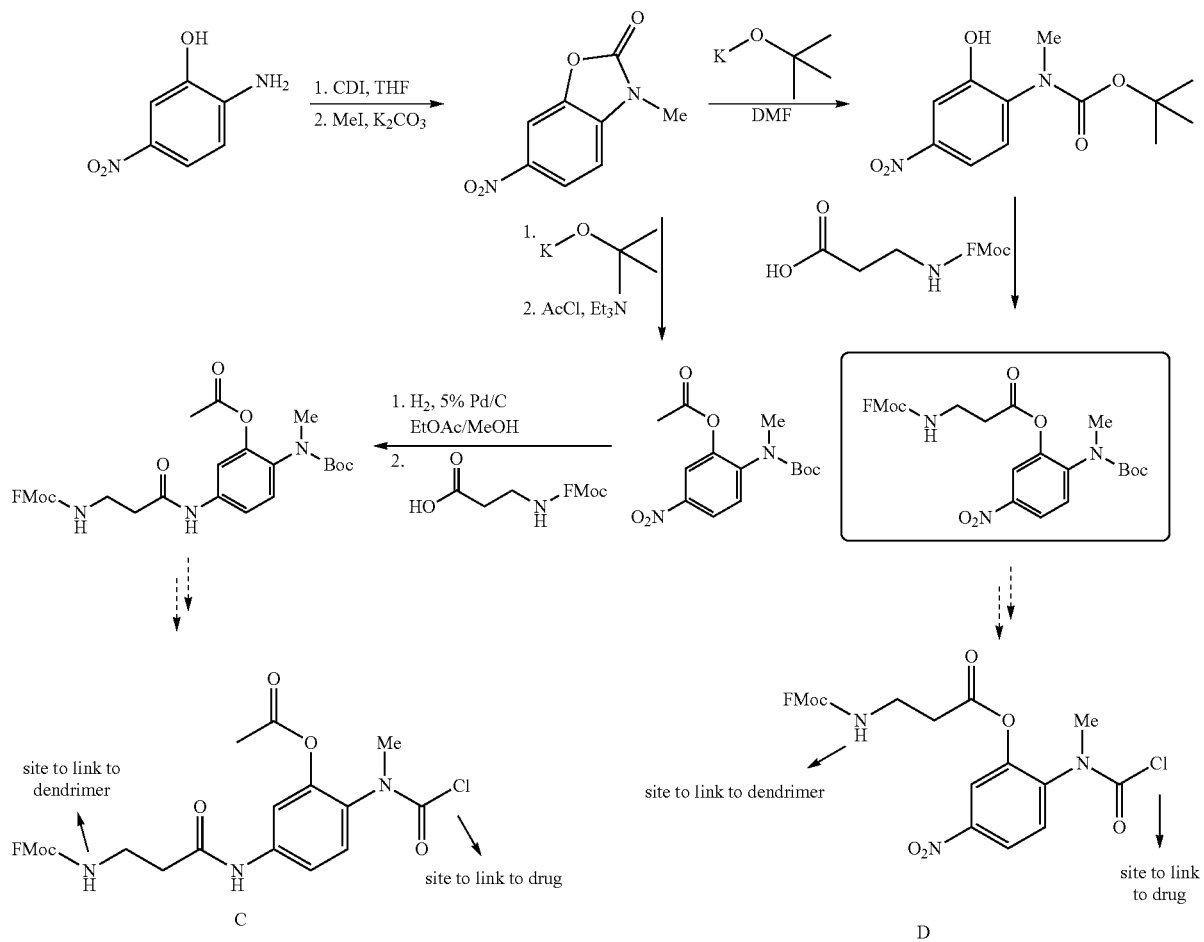

Example 6

Characterization of Dendrimer Conjugates

Experiments were conducted during development of embodiments of the invention in order to characterize release of drug from a dendrimer conjugate comprising a linker-drug component. The linker-drug components were characterized under esterase incubation conditions, utilizing HPLC as an analytical tool to monitor drug release. This approach provides an assessment regarding structural influences of the linkers. For example, characteristics of drug release from a linker (e.g., in the absence of a dendrimer) provides information regarding drug release from a linker conjugated to a dendrimer.

For example, the experiments were conducted to characterize the following two conjugates:

First Generation Linker-Drug(-Dendrimer) Conjugates

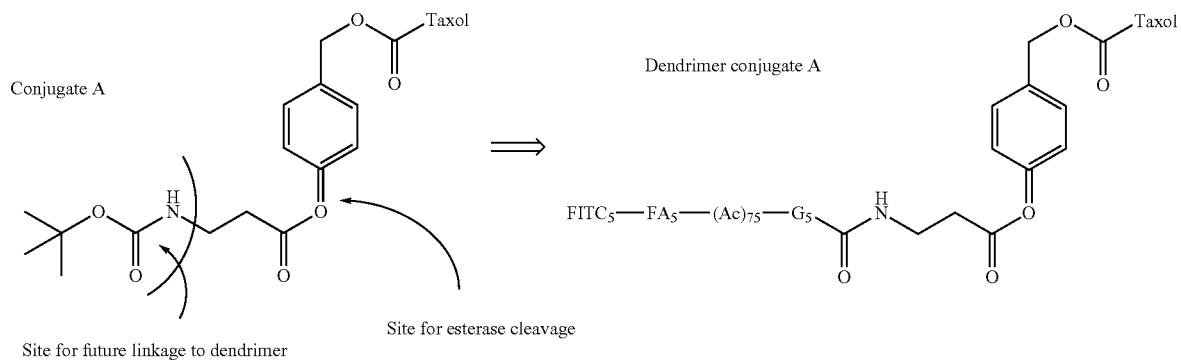

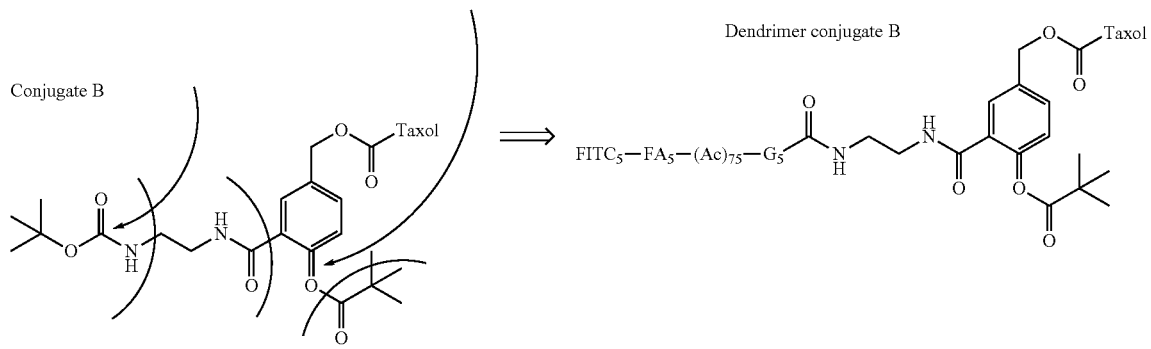

Figure 12:
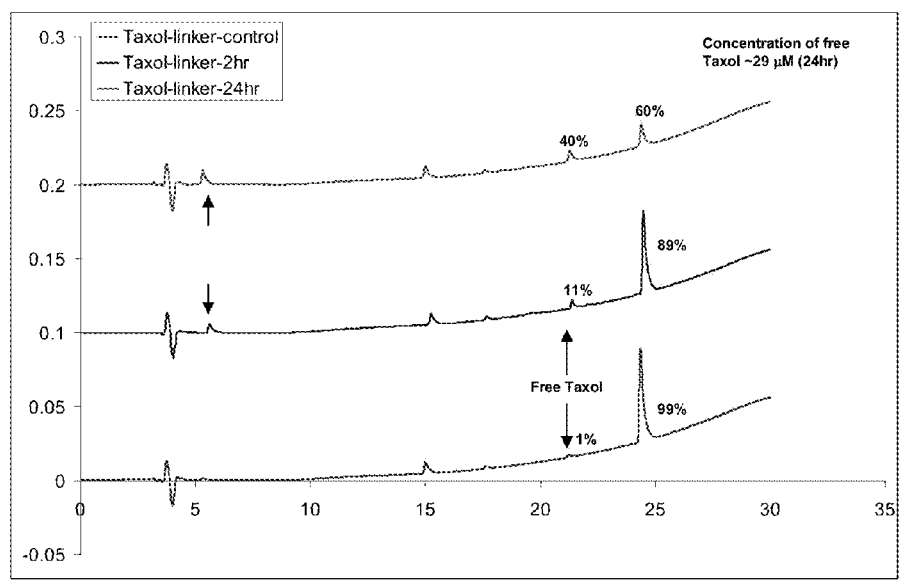
FIG. 12 shows the characterization of therapeutic compound release from dendrimer conjugates of the present invention.

When incubated with pig liver esterase for 2 hours, conjugate B showed minimal release and conjugate A showed ~11% release. Furthermore, conjugate A showed around 40% release at 24 h (See, e.g., FIG. 12).

Example 7

Second Generation Linkers

Characterization of linkers as described in Example 6 indicated that steric hindrance issues were inhibiting release of a therapeutic from the conjugates (e.g., due, in some embodiments, to inaccessibility of esterase to the linker). Based on this data, alternative approaches were generated and characterized. For example, in some embodiments, in order to relieve steric hindrance, lengths of the linkers were extended. Thus, the present invention provides additional, "second generation" linkers as described below.

Second Generation Linker-Drug(-Dendrimer) Conjugates Rational

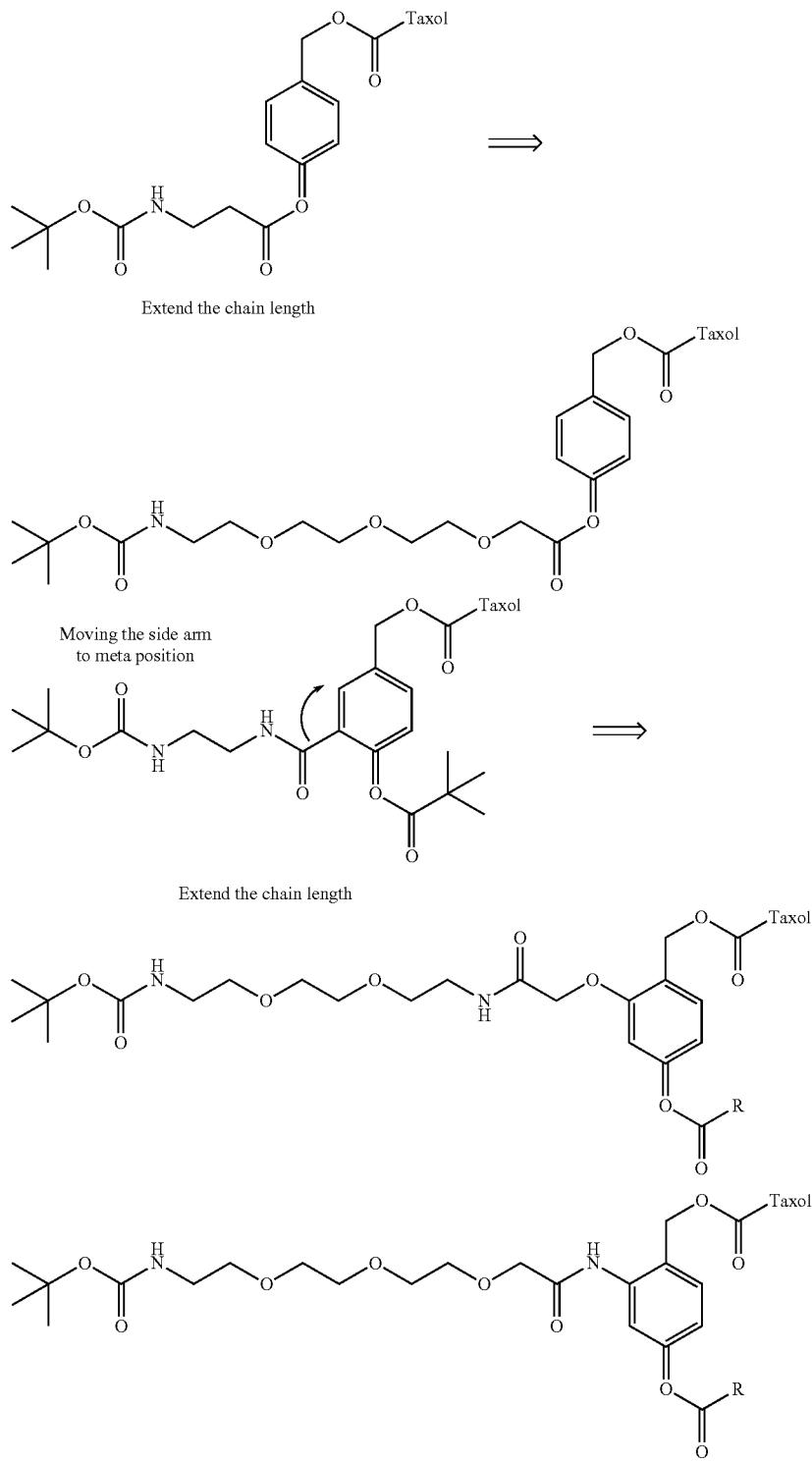

-continued

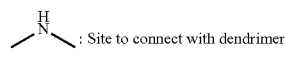: Site to connect with dendrimer

R = Me, t-Bu

Figure 15:
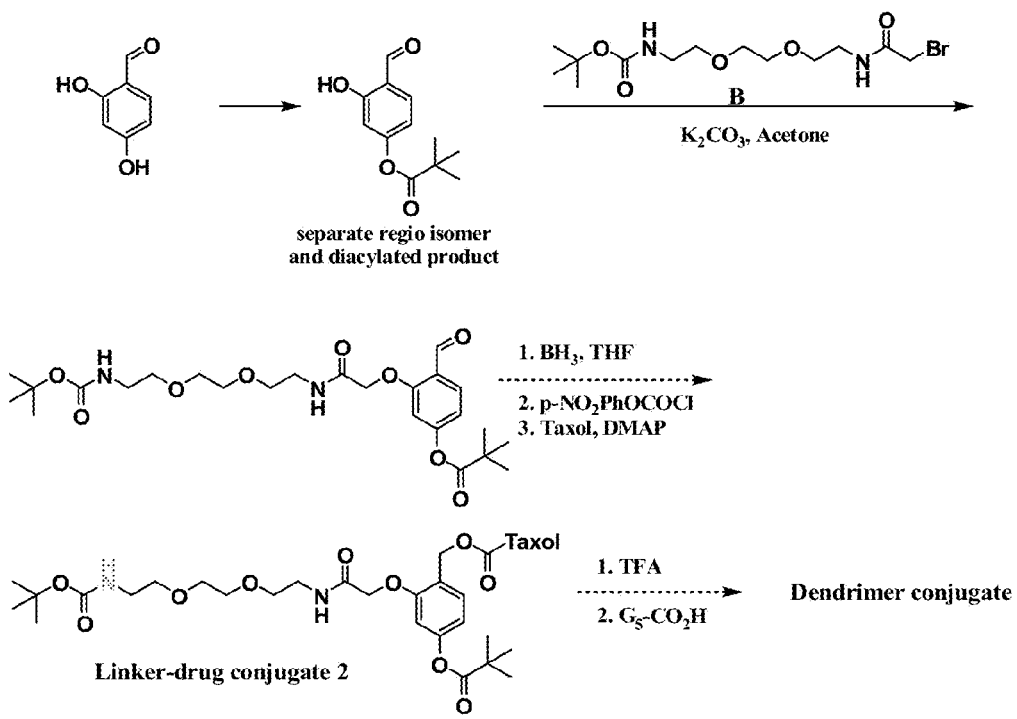
FIG. 15 shows a diagram of a dendrimer conjugate provided in some embodiments of the present invention.
Figure 16:
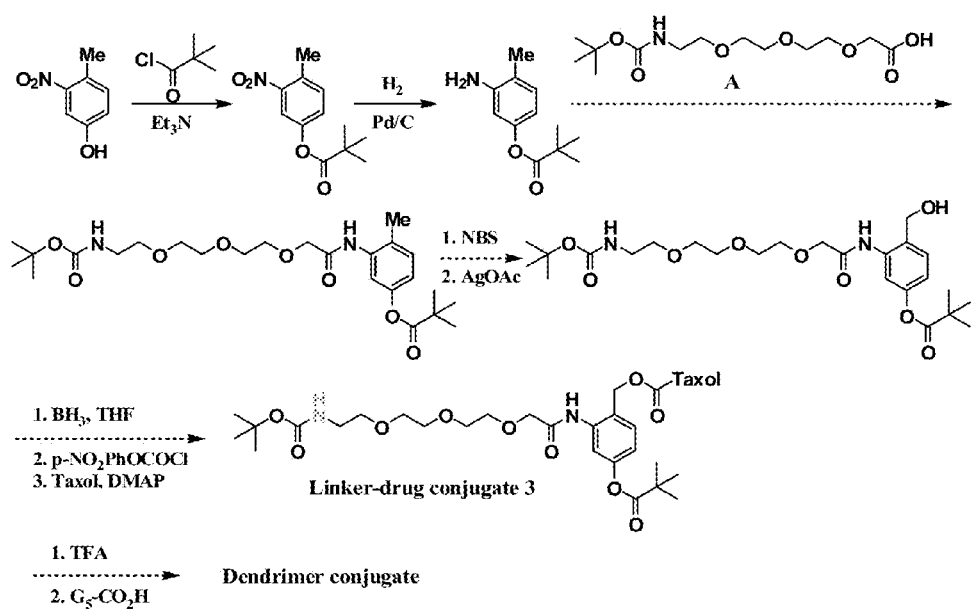
FIG. 16 shows a diagram of a dendrimer conjugate provided in some embodiments of the present invention.

Thus, in some embodiments, the present invention provides conjugates and methods of synthesizing and utilizing (e.g., therapeutically) the same with extended linkages as shown in FIG. 13. In some embodiments the present invention provides conjugates as shown in FIGS. 14-16.

Example 8

Hypoxia induced linkers

Figure 29:
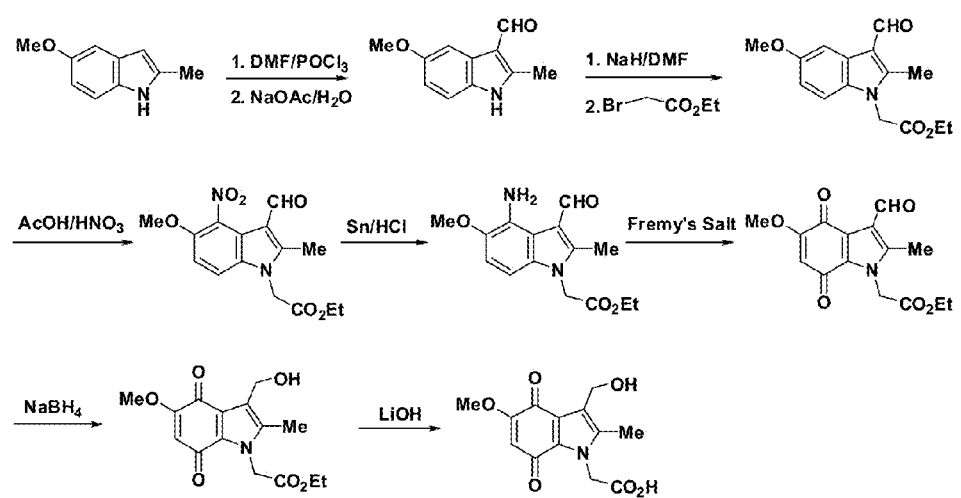
FIG. 29 shows a synthesis scheme for generating a dendrimer comprising a hypoxia induced linker.
Figure 30:
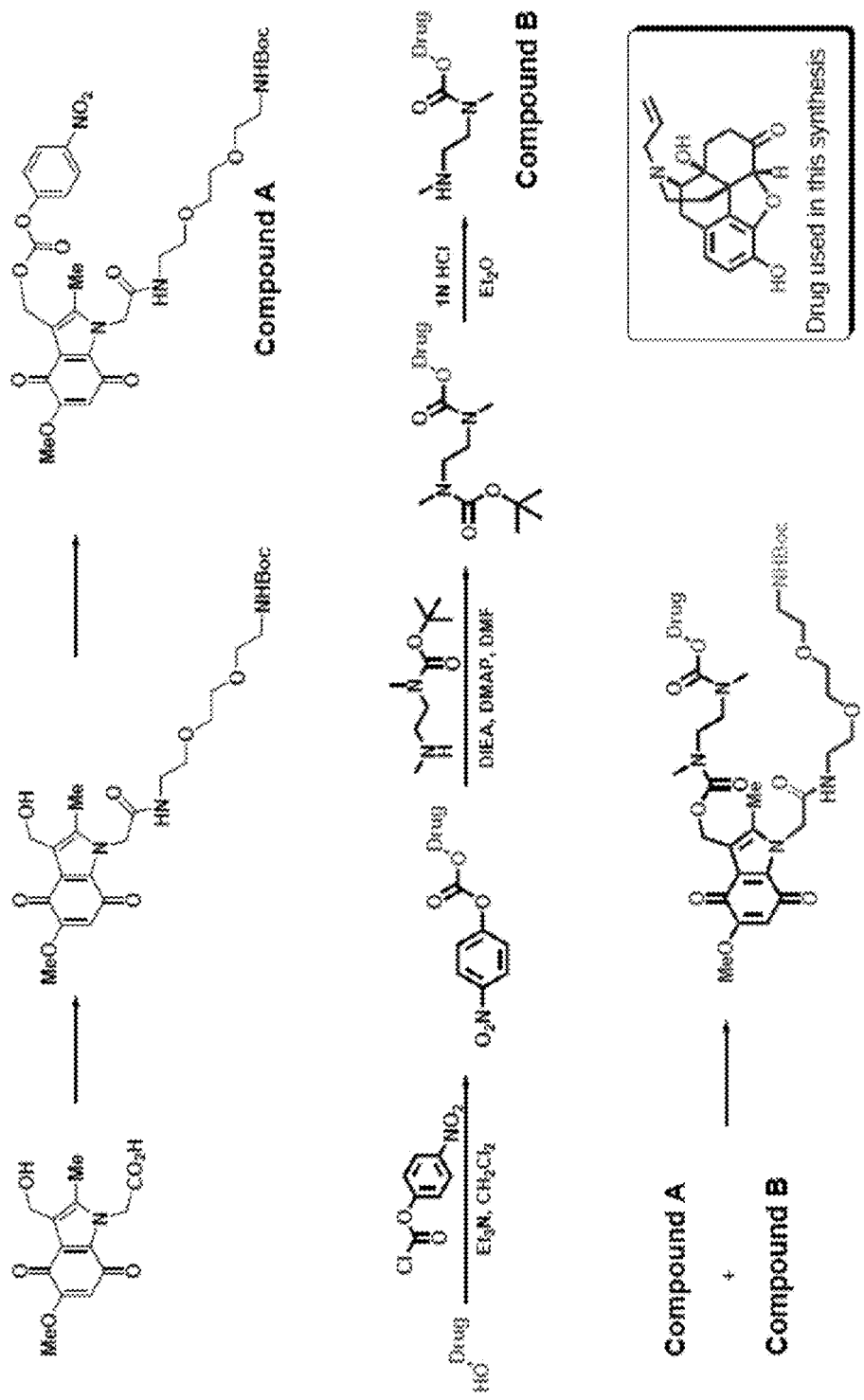
FIG. 30 shows a synthesis scheme for generating a dendrimer comprising a hypoxia induced linker.
Figure 31:
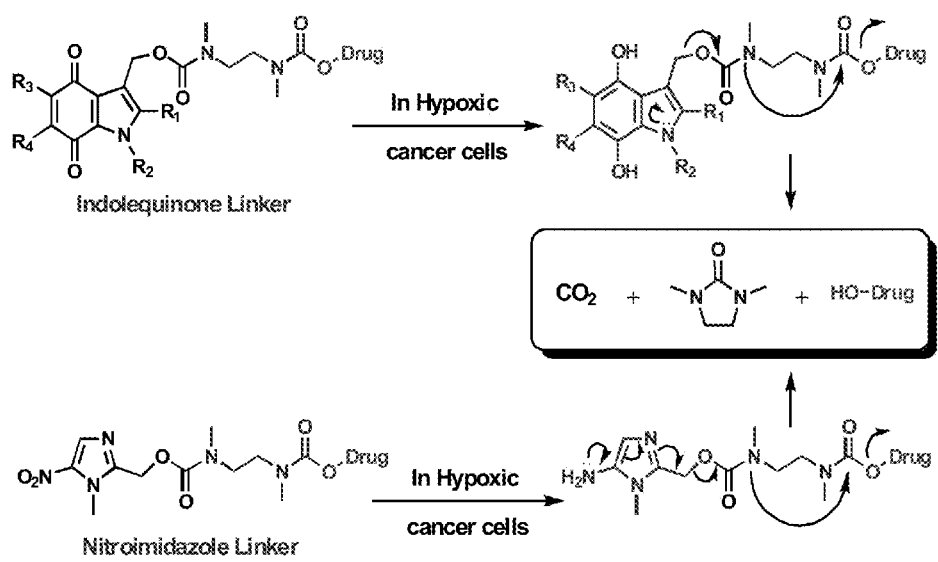
FIG. 31 shows a diagram depicting a mechanism of release of a therapeutic agent from a dendrimer comprising a hypoxia sensitive linker.

The present invention also provides dendrimers comprising small molecule linkers triggered by hypoxic environments (e.g., in and/or around cancer cells). In some embodiments, a dendrimer of the present invention comprises a indolequinone linker. In some embodiments, a dendrimer comprising a hypoxia cleavable linker is generated according to the synthesis scheme shown in FIG. 29. In some embodiments, a dendrimer comprising a hypoxia cleavable linker is generated according to the synthesis scheme shown in FIG. 30. The present invention is not limited to any particular mechanism of release of a therapeutic agent from a dendrimer comprising a linker triggered by a hypoxic environment. Indeed, a variety of mechanisms are contemplated including, but not limited to, a mechanism shown in FIG. 31.

Example 9

Synthesis and Conjugation of Locking Agent

For the synthesis of the locking module (tetrahydropyridinium, 3-[[(3-carboxypropyl)amino]carbonyl]-1-methyl), γ-aminobutyric acid (GABA), benzyl ester is linked to an interconvertible tetrahydronicotinamide/quaternary nicotinamide salt structure that is able to participate in a re-dox type reaction. The tetrahydronicotinamides are lipophilic stable compounds that readily oxidize back to precursor quaternary salts by oxidase and peroxidase enzymes in vivo. The synthesis of this compound is performed according to a modified literature procedure (see, e.g., Carelli, V., et al., Bioorganic & Medicinal Chemistry Letters, 2003. 13(21): p. 3765-3769; herein incorporated by reference in its entirety) (Scheme 4). Reaction of the GABA ester with nicotinoyl chloride gives the corresponding nicotinamide derivative. The deprotection of the benzyl ester by hydrogenation using Pd/C catalyst yields the GABA derivative that is transformed to a quaternary salt by treatment with dimethyl-sulfate. The pyridinium salt is reduced with $Na_2S_2O_4$ or electrochemically to give a tetrahydronicotinamide derivative. This compound is conjugated in varying ratios to partially acetylated dendrimer using carbodimide coupling to give the desired locking function to the dendrimer conjugate.

Scheme 4. Synthesis of locking module.

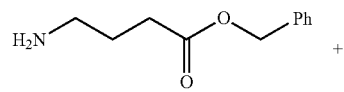

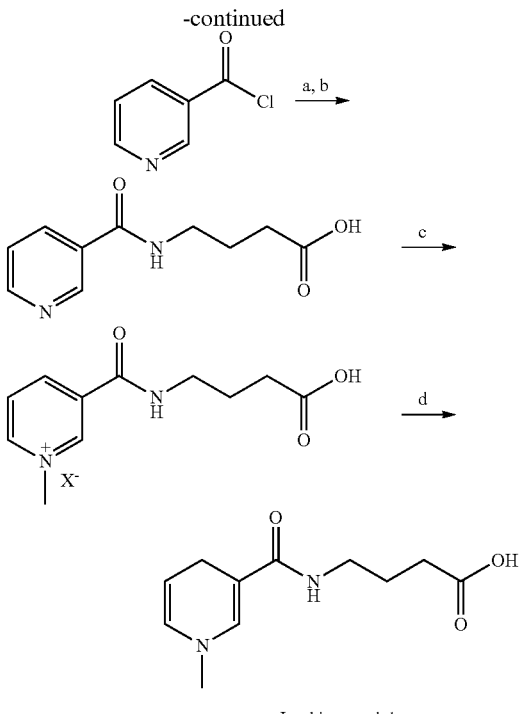

Locking module a) $Et_3N$, $CHCl_3$ b) $H_2$, Pd/C c) $(CH_3)_2SO_4$ d) $NaS_2O_4$ Example 10

Synthesis and Conjugation of Drug-Linkers

Syntheses of Esterase Sensitive Morphine-linker for Conjugated to the CNS Targeting Dendrimer Prodrug approaches have been applied to Morphine in many studies in order to improve solubility, absorption, tissue selectivity, and other drug delivery properties. Generally, either or both 3- and 6-hydroxyl groups are converted to an ester (see, e.g., Christrup, L. L., et al., International Journal of Pharmaceutics, 1997. 154(2): p. 157-165; Drustrup, J., et al., International Journal of Pharmaceutics, 1991. 71(1-2): p. 105-116; Groth, L., et al., International Journal of Pharmaceutics, 1997. 154(2): p. 149-155; Mignat, C., et al., Journal of Pharmaceutical Sciences, 1996. 85(7): p. 690-694; each herein incorporated by reference in their entireties). The kinetics of ester enzymatic hydrolysis have been studied well. The present invention provides dendrimer conjugates wherein ester prodrugs are attached to a dendrimer platform that possesses CNS targeting characteristics. Since the structural features of the ester significantly affect the rate of hydrolysis, three different ester linkages between Morphine and the dendrimer are provided. Serum esterase catalyzed drug release reactions are carried out to find the desired hydrolysis profile.

Morphine-linker A, a 3-Aliphatic Acid Ester (See, e.g., Daniels, T. R., et al., Clinical Immunology, 2006. 121(2): p. 159-176; Daniels, T. R., et al., Clinical Immunology, 2006.

121(2): p. 144-158; Carelli, V., et al., Bioorganic & Medicinal Chemistry Letters, 2003. 13(21): p. 3765-3769; each herein incorporated by reference in their entireties).

Synthesis of the Morphine-linker A is straightforward as shown in Scheme 5. Morphine hydrochloric acid salt will be reacted with glutaric anhydride in basic aqueous solution to afford the desired product.

Scheme 5: Morhpine-linker A.

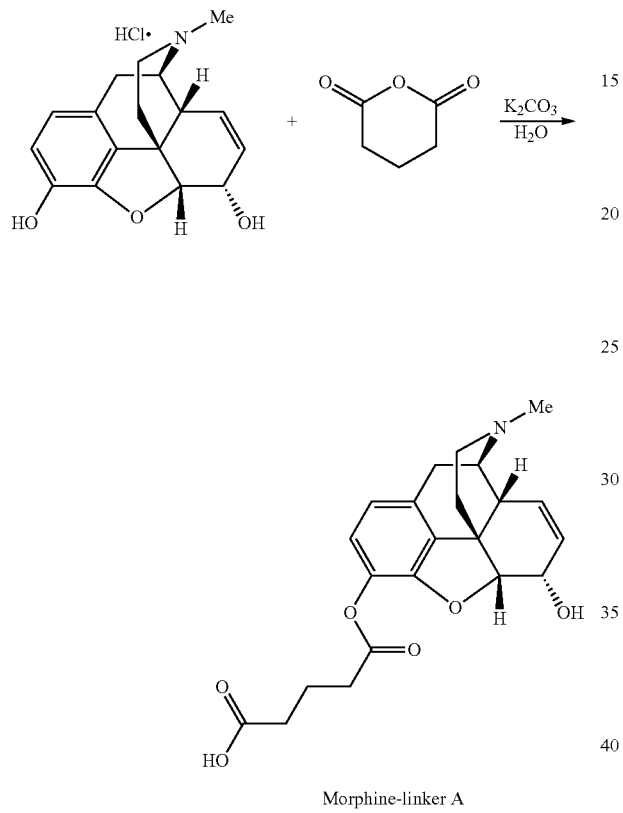

Morphine-linker A

Morphine-linker B, a 3-Aromatic Acid Ester (see, e.g., Majoros, I. J., et al., Biomacromolecules, 2006. 7(2): p. 572-579; herein incorporated by reference in its entirety).

The 3-morphine ester of the 4-N-Boc-benzoic acid is formed in a reaction with carbonyldiimidazole (CDI) in the presence of a base. The Boc group is removed by treatment with 1N HCl in ether. The free amino group is immediately reacted with glutaric anhydride to obtain the morphine-linker B (Scheme 6).

Scheme 6. Morphine-linker B

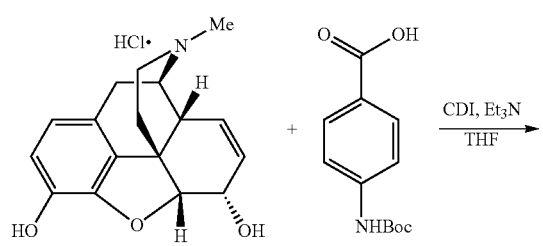

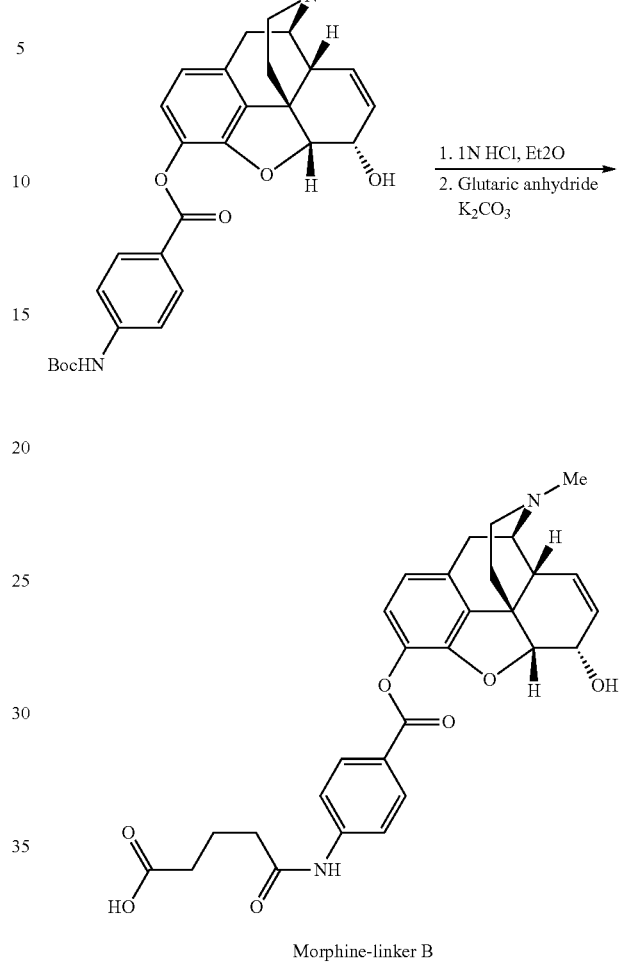

Morphine-linker B

Morphine-linker C Through a Self-Immolative Linker

Self-immolative linkers have been proven to be a critical factor in the success of the widely applied tripartite prodrug approach. A 1,6-elimination linker (Linker A in Scheme 7), is activated by serum esterases and used to conjugate Morphine to dendrimers. Synthesis of this linker is well documented and its reaction with morphine is carried out in methylene chloride in the presence of diisopropyl ethyl amine and 4-(dimethylamino) pyridine (DMAP). The N-Boc group is removed under mild acidic conditions and the resulting amino group reacted with glutaric anhydride to form the desired product (Scheme 7).

Scheme 7. Morphine-linker C.

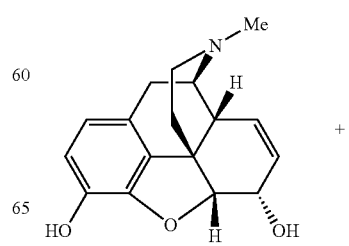

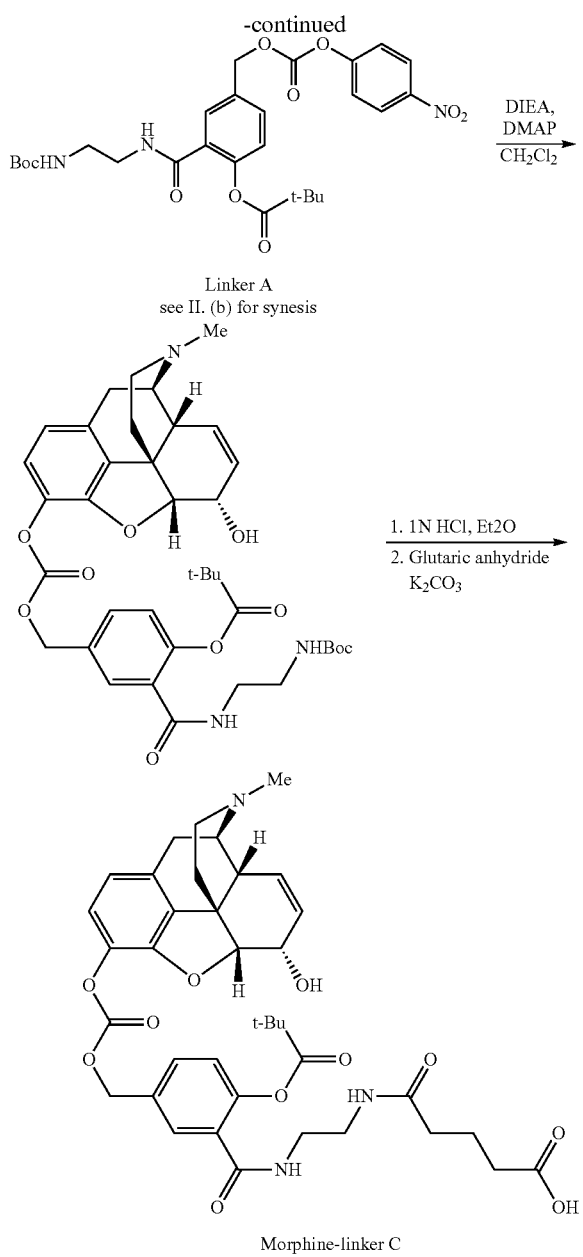

Conjugation of the Morphine-linker Compounds to the Dendrimer Attached with a Locking Module Each of the Morphine-linker units are conjugated to the dendrimer which has already been attached with the locking module. EDC chemistry is employed to promote the amide bond formation. The conjugates are isolated and purified using ultrafiltration and HPLC techniques.

Example 11

Conjugation of CNS Targeting Moiety

Small molecules such as folic acid (see, e.g., Majoros, I. J., et al., Biomacromolecules, 2006. 7(2): p. 572-579; Majoros, I. J., et al., Journal of Medicinal Chemistry, 2005. 48(19): p. 5892-5899; each herein incorporated by reference in their entireties), peptides (RGD and EGF) (see, e.g., Shukla, R., et al., Chemical Communications, 2005(46): p. 5739-5741; herein incporoated by reference in its entirety) and Her2 antibodies (see, e.g., Shukla, R., et al., Bioconjugate Chemistry, 2006. 17(5): p. 1109-1115; herein incorporated by reference in its entirety) target partially acetylated dendrimer conjugates to tumor cells expressing these antigens. Transferrin is used to cross the BBB and a small peptide (Tet 1) to target neurons in the CNS. Transferrin has been utilized as a targeting vector to transport a drugs, liposomes and proteins across the BBB by receptor mediated transcytosis (see, e.g., Smith, M. W. and M. Gumbleton, Journal of Drug Targeting, 2006. 14(4): p. 191-214; herein incorporated by reference in its entirety). Fluorescein-conjugated, synthetic Tet1 peptide binds strongly to cultured PC 12, primary motor neurons, and dorsal root ganglion (DRG) cells. Tet1 peptide also binds and internalizes in DRG and motor neurons, but not muscles in tissue sections. As such, Tet1 can be used to target neurons once the complex reaches the CNS.

Conjugation of Transferrin

Transferrin is conjugated to the dendrimer in two steps as described in the literature (see, e.g., Smith, M. W. and M. Gumbleton, Journal of Drug Targeting, 2006. 14(4): p. 191-214; herein incorporated by reference in its entirety). First, a thiol reactive maleimide group is introduced on the dendrimer by reacting with sulfo-SMCC at room temperature for 2 h. The dendrimer conjugate is purified by gel filtration on a Sephadex G-25 column and subsequent dialysis. Next, sulfhydryl groups are introduced using Traut's reagent. Briefly, a cold solution of human holotransferrin in PBS-EDTA buffer (pH 7.4) is mixed with iminothiolane and allowed to react for 1 h. The modified transferrin is purified by eluting the mixture on a PD-10 column using PBS-EDTA buffer. The degree of thiol modification is determined using Ellman assay. The maleimide derivatized dendrimer is reacted with thiol-modified transferrin (Tf-SH) for 2 h. to give a stable thioether bond. The reaction is stopped by quenching unreacted thiol groups with N-ethylmaleimide. The final conjugate is purified by ultrafiltration (MWCO 100,000) and analyzed by HPLC, PAGE and UV-vis spectroscopy.

Conjugation of Peptide (Tet 1)

Multiple peptide ligands on the dendrimer allow for polyvalent interactions between the ligands and cell surface targeting molecules in a way that provides a much stronger interaction than what is achieved with a single peptide interaction. Recently, a linear peptide (Tet 1, HLNILSTLWKYR (SEQ ID NO:1) with the binding characteristics of tetanus toxin was identified by using phage display. Tet1 is used for targeted delivery of the narcotic analgesic/antagonist to the CNS. The peptide is synthesized with a terminal sulphydral linker. This peptide-SH molecule is conjugated to the dendrimer using standard protocols, and the conjugate is purified by dialysis or gel-filtration to remove excess reagents. PAGE and other analytical techniques are employed to determine the extent of peptide conjugation in the product.

Conjugation of the Morphine-Linker Compounds to the CNS Targeted Dendrimer

The narcotic analgesic, Morphine, is conjugated to the dendrimer using different esterase sensitive linkers. Morphine-linker compounds can be conjugated to the dendrimer in two reaction steps. First, an active ester of the drug-linker is prepared using EDC in a DMF/DMSO solvent mixture in the presence of HOBt. This active ester solution is then be added to the aqueous solution of the dendrimer modified with a targeting and locking function. The reaction mixture is allowed to react for 24 h. (Scheme 8). The final conjugate is purified using ultrafiltration and characterized.

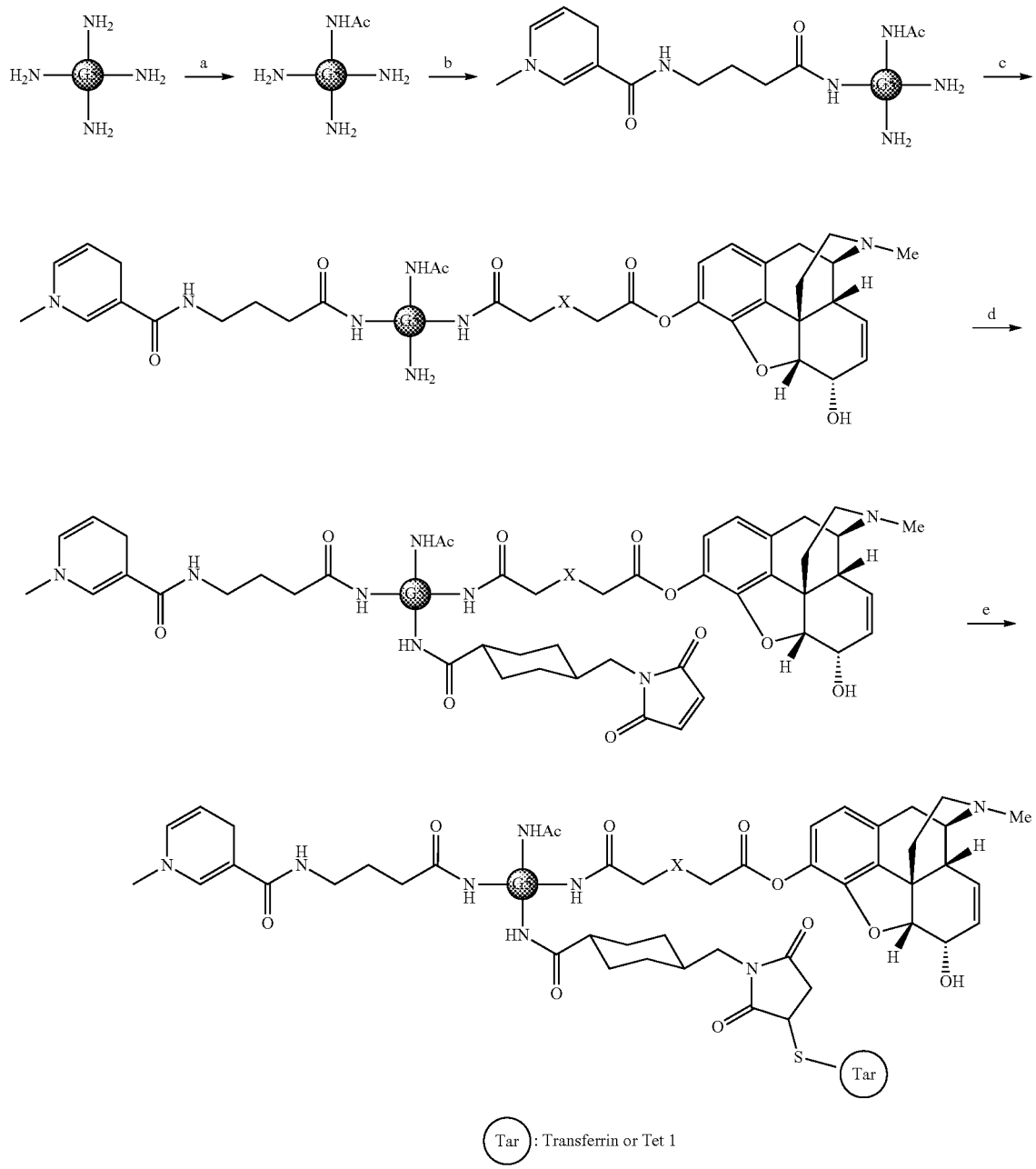

Scheme 8. Conjugation of the Morphine-linker compounds to the CNS targeted dendrimer.

(Tar): Transferrin or Tet 1 a) Ac₂O, Et₃N b) Locking compound, EDC, HOBt c) Morphine-linker, EDC, HOBt
d) Sulfo-LC-SMCC e) Tf—SH or Pep—SH

Example 12

Syntheses of Hypoxia Triggered Naloxone-linker Units to be Conjugated with CNS Targeting Dendrimer Naloxone-indoquinone Linker (see, e.g., Naylor, M. A., et al., Journal of Medicinal Chemistry, 1997. 40(15): p. 2335-2346; Zhang, Z., et al., Organic & Biomolecular Chemistry, 2005. 3(10): p. 1905-1910).

Synthesis of the indoquinone-Naloxone linker involves multiple steps. Starting from 2-methyl-5-methoxyindole, alkylation on nitrogen with sodium hydride and t-butyl 4-bromobutanoate, followed by formylation provides the 3-formyl indole. After the nitration reaction, the 4-NO₂ group is reduced to the amino group. Treatment with Fremy's salt produces the indoquinone structure. The 3-formyl group is reduced and converted to 4-NO₂-phenyl carbonate compound A. Morphine is converted to the carbamate compound B through an activated carbonate intermediate. Compounds A and B are combined in the presence of an amine in DMF to provide the completed drug-linker unit after an acid catalyzed t-butyl ester hydrolysis (Scheme 9).

Scheme 9. Synthesis of the indoquinone-Naloxone linker.
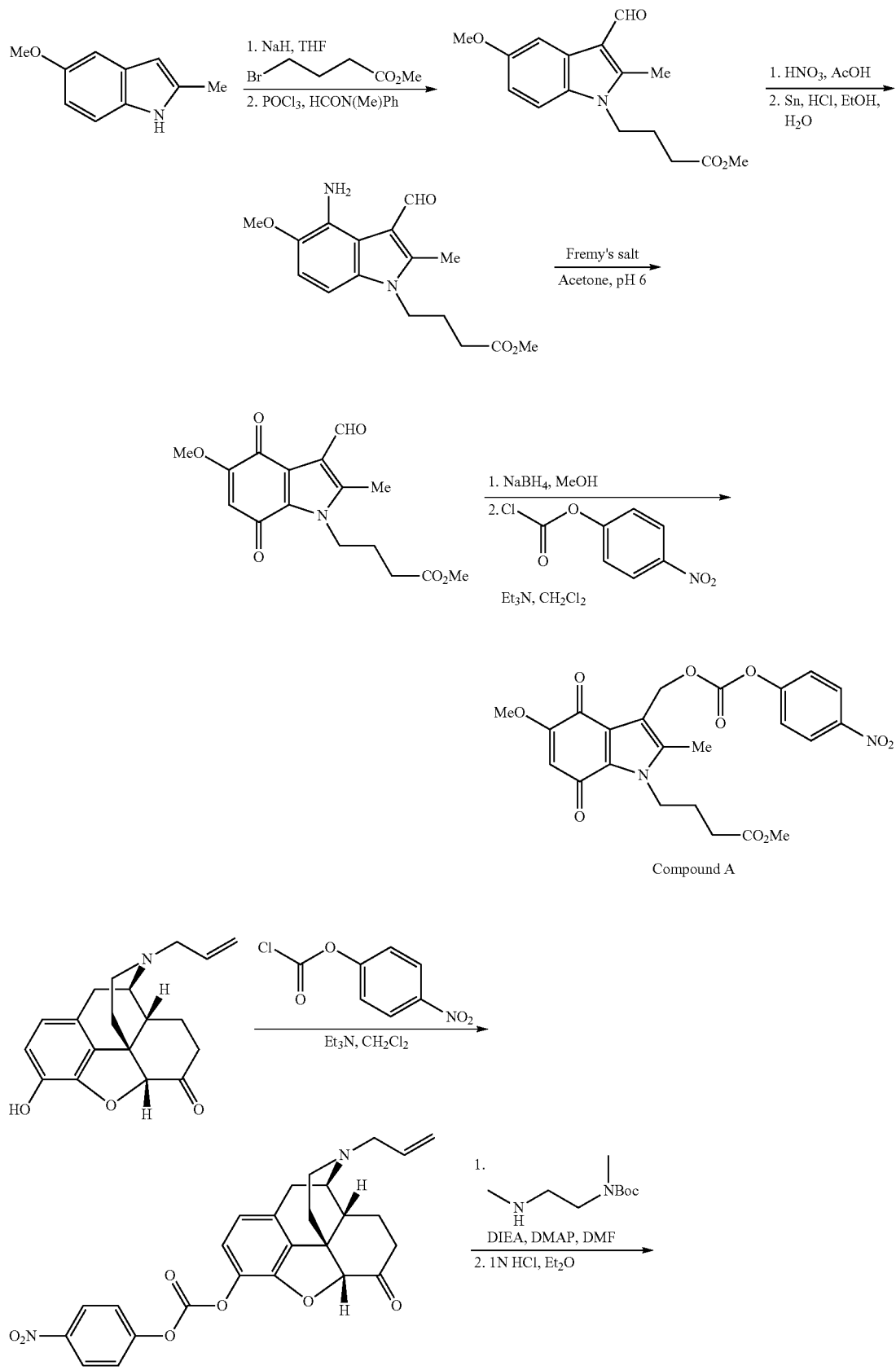

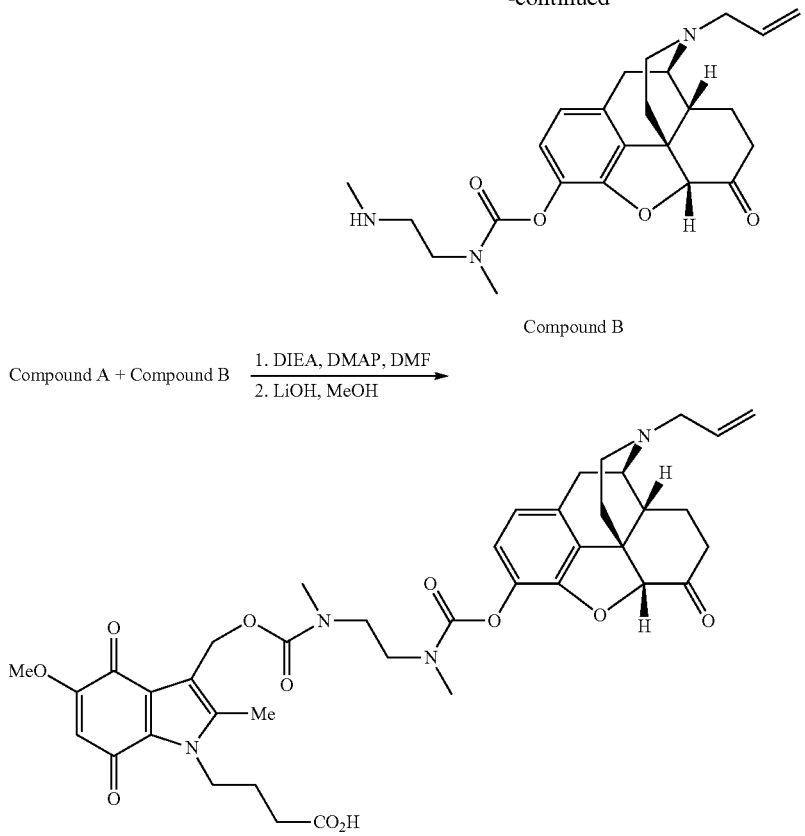

Compound B

Compound A + Compound B  →  1. DIEA, DMAP, DMF
                               2. LiOH, MeOH Naloxone-nitroimidazole Linker (see, e.g., Hay, M. P., et al., Journal of Medicinal Chemistry, 2003. 46(25): p. 5533-5545; Hay, M. P., W. R. Wilson, and W. A. Denny, Tetrahedron, 2000. 56(4): p. 645-657; each herein incorporated by reference in their entireties).

A nitroimidazole template is used as a reductive drug releasing system to couple Naloxone. The one position on the drug is alkylated with t-butyl 4-bromobutanoate and the 2-hydroxymethyl group is introduced by a reaction with paraformaldehyde. After conversion of the hydroxyl group to an activated carbonate, it is coupled with a dendrimer previously mentioned compound B (see Scheme 9) in the presence of a base. The t-butyl ester is removed to yield the Naloxone-linker unit that is ready to be conjugated to the dendrimer carrier (Scheme 10).

Scheme 10. Naloxone-nitroimidazole linker.

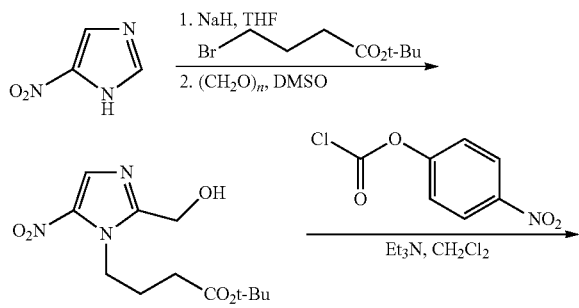

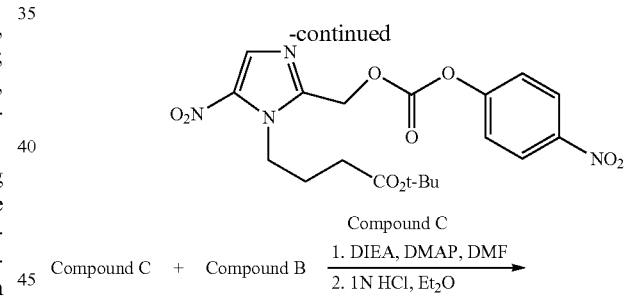

Compound C

Compound C + Compound B  →  1. DIEA, DMAP, DMF
                               2. 1N HCl, Et₂O

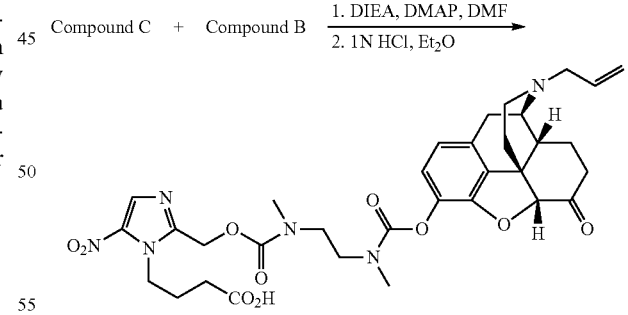

Example 13

Design and Syntheses of Peripherally Active Drug-Dendrimer Conjugates Tripartite Prodrug Linker Design Strategy The tripartite prodrug strategy has been well studied and successfully applied to numerous drug delivery systems especially in targeted cancer therapeutics (see, e.g., de Groot, F. M. H., E. W. P. Damen, and H. W. Scheeren, Curr. Med.

Chem.—Anti-Cancer Agents, 2001. 8 p. 1093-1122; Dubowchik, G. M. and M. A. Walker, Pharmacology & Therapeutics, 1999. 83: p. 67-123; Papot, S., et al., Curr. Med. Chem.—Anti-Cancer Agents, 2002. 2: p. 155-185; each herein incorporated by reference in their entireties). The general principle of drug release is shown in the following simplified scheme. Namely, a trigger unit is attached to a hetero atom, such as an oxygen or nitrogen, on a unique linker, which is in turn attached to the drug of interest through a carbonate or a carbamate linkage. Once the trigger is recognized and cleaved by an enzyme in the body, the linker spontaneously decomposes to lead a facile liberation of the drug. This strategy has been proven to be effective as a powerful delivery system for various hydroxyl and amino group containing drug (X=O, NH). In Scheme 11, an 1,6-elimination linker is used for illustration purposes although many other types are available to accomplish the similar goals of drug release (see, e.g., de Groot, F. M. H., et al., Angew. Chem. Int. Ed., 2003. 42: p. 4490-4494; de Groot, F. M. H., et al., J. Org. Chem., 2001. 66: p. 8815-8830; Greenwald, R. B., et al., J. Med. Chem., 1999. 42: p. 3657-3667; Greenwald, R. B., et al., Bioconjugate Chem., 2003. 14: p. 395-403; Zhang, Z., et al., Pharmaceutical Research, 2005. 22: p. 381-389; each herein incorporated by reference in their entireties). As shown in Scheme 11, the dendrimer conjugates takes advantage of the serum esterase (see, e.g., Antczak, C., et al., Bioorg. & Med. Chem., 2001. 9: p. 2843-2848; Pohl, T. and H. Waldmann, J. Am. Chem. Soc., 1997. 119: p. 6702-6710; Sauerbrei, B., V. Jungmann, and H. Waldmann, Angew. Chem. Int. Ed., 1998. 37: p. 1143-1146; each herein incorporated by reference in their entireties) to activate the trigger unit in the prodrug constructs. Furthermore, the prodrug construct is conjugated to the unique dendrimer platform as a drug delivery carrier.

Synthesis of the Esterase Sensitive Linker Moieties

Typical 1,6-elimination linkers are used that can be activated by serum esterase. Since the rate of the ester bond cleavage can be significantly affected by the structural features at the acid side, the pivalate (see, e.g., Antczak, C., et al., Bioorg. & Med. Chem., 2001. 9: p. 2843-2848; herein incorporated by reference in its entirety) and phenylacetate (see, e.g., Pohl, T. and H. Waldmann, J. Am. Chem. Soc., 1997. 119: p. 6702-6710; herein incorporated by reference in its entirety) are used as the first set of templates to test the rate of drug release. Further Structure-Activity-Relationship (SAR) studies on the linkers is carried out in order to achieve the optimal drug releasing profile.

As shown in Scheme 12, therapeutics are attached to the linker with R=t-Bu. The 5-formylsalicyclic acid is coupled with mono-Boc-ethylenediamine under an EDC catalyzed condition in DMF. The crude product is treated with an acyl chloride (2 eq) and triethyl amine (2.5 eq) simultaneously. After isolation and purification by silica gel chromatography, the product is reduced by boran in THF. The benzyl alcohol product is treated with p-nitrobenzyl chloroformate in the presence of pyridine and 4-(dimethylamino)pyridine (DMAP). The product is isolated and purified by silica gel chromatography.

Scheme 11. Drug releasing mechanism of the tripartite prodrug strategy.

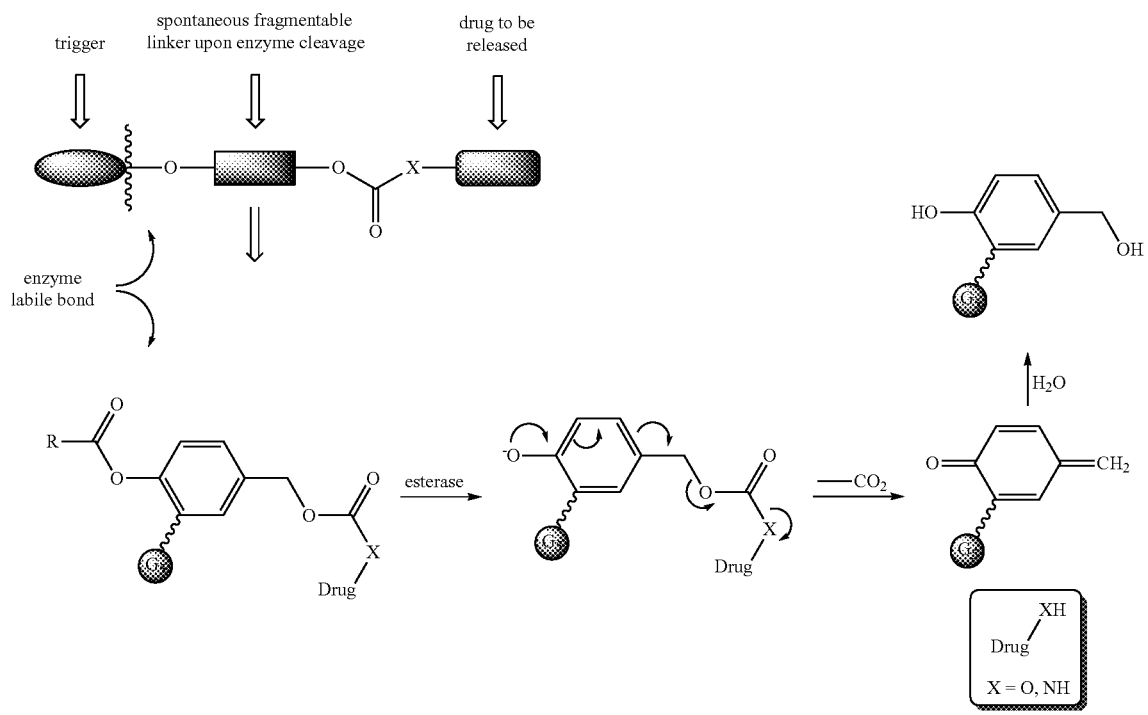

Scheme 12. Synthesis of the esterase cleavable linker.

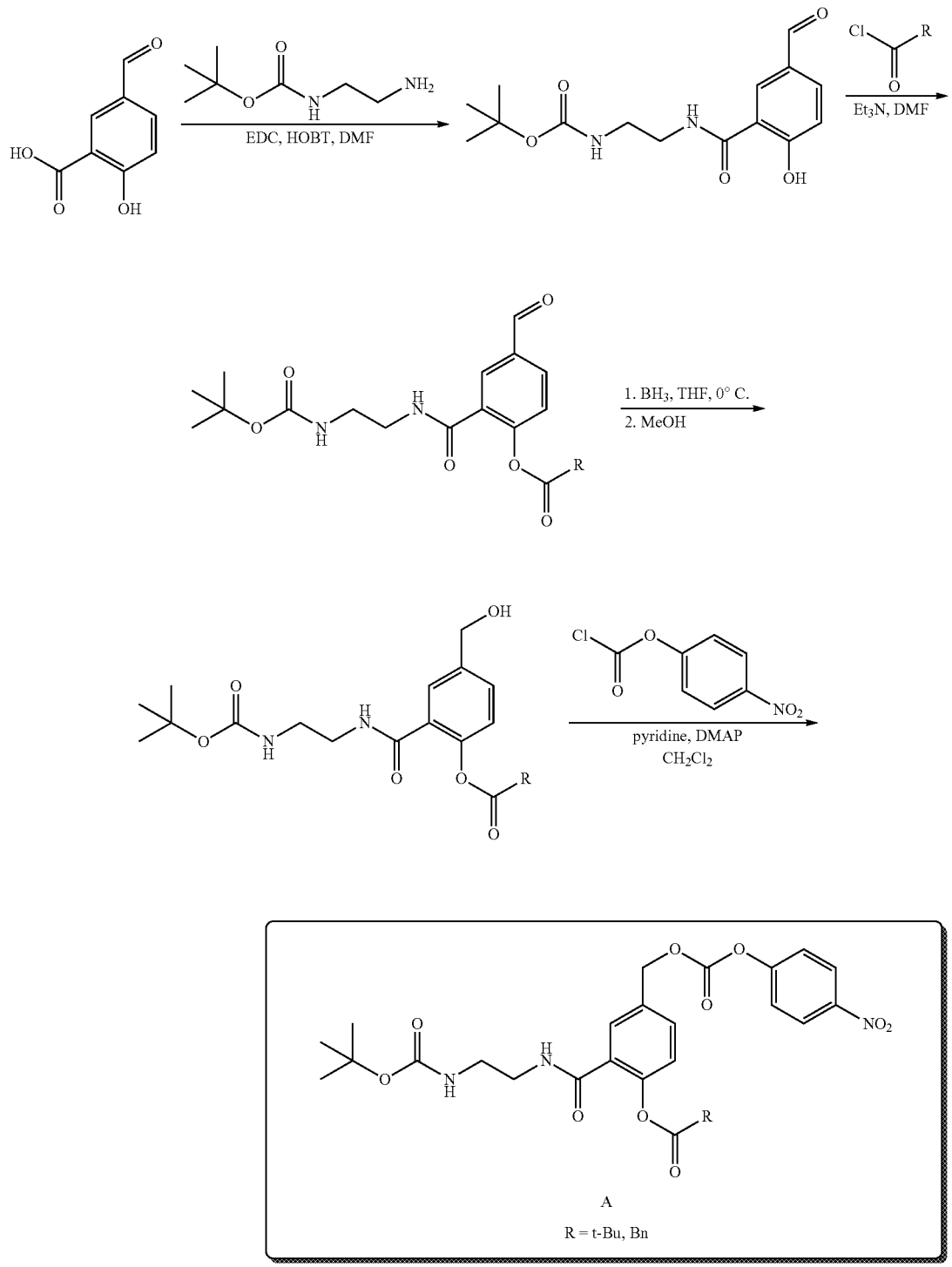

A
R = t-Bu, Bn

Attachments of Ketamine and Lorazepam to the Esterase Sensitive Linker Units

The drugs for this study, Ketamine and Lorazepam, will be attached to the above mentioned linkers through a displacement reaction of the 4-nitrophenol group to form a carbamate linkage (Ketamine (see, e.g., Leung, L. Y. and T. A. Baillie, J. Med. Chem., 1986. 29: p. 2396-2399; Woolf, T., et al., J. Org. Chem., 1984. 49: p. 3305-3310; each herein incorporated by reference in their entireties)) and a carbonate linkage (Lorazepam (see, e.g., Nudelman, A., R. J. McCaully, and S. C. Bell, J. Pharm. Sci., 1974. 63: p. 1880-1885; herein incorporated by reference in its entireties)), respectively, in the presence of N,N-diisopropylethyl amine (DIEA) and DMAP in DMF (Scheme 13).

Scheme 13. Synthesis of the drug-linker units.

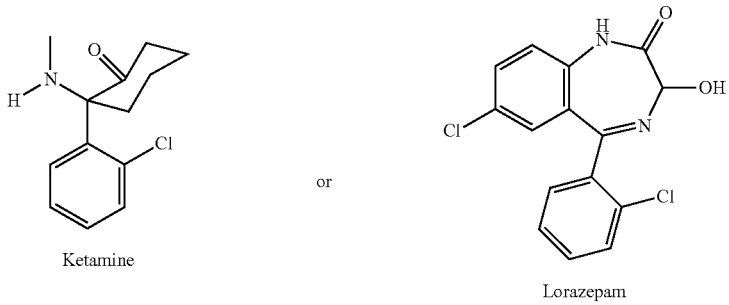

Ketamine or Lorazepam

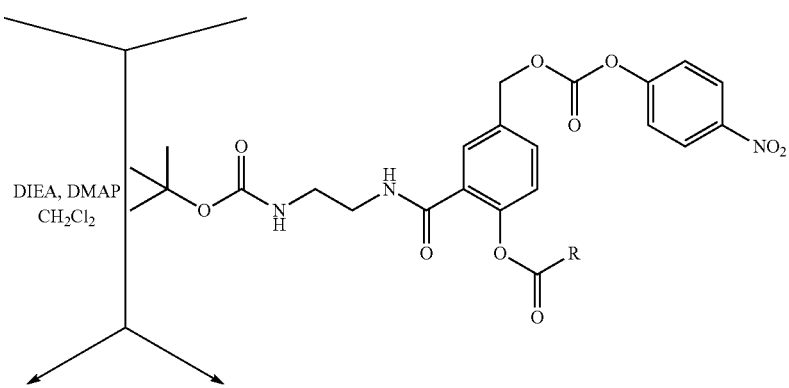

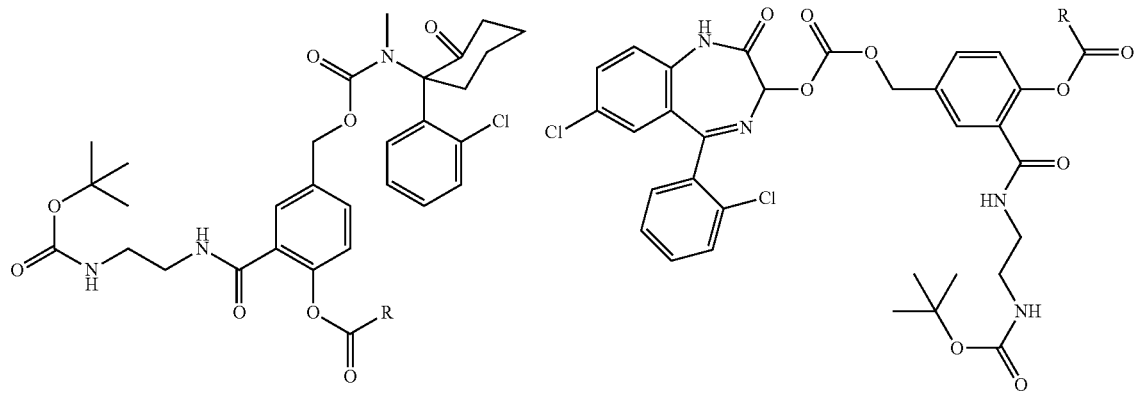

R = t-Bu, Bn, respectively

Conjugation of the Drug-linker Units to the Appropriately Functionalized Dendrimer The partially acetylated G5 dendrimer is further modified to have carboxylic acid at the terminal of each branch. This is achieved by reacting the partially acetylated G5 dendrimer with large excess of glutaric anhydride. The t-Boc protecting group on the drug-linker unit is removed by treatment with 1 equivalent of 1N HCl in ether. The freed amino group is immediately conjugated with the appropriately functionalized dendrimer through an EDC catalyzed coupling reaction as shown in Scheme 14:

Scheme 14. Drug-linker conjugation to dendrimer.

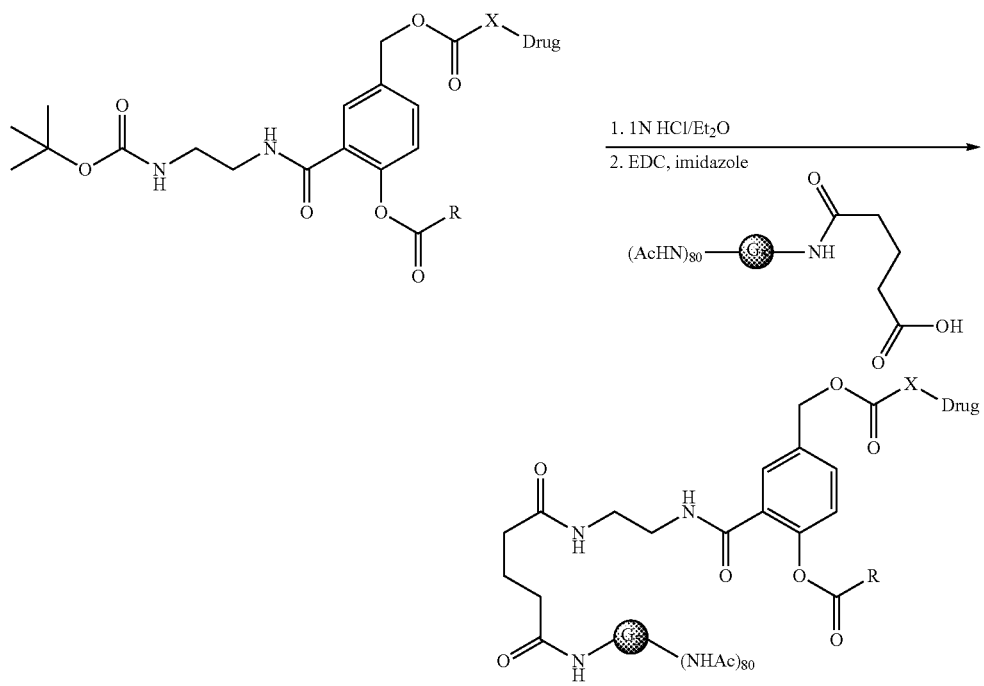

Drug = ketamine, X = NH
Drug = lorazepam, X = O
R = t-Bu and Bn, respectively

All the dendrimer-drug conjugates are isolated, purified, and characterized through methods including GPC, NMR, HPLC, UV, and CE.

Example 14

Design and Synthesis of Doxapram-dendrimer Complex to Counter Respiratory Depression Doxapram (Scheme 3), used for reversal of respiratory depression that is induced by Ketamine/Lorazapram treatment, cannot be covalently conjugated onto dendrimer surface amines due to its structural characteristics. An alternative approach is to formulate Doxapram as a dendrimer complex for acid-triggered release. Dendrimer-drug complexes are formed through, for example, hydrogen bonding, hydrophobic interactions, electrostatic interactions, or a combination of these approaches (see, e.g., Esfand, R. and D. A. Tomalia, Drug Discovery Today, 2001.6: p. 427-436; Jansen, J. F. G. A., E. M. M. de Brabander van den Berg, and E. W. Meijer, Science, 1994. 266: p. 1226-1229; Kolhe, P., et al., International Journal of Pharmaceutics, 2003. 259: p. 143 160; Man, N., et al., European Journal of Medicinal Chemistry, 2006. 41: p. 670-674; Morgan, M. T., et al., J. Am. Chem. Soc., 2003. 125(50): p. 15485-15489; Naylor, A. M., et al., J. Am. Chem. Soc., 1989. 111: p. 2339-2341; Papagiannaros, A., et al., International Journal of Pharmaceutics, 2005. 302: p. 29 38; Patri, A. K., J. F. Kukowska-Latallo, and J. R. Baker, Advanced Drug Delivery Reviews, 2005. 57(15): p. 2203-2214; Patri, A. K., I. J. Majoros, and J. R. Baker, Jr., Current Opinion in Chemical Biology, 2002. 6: p. 466-471; Qiu, L. Y. and Y. H. Bae, Pharmaceutical Research, 2006. 23: p. 1 30; Shcharbin, D. and B. M., Biochimica et Biophysica Acta, 2006. 1760: p. 1021-1026; each herein incorporated by reference in their entireties). In order to prepare dendrimer-Doxapram complexes that release drug during acidosis, poly (amidoamine) (PAMAM) dendrimers with surface succinamic acid substitutions are synthesized to facilitate both electrostatic and hydrophobic interactions with Doxapram.

Synthesis and Characterization of G5 Dendrimers with Varying Numbers of Succinamic Acid G5 dendrimers with different succinamic acid termini are synthesized (e.g., Shi, X., et al., Electrophoresis, 2006. 27(9): p. 1758-1767; herein incorporated by reference in its entireties). The amine-terminated $G5.NH_2$ dendrimers are first acetylated in different percentages, followed by reaction with succinic anhydride to transfer the remaining amine groups to carboxylic acid groups (Scheme 15). The acetylation reaction (see, e.g., Majoros, I. J., et al., Macromolecules, 2003. 36: p. 5526-5529; herein incorporated by reference in its entirety), involves addition of 0.5 mL of pyridine to a 10-mL methanol solution containing 100 mg $G5.NH_2$ dendrimer. Methanolic solutions (10 mL) of acetic anhydride with different calculated molar ratios (25, 50, 75, and 100% of the total primary amines of $G5.NH_2$) are added in parallel into the dendrimer/pyridine mixture solutions while vigorously stirring, and the mixture are allowed to react for 24 h. Methanol is then removed from the reaction mixture with a rotary evaporator. The oily crude product is diluted with $H_2O$ and dialyzed against water (6×4 liters) for three days to remove the excess of reactants and byproducts. Water is removed from the retentate and the product is re-dissolved in water, then lyophilized. The final G5 acetamides are annotated by using their theoretical composition numbers as G5.25Ac, G5.50Ac, G5.75Ac, and G5.100Ac. For the carboxylation reaction, 50 mg dry polycationic G5 acetamide derivative (acetylation percentages 0%, 25%, 50%, and 75%) is dissolved in 10 mL DMSO. Into each of the G5 acetamide solution is added under vigorous stirring 10 mL of DMSO solution containing succinic anhydride with 2-3 times molar excess of the remaining primary amine groups of the particular G5 acetamide. The reaction is maintained at room temperature for 24 h. Then, the final DMSO solution is dialyzed against water (6×4 liters) to remove the excess succinic anhydride as well as the organic solvent. The aqueous retentate is filtered and lyophilized. The final G5 succinamic acids are denoted as G5.25SAH, G5.50SAH, G5.75SAH, and G5.100SAH. The synthesized dendrimer acetamides and succinamic acids are characterized using high performance liquid chromatography (HPLC), gel permeation chromatography (GPC), matrix-assisted laser desorption ionization-time of flight (MALDI-TOF) mass spectrometry, capillary electrophoresis (CE), and NMR (see, e.g., Shi, X., et al., Electrophoresis, 2006. 27(9): p. 1758-1767; Islam, M. T., I. J. Majoros, and J. R. Baker, Journal of Chromatography B-Analytical Technologies in the Biomedical and Life Sciences, 2005. 822(1-2): p. 21-26; Islam, M. T., et al., Analytical Chemistry, 2005. 77(7): p. 2063-2070; Shi, X., et al., Polymer, 2005. 46: p. 3022-3034; Shi, X., et al., Colloids Surf., A, 2006. 272: p. 139-150; Shi, X., I. J. Majoros, and J. R. Baker, Jr., Mol. Pharm., 2005. 2: p. 278-294; Shi, X. Y., et al., Electrophoresis, 2005. 26(15): p. 2949-2959; Shi, X. Y., et al., Analyst, 2006. 131(7): p. 842-848; Shi, X. Y., et al., Analyst, 2006. 131(3): p. 374-381; Shi, X. Y., et al., Electrophoresis, 2005. 26(15): p. 2960-2967; each herein incorporated by reference in their entireties).

Scheme 15. Schematic representation of acetylation and carboxylation reactions with G5•NH$_2$ PAMAM dendrimer.

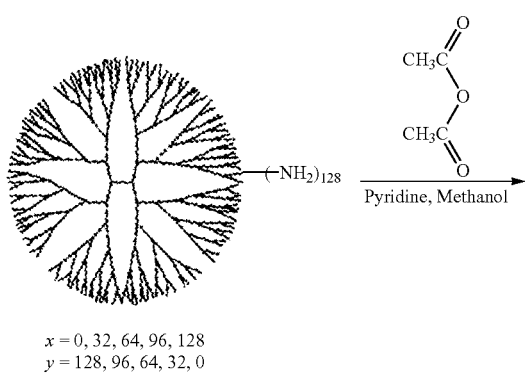

$x = 0, 32, 64, 96, 128$
$y = 128, 96, 64, 32, 0$

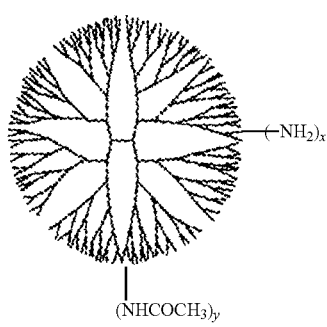

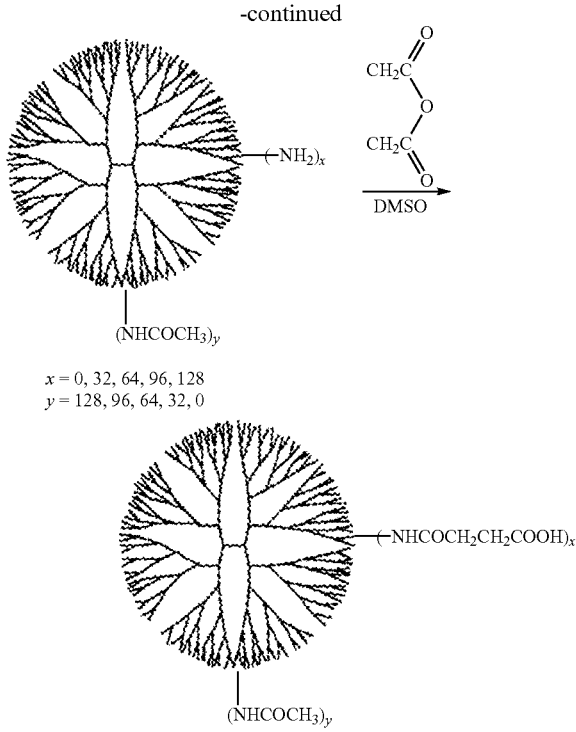

$x = 0, 32, 64, 96, 128$
$y = 128, 96, 64, 32, 0$

Formation and Characterization of G5 Dendrimer Succinamic Acid/Doxapram Complexes Dendrimer-Doxapram complexes are prepared (see, e.g., Kolhe, P., et al., International Journal of Pharmaceutics, 2003. 259: p. 143-160; Morgan, M. T., et al., J. Am. Chem. Soc., 2003. 125(50): p. 15485-15489; each herein incorporated by reference in their entireties). 27 mg ($8.2 \times 10^{-7}$ mol) of the G5.25SAH dendrimer (molecular weight is estimated from previous publication, Mw=32,910) is dissolved in 2.0 mL of $CH_3OH$. Doxapram hydrochloride (Mw=0.34 mg, $8.2 \times 10^{-7}$ mol) is added to the $CH_3OH$ solution and stirred for 10 min. $H_2O$ (1.0 mL) is added to the solution and the solution is stirred for 1 h. Next, the $CH_3OH$ is removed via evaporation over several hours. The encapsulated drug-dendrimer solution is then be stored at room temperature until further use. Samples for NMR analysis are prepared using deuterated solvents. The amount of Doxapram complexed with G5 dendrimer succinamic acids is determined using UV-Vis spectroscopy. The maximum loading capacity of Doxapram in G5 succinamic acids with different percentages of carboxyl modification is determined. Additional methods for characterization of the complexes include NMR techniques, zeta potential, and FTIR spectroscopy.

Example 15

Functional Analysis of Dendrimer-Opioid Conjugates and Released Free Drug Functional Analysis of Dendrimer-Opioid Conjugates and Released Free Drug Binding of Morphine to a cell surface receptor initiates a series of signal transduction events, which lead to cellular responses. An early event in the signal transduction pathway is the activation of Gi/Go proteins leading to the inhibition of adenylate cyclase activity and decrease in the cellular cAMP levels (see, e.g., Childers, S. R. and S. R. Childers, *Opioid*

*receptor-coupled second messenger systems.* Life Sciences, 1991. 48(21): p. 1991-2003; herein incorporated by reference in its entirety). The biological functionality of the dendrimer-opioid conjugates can be determined by i) monitoring the in vitro binding of the conjugate onto live cells or isolated cell membranes, ii) determining the activation/inactivation of G-proteins in isolated membranes, and iii) quantifying the cAMP content in intact cells.

Determination of the Activation of G-proteins Using Cell-free Membrane System

The rate-limiting step in the activation of G-protein is the dissociation of bound GDP, which enables the binding of GTP at the displaced site. This is followed by the dissociation of G-protein subunits that facilitates the activation of adenlyate cyclase, and the subsequent hydrolysis of the bound GTP by the inherent GTPase of the G-protein (see, e.g., Pierce, K. L., et al., Nature Reviews Molecular Cell Biology, 2002. 3(9): p. 639-50; herein incorporated by reference in its entirety). The activity of an opioid agonist can be determined in cell-free systems using partially purified membrane from opioid receptor-expressing cells that contains the G-proteins. This is done by measuring the rate of agonist-stimulated membrane binding of a non-hydrolyzable analog of GTP such as the GTPγS (see, e.g., Traynor, J. R., et al., Journal of Pharmacology & Experimental Therapeutics, 2002. 300(1): p. 157-61; herein incorporated by reference in its entirety), or by monitoring the membrane GTPase activity (see, e.g., Sun, H., et al., Proceedings of the National Academy of Sciences of the United States of America, 1995. 92(6): p. 2229-33; herein incorporated by reference in its entirety). The biochemical functionality of dendrimer-opioid conjugates is determined before and after pre-treatment with purified esterase by G-protein-based assays.

Evaluating Opioid Conjugate Ability to Stimulate [$^{35}$S] GTPγS Binding

A procedure similar to that described by Traynor et al is used (see, e.g., Traynor, J. R., et al., Journal of Pharmacology & Experimental Therapeutics, 2002. 300(1): p. 157-61; herein incorporated by reference in its entirety). Cells are rinsed with PBS and scraped into Tris-HCl buffer pH 7.4 containing 0.3 M sucrose in presence of protease inhibitors, and homogenized in a dounce homogenizer. The nuclei and unbroken cells are removed by low-speed centrifugation at 200 g and the supernatant is spun again at 15,000 g for 20 min. The membrane preparation obtained is washed with Tris-HCl buffer and used for binding studies. The protein concentration of the membrane is determined using standard protocols. 100 μg of the partially purified membrane preparation is incubated for 10 min at 37° C. in a buffer containing [$^{35}$S] GTPγS and GDP. The 'dendrimer-opioid agonist' conjugate is then added and at different time points, aliquots of the reaction mixture removed and rapidly filtered through a glass fiber filter. The filters are rinsed and the bound radioactivity determined by scintillation counting. Non-specific binding is determined in presence of excess (50 μM) non-radioactive GTPγS. The rate constants and maximal binding of the [$^{35}$S] GTPγS is determined using the GraphPad Prism program (GraphPad, San Diego, Calif.). Appropriate controls are run in the absence of ligands, and in the presence of free agonists. The effect of 'dendrimer-opioid antagonist' on the agonist-induced binding is then verified.

The results of the studies described above indicate if the intact dendrimer-opioid conjugates have any in vitro biological activity. The [$^{35}$S] GTPγS binding studies using dendrimer-Morphine conjugate that had been pre-incubated with purified esterase are performed to demonstrate the biological activity of the ligand that is released by esterase. For this, the conjugate is incubated with commercially available esterase for different time-periods and adding ice-cold buffer will stop the esterase action. The reaction mixture is immediately filtered through a 10 kDa filter at 4° C., and the filtrate used as the ligand in the [$^{35}$S] GTPγS binding assay. Similarly, the filtrates obtained following hypoxic treatment of dendrimer-Naloxone conjugates are used to test whether the released free Naloxone inhibits agonist-induced Gi-protein activation.

Functional Determination of Opioid-induced GTPase Activity

GTPase activity is determined (see, e.g., Sun, H., et al., Proceedings of the National Academy of Sciences of the United States of America, 1995. 92(6): p. 2229-33; herein incorporated by reference in its entirety). Cell membranes are partially purified. 10 to 100 μg of the membrane protein are incubated in HEPES buffer pH 8.0 containing dithiothrietol and different concentrations of the 'dendrimer-opioid agonist.' The reaction is initiated by adding 100 nM GTP[γ-$^{32}$P] and aliquots withdrawn at different time intervals into tubes containing ice cold 5% Norit A in phosphate buffer. After centrifugation of the mixture, the radioactivity of the liberated [$^{32}$P]-phosphate in the supernatant is quantified by scintillation counting. The binding constants are determined. Appropriate controls are run in parallel, and the effect of 'dendrimer-opioid antagonists' and esterase- and hypoxia-treated conjugates are also be determined. If needed, the specificity for Gi-protein activation is verified by using membranes isolated from cells that had been pre-treated with pertussis toxin (200 ng/ml for 24 hrs), a treatment that inactivates the GTPase activity of the Gi-protein.

Determination of Opioid Mediated Cyclase Activity

Dendrimer-conjugates with either Morphine or Naloxone and in combination are tested in vitro on opioid-responsive neuronal cell lines. Opiate Morphine binds to the mu opioid receptor (MOR), also known as the enkephalin G-protein-coupled receptor on the subsynaptic membrane of neurons involved in the transmission of pain signals. By binding to the enkephalin receptor, Morphine enhances the analgesic effects of enkephalin neurons. Opiate antagonists such as Naloxone bind to mu receptors, but do not activate them and prevent the binding of opiates. Morphine's relative efficacy to promote MOR internalization is much less than its relative efficacy to activate a G protein associated with the cytoplasmic C-terminal of the receptor (see, e.g., Borgland, S. L., et al., Journal of Biological Chemistry, 2003. 278(21): p. 18776-84; herein incorporated by reference in its entirety). Morphine binding to a receptor triggers an allosteric change in the Ga subunit of the G protein, causing replacement of GDP with GTP and activation of the Ga subunit. Activated Ga, in turn, activates an effector molecule, cyclase, an enzyme in the inner side of the plasma membrane, and this enzyme then catalyzes the conversion of ATP into the "second messenger" cyclic AMP (cAMP). Changes in the activity of Morphine and antagonism by Naloxone of intracellular generation of cAMP will be used as a marker of the function of dendrimer-conjugated and released opioids. Responsive neuronal cells in vitro are measured by cyclase ELISA (see, e.g., Horton, J. K., et al., Journal of Immunological Methods, 1992. 155(1): p. 31-40; herein incorporated by reference in its entirety).

Example 16

Chemical Analysis of Dendrimer Conjugate and Free Drug Concentrations for Release Kinetic Studies Characterization of Generation 5 PAMAM Dendrimer-Drugs Conjugates PAMAM dendrimers conjugated and/or complexed to drugs such as Ketamine, Lorazepam, Doxapram, Morphine and Naloxone are characterized. Methods for characterizing such conjugates have been developed (see, e.g., Majoros, I. J., et al., Biomacromolecules, 2006. 7(2): p. 572-579; Majoros, I. J., et al., Journal of Medicinal Chemistry, 2005. 48(19): p. 5892-5899; Shi, X., et al., Electrophoresis, 2006. 27(9): p. 1758-1767; Islam, M. T., I. J. Majoros, and J. R. Baker, Journal of Chromatography B-Analytical Technologies in the Biomedical and Life Sciences, 2005. 822(1-2): p. 21-26; Islam, M. T., et al., Analytical Chemistry, 2005. 77(7): p. 2063-2070; Shi, X.Y., et al., Electrophoresis, 2005. 26(15): p. 2949-2959; Shi, X. Y., et al., Analyst, 2006. 131(3): p. 374-381; Shi, X.Y., et al., Electrophoresis, 2005. 26(15): p. 2960-2967; each herein incorporated by reference in their entireties). High Performance Liquid Chromatography (HPLC), Size Exclusion Chromatography (SEC), Capillary electrophoresis (CE), and Matrix Assisted Laser Desorption Ionization-Time of flight (MALDI-TOF) mass spectrometric techniques are utilized.

High Performance Liquid Chromatography (HPLC)

HPLC is a widely accepted analytical method for separation and purification of various compounds. PAMAM dendrimer and its conjugates have been successfully characterized and analyzed using a gradient HPLC elution (see, e.g., Islam, M. T., I. J. Majoros, and J. R. Baker, Journal of Chromatography B-Analytical Technologies in the Biomedical and Life Sciences, 2005. 822(1-2): p. 21-26; Islam, M. T., et al., Analytical Chemistry, 2005. 77(7): p. 2063-2070; each herein incorporated by reference in their entireties). Briefly, HPLC analysis is carried out on a Waters Delta 600 HPLC system equipped with a Waters 2996 photodiode array detector, a Waters 717 Plus auto sampler, and Waters Fraction collector III. The instrument is controlled by Empower 2 software. For analysis of the conjugates, a C5 silica-based RP-HPLC column (250×4.6 mm, 300 Å) connected to a C5 guard column (4×3 mm) is used. The mobile phase for elution of different generations of PAMAM dendrimers is a linear gradient beginning with 100:0 (v/v) water/acetonitrile (ACN) at a flow rate of 1 mL/min. Trifluoroacetic acid (TFA) at 0.14 wt % concentration in water as well as in ACN is used as a counter ion to make the dendrimer surfaces hydrophobic.

Capillary Electrophoresis (CE)

An Agilent Technologies CE instrument is used for this work. A procedure similar to as described by Shi, et. al. (see, e.g., Shi, X.Y., et al., Electrophoresis, 2005. 26(15): p. 2949-2959; Shi, X.Y., et al., Analyst, 2006. 131(3): p. 374-381; Shi, X. Y., et al., Electrophoresis, 2005. 26(15): p. 2960-2967; each herein incorporated by reference in their entireties) is used to characterize dendrimer conjugates. Samples are introduced by hydrodynamic injection. Detection is done by an online PDA detector installed in the system.

Size Exclusion Chromatography (SEC)

SEC experiments for dendrimers and their conjugates are performed using an Alliance Waters 2690/2695 separations module (Waters Corp., Milford, Mass.) equipped with a Waters 2487 UV absorbance detector (Waters Corp.), a Wyatt Dawn DSP laser photometer (Wyatt Technology Corp., Santa Barbara, Calif.), an Optilab DSP interferometric refractometer (Wyatt Technology Corp.), and TosoHaas TSK-Gel Guard PHW 06762 (75×7.5 mm, 12 µm), G 2000 PW 05761 (300×7.5 mm, 10 µm), G 3000 PW 05762 (300×7.5 mm, 10 µm), and G 4000 PW (300×7.5 mm, 17 µm) columns. Citric acid buffer (0.1 M concentration) with 0.025% sodium azide in water is used as a mobile phase, pH 2.74, using NaOH. Molar mass moments of the PAMAM dendrimers is determined using Astra software (version 4.9) (Wyatt Technology Corp.).

MALDI-TOF Mass Spectrometry

MALDI-TOF mass spectra is acquired using a Waters Tof-Spec-2E spectrometer in a reflection mode. Each sample is dissolved in 50:50 mixture of methanol/water to obtain an approximate concentration of 0.25 mg/mL. The samples is then mixed with equal volumes (5 µL) of the matrix solution (10 mg/mL R-cyano-4-hydroxycinnamic acid (CHCA) dissolved in ACN/ethanol (50:50)). The TFA salt form of the separated samples is isolated and collected. A 1-µL solution of the mixture is injected on the spots of the target plate and evaporated to dryness. Calibration of the spectrometer is done using a mixture of known peptides in the CHCA matrix.

NMR Spectroscopy $^1$H and $^{13}$C and HMQC NMR spectra is taken in $D_2O$ and used to provide integration values for structural analysis by means of a Bruker AVANCE DRX 500 instrument. Shifts and integration of signals in the $^1$H NMR spectra are used for quantitative analysis of the conjugation reactions and for structural characterization, while the signals and shifts in the $^{13}$C NMR spectra are used for qualitative characterization.

Example 17

Determination of In-vitro Release Kinetics of Drugs Using HPLC Ketamine, Lorazepam (in Serum) and Morphine (in CSF)

Figure 34:
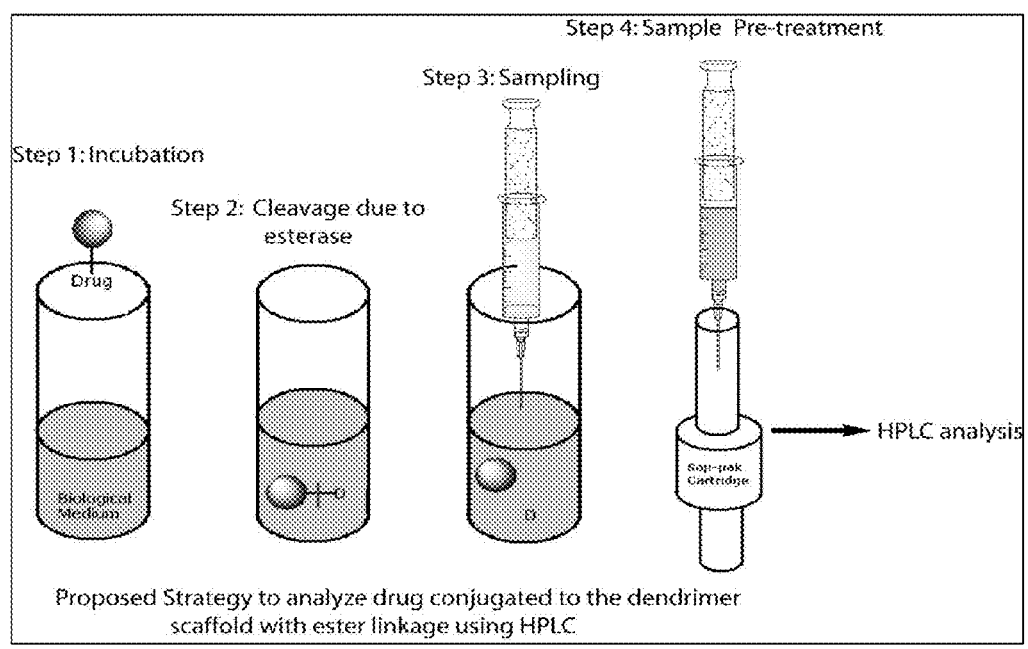
FIG. 34 shows a strategy to analyze drug conjugated to the dendrimer scaffold with ester linkage using HPLC.

HPLC is widely used in the pharmaceutical field to analyze a variety of drugs. Ketamine, Lorazepam and Morphine have been extensively characterized using HPLC (see, e.g., Kuracka, L., et al., Clinical Chemistry, 1996. 42(5): p. 756-760; Orlovic, D., et al., Chromatographia, 2000. 52(11/12): p. 732-734; Svensson, J., et al., Journal of Chromatography B: Biomedical Sciences and Applications, 1982. 230(2): p. 427-432; Svensson, J.-O., Journal of Chromatography B: Biomedical Sciences and Applications, 1986. 375: p. 174-178; Tebbett, I. R., Chromatographia, 1987. 23(5): p. 377-378; each herein incorporated by reference in their entireties). These drugs are conjugated to the dendrimer scaffold using an ester linkage. The drugs are released from the carrier molecule into the biological matrix after cleavage by cellular esterase, tested both as purified enzyme and cellular extract. HPLC is used to qualitatively and quantitatively analyze free drug content in the biological medium after its release (FIG. 34). Quantitative analysis is done by a calibration curve method generated by a standard sample of the free drugs.

Sample Preparation

To study drug release using HPLC, the drug conjugated to the dendrimer scaffold is incubated with serum at 37° C. in a heparinized tube for 72 hrs. Once the drug is released from the scaffold by the esterase, aliquots at various time points are collected and frozen until HPLC analysis. Prior to HPLC analysis for free drug content, the serum sample and cerebrospinal fluid (with and without drug conjugate) are pre-treated using the Solid Phase Extraction method carried out by using $C_{18}$ Sep-pak cartridges to remove any interfering matrix impurities. After pre-treatment, the samples are reconstituted with the HPLC eluent and injected into a reverse phase column.

Quantitative Analysis—Calibrator Solutions

For quantitative analysis, standard drug samples are obtained and stock solutions for each of these drugs are made in an appropriate solvent. Using a serial dilution method, standards for each drug at various concentrations are prepared to generate a calibration curve. Concentration of free drug after its release is calculated using a regression equation. Simultaneous analysis of Ketamine and Lorazepam are carried out by preparing a sample containing both drugs. This is then analyzed under the specified HPLC conditions.

Recovery of the Sample (see, e.g., Kuracka, L., et al., Clinical Chemistry, 1996. 42(5): p. 756-760; Kimiskidis, V., et al., Journal of Pharmaceutical and Biomedical Analysis, (in press); each herein incorporated by reference in their entireties)

An important step for HPLC analysis of the drug in biological medium is its extraction. The percent recovery of the sample by an extraction process is crucial. To check for the percent recovery of a drug sample from the biological medium, a standard drug sample of a known concentration is spiked into serum and/or cerebrospinal fluid. This spiked sample is then subjected to sample pre-treatment. An HPLC analysis is performed on the pre-treated spiked sample and a standard drug sample. From the calibration curve and the regression equation the percent recovery is computed.

Doxapram

The synthetic approach for Doxapram involves formation of a complex with the dendrimer, which releases the drug on lower pH (pH-trigger). Doxapram release from the dendrimer is studied in complexes formed with different ratios of dendrimer and drug, and with different dendrimers with varied amounts of succinamide substitution. The dendrimer-drug complex is subjected to dialysis against various buffer systems (pH ranging from 7.4 to 6.8) and the dialysate subjected to HPLC analysis to determine drug release and release kinetics. Ultrafiltration of complexes mixed with serum buffered to different pH is also employed to determine the exact drug release at varied serum pH.

Experimental Step-up

Concentrated sample of the dendrimer-Doxapram complex is prepared in saline. 500 µL of this solution is then placed in a dialysis tube (MWCO=10 KD). This sample is dialyzed against buffers of various pH ranging from 6.8 to 7.4. The volume of the buffers in the outer phase is 100 mL. Permeates at various time points are withdrawn from the outer phase and centrifuged against a molecular weight cut off filter to remove buffers and to concentrate the sample. The retentate is reconstituted with the eluent and subjected to analysis using HPLC. A series of Doxapram standards are prepared in an appropriate solvent using a serial dilution to generate a calibration curve. Quantitative analysis for the amount of drug release is computed using a regression equation. In an alternative approach, to mimic physiological conditions, Doxapram release is studied in serum.

Naloxone

Release of Naloxone is triggered by hypoxia induction due to exceeding limits of Morphine dosage. An in vitro hypoxia model that facilitates drug release is used for naloxone release. An in vitro hypoxia model for measuring a neurotransmitter (Dopamine) release is used (see, e.g., Stamford, J. A., Journal of Neuroscience Methods, 1990. 34(1-3): p. 67-72; Toner, C. C. and J. A. Stamford, Journal of Neuroscience Methods, 1996. 67(2): p. 133-140; Toner, C. C. and J. A. Stamford, Neuroscience, 1997. 81(4): p. 999-1007; each herein incorporated by reference in their entireties). A quantitative method for determination of drug content in artificial CSF (ACSF) using HPLC (see, e.g., Kimiskidis, V., et al., Journal of Pharmaceutical and Biomedical Analysis, (in press); herein incorporated by reference in its entirety). Also, Naloxone has been thoroughly characterized and analyzed using HPLC (see, e.g., Achilli, G., et al., Journal of Chromatography A, 1996. 729(1-2): p. 273-277; herein incorporated by reference in its entirety). Accordingly, an in vitro model using HPLC to study the CSF release kinetics of Naloxone under hypoxic conditions is provided.

Experimental Design

An in vitro hypoxia model is provided. The sample vials are placed in an enclosed chamber that has the capability to continuously allow the flow of required gases and alternatively facilitates ease of sampling. The amount of gas that pumped into this chamber is maintained and controlled through a peristaltic pump. The temperature of the system is maintained at 37° C. Using this set-up, the sample vials containing dendrimer-drug conjugate in CSF are incubated in this enclosed chamber. Varying concentrations of human DT-diaphorase (Sigma), the brain enzyme responsible for the bioreduction catalysis of the indolequinone-Naloxone conjugate that is regulated by hypoxia, are provided. Initially, hypoxia is induced by gassing the chamber with 95% $N_2$/5% $CO_2$ gas for about 30 minutes at 400 ml/hr (see, e.g., Toner, C. C. and J. A. Stamford, Neuroscience, 1997. 81(4): p. 999-1007; herein incorporated by reference in its entirety). Simultaneously, another sample vial is oxygenated by flowing 95% $O_2$/5% $CO_2$ that serves as a control. After sample incubation under hypoxic condition, aliquots from each sample (oxygenated and deoxygenated) are taken and stored until analysis. For sample incubated under hypoxic conditions, storage of the aliquots, sample pre-treatment and sample preparation are carried out in a glove box to maintain hypoxic conditions. HPLC of these samples is then carried out to check for free drug content.

Drug Release Kinetics

The sample is incubated under 95% $N_2$/5% $CO_2$ atmosphere for different time periods and aliquots are collected at the end of each incubation time period to study the amount of drug release. Also, the rate of gassing (the amount of gas passing through the chamber) is critical. To optimize these conditions, the chamber is gassed at various speeds and at the end of each run, the aliquots are taken for analysis using HPLC. Once the conditions for hypoxia induced drug release are optimized, the samples in CSF are subjected to the set conditions to characterize the kinetics of drug release. The samples are pre-treated prior to HPLC analysis. Complete quantitative analysis using standard samples of Naloxone is carried out in a similar fashion.

Example 18

Apparatus and Chromatographic Conditions to Study Release Kinetics of Drugs

The complete qualitative and quantitative analysis using HPLC is carried out on a Waters Delta 600 HPLC system equipped with a Waters 2996 photodiode array detector, a Waters 717 Plus auto sampler, Waters Fraction collector III and Empower 2 software. An analytical size column (C8 or C18) with a particle size of 5µ is used. Initially, an isocratic elution using acetonitrile/phosphate buffer, pH 7.0, is used. The conditions for an HPLC experiment, if required, are modified in order to incorporate various analyses and generate efficient results.

Example 19

Synthesized analgesic nanodevices should be stable and biologically inactive. The biological activity (or lack thereof) is tested using the radio-ligand competition-binding assay. If no binding competition is observed, the nanodevices are treated to release fully functional drugs. The drugs' release kinetics and biological activity is further evaluated using fluorescence polarization immunoassay (FPIA) analysis and the radioligand competition-binding assay. This assay is used to study the ability of released drug and drug conjugates to bind to the respective receptors.

The assay is performed using membrane preparations from cell lines, shown in Table 2, that express various receptors. Prior to membrane preparation, the cells are maintained in RPMI 1640 medium supplemented with 10% heat-inactivated bovine calf serum, 2 mM L-glutamine, as well as penicillin and streptomycin. The cells are grown at 37° C. in a 5% $CO_2$ incubator. Cell membranes are prepared as described previously (see, e.g., Horner, K. A., et al., Brain Research, 2004. 1028(2): p. 121-32; herein incorporated by reference in its entirety). Total protein concentration is determined with bovine serum albumin (BSA) as a standard. Cell membrane binding assays for receptors are performed as described previously (see, e.g., Horner, K. A., et al., Brain Research, 2004. 1028(2): p. 121-32; herein incorporated by reference in its entirety). Briefly, cell membranes (0.1 mg protein) are incubated in 100 mM Trizma/0.3% bovine serum albumin containing a constant concentration of $^3H$ drug and various concentrations of unlabeled drug either coupled to or released from the dendrimer. Nonspecific binding is defined as that measured in the presence of 1 µM of cold drug. The membranes are filtered onto Skatron glass fiber filters that have been soaked in 50 mM Trizma, using a Skatron harvester (Molecular Devices, Sunnyvale, Calif.). Filter disks are placed in scintillation cocktail (Ready-Protein Plus, Beckman Coulter, Fullerton, Calif.) and counted. Total binding is defined as dpm of $^3H$ drug bound by each sample. Each concentration of drug is assayed in triplicate and the experiment repeated at least 2 times. Nonlinear regression analysis of $^3H$ drug competition assays is performed with GraphPad Prism (GraphPad Software, San Diego, Calif., USA). $^3H$-Ketamine and $^3H$-Doxapram is radio-labeled as described previously (see, e.g., Adams, J. D., Jr., et al., Biomedical Mass Spectrometry, 1981. 8(11): p. 527-38; herein incorporated by reference in its entirety).

TABLE 2 shows drugs, receptors and cell lines expressing these receptors.

| Drugs | Receptors/ transporters | Cell lines | Cell line availability | References |
|---|---|---|---|---|
| Morphine | µ opioid receptor | SH-SY5Y, SK-N-SH, T47D | From ATCC | Horner, K. A., et al., Brain Research, 2004. 1028(2): p. 121-32; herein incorporated by reference in its entirety |
| Naloxone | µ opioid receptor | SH-SY5Y, SK-N-SH, T47D | From ATCC | Horner, K. A., et al., Brain Research, 2004. 1028(2): p. 121-32; herein incorporated by reference in its entirety |
| Doxapram | $CO_2$ chemoreceptor | PC12 | From ATCC | Millhorn, D. E., et al., Advances in Experimental Medicine & Biology, 1996. 410: p. 135-42; herein incorporated by reference in its entirety |
| Ketamine | N-methyl-D-aspartate receptor | NG108-15 | From ATCC | Cai, Y. C., et al., Molecular Pharmacology, 1997. 51(4): p. 583-7; herein incorporated by reference in its entirety |
| Lorazepam | glutamate transporter EAAC1 | PC-3 | From ATCC | Franklin, R. B., et al., BMC Biochemistry, 2006. 7: p. 10; herein incorporated by reference in its entirety |

Fluorescence Polarization Immunoassay (FPIA) Analysis

To evaluate of kinetics of Morphine and Naloxone release from the nanodevice, the fluorescence polarization immunoassay is performed as described previously (see, e.g., KuKanich, B., et al., Therapeutic Drug Monitoring, 2005. 27(3): p. 389-92; herein incorporated by reference in its entirety). FPIA samples are prepared by mixing of 100 µL standard solution or supernatant of drug filtered through a 10 kDa cutoff membrane to separate drug released from nanodevice. The materials are mixed with 100 µL of the tracer solution in borate buffer and 300 µL of optimal dilution of MAb. The reaction mixture is vortexed and fluorescence polarization will be measured using a Beacon 2000 instrument with a variable temperature unit (Pan Vera Corp., Madison, Wis.). Standard curves are obtained by plotting normalized fluorescence polarization signal ($100 \times B/B_0$, where $B_0$=fluorescence polarization of "zero" standard, B=fluorescence polarization of each standard or rested drug solution) against the logarithm of the analyte concentration. Sigmoidal curves are fitted to a four-parameter logistic equation.

Example 20

Testing the Movement of Dendrimer-Drug Conjugates Across an Artificial BBB

To demonstrate that the CNS targeted dendrimer conjugate is transported across the BBB, the DIV-BBB system (Flocel Inc., Cleveland, Ohio) that closely mimics the in vivo BBB is used (see, e.g., Cucullo, L., et al., Current Opinion in Drug Discovery & Development, 2005. 8 (1): p. 88-99; herein incorporated by reference in its entirety). Briefly, the DIV-BBB is characterized by tight junctions, segregated lumenal/ablumenal transporters (i.e. potassium, amino acids, glucose GLUT-1), a negligible permeability to 14C sucrose, and a high transendothelial electrical resistance (TEER>1000 Ωcm2). The dendrimer-drug conjugate is dissolved in saline and injected through the luminal side of the DIV-BBB cartridge. The conjugate is allowed to pass through the endothelial capillaries (EC) to the ablumenal side. The samples are then be collected from the ablumenal side at various time intervals and analyzed for the presence of conjugate using HPLC.

Evaluation of Locking Module

Dendrimers with varying degrees of substitution with the tetrahydronicotinamide derivative are exposed to horseradish peroxidase enzymes (Sigma) in varying buffers, neuronal cell lines, enzyme and protein concentrations to simulate the CNS environment. MS and proton NMR determine the amount of charged material on the dendrimer. This material is tested for the ability to cross the BBB. Transport before and after treatment is compared, as is activity with different levels of conjugate to determine an optimal degree of conjugation to develop inducible locking activity.

Neuronal Cell Binding Assays

The ability of transferrin and Tet1 dendrimer conjugates to bind to neurons is evaluated using several techniques. Neuronal cell lines (SH-SY5Y, SK-N-SH, T47D, see Table 2 above) are cultured and incubated with radio-labeled transferrin and Tet1 dendrimer conjugates. Cells are washed and the cell pellets collected and assayed for bound radioactivity. Non-labeled transferrin and tet peptides are employed in an effort to block binding. Conjugates having both drug and targeting ligand are employed to determine if there is cooperative binding. Alternatively, the dendrimer conjugates are labeled with fluorescein and the binding and uptake in the neuronal cells tested using confocal microscopy and flow cytometry (see, e.g., Majoros, I. J., et al., Biomacromolecules, 2006. 7(2): p. 572-579; Shukla, R., et al., Bioconjugate Chemistry, 2006. 17(5): p. 1109-1115; each herein incorporated by reference in their entireties). These techniques allow for rapid "dose ranging" studies.

Example 21

Figure 35:
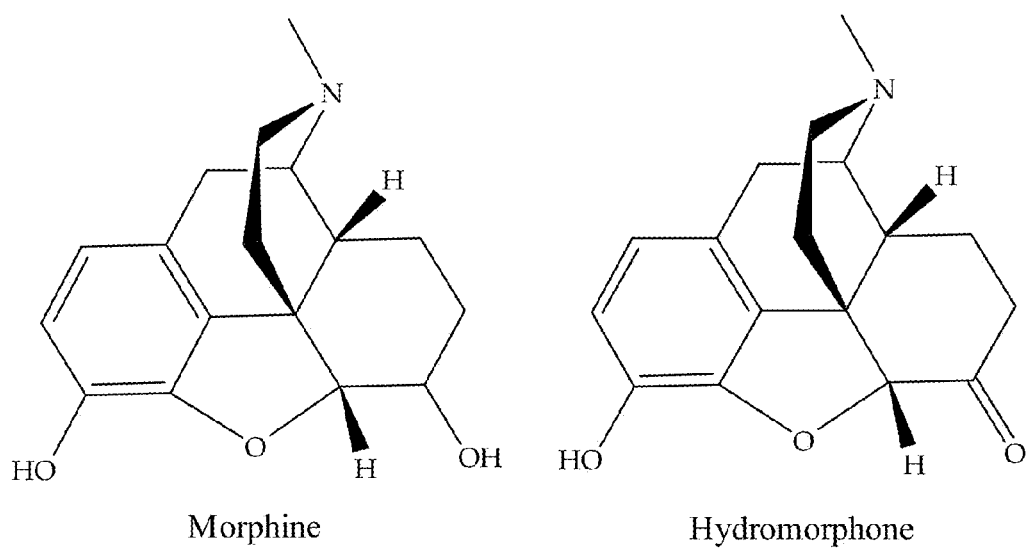
FIG. 35 shows structures of pain relief agents.
Figure 36:
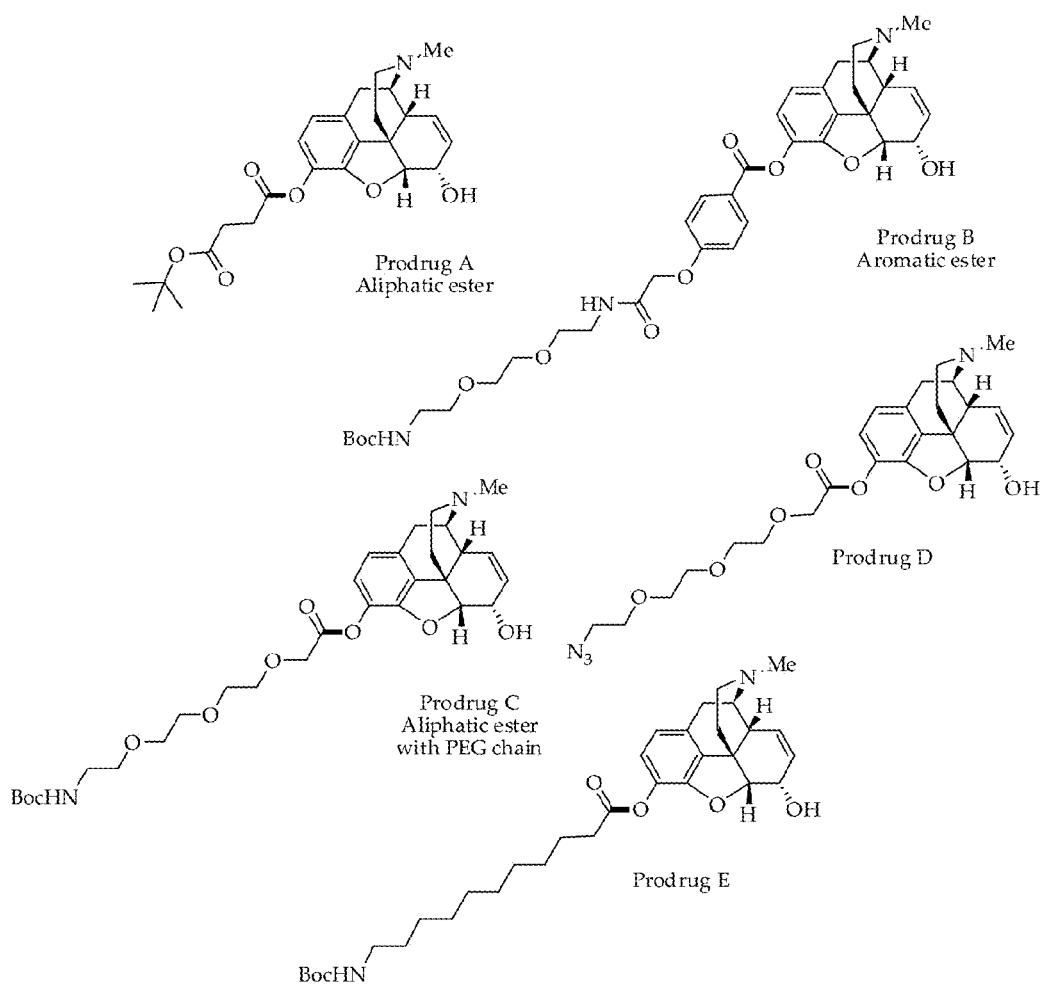
FIG. 36 shows structures of morphine pro-drugs.
Figure 37:
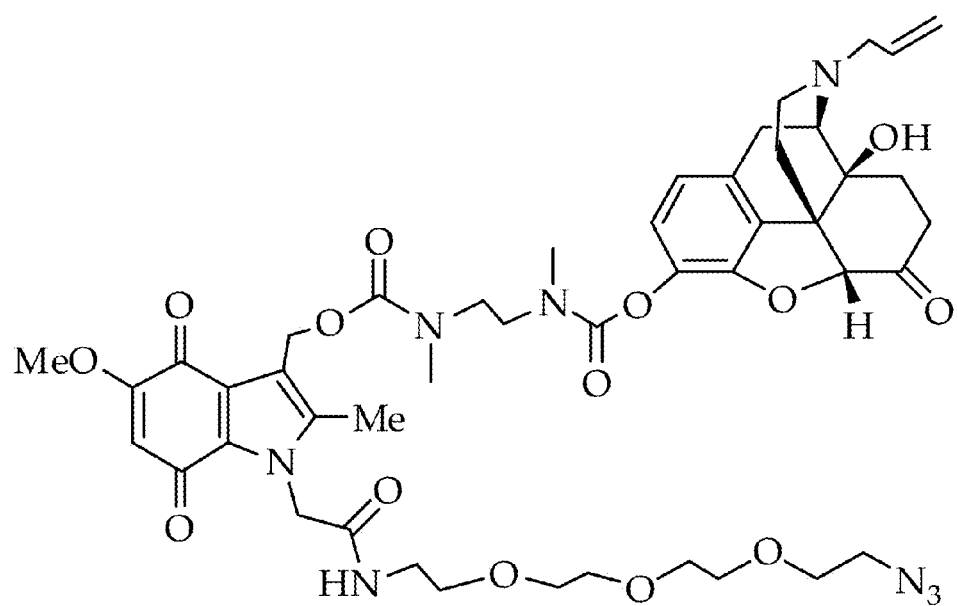
FIG. 37 shows the structure of a Naloxone pro-drug where the length of the spacer was varied to produce 3 additional Naloxone pro-drugs.
Figure 38:
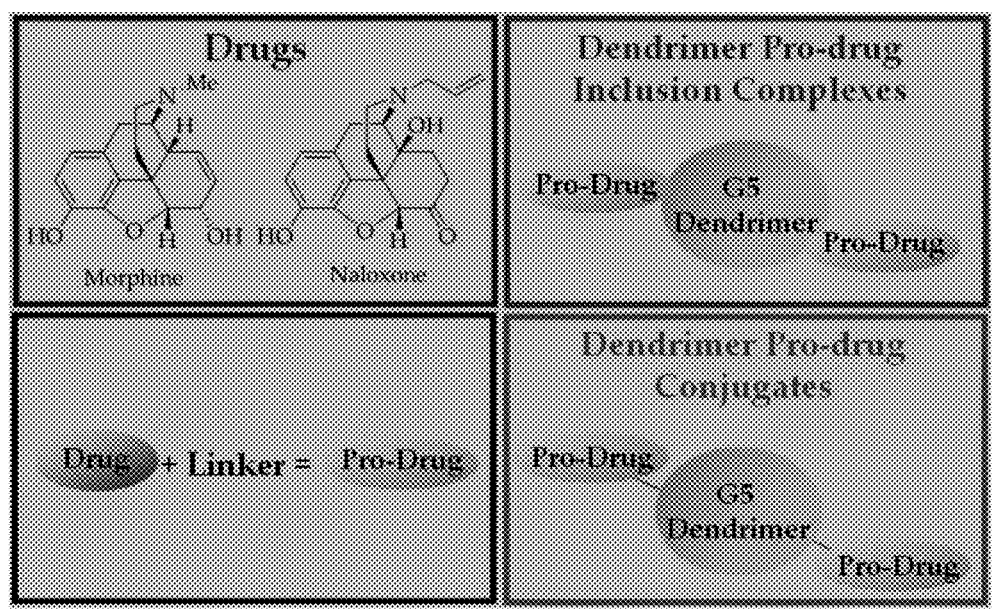
FIG. 38 shows drug formulations.

Morphine and Naloxone Pro-drugs, Dendrimer-Pro-Drug Complexes and Dendrimer-Pro-Drug Conjugates Synthesized Morphine and Naloxone were first modified to form pro-drugs through the attachment of rationally designed chemical modifications (FIGS. 35, 36, and 37). The modifications used for the Morphine pro-drugs were designed to be progressively and consistently cleaved by the esterases present in plasma, while those used in the formation of the Naloxone pro-drugs were cleaved to yield active drug by reduction only under hypoxic conditions, therefore serving as the feedback mechanism. Structural variations in the linkers resulted in variations in the rate of the continuous release of Morphine and the hypoxia-activated release of Naloxone. Both sets of pro-drugs were then associated with G5 PAMAM dendrimers to form a delivery platform through either i) non-covalent complexation with the polymer or ii) covalent conjugation to the dendrimer. A schematic illustrating the family of resulting formulations is in vivo displayed in FIG. 38.

Morphine Pro-drug Complexes and Dendrimer Morphine Pro-drug Conjugates can be Used to Obtain a Release of 2.25 mg Morphine/Hour in Human Plasma.

Figure 39:
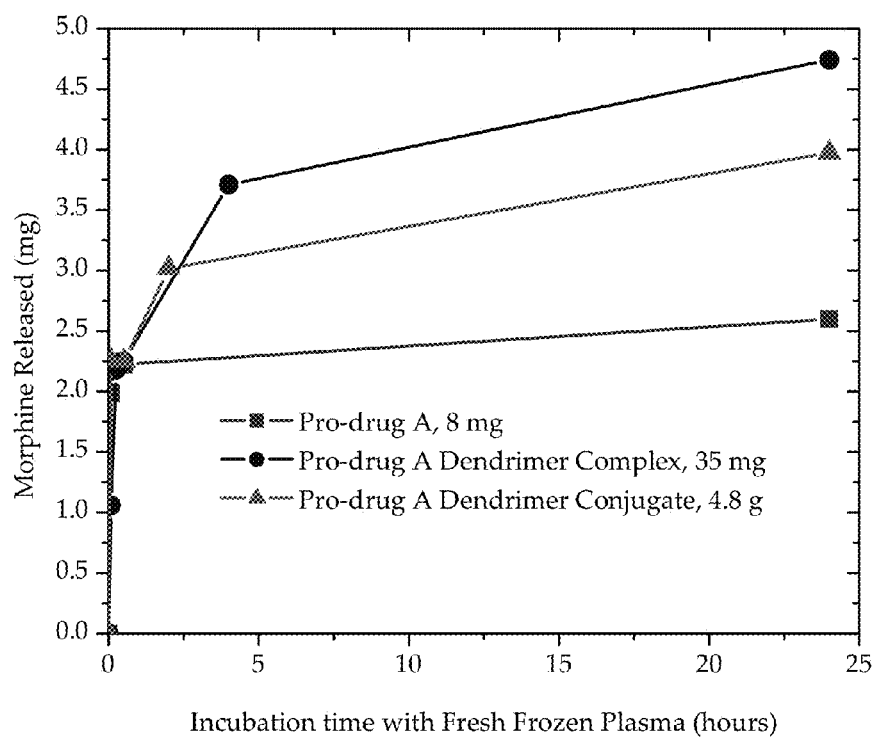
FIG. 39 shows time-dependent release kinetics of Morphine compounds incubated in fresh frozen plasma.

Release rates of Morphine from Morphine-pro-drug, dendrimer Morphine pro-drug complexes and dendrimer-Morphine pro-drug conjugates were obtained. These studies were completed by incubating each compound with human plasma for a given period of time. Following incubation with plasma, the release of Morphine from the Morphine compounds was quantified using HPLC. The identities of the HPLC peaks were confirmed using mass spectrometry analysis and the amount of Morphine released was calculated using a calibration curve. FIG. 39 shows the time-dependent release of Morphine from the different Morphine compounds after incubation with human plasma. These formulations were used in combination to achieve 2.25 mg Morphine/hour and demonstrate the feasibility of achieving the controlled release of Morphine.

Naloxone Pro-Drug can be Used to Obtain a Release of 6 mg Naloxone/Hour in Human Plasma Under Hypoxic Conditions ($pO_2$ of 18 mmHg).

Figure 40:
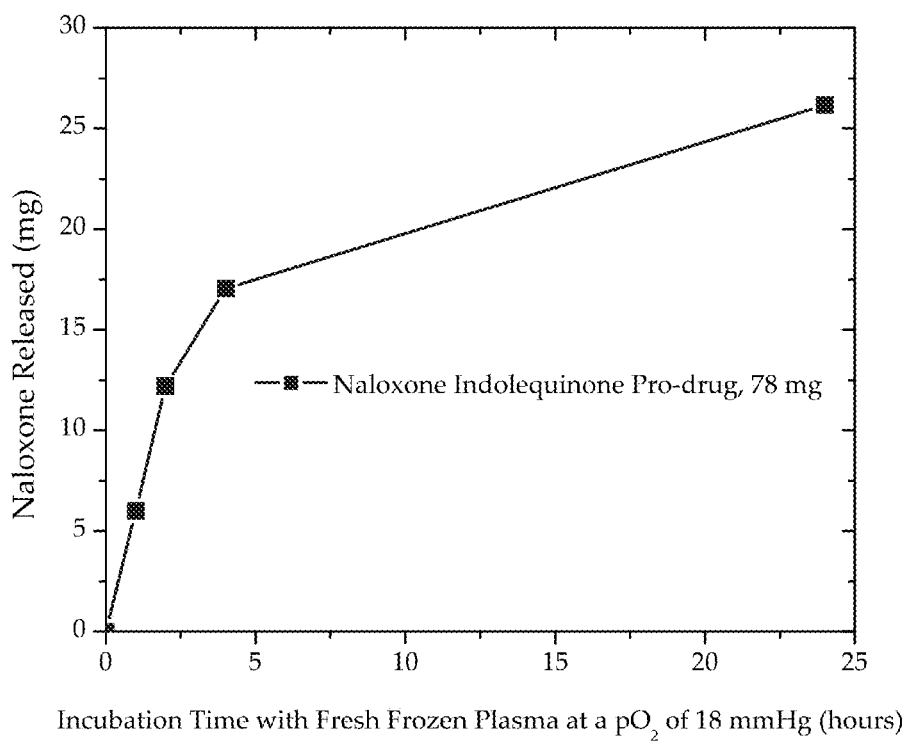
FIG. 40 shows time-dependent release kinetics of Naloxone pro-drug incubated in fresh frozen plasma under hypoxia.

The release rate of Naloxone from an indolequinone linker-based Naloxone pro-drug was obtained. This study was completed by incubating the Naloxone pro-drug with human plasma for a given period of time at a $pO_2$ of 18 mmHg. Following this incubation, the release of Naloxone from the Naloxone pro-drug was quantified using HPLC. The identities of the HPLC peaks were confirmed using mass spectrometry analysis and the amount of Naloxone released was calculated using a calibration curve. FIG. 40 shows the time-dependent release of Naloxone from the Naloxone pro-drug after incubation with human plasma. Based on this release study, it was determined that 78 mg of the indolequinone linker-based Naloxone pro-drug are required to achieve a release of 6 mg Naloxone/hour.

Example 22

Scale-Up of Synthesized Morphine/Hydro-morphone and Naloxone Compounds

In order to provide effective narcotic (Morphine/Hydromorphone) analgesia over prolonged periods, scale-up synthesis processes for the compounds are developed. Three (3) grams of each compound are synthesized. These compounds are used in combination to obtain the desired release kinetics of the analgesic and narcotic antagonist.

Synthesis of Morphine/Hypdromorphone Pro-drugs.

All of the Morphine pro-drugs (A, B, C, D, E, F, G; see FIG. 36) were synthesized through conventional organic chemistry (FIG. 35). Yields for each step were moderate to excellent. To minimize the number of permeatations, four of the six Morphine pro-drugs synthesized are selected for scale-up. Given the increased potency of Hydromorphone as compared to Morphine, two esterase-s7ensitive Hydromorphone pro-drugs are sythesized on gram scales.

Synthesis of Naloxone Pro-drugs.

The synthesis of indolequinone linker-based Naloxone pro-drugs was achieved on the 10-20 mg scale. Although 8 indolequinone-based Naloxone pro-drugs were originally synthesized, only the 4 pro-drugs containing diamine spacers were shown to be stable in PBS buffer. Therefore, only these 4 pro-drugs are scaled up to gram quantities (FIG. 36). The final indolequinone-Naloxone products are further purified by preparation TLC (0.25 mm thick, 20×20 cm, Whatman).

Synthesis of Dendrimer-Pro-Drug Complexes.

Figure 41:
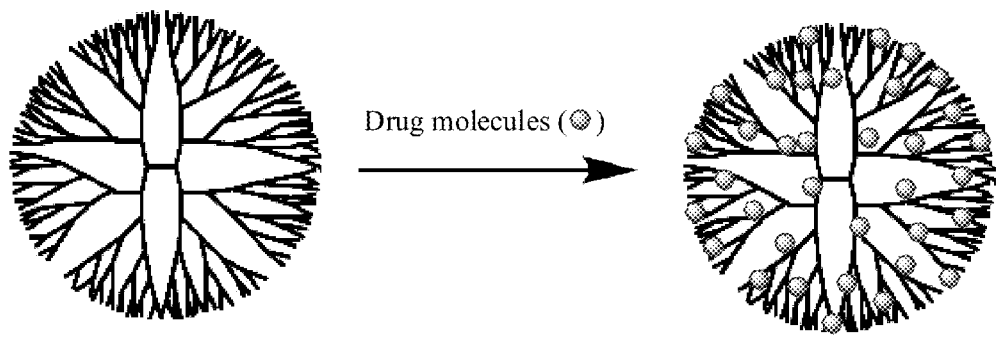
FIG. 41 shows a schematic depicting the complexation of drug to G5 PAMAM dendrimer.

An advantage of using dendrimer/drug complexes for drug delivery applications is generally known (1) to make water-insoluble drugs water soluble, and (2) to achieve high drug loading capacity. The hydrophobic interior of dendrimers along with their unique surface functional groups allow for effective complexation of drugs (FIG. 41). The mechanism to form dendrimer/drug complexes is based on the hydrophobic interaction, electrostatic interaction, hydrogen bonding, Van der Waals force, and/or the combination thereof (see, e.g., Esfand, R. and D. A. Tomalia, Drug Discovery Today, 2001. 6: p. 427-436; Kolhe, P., et al., International Journal of Pharmaceutics, 2003. 259: p. 143-160; Morgan, M. T., et al., J. Am. Chem. Soc., 2003. 125(50): p. 15485-15489; Papagiannaros, A., et al., International Journal of Pharmaceutics, 2005. 302: p. 29-38; Patri, A. K., J. F. Kukowska-Latallo, and J. R. Baker, Jr., Advanced Drug Delivery Reviews, 2005. 57: p. 2203-2214; Shcharbin, D. and B. M., Biochimica et Biophysica Acta, 2006. 1760: p. 1021-1026; each herein incorporated by reference in their entireties. In experiments conducted during the course of the present invention it was shown that Morphine and Naloxone pro-drugs can be complexed with G5 dendrimers with very high payload (40-70 pro-drug molecules/per dendrimer molecule). The novel concept to use dendrimer/pro-drug complexes allows one to design desired bimodal release profiles of drugs through different mechanisms. For example, a dendrimer/Morphine pro-drug complex can be first released through a general diffusion-driven mechanism, followed by the cleavage of the ester bond of the pro-drugs to release Morphine drug.

To obtain gram scales of the Morphine/Hydromorphone or Naloxone pro-drug complexes, a G5 dendrimer with 80 amine groups acetylated and the remaining amines carboxylated (G5.NHAc80-SAH) is used for complexation. G5.NHAc$_{80}$-SAH dendrimer (1.0 g) is dissolved in 50-mL water, and a specific pro-drug (molar ratio of dendrimer/pro-drug=1:80) dissolved into 5 mL methanol. The two solutions are mixed together and magnetically stirred over night to allow the evaporation of methanol. Then, the solution is centrifuged to remove possible precipitates related to non-complexed Morphine or Naloxone pro-drugs as the pro-drugs are hydrophobic and insoluble in water. The precipitate is collected and dissolved into methanol for HPLC analysis. The supernatant is lyophilized. The loading capacity of drugs is determined using HPLC. The final complexes are characterized using NMR, zeta potential measurements, and light scattering.

Synthesis of Dendrimer Pro-drug Conjugates.

Figure 42:
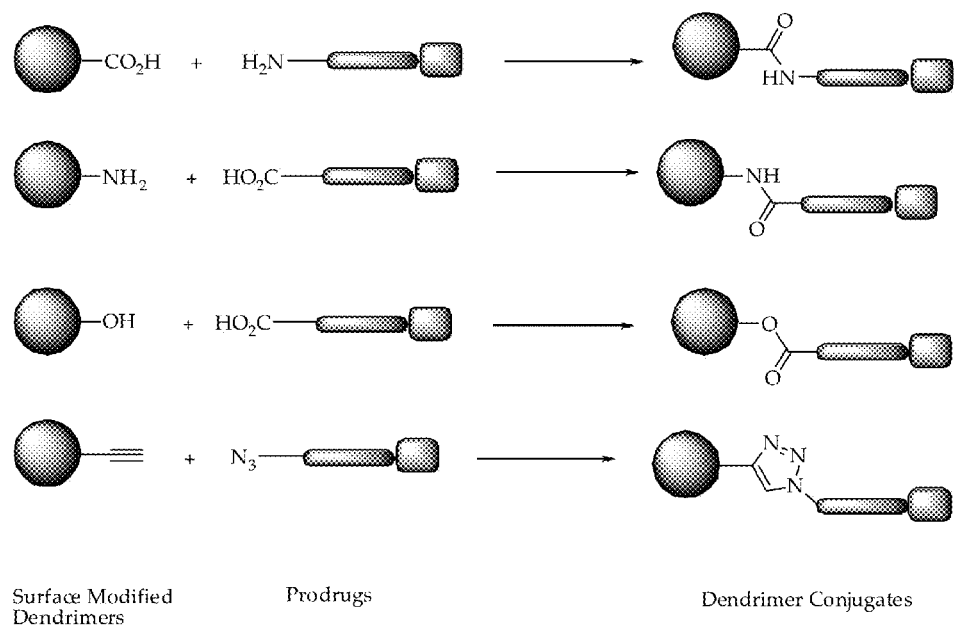
FIG. 42 shows a scheme depicting synthesis used to form pro-drug dendrimer conjugates.

In experiments conducted during the course of the present invention, several dendrimer pro-drug conjugates were synthesized. The pro-drugs containing acid, amine or azide functional groups were reacted with carboxyl, amine, hydroxyl or alkyne surface modified dendrimers, respectively, to afford the desired dendrimer drug compounds (FIG. 42). A similar strategy is utilized to scale up these compounds (100 mg-1 g).

In experiments conducted during the course of the present invention, it was shown that the synthesis of folic acid targeted dendrimer-drug conjugates can be scaled up to 100 g without any significant purification problems. A G5 PAMAM dendrimer is used as a general platform. G5 PAMAM dendrimer is first partially acetylated using a calculated amount acetic anhydride in presence of triethylamine as base. The remaining amino groups of the dendrimer are further modified to have either carboxylic acid or alkyne groups at the terminus of each branch. The carboxyl surface modification is achieved by reaction of the partially acetylated G5 dendrimer with a large excess of succinic/glutaric anhydride in methanol. The partially acetylated G5 dendrimer is reacted with 3-(4-(ethynyloxy)phenyl)propanoic acid to give alkyne functionalized partially acetylated dendrimer. Pro-drugs containing a carboxyl functional group are reacted with partially acetylated dendrimer to provide amide linked dendrimer-drug conjugate. The carboxyl surface modified dendrimer is attached to the pro-drugs having amine functional groups using standard carbodiimide coupling reaction. In experiments conducted during the course of the present invention, a method was developed for reacting azide functionalized drug linkers with alkyne terminated dendrimers using Cu(I) as catalyst. All these conjugate syntheses are readily scaled-up to gram quantities using a variety of coupling conditions. The synthesized conjugates are purified by gel filtration, large scale ultrafiltration using membranes of large surface area and dialysis, and characterized using NMR, mass spectroscopy and UV-vis.

Chemical Analysis of Dendrimer Complexes/Conjugates and Free Drug Concentration for Release Kinetic Studies.
Characterization of Generation 5 PAMAM Dendrimer-drugs Conjugates.

In experiments conducted during the course of the present invention, successful methods were developed to characterize PAMAM dendrimers (see, e.g., Majoros, I. J., et al., Biomacromolecules, 2006. 7(2): p. 572-579; Majoros, I. J., et al., Journal of Medicinal Chemistry, 2005. 48(19): p. 5892-5899; Islam, M. T., I. J. Majoros, and J. R. Baker, Journal of Chromatography B-Analytical Technologies in the Biomedical and Life Sciences, 2005. 822(1-2): p. 21-26; Islam, M. T., et al., Analytical Chemistry, 2005. 77(7): p. 2063-2070; Shi, X., et al., Electrophoresis, 2006. 27(9): p. 1758-1767; Shi, X. Y., et al., Electrophoresis, 2005. 26(15): p. 2949-2959; Shi, X. Y., et al., Analyst, 2006. 131(3): p. 374-381; Shi, X. Y., et al., Electrophoresis, 2005. 26(15): p. 2960-2967; each herein incorporated by reference in their entireties). High Performance Liquid Chromatography (HPLC), Size Exclusion Chromatography (SEC), Capillary electrophoresis (CE), and Matrix Assisted Laser Desorption Ionization-Time of flight (MALDI-TOF) mass spectrometric techniques are utilized.
High Performance Liquid Chromatography (HPLC)

HPLC is a widely accepted analytical method for separation and purification of various compounds. PAMAM dendrimer and its conjugates have been successfully characterized and analyzed using a gradient HPLC elution (see, e.g., Islam, M. T., I. J. Majoros, and J. R. Baker, Journal of Chromatography B-Analytical Technologies in the Biomedical and Life Sciences, 2005. 822(1-2): p. 21-26; Islam, M. T., et al., Analytical Chemistry, 2005. 77(7): p. 2063-2070; each herein incorporated by reference in their entireties). Briefly, HPLC analysis is carried out on a Waters Delta 600 HPLC system equipped with a Waters 2996 photodiode array detector, a Waters 717 Plus auto sampler, and Waters Fraction collector III. The instrument is controlled by Empower 2 software. For analysis of the conjugates, a C5 silica-based RP-HPLC column (250×4.6 mm, 300 Å) connected to a C5 guard column (4×3 mm) is used. The mobile phase for elution of different generations of PAMAM dendrimers is a linear gradient beginning with 100:0 (v/v) water/acetonitrile (ACN) at a flow rate of 1 mL/min. Trifluoroacetic acid (TFA) at 0.14 wt % concentration in water as well as in ACN are used as a counter ion to make the dendrimer surfaces hydrophobic.
Capillary Electrophoresis (CE)

An Agilent Technologies CE instrument is used for capillary electrophoresis. A procedure is used to characterize dendrimer conjugates (see, e.g., Shi, X. Y., et al., Electrophoresis, 2005. 26(15): p. 2949-2959; Shi, X. Y., et al., Analyst, 2006. 131(3): p. 374-381; Shi, X. Y., et al., Electrophoresis, 2005. 26(15): p. 2960-2967; each herein incorporated by reference in their entireties). Samples are introduced by hydrodynamic injection. Detection is done by an online PDA detector installed in the system.

Size Exclusion Chromatography (SEC)

SEC experiments for dendrimers and their conjugates are performed using an Alliance Waters 2690/2695 separations module (Waters Corp., Milford, Mass.) equipped with a Waters 2487 UV absorbance detector (Waters Corp.), a Wyatt Dawn DSP laser photometer (Wyatt Technology Corp., Santa Barbara, Calif.), an Optilab DSP interferometric refractometer (Wyatt Technology Corp.), and TosoHaas TSK-Gel Guard PHW 06762 (75×7.5 mm, 12 µm), G 2000 PW 05761 (300× 7.5 mm, 10 µm), G 3000 PW 05762 (300×7.5 mm, 10 µm), and G 4000 PW (300×7.5 mm, 17 µm) columns. Citric acid buffer (0.1 M concentration) with 0.025% sodium azide in water is used as a mobile phase, pH 2.74, using NaOH. Molar mass moments of the PAMAM dendrimers are determined using Astra software (version 4.9) (Wyatt Technology Corp.).

MALDI-TOF Mass Spectrometry

MALDI-TOF mass spectra is acquired using a Waters Tof-Spec-2E spectrometer in a reflection mode. Each sample is dissolved in a 50:50 mixture of methanol/water to obtain an approximate concentration of 0.25 mg/mL. The samples are then mixed with equal volumes (5 µL) of the matrix solution (10 mg/mL R-cyano-4-hydroxycinnamic acid (CHCA) dissolved in ACN/ethanol (50:50)). The TFA salt form of the separated samples is isolated and collected. A 1-µL solution of the mixture is injected on the spots of the target plate and evaporated to dryness. Calibration of the spectrometer is done using a mixture of known peptides in the CHCA matrix.

NMR Spectroscopy $^1$H and $^{13}$C and HMQC NMR spectra is taken in $D_2O$ and used to provide integration values for structural analysis by means of a Bruker AVANCE DRX 500 instrument. Shifts and integration of signals in the $^1$H NMR spectra are used for quantitative analysis of the conjugation reactions and for structural characterization, while the signals and shifts in the $^{13}$C NMR spectra are used for qualitative characterization.

Example 23

Perform In Vitro Binding and Cytotoxicity Studies of Morphine/Hydromorphone and Naloxone Compounds The controlled drug release is based on the premise that the synthesized pro-drugs remain biologically minimally active or inactive and the free drug is released to an active form by a physiological trigger such as an esterase action or hypoxia. The biological function of the pro-drugs and the released drugs by bioassays are monitored. The binding characteristics of the released drugs on appropriate cells which express the receptors for these drugs are tested. Ligands with established biochemical signal effects following their binding are studied by monitoring these signals. For example, the binding of Morphine to a cell surface receptor initiates a series of signal transduction events, which lead to several cellular responses. An early event in the signal transduction pathway is the activation of Gi/Go proteins leading to the inhibition of adenlyate cyclase activity and decrease in the cellular cAMP levels (see, e.g., Childers, S. R. and S. R. Childers, Life Sciences, 1991. 48(21): p. 1991-2003; herein incorporated by reference in its entirety). The biological functionality of the dendrimer-opioid conjugates are determined in vitro by, for example, i) monitoring the binding of the conjugate onto live cells or isolated cell membranes, ii) determining the activation/inactivation of G-proteins in isolated membranes, and iii) quantifying the cAMP content in intact cells.

Radio-ligand Competition-Binding Assay

This assay is performed using membrane preparations from cell lines, shown in Table 3, that express various receptors.

TABLE 3

Analgesic drugs, receptors and cell lines expressing these receptors.

| Drugs | Receptors/ transporters | Cell lines | Cell line availability | References |
|---|---|---|---|---|
| Morphine/ Hydromorphone | µ opioid receptor | SH-SY5Y, SK-N-SH, T47D | From ATCC | Horner, K. A., et al., Brain Research, 2004. 1028(2): p. 121-32; herein incorporate by reference in its entirety |
| Naloxone | µ opioid receptor | SH-SY5Y, SK-N-SH, T47D | From ATCC | Horner, K. A., et al., Brain Research, 2004. 1028(2): p. 121-32; herein incorporate by reference in its entirety |

Cells are maintained in appropriate culture medium supplemented with 10% heat-inactivated bovine calf serum, 2 mM L-glutamine, as well as penicillin and streptomycin, and grown at 37° C. in a 5% $CO_2$ incubator. Cell membranes are prepared as described previously (see, e.g., Horner, K. A., et al., Brain Research, 2004. 1028(2): p. 121-32; herein incorporate by reference in its entirety). Total protein concentration is determined and membrane binding assays for receptors are performed as described previously (see, e.g., Horner, K. A., et al., Brain Research, 2004. 1028(2): p. 121-32; herein incorporate by reference in its entirety). Briefly, cell membranes (0.1 mg protein) are incubated in 50 mM Tris-HCl pH 7.4/0.3% bovine serum albumin containing a constant concentration of $^3$H-drug and various concentrations of unlabeled drug either coupled to or released from the dendrimer. Nonspecific binding is defined as that measured in the presence of 1 µM of cold drug. The membranes are then filtered onto Skatron glass fiber filters that have been soaked in 50 mM Tris-HCl, pH 7.4, using a Skatron harvester (Molecular Devices, Sunnyvale, Calif.). Filter disks are placed in scintillation cocktail (Ready-Protein Plus, Beckman Coulter, Fullerton, Calif.) and counted. Total binding is defined as dpm of $^3$H drug bound by each sample. Each concentration of drug is assayed in triplicate and the experiment repeated at least two times. Nonlinear regression analysis of $^3$H-drug competition assays is performed with GraphPad Prism (GraphPad Software, San Diego, Calif., USA).

Determination of Receptor Binding of Drug Compounds by Surface Plasmon Resonance (SPR).

The binding of the synthesized pro-drugs and dendrimer-drug compounds onto receptors of these drugs in partially purified membrane fractions of cell lines listed in Table 3 is tested. For this, membrane is extracted with 0.5% Triton-X in buffer containing protease inhibitors and centrifuged at 100,000×g for 1 h. The supernatant is ultra filtered to remove the detergent and other small molecules, and the protein extract used as a source of receptors for drug-conjugate binding. If needed, the opioid receptor is further purified by affinity chromatography of the Triton-X-solubilized fraction. The binding of the conjugates is tested using a BIAcore X instrument (BIAcore AB, Uppsala, Sweden) (see, e.g., Hong, S., et al., Chemistry & Biology, 2007. 14(1): p. 105-113; herein incorporated by reference in its entirety). The conditions for receptor immobilization and ligand binding is optimized using different BIAcore sensor chips and buffer solutions as suggested by the vendor. The data obtained is analyzed by a global fitting binding model using the BIAevaluation 3.2 software. The apparent equilibrium dissociation constants ($K_d$) are calculated from the ratio of the dissociation and association rate constants ($k_{off}/k_{on}$). The data obtained displays the efficacy for binding of the conjugates vs. free drugs on their respective receptors.

Determination of the Opioid Receptor Activation.

The rate-limiting step in the activation of G-protein is the dissociation of bound GDP, which enables the binding of GTP at the displaced site. This is followed by the dissociation of G-protein subunits that facilitates the activation of adenlyate cyclase and the subsequent hydrolysis of the bound GTP by the inherent GTPase of the G-protein (see, e.g., Pierce, K. L., et al., Nature Reviews Molecular Cell Biology, 2002. 3(9): p. 639-50; herein incorporated by reference in its entirety). The activity of an opioid agonist is determined in cell-free systems using partially purified membrane from opioid receptor-expressing cells that contains the G-proteins. This is done by measuring the rate of agonist-stimulated membrane binding of a non-hydrolyzable analog of GTP such as the GTPγS (see, e.g., Traynor, J. R., et al., Journal of Pharmacology & Experimental Therapeutics, 2002. 300(1): p. 157-61; herein incorporated by reference in its entirety), or by monitoring the membrane GTPase activity (see, e.g., Sun, H., et al., Proceedings of the National Academy of Sciences of the United States of America, 1995. 92(6): p. 2229-33; herein incorporated by reference in its entirety). The biochemical functionality of dendrimer-opioid conjugates before and after pre-treatment with purified enzymes and plasma is determined by G-protein-based assays.

Evaluating Opioid Conjugate Ability to Stimulate [$^{35}$S] GTPγS Binding.

Cells are rinsed with PBS and scraped into 50 mM Tris-HCl buffer pH 7.4 containing 0.3 M sucrose in presence of protease inhibitors, and homogenized in a dounce homogenizer. The nuclei and unbroken cells are removed by low-speed centrifugation at 200×g and the supernatant is spun again at 15,000×g for 20 min. The membrane preparation obtained is washed with Tris-HCl buffer and used for binding studies. The protein concentration of the membrane is determined using standard protocols. 100 μg of the partially purified membrane preparation is incubated for 10 min at 37° C. in a buffer containing [$^{35}$S] GTPγS and GDP. The pro-drugs are then added and at different time points, aliquots of the reaction mixture removed and rapidly filtered through a glass fiber filter. The filters are rinsed and the bound radioactivity determined by scintillation counting. Non-specific binding is determined in presence of excess (50 μM) non-radioactive GTPγS. The rate constants and maximal binding of the [$^{35}$S] GTPγS is determined using the GraphPad Prism program (GraphPad, San Diego, Calif.). Appropriate controls are run in the absence of ligands, and in the presence of free agonists. The effect of the 'dendrimer-opioid antagonist' on the agonist-induced binding is then be verified.

The results of the studies described above indicate if the intact pro-drugs have any in vitro biological activity. The [$^{35}$S] GTPγS binding studies using pro-drugs that had been pre-incubated with purified esterase/plasma are done in order to demonstrate the biological activity of the ligand that is released by esterase. For this, the conjugate/complex is incubated with the enzymes for different time-periods and adding ice-cold buffer to stop the esterase action. The reaction mixture is immediately filtered through a 10 kDa filter at 4° C., and the filtrate used as the ligand in the [$^{35}$S] GTPγS binding assay (see, e.g., Traynor, J. R., et al., Journal of Pharmacology & Experimental Therapeutics, 2002. 300(1): p. 157-61; herein incorporated by reference in its entirety). Similarly, the filtrates obtained following hypoxic treatment of dendrimer-Naloxone pro-drug complexes/conjugates are used to test whether the released free Naloxone inhibits agonist-induced Gi-protein activation.

Functional Determination of Opioid-induced GTPase Activity.

GTPase activity will be determined as previously described (see, e.g., Sun, H., et al., Proceedings of the National Academy of Sciences of the United States of America, 1995. 92(6): p. 2229-33; herein incorporated by reference in its entirety). Cell membranes are partially purified. 10 to 100 μg of the membrane protein are incubated in HEPES buffer pH 8.0 containing dithiothrietol and different concentrations of pro-drugs. The reaction is initiated by adding 100 nM GTP[γ-$^{32}$P] and aliquots withdrawn at different time intervals into tubes containing ice cold 5% Norit A in phosphate buffer. After centrifugation of the mixture, the radioactivity of the liberated [$^{32}$P]-phosphate in the supernatant is quantified by scintillation counting. The binding constants are determined. Appropriate controls are run in parallel, and the effect of respiratory stimulants and esterase- and hypoxia-treated conjugates are also determined. If needed, the specificity for Gi-protein activation is verified by using membranes isolated from cells that had been pre-treated with pertussis toxin (200 ng/ml for 24 hrs), a treatment that inactivates the GTPase activity of the Gi-protein.

Determination of Adenylate Cyclase Activity.

Dendrimer-based pro-drugs with either Morphine/Hydromorphone or Naloxone and in combination are tested in vitro on opioid-responsive neuronal cell lines. Morphine binding and G-protein mediated signal transduction events leads to the activation of the enzyme adenlyate cyclase and generation of the second messenger cyclic AMP (cAMP). Changes in the activity of Morphine and antagonism by Naloxone of intracellular generation of cAMP are used as a marker of the function of dendrimer-conjugated and released opioids. Responsive neuronal cells are measured by cyclase ELISA (see, e.g., Horton, J. K., et al., Journal of Immunological Methods, 1992. 155(1): p. 31-40; herein incorporated by reference in its entirety).

In Vitro Cytotoxicity Studies.

The cytotoxicity of the free drugs and the conjugates is determined by multiple biochemical assays such as XTT assay, Clonogenic assay and lactate dehydrogenase (LDH) release assay, using the cells lines given in Table 3. As some indolequinones have variable cytotoxic potential in the oxidized and reduced state (see, e.g., Newsome et al, Organic & Biomolecular Chemistry 5(10): 1629-40, 2007; herein incorporated by reference in its entirety), the cytotoxicity of the compounds before and after reduction by reductases is tested.

XTT assay.

This assay is based on the conversion of XTT (sodium 3'-[1-(phenylaminocarbonyl)-3,4-tetrazolium]-bis(4-methoxy-6-nitro)benzene sulfonic acid hydrate; Roche Diagnostics) to formazan by mitochondria of live cells. Cells are placed in 96-well microtiter plates and incubated with various concentrations of the drug conjugates for different time periods. The drugs are removed and the cells are allowed to recover for 3 days. The cells are incubated with XTT reagent for 2 hours and the absorbance of the formazan product formed is measured at 492 nm on ELISA reader, using a reference wavelength of 690 nm.

Clonogenic Assay.

This is based on inhibiting colony formation initiated by single cells. 100 cells are plated in 60 mm dishes and incubated drug conjugates under various conditions, and allowed the singles cells to form colonies over a period of 7-10 days. Cells are rinsed and stained with methylene blue. Cell colonies (>20 cells) are counted using an AcuCount1000 (Bio Logics) counter.

LDH Release Assay.

This is based on the determination of cell membrane integrity and the leakage of LDH from dead cells. Cells are plated in 96 wells and exposed to drug conjugates for varying times. The conjugates are removed and incubated with a fluorogenic substrate for LDH ("Cyto Tox-One", Promega). The generated fluorescence is measured (excitation 560 nm and emission 590 nm) as a function of the concentration of LDH in the media.

Apoptosis Sensing Assay.

If needed, in order to differentiate between apoptosis vs. necrosis, apoptosis-sensing assays such as "Annexin V-PS staining" (BD Sciences) and "CaspaTag" Caspase 3 binding (Chemicon) assays are conducted.

Example 24

Demonstrate Release of Morphine/Hydromorphone and Naloxone Compounds In Vivo at Concentrations and Conditions Required for Clinical Effect Methods were designed to evaluate the release kinetics and activity of drugs, prodrugs, and conjugated drugs with dendrimers. This is done to document that both the specific activity and dosage of drug achievable with these systems are adequate for the desired therapeutic and feedback effects. These studies are performed with parallel development of both the Morphine/Hydromorphone and Naloxone arms with combination testing as an ongoing process. It is anticipated that a number of additional compounds will be created as well as modifications to promising candidates in order to arrive at optimal release kinetics. Ultimately, utilizing a down selection process based on efficacy testing and ADMET, the best compounds will be placed in a preclinical simulation providing evidence for an IND submission to the FDA.

The components of each phase possess unique requirements in animal model design and testing which have been considered to enhance our capability for success.

Selection of Animals for Separately Examining Morphine/Hydromorphone and Naloxone Pharmaco-Kinetics.
(a) Hartley Guinea Pigs (see, e.g., Nambiar, M. P., et al., Toxicology and Applied Pharmacology, 2007. 219(2-3): p. 142-150; Shih, T. M., T. C. Rowland, and J. H. McDonough, Journal of Pharmacology and Experimental Therapeutics, 2007. 320(1): p. 154-161; each herein incorporated by reference in their entireties).

Adult male Hartley guinea pigs weighing 500 grams are an accepted model utilized by the esterase scientific community. Guinea pigs allow for initial testing of large numbers of prodrug/conjugates which can be studied in an economical and effective way. In addition, these animals are adequate size to be intubated under general anesthetic conditions for airway control and hypoxia induction. Invasive hemodynamic monitoring is required to validate hypoxic release of Naloxone is also possible in this animal model. Animal size allows for the collection of approximately 5 ml whole blood prior to an end terminal bleed which limits the number of time points for collection of an otherwise optimal small animal model for study.

(b) Alternative Strategy: Esterase Knockout Mouse.

An esterase knockout mouse, bred specifically to simulate in-vivo human esterase conditions, is provided. This model provides highly translatable data to the human condition. This model serves as a backup to guinea pig for Morphine/Hydromorphone release.

In Vivo Morphine/Hydromorphone Pharmacokinetics Studies.

A total of 12 pro-drug/pro-drug compounds are tested at 6 dosage levels, utilizing 2 delivery methods, with 6 evaluation time points per animal. Three animals for each group for statistical validity are used. Blood samples are drawn at time 0 prior to drug administration and at serial time points of 10, 30, 60 min and 6, 12, 24 hours via a placed indwelling catheter. For the first 6 time points 0.5 ml are withdrawn. This is followed by an end terminal bleed for approximately 10 ml final whole blood. These samples immediately undergo analysis for Morphine/Hydromorphone levels in serum using an ELISA assay. For the best 2 drugs only, recovery procedures are carried out with continued blood sampling at 2 weeks and 1 month followed by sacrifice and histopathology to validate the lack of long-term toxicity.

For serum Morphine/Hydromorphone level determination, the Calbiotech Morphine Specific Direct ELISA Kit is utilized. In 96 well plates, 20 ul serum is incubated per manufacturer instructions. Both positive and negative controls are analyzed as provided in the assay. The resulting products are read utilizing a 96 well plate reader Bio-Rad 680 XR Microplate Reader and analyzed using provided statistical software. The assay's reported sensitivity is to 1 ng/mL, which is more than adequate for the anticipated in-vivo serum levels.

In Vivo Naloxone Pharmacokinetics Studies.

Guinea Pigs are anesthetized and the carotid artery accessed for placement of an invasive oxygen monitor catheter which provides direct measurement of blood oxygenation during the study. Blood is drawn as a preoperative standard and then 6 prodrug/conjugates are administered using 6 different dosage schedules via 2 delivery methods. Hypoxia is then induced using a gas mixture to obtain the desired levels of SaO2 (10, 20, 40, 70, 100). Blood is collected and analyzed at each of these levels to confirm appropriate drug release at the desired hypoxic levels. These samples immediately undergo analysis for Naloxone levels using HPLC. For the best 2 drugs only, recovery procedures are carried out with continued blood sampling at 2 weeks and 1 month followed by sacrifice and histopathology to validate the lack of long-term toxicity.

HPLC (see, e.g., Kuracka, L., et al., Clinical Chemistry, 1996. 42(5): p. 756-760; Orlovic, D., et al., Chromatographia, 2000. 52(11/12): p. 732-734; Svensson, J., et al., Journal of Chromatography B: Biomedical Sciences and Applications 1982. 230(2): p. 427-432; Svensson, J.-O., Journal of Chromatography B: Biomedical Sciences and Applications, 1986. 375: p. 174-178; Tebbett, I. R., Chromatographia, 1987. 23(5): p. 377-378; each herein incorporated by reference in their entireties) is utilized to quantitatively analyze Naloxone content in the serum samples. Prior to HPLC analysis of the reaction mixtures, the samples are pre-treated by protein precipitation by organic solvents. If needed, Solid Phase Extraction method carried out by using $C_{18}$ Sep-pak cartridges to remove proteins and any other interfering matrix impurities is also performed. After pre-treatment, the samples are reconstituted with the HPLC eluent and injected into a reverse phase column. The complete qualitative and quantitative analysis using HPLC is carried out on a Waters Delta 600 HPLC system equipped with a Waters 2996 photodiode array detector, a Waters 717 Plus auto sampler, Waters Fraction collector III and Empower 2 software. An analytical size column (C8 or C18) with a particle size of 5 µm is used. Initially, an isocratic elution using acetonitrile/phosphate buffer, pH 7.0 is used. The conditions for an HPLC experiment, if required, are modified in order to incorporate various analyses and generate efficient results. To determine the percent recovery of a drug sample from the serum, a standard drug sample of a known concentration is spiked into serum and/or cerebrospinal fluid. This spiked sample is then subjected to sample pre-treatment. A HPLC analysis is performed on this pre-treated spiked sample and a standard drug sample. From the calibration curve and the regression equation, the percent recovery is computed.

For quantitative analysis, standard drug samples are obtained and stock solutions for each of these drugs made in an appropriate solvent. Using a serial dilution method, standards for each drug at various concentrations are prepared to generate a calibration curve. Concentration of free drug after its release is calculated using a regression equation.

Example 25

Survey ADMET Characteristics of Those Compounds that Showed Desirable Release Kinetics ADMET data has already been obtained for Morphine/Hydromorphone, Naloxone and the dendrimers themselves. Therefore, toxicity issues from these compounds will not be a limiting factor in selection of the final compound. Analysis of the final formulations is conducted to assure that they are also not toxic. Therefore, ADMET characteristics of only those compounds that show desirable release kinetics will need to be surveyed. Three adult male Hartley pigs (500 grams) per compound are used to ensure statistical validity. Six dosage levels with 2 delivery methods are explored with the goal of achieving dose related-toxicity in the highest group for definition of the therapeutic threshold. Morphine/Hydromorphone, and 2 Naloxone, $^{13}C$ radio-labeled compounds will undergo ADMET testing.

An indwelling port is placed to assist with scheduled blood draws. Following drug administration, blood samples are drawn at serial time points of 1, 4, 7, and 14 days. An end terminal bleed is completed and animals will be sacrificed with 10 organ harvest for histopathological examination to determine distribution and toxicity effects. Blood samples undergo HPLC analysis for evaluation of compound/conjugate levels.

Example 26

Figure 43:
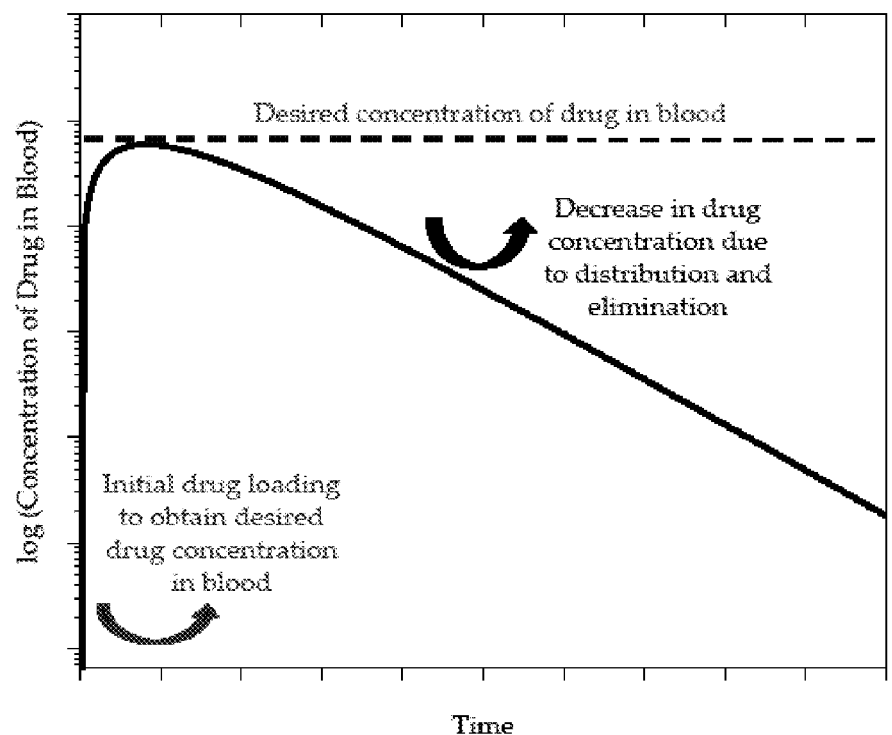
FIG. 43 shows a schematic showing the initial loading and subsequent decrease of drug concentration in blood due to distribution and elimination. Models are used to determine an appropriate mixture of compounds needed to maintain the desired drug concentration.

Perform In Vivo Studies Simultaneously Examining the Effect of the Morphine/Hydromorphone and Naloxone Compounds A component of developing a controlled analgesic release system is determining the mixture of Morphine/Hydromorphone and Naloxone necessary obtain the desired clinical effects. Due to the fast drug-release kinetics, pro-drugs are used for the initial loading bolus to reach the desired drug-serum concentration. Pro-drug dendrimer complexes and conjugates, both of which have shown slower drug release kinetics, are used for maintenance to replace drug lost during the distribution and elimination phases (FIG. 43). Previously published literature (see, e.g., Schulte, H., A. Sollevi, and M. Segerdahl, Pain, 2005. 116(3): p. 366-374; Loetsch, J., et al., Clinical Pharmacology and Therapeutics, 1996. 60(3): p. 316-325; Hill, H. F., et al., Pain, 1990. 43(1): p. 57-67; Hill, H. F., et al., Pain, 1990. 43(1): p. 69-79 each herein incorporated by reference in their entireties) and commercially available software are used to guide decisions in determining the appropriate ratios of pro-drug, pro-drug dendrimer complexes and pro-drug dendrimer-conjugates.

Selection of Animal for Separately Examining Morphine/Hydromorphone and Naloxone Pharmacokinetics.

(a) Gottingen Mini-Pigs (see, eg., Worek, F., et al., Toxicology, 2008. 244: p. 35-41; herein incorporated by reference in its entirety)

Gottingen pigs are 20 kg and offer a translatable model to human condition with the ability for both intubation and invasive hemodynamic monitoring as well as a large quantity of blood for analysis of drug release. Data obtained from pigs is adequate for proof of concept validation. This model allows evaluation of numerous time points both for Morphine/Hydromorphone release via esterase and Naloxone release via hypoxia.

In Vivo Morphine/Hydromorphone and Naloxone Pharmacokinetics Studies.

In vivo studies simultaneously examining the activity Morphine/Hydromorphone- and Naloxone-based compounds is conducted. Due to the complex monitoring required for these studies, they need to be performed in Gottingen pigs. Combinations of both Morphine/Hydromorphone- and Naloxone-based compounds are administered to the pigs. Pigs are dosed five times (5) over a period of one hour. This is done to simulate a potential overdose scenario and therefore enable evaluation of the feedback mechanism within the controlled analgesic release system. The pigs are bled regularly for over the course of 12 hours.

Gottingen mini pigs are anesthetized and the carotid artery accessed for placement of an invasive oxygen monitor catheter which provides direct measurement of blood oxygenation during the study. Blood is drawn as a preoperative standard. Eight combinations of the best 2 drugs from each category (narcotic and anti-narcotic) are evaluated using a clinical simulation model applicable to direct in field application. Pigs receive serial administration of the combination of drugs at time 0, 15, 30, 45, 60 min for a total of 5 doses. This simulates a potential overdose scenario and therefore enables evaluation of the feedback mechanism within the controlled analgesic release system. If hypoxia has not occurred following the final dosage, a gas mixture is administered with reduced oxygen concentrations to simulate hypoxia due to analgesic overdose. Blood samples are taken at 0, 15, 30, 45, 60, and 120 minutes, as well as at $SaO_2$ values of 10, 20, 40, 70, 100. The serum collected is analyzed using an ELISA assay (Morphine/Hydromorphone) and HPLC (Naloxone) to confirm obtainment of appropriate drug release levels. For the 2 most promising compound combinations, recovery procedures are carried out with continued blood sampling at 2 weeks and 1 month. Following a terminal bleed, the pigs are sacrificed and undergo histopathological examination to determine long-term distribution and toxicity effects.

Example 27

This example demonstrates in vitro sustained release of morphine using a morphine pro-drug. Pro-drug A (20 µM)

Prodrug A Aliphatic ester

Figure 44:
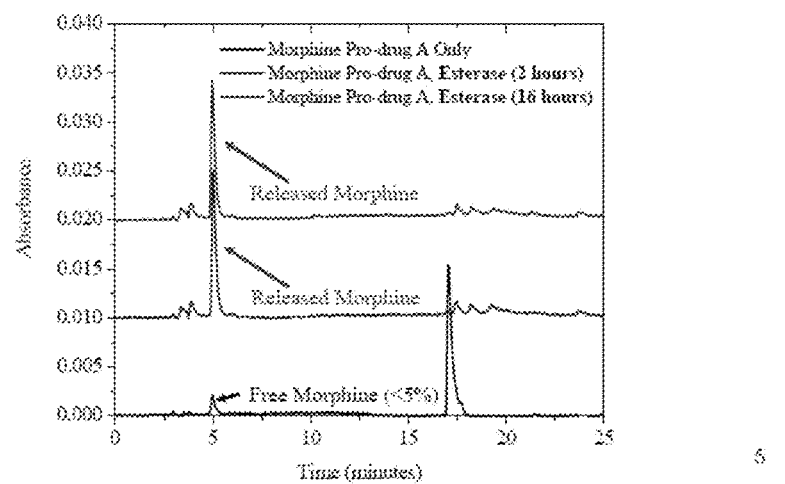
FIG. 44 shows in vitro sustained release of morphine using a morphine pro-drug.

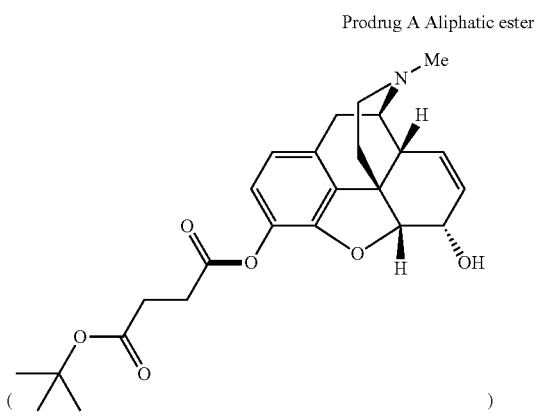

was incubated with porcine liver esterase (Sigma, 0.01 U) in 20 mM phosphate buffer pH 7.0 for 2 and 16 hours. At the end of the time periods the samples were frozen at −20° C. and were thawed prior to loading onto the HPLC column. HPLC analysis was performed within 24 hours of the incubation. The analysis was performed on a reverse phase column (250× 4.6 mm, C5, 300A) with a flow rate of 1 mL/min using a gradient elution beginning at 90/10 Water/Acetonitrile with 0.14% TFA and ending at 10/90 within 30 minutes. Released Morphine was monitored and detected using a PDA detector at wavelength of 280 nm. As shown in FIG. 44, the morphine prog-drug A without esterase is shown with absorbance starting at 0.000, the morphine pro-drug A with esterase (2 hours) is shown with absorbance starting at 0.010, and the morphine pro-drug A with esterase (16 hours) is shown with absorbance starting at 0.020.

Example 28

Figure 45:
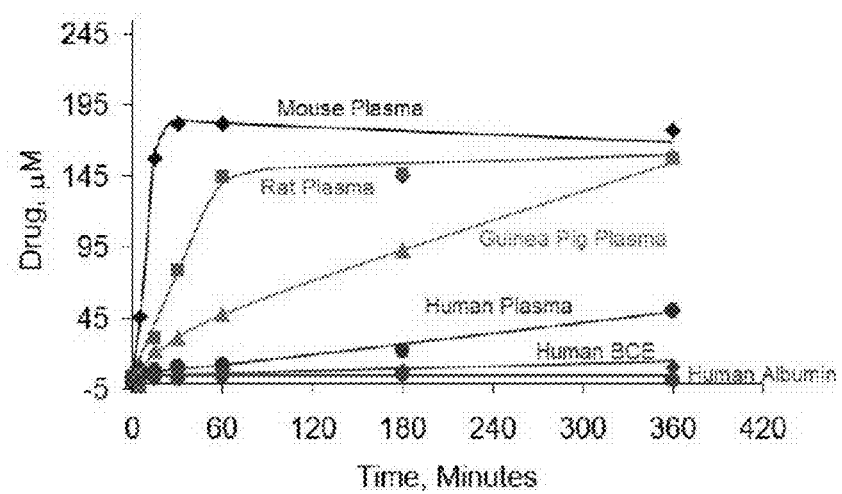
FIG. 45 shows the release kinetics of free morphine from the prodrug in the various plasma samples.

This example demonstrates in vitro release of free morphine from prodrug in different plasma samples. Pro-drug B (250 µM)
was incubated with 50% fresh frozen plasma collected from the indicated species, or with Human Butyryl Choline Esterase (Human BCE, 0.5 U/ml), or with Human Albumin (Sigma, 25 mg/ml) in 50 mM phosphate buffer pH 7.0. The samples were incubated at 37° C. and aliquots were withdrawn at the indicated time-points and the proteins were precipitated with 2 volumes of ice-cold 10% DMSO in acetonitrile. The samples were micro-centrifuged at high speed for 10 minutes at 4° C. and the supernatants were frozen at −20° C. The samples were thawed prior to loading onto the UPLC column. UPLC analysis was performed within 24 hours of the incubation using an Acquity HSS T3 column (2.1×10 mm). Flow rate was maintained at 0.5 ml/min. Released Morphine was monitored using a PDA detector at 280 nm. The gradient elution used for this method began at 98/2 Water/Acetonitrile containing 0.14% TFA and ended with 2/98 Water/Acetonitrile containing 0.14% TFA in 6.5 minutes. The amount of free morphine released was calculated from a standard curve generated using different concentrations of morphine subjected to UPLC under identical conditions. FIG. 45 shows the release kinetics of free morphine from the prodrug in the various plasma samples.

Example 29

This example demonstrates that naloxone is released from an indolequinone based naloxone prodrug only under low oxygen conditions. Naoxone pro-drug (125 µM) was incubated with 30% fresh frozen human plasma in 50 mM phosphate buffer pH 7.0 in the presence of 133 µM each of NADH and NADPH. The reaction mixture was divided into two portions, and to one portion Argon gas was slowly bubbled using a capillary tube until the oxygen pressure reached 18 mm Hg, monitored using a Blood Gas Analyzer. The tube was tightly sealed and transferred into a hypoxia chamber with a pO$_2$ that was maintained at 18 mm Hg by continuously passing Argon gas. The sample was incubated overnight at room temperature with the second portion incubated under normoxia condition kept outside the chamber. At the end of the Prodrug B Aromatic ester

Figure 46:
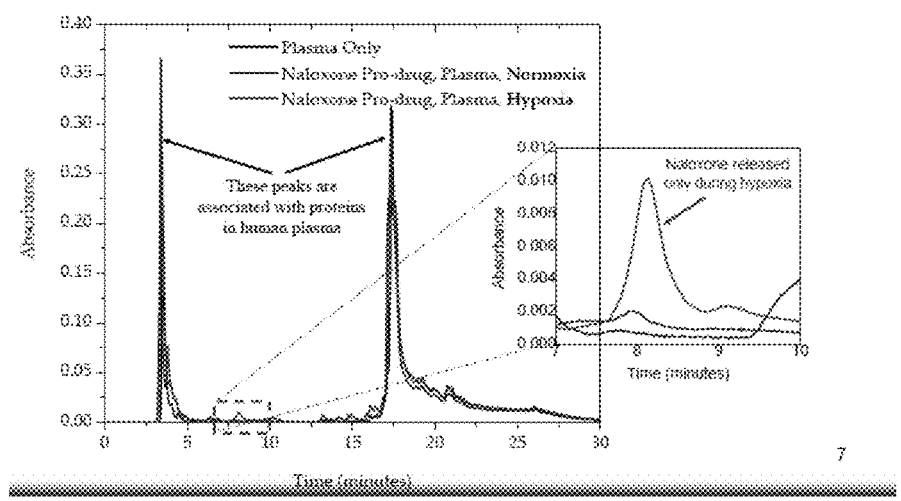
FIG. 46 shows that naloxone is released from an indolequinone based naloxone prodrug only under low oxygen conditions.

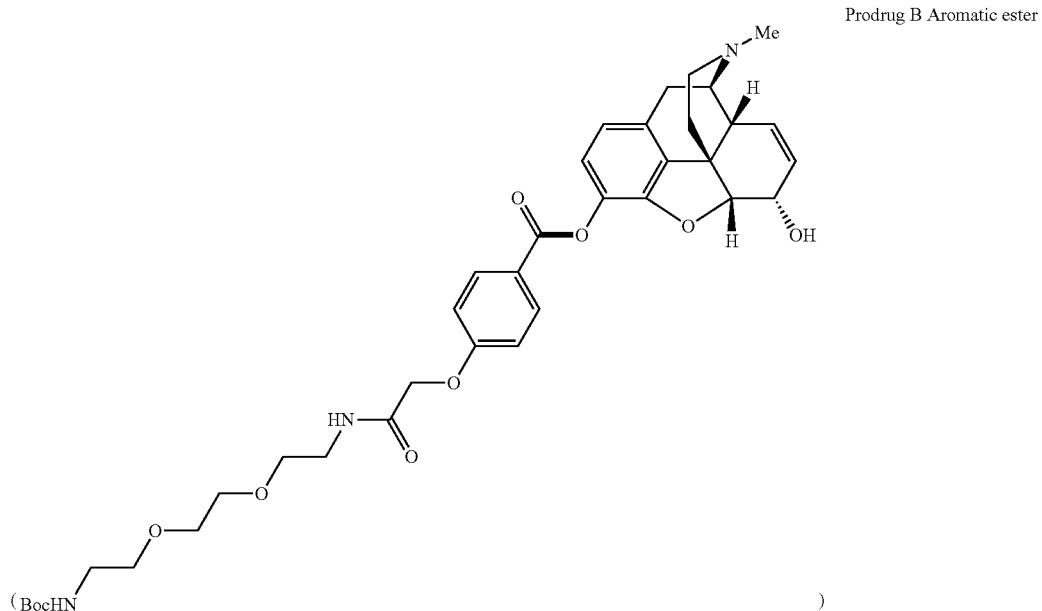

time period the samples were frozen at −20° C. and the samples were thawed prior to loading onto the HPLC column. HPLC analysis was performed within 24 hours of the incubation. The analysis was performed on a reverse phase column (250×4.6 mm, C5, 300 A) with a flow rate of 1 mL/min using a gradient elution beginning at 90/10 Water/Acetonitrile with 0.14% TFA and ending at 10/90 within 30 minutes. Released Naloxone was monitored and detected using a PDA detector at wavelength of 280 nm. FIG. 46 shows that naloxone is released from an indolequinone based naloxone prodrug only under low oxygen conditions.

Example 30

This example demonstrates in vivo sustained release of morphine in a guinea pig model. Male Hartley guinea pigs (375-475 g) from Elm Hill labs were allowed free access to food and water before being used in the testing of analgesia effects free morphine, morphine complex, and morphine prodrug A complex

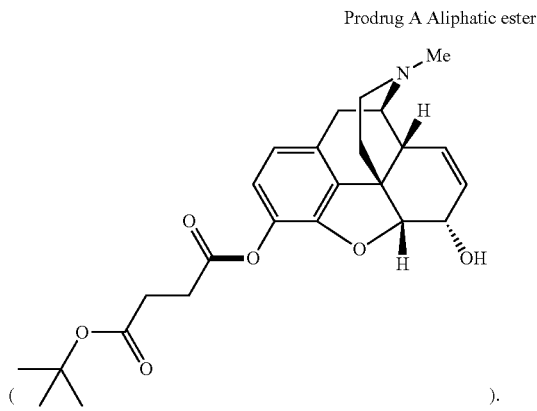

Prodrug A Aliphatic ester

Figure 47:
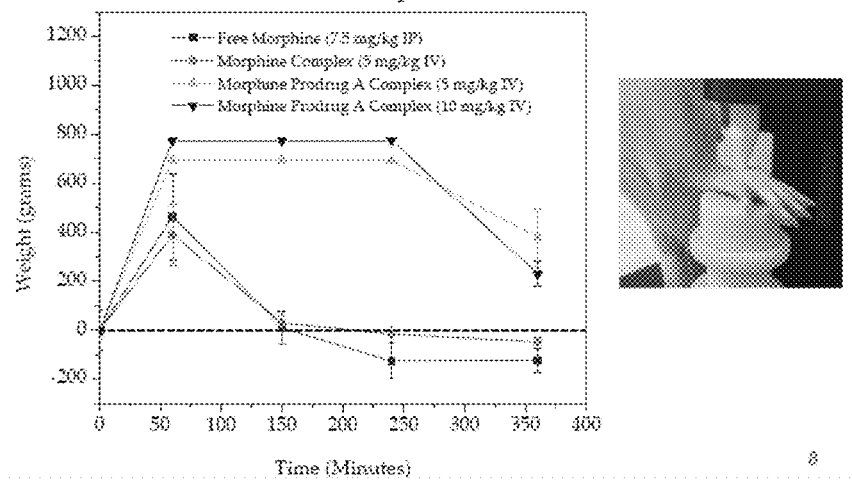
FIG. 47 shows sustained release of morphine in the guinea pig model over a six hour period with prodrug A.

The Randall & Selitto test apparatus (Harvard Instruments) is used to measure analgesia and is based on determination of the animal threshold response to pain induced in the paw by the application of a uniformly increasing pressure from a conical tip upon the dorsal surface of the rear paw which rests on a platform. The weight in grams is taken upon withdrawal of the animals paw from the platform with five repeated measurements of pain threshold recorded for each time point (control, 60, 150, 240, and 360 min) after drug administration. Values are normalized to control and the mean±SEM for each time point are recorded. To reduce tissue damage to the animal a weight limit is used for all animals. FIG. 47 shows sustained release of morphine in the guinea pig model over a six hour period with prodrug A.

Figure 48:
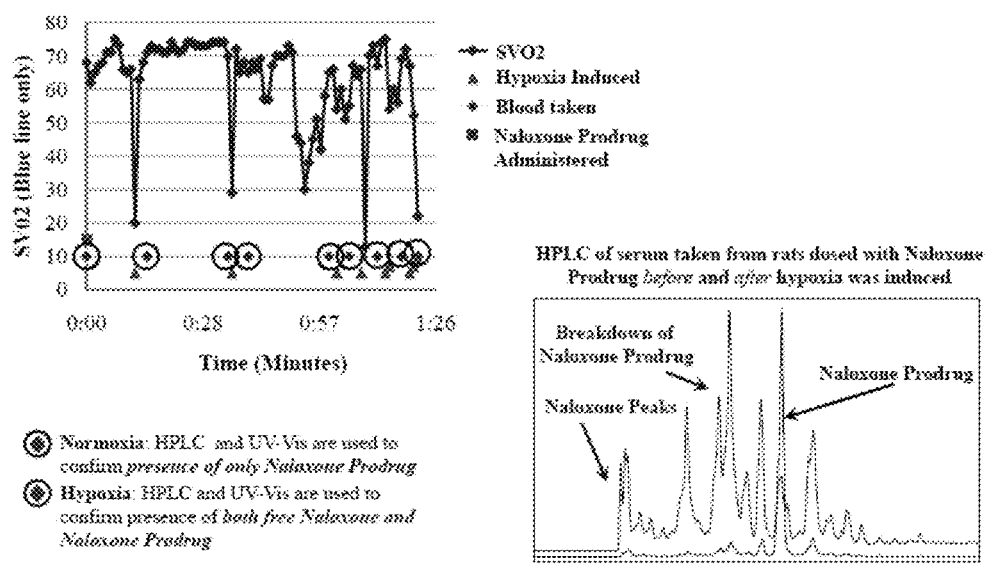
FIG. 48 shows in vivo studies with a guinea pig model demonstrating that naloxone is release from naloxone-prodrug only under low oxygen conditions.

After collecting the blood samples from the animals, the blood samples were spun down and the supernatant (plasma) was taken for further analysis using UPLC (ultra performance liquid chromatography). Prior to subjecting the samples to UPLC, the samples were pre-treated to remove the plasma proteins using a solid phase extraction protocol. Using a Waters HLB micro elution plates, the samples were passed through the cartridge following a washing and an equilibration step with Water and methanol respectively, the samples were then loaded on to the cartridge and followed by elution with 40/60 Acetonitrile/Isopropanol. The solvent was evaporated over night and the samples were reconstituted in UPLC eluent for analysis. UPLC analysis was performed using an Acquity HSS T3 column (2.1×10 mm). Flow rate was maintained at 0.5 ml/min. Released Morphine was monitored using a PDA detector at 280 nm. The gradient elution used for this method began at 98/2 Water/Acetonitrile containing 0.14% TFA and ended with 2/98 Water/Acetonitrile containing 0.14% TFA in 6.5 minutes. FIG. 48 shows in vivo studies with a guinea pig model demonstrating that naloxone is release from naloxone-pro-drug only under low oxygen conditions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method for simultaneously ameliorating pain and preventing respiratory depression in a subject, comprising providing a composition comprising pain relief complexes and pain relief antagonist complexes;

wherein said pain relief complexes consist of dendrimers separately conjugated with 1) a pain relief agent via an ester linkage agent, wherein said pain relief agent is morphine, 2) a locking agent, wherein said locking agent is trigonelline, and 3) a targeting agent, wherein said targeting agent is transferrin;

wherein said pain relief antagonist complexes consist of dendrimers separately conjugated with 1) a pain relief agent antagonist via an indolequinone trigger agent, wherein said pain relief agent antagonist is naloxone, 2) a locking agent, wherein said locking agent is trigonelline, and 3) a targeting agent, wherein said targeting agent is transferrin;

wherein said dendrimers within said pain relief complexes and pain relief antagonist complexes are separate within said composition;

administering said composition to a subject experiencing pain such that said pain relief complexes and pain relief antagonist complexes cross the blood brain barrier and are locked within the central nervous system, releasing said morphine from said pain relief complexes upon interaction between an endogenous esterase and said ester linkage agent, wherein said release of said morphine results in pain amelioration, and releasing said naloxone from said pain relief antagonist complexes upon endogenous hypoxic conditions within said subject, wherein said release of said naloxone results in prevention of respiratory depression.

2. The method of claim 1, wherein said subject is a human subject.

3. The method of claim 1, wherein said dendrimers are selected from the group consisting of a polyamideamine (PAMAM) dendrimer, a polypropylamine (POPAM) dendrimer, and a PAMAM-POPAM dendrimer.

4. The method of claim 1, wherein the linkage agent comprises a spacer comprising between 1 and 8 straight or branched carbon chains, wherein said straight or branched chains are selected from the group consisting of i) unsubstituted, and ii) substituted with alkyls.

5. The method of claim 1, wherein said dendrimers are acetylated.

* * * * *